United States Patent
Reed et al.

(10) Patent No.: US 7,671,183 B2
(45) Date of Patent: Mar. 2, 2010

(54) PAAD DOMAIN-CONTAINING POLYPEPTIDES, ENCODING NUCLEIC ACIDS, AND METHODS OF USE

(75) Inventors: John C. Reed, Rancho Santa Fe, CA (US); Adam Godzik, San Diego, CA (US)

(73) Assignee: Burnham Institute for Medical Research, La Jolla, CA (US)

( * ) Notice: Subject to any disclaimer, the term of this patent is extended or adjusted under 35 U.S.C. 154(b) by 0 days.

(21) Appl. No.: 11/496,017

(22) Filed: Jul. 27, 2006

(65) Prior Publication Data

US 2007/0020708 A1    Jan. 25, 2007

Related U.S. Application Data

(62) Division of application No. 10/407,866, filed on Apr. 4, 2003, now abandoned.

(60) Provisional application No. 60/370,538, filed on Apr. 4, 2002.

(51) Int. Cl.
*C07H 21/02* (2006.01)
(52) U.S. Cl. .................................. 536/23.1
(58) Field of Classification Search ................. 536/23.1
See application file for complete search history.

(56) References Cited

U.S. PATENT DOCUMENTS

2003/0077699 A1* 4/2003 Reed et al. ................. 435/69.1
2005/0191624 A1* 9/2005 Bertin et al. .................... 435/6

FOREIGN PATENT DOCUMENTS

| WO | WO 01/14564 A2 | | 3/2001 |
|---|---|---|---|
| WO | WO 01/57188 A2 | * | 8/2001 |
| WO | WO 01/61005 | | 8/2001 |
| WO | WO 01/57188 A2 | * | 9/2001 |
| WO | WO 01/75067 A2 | * | 10/2001 |
| WO | WO 01/83753 A2 | * | 11/2001 |
| WO | WO 01/92527 A2 | * | 12/2001 |
| WO | WO 02/40668 A2 | * | 5/2002 |
| WO | WO 02/061049 A2 | * | 8/2002 |

OTHER PUBLICATIONS

Aderem et al., "Toll-like receptors in the induction of the innate immune responses," *Nature* 406:782-787 (2000).
Aravind et al., "The domains of death: evolution of the apoptosis machinery," *TIBS* 24(2):47-53 (1999).
Bertin and DiStefano, "The PYRIN domain: a novel motif found in apoptosis and inflammation proteins," *Cell Death Differ*. 7(12):1273-1274 (2000).
Beutler, "Autoimmunity and apoptosis: The Crohn's connection," *Immunity* 15:5-14 (2001).
Bork, P. "Powers and pitfalls in sequence (2000) analysis: the 70% hurdle," *Genome Res*. 10:398-400 (2000).
Bowie et al., "Deciphering the message in protein sequences: tolerance to amino acid substitutions," *Science* 257:1306-1310 (1990).
Burgess et al., "Possible dissociation of the heparin-binding and mitogenic activities of heparin-binding (acidic fibroblast) growth factor-1 form its receptor-binding activities by site-directed mutagenesis of a single lysine reside," *J. Cell. Biol*. 111:2129-2138 (1990).
Carpentier et al., "TRAF1 is a TNF inducible regulator of NF-κB activation," *FEBS Letters* 460:246-250 (1999).
Chu et al, "A novel enhancer of the Apaf1 apoptosome involved in cytochrome c-dependent caspase activation and apoptosis," *J. Biol. Chem* 276:9239-9245 (2001).
Damiano et al., "CLAN, a novel human CED-4-like gene," *Genomics* 75:77-83 (2001).
Dawson and Trapani, "The interferon-inducible autoantigen, IFI 16: localization to the nucleolus and identification of a DNA-binding domain," *Biochem Biophys. Res. Commun*. 214:152-162 (1995).
DeYoung et al., "Cloning a novel member of the human interferon-inducible gene family associated with control of tumorigenicity n a model of human melanoma," *Oncogene* 15:453-457 (1997).
Fairbrother et al., "The PYRIN domain: a member of the death domain-fold superfamily," *Protein Science* 10:1911-1918 (2001).
French FMF Consortium, "The A candidate gene for familial mediterranean fever," *Nature Genetics* 17:25-31 (1997).
Hayashi et al., "The innate immune response to bacterial flagellin is mediated by Toll-like receptor 5," *Nature* 410:1099-1103 (2001).
Hlaing et al., "Molecular cloning and characterization of DEFCAP-L and -S, two isoforms of a novel member of the mammalian Ced-4 family of apoptosis proteins," *J. Biol. Chem*. 276:9230-9238 (2001).
Hoffman et al, "Mutation of a new gene encoding a putative pyrin-like protein causes familial cold autoinflammatory syndrome and Muckle-Wells syndrome," *Nature Genetics* 29:301-305 (2001).
Inohara and Nunez, "Genes with homology to mammalian apoptosis regulators identified in zebrafish," *Cell Death Differ*. 7:509-510 (2000).
Inohara et al., "Nod1, an Apaf-1-like activator of caspase-9 and nuclear factor-κB," *J. Biol. Chem*. 274:14560-14567 (1999).

(Continued)

*Primary Examiner*—Sean E Aeder
(74) *Attorney, Agent, or Firm*—McDermott Will & Emery LLP

(57) ABSTRACT

The invention provides isolated nucleic acid molecules encoding PAAD-domain containing polypeptides and functional fragments thereof, including fragments containing PAAD domains, NACHT domains and ARED domains, encoded polypeptides, and antibodies. Also provided are methods of identifying polypeptides and agents that associate with a PAAD-domain containing polypeptide or fragment thereof, or that alter an association of a PAAD domain-containing polypeptides. Further provided are methods of identifying agents that modulate PAAD domain-mediated inhibition of NFκB activity, or modulate an activity of a NACHT domain of a PAAD domain-containing polypeptide. Also provided are methods of modulating NFκB transcriptional activity in a cell, and methods of altering expression of a PAAD domain-containing polypeptide in a cell.

9 Claims, 33 Drawing Sheets

OTHER PUBLICATIONS

Johnstone et al., "The human interferon-inducible protein, IFI 16, is a repressor of transcription," *J. Biol. Chem.* 273:17172-17177 (1998).

Jones, "GenTHREADER: an efficient and reliable protein fold recognition method for genomic sequences," *J. Mol. Biol.* 287:797-815 (1999).

Karin et al., "Phosphorylation meets ubiquitination: The control of NF-κB activity," *Ann. Rev. Immunol.* 18:621-663 (2000).

Karplus et al., "Hidden Markov models for detecting remote protein homologies," *Bioinformatics* 14(10):846-856 (1998).

Koonin and Aravind, "The NACHT family—a new group of predicted NTPases implicated in apoptosis and MHC transcription activation," *TIBS* 25:223-224 (2000).

Lawrence et al, "Detecting subtle sequence signals: a Gibbs sampling strategy for multiple alignment," *Science* 262:208-214 (1993).

Lee et al., "COP, a caspase recruitment domain-containing protein and inhibitor of caspase-1 activation processing," *J. Biol. Chem.* 276:34495-34500 (2001).

Lennon et al., "The I.M.A.G.E. consortium: an integrated molecular analysis of genomes and their expression," *Genomics* 33:151-152 (1996).

Manji et al, "PYPAF1, a Pyrin-containing Apaf1-like protein that assembles with ASC and regulates activation of NF-kappa B," *J. Boi. Chem.* 277(13):11570-11575 (2002) (epub ahead of print).

Martinon et al., "The pyrin domain: a possible member of the death domain-fold family implicated in apoptosis and inflammation," *Curr. Biol.* 10(4):R118-R120 (2001).

Masumoto et al., "ASC, a novel 22-kDa protein, aggregates during apoptosis of human promyelocytic leukemia HL-60 cells," *J. Biol. Chem.* 274:33835-33838 (1999).

Masumoto et al., "Pyrin N-terminal homology domain- and caspase recruitment domain-dependent oligomerization of ASC," *Biochem. Biophys. Res. Commun.* 280(3):652-655 (2001).

Masumoto et al., "Murine ortholog of ASC, a CARD-containing protein, self-associates and exhibits restricted distribution in developing mouse embryos," *Exp. Cell Res.* 262(2):128-133 (2001).

Masumoto et al, "Expression of apoptosis-associated speck-like protein containing a Caspase Recruitment domain, a pyrin N-terminal Homology domain-containing protein, in normal human tissues," *J. Histochem. and Cytochem.* 49(10):1269-1275 (2001).

Pawloski et al., "PAAD—a new protein dmain associated with apoptosis, cancer and autoimmune diseases," *Trends Biochem. Sci.* 26(2):85-87 (2001).

Pras, "Familial mediterranean fever: from the clinical syndrome to the cloning of the pyrin gene," *Scand. J. Rheumatol.* 27:92-97 (1998).

Richards et al, "Interaction between Pyrin and the apoptotic speck protein (ASC) modulates ASC-induced apoptosis " *J. Biol. Chem.* 276(42):39320-39329 (2001).

Rost et al., "PHD—an automatic mail server for protein secondary structure prediction," *CABIOS* 10:53-60 (1994).

Ruiz-Opazo et al., "Identification of a novel dual angiotensin II/vasopressin receptor on the basis of molecular recognition theory," *Nature Med.* 1:1074-1081 (1995).

Rychlewski et al., "Comparison of sequence profiles. Strategies for structural predictions using sequence information," *Protein Science* 9:232-241 (2000).

Sali and Blundell, "Comparative protein modelling by satisfaction of spatial restraints," *J. Mol. Biol.* 234:779-815 (1993).

Scott et al., "The Pendred syndrome gene encodes a chloride-iodide transport protein," *Nat. Genet.* 21:440-443 (1999).

Staub et al., "The Dapin family: a novel domain links apoptotic and interferon response proteins," *TIBS* 26(2): 83-85 (2001).

Takeuchi et al., "TLR6: A novel member of an expanding Toll-like receptor family," *Gene* 231:59-65 (1999).

Thompson et al., "CLUSTAL W: improving the sensitivity of progressive multiple sequence alignment through sequence weighting, position-specific gap penalties and weight matrix choice," *Nucleic Acids Research* 22 (22):4673-4680 (1994).

van der Biezen and Jones, "The NB-ARC domain: a novel signalling motif shared by plant resistance gene products and regulators of cell death in animals," *Curr. Biol.* 8:R226-R227 (1998).

Xie et al., "MNDA dimerizes through a complex motif involving an N-terminal basic region," *FEBS Letters* 408:151-155 (1997).

Genbank Accession No. 4557743, Aug. 1, 2007.
Genbank Accession No. 5094556, Aug. 1, 2007.
Genbank Accession No. 7019331, Aug. 1, 2007.
Genbank Accession No. 7689912, Aug. 1, 2007.
Genbank Accession No. 7020664, Aug. 1, 2007.
Genbank Accession No. 7382417, Aug. 1, 2007.
Genbank Accession No. 2335202, Aug. 1, 2007.
Genbank Accession No. 7690109, Aug. 1, 2007.
Genbank Accession No. 8099799, Aug. 1, 2007.
Genbank Accession No. 8655944, Aug. 1, 2007.
Genbank Accession No. 7662386, Aug. 1, 2007.
Genbank Accession No. 5902751, Aug. 1, 2007.
Genbank Accession No. 2833279, Aug. 1, 2007.
Genbank Accession No. 6523868, Aug. 1, 2007.
Genbank Accession No. 3483677, Aug. 1, 2007.
Genbank Accession No. 10440263, Aug. 1, 2007.
Genbank Accession No. 14731965, Aug. 1, 2007.
Genbank Accession No. 15488764, Aug. 1, 2007.
Genbank Accession No. 202805, Aug. 1, 2007.
Genbank Accession No. 9211204, Aug. 1, 2007.
Genbank Accession No. 15488878, Aug. 1, 2007.
Genbank Accession No. 14779445, Aug. 1, 2007.
Genbank Accession No. 14779455, Aug. 1, 2007.
Genbank Accession No. 14488058, Aug. 1, 2007.
Genbank Accession No. 11096298, Aug. 1, 2007.
Genbank Accession No. 9802275, Aug. 1, 2007.
Genbank Accession No. 9863861, Aug. 1, 2007.
Genbank Accession No. 986863, Aug. 1, 2007.
Genbank Accession No. 10835255, Aug. 1, 2007.
Genbank Accession No. 10801601, Aug. 1, 2007.
Genbank Accession No. 7020146, Aug. 1, 2007.
Genbank Accession No. 14779447, Aug. 1, 2007.
Genbank Accession No. 13325315, Aug. 1, 2007.
Genbank Accession No. 15215377, Aug. 1, 2007.
Genbank Accession No. 11230601, Aug. 1, 2007.
Genbank Accession No. 9937751, Aug. 1, 2007.
Genbank Accession No. 14758026, Aug. 1, 2007.
Genbank Accession No. 15193291, Aug. 1, 2007.
Genbank Accession No. 13182796, Aug. 1, 2007.
Genbank Accession No. 14731967, Aug. 1, 2007.
Genbank Accession No. 4757727, Aug. 1, 2007.
Genbank Accession No. 3341995, Aug. 1, 2007.
Genbank Accession No. 14253110, Aug. 1, 2007.
Genbank Accession No. 9153913, Aug. 1, 2007.
Genbank Accession No. 1383656, Aug. 1, 2007.
Genbank Accession No. BE278926, Aug. 1, 2007.
Genbank Accession No. W73523 (GI:1383656), Aug. 1, 2007.
Genbank Accession No. P29315, Aug. 1, 2007.
Genbank Accession No. AF442488, Aug. 1, 2007.
Genbank Accession No. AC022066, Aug. 1, 2007.

* cited by examiner

FIGURE 1

ASC

PAN1 - PAN6 (only some contain leucine rich repeats - LRR)

NAC zebrafish caspase pyrin

IFI16,

AIM2, MNDA

ASC2

PAN 3

Nucleotide Sequence: SEQ ID NO:65 atggaccagccagaggcccctgctccagcacggggccgcgcctcgcggtggcccgcgag
ctgctcctggctgcgctggaggaactgagccaagagcagctgaagcgcttccgccacaag
ctgcgcgacgtgggcccggacggacgcagcatcccgtggggcggctggagcgcgcggac
gccgtggacctcgcggagcagctggcccagttctacggcccggagcctgccctggaggtg
gcccgcaagaccctcaagagggcggacgcgcgcgacgtggcggcgcagctccaggagcgg
cggctgcagcggctcgggctcggctccgggacgctgctctccgtgtccgagtacaagaag
aagtaccgggagcacgtgctgcagctgcacgctcgggtgaaggagaggaacgcccgctcc
gtgaagatcaccaagcgcttcaccaagctgctcatcgcgcccgagagcgccgccccggag
gaggcgctggggcccgcggaagagcctgagccggggcgcgcgcggcgctcggacacgcac
actttcaaccgcctcttccgccgcgacgaggagggccggcggccgctgaccgtggtgctg
cagggcccggcgggcatcggcaagaccatggcggccaaaaagatcctgtacgactgggcg
gcgggcaagctgtaccagggccaggtggacttcgccttcttcatgccctgcggcgagctg
ctggagaggccgggcacgcgcagcctggctgacctgatcctggaccagtgccccgaccgc
ggcgcgccggtgccgcagatgctggcccagccgcagcggctgctcttcatcctggacggc
gcggacgagctgccggcgctgggggccccgaggccgcgccctgcacagacccttcgag
gcggcgagcggcgcgcgggtgctaggcgggctgctgagcaaggcgctgctgcccacggcc
ctcctgctggtgaccacgcgcgccgccgcccccgggaggctgcagggccgcctgtgttcc
ccgcagtgcgccgaggtgcgcggcttctccgacaaggacaagaagaagtatttctacaag
ttcttccgggatgagaggagggccgagcgcgcctaccgcttcgtgaaggagaacgagacg
ctgttcgcgctgtgcttcgtgcccttcgtgtgctggatcgtgtgcaccgtgctgcgccag
cagctggagctcggtcgggacctgtcgcgcacgtccaagaccaccacgtcagtgtacctg
cttttcatcaccagcgttctgagctcggctccggtagccgacgggccccggttgcagggc
gacctgcgcaatctgtgccgcctggcccgcgagggcgtcctcggacgcagggcgcagttt
gccgagaaggaactggagcaactggagcttcgtggctccaaagtgcagacgctgtttctc
agcaaaaaggagctgccgggcgtgctggagacagaggtcacctaccagttcatcgaccag
agcttccaggagttcctcgcggcactgtcctacctgctggaggacggcggggtgcccagg
accgcggctggcggcgttgggacactcctgcgtggggacgcccagccgcacagccacttg
gtgctcaccacgcgcttcctcttcggactgctgagcgcggagcggatgcgcgacatcgag
cgccacttcggctgcatggtttcagagcgtgtgaagcaggaggccctgcggtgggtgcag
ggacagggacagggctgccccggagtggcaccagaggtgaccgaggggggccaaagggctc
gaggacaccgaagagccagaggaggaggaggagggagaggagcccaactacccactggag
ttgctgtactgcctgtacgagacgcaggaggacgcgtttgtgcgccaagccctgtgccgg
ttcccggagctggcgctgcagcgagtgcgcttctgccgcatggacgtggctgttctgagc
tactgcgtgaggtgctgccctgctggacaggcactgcggctgatcagctgcagattggtt
gctgcgcaggagaagaagaagaagagcctggggaagcggctccaggccagcctgggtggc
ggcagctggctggggacccaactggctccagaagtacccttttcgaccaccctgctgtgac
atctgccccacacctccaccagaccctcggctcctccagggcaaggcttttgccagagtt
cctttgaatatagctccaattcagccctgcccaggggcttggcatctgttgagaggatg
aatgtcacggtgttggcaggggctgggcctggggacccaaagacccatgcaatgactgac
ccactgtgccatctgagcagcctcacgctgtcccactgcaaactccctgacgcggtctgc
cgagacctttctgaggccctgagggcagccccgcactgacggagctgggcctcctccac
aacaggctcagtgaggcaggactgcgtatgctgagtgagggcctagcctggccgcagtgc
agggtgcagacggtcagggtacagctgcctgaccccagcgagggctccagtacctggtg
ggtatgcttcggcagagccctgccctgaccaccctggatctcagcggctgccaactgccc
gcccccatggtgacctacctgtgtgcagtcctgcagcaccagggatgcggcctgcagacc
ctcagcct

FIGURE 12A

PAN 3

Amino Acid Sequence: SEQ ID NO:66

```
MDQPEAPCSSTGPRLAVARELLLAALEELSQEQLKRFRHKLRDVGPDGRSIPWGRLERAD
AVDLAEQLAQFYGPEPALEVARKTLKRADARDVAAQLQERRLQRLGLGSGTLLSVSEYKK
KYREHVLQLHARVKERNARSVKITKRFTKLLIAPESAAPEEALGPAEEPEPGRARRSDTH
TFNRLFRRDEEGRRPLTVVLQGPAGIGKTMAAKKILYDWAAGKLYQGQVDFAFFMPCGEL
LERPGTRSLADLILDQCPDRGAPVPQMLAQPQRLLFILDGADELPALGGPEAAPCTDPFE
AASGARVLGGLLSKALLPTALLLVTTRAAAPGRLQGRLCSPQCAEVRGFSDKDKKKYFYK
FFRDERRAERAYRFVKENETLFALCFVPFVCWIVCTVLRQQLELGRDLSRTSKTTTSVYL
LFITSVLSSAPVADGPRLQGDLRNLCRLAREGVLGRRAQFAEKELEQLELRGSKVQTLFL
SKKELPGVLETEVTYQFIDQSFQEFLAALSYLLEDGGVPRTAAGGVGTLLRGDAQPHSHL
VLTTRFLFGLLSAERMRDIERHFGCMVSERVKQEALRWVQGQGQGCPGVAPEVTEGAKGL
EDTEEPEEEEGEEPNYPLELLYCLYETQEDAFVRQALCRFPELALQRVRFCRMDVAVLS
YCVRCCPAGQALRLISCRLVAAQEKKKKSLGKRLQASLGGGSWLGTQLAPEVPFRPPCCD
ICPTPPPDPRLLQGKAFARVPLNIAPIQPLPRGLASVERMNVTVLAGAGPGDPKTHAMTD
PLCHLSSLTLSHCKLPDAVCRDLSEALRAAPALTELGLLHNRLSEAGLRMLSEGLAWPQC
RVQTVRVQLPDPQRGLQYLVGMLRQSPALTTLDLSGCQLPAPMVTYLCAVLQHQGCGLQT
LS
```

FIGURE 12B

PAN 6

Nucleotide Sequence: SEQ ID NO:67

```
CTCTCCGCCCGCTGCCTGTGAATGA
TGCAATGGAAGGTGTGCTGGGGTCGCCCTGTGTCCCGTGCATAGGAGCAT
CTCAGCCTCCAGGTCCTCTCCTTTGGGGCTCACGGCACCCCATGCTACG
AACCGCAGGCAGGGACGGCCTCTGTCGCCTGTCCACCTACTTGGAAGAAC
TCGAGGCTGTGGAACTGAAGAAGTTCAAGTTATACCTGGGGACCGCGACA
GAGCTGGGAGAAGGCAAGATCCCCTGGGGAAGCATGGAGAAGGCCGGTCC
CCTGGAAATGGCCCAGCTGCTCATCACCCACTTCGGGCCAGAGGAGGCCT
GGAGGTTGGCTCTCAGCACCTTTGAGCGGATAAACAGGAAGGACCTGTGG
GAGAGAGGACAGAGAGAGGACCTGGTGAGGGATACCCCACCTGGTGGCCC
GTCCTCACTTGGGAACCAGTCAACATGCCTTCTGGAAGTCTCTCTTGTCA
CTCCAAGAAAAGATCCCCAGGAAACCTACAGGGACTATGTCCGCAGGAAA
TTCCGGCTCATGGAAGACCGCAATGCGCGCCTAGGGGAATGTGTCAACCT
CAGCCACCGGTACACCCGGCTCCTGCTGGTGAAGGAGCACTCAAACCCCA
TGCAGGTCCAGCAGCAGCTTCTGGACACAGGCCGGGGACACGCGAGGACC
GTGGGACACCAGGCTAGCCCCATCAAGATAGAGACCCTCTTTGAGCCAGA
CGAGGAGCGCCCCGAGCCACCGCGCACCGTGGTCATGCAAGGCGCGGCAG
GGATAGGCAAGTCCATGCTGGCACACAAGGTGATGCTGGACTGGGCGGAC
GGGAAGCTCTTCCAAGGCAGATTTGATTATCTCTTCTACATCAACTGCAG
GGAGATGAACCAGAGTGCCACGGAATGCAGCATGCAAGACCTCATCTTCA
GCTGCTGGCCTGAGCCAGCGCGCCTCTCCAGGAGCTCATCCGAGTTCCC
GAGCGCCTCCTTTTCATCATCGACGGCTTCGATGAGCTCAAGCCTTCTTT
CCACGATCCTCAGGGACCCTGGTGCCTCTGCTGGGAGGAGAAACGGCCCA
CGGAGCTGCTTCTTAACAGCTTAATTCGGAAGAAGCTGCTCCCTGAGCTA
TCTTTGCTCATCACCACACGGCCCACGGCTTTGGAGAAGCTCCACCGTCT
GCTGGAGCACCCCAGGCATGTGGAGATCCTGGGCTTCTCTGAGGCAGAAA
GGAAGGAATACTTCTACAAGTATTTCCACAATGCAGAGCAGGCGGGCCAA
GTCTTCAATTACGTGAGGGACAACGAGCCTCTCTTCACCATGTGCTTCGT
CCCCCTGGTGTGCTGGGTGGTGTGTACCTGCCTCCAGCAGCAGCTGGAGG
GTGGGGGGCTGTTGAGACAGACGTCCAGGACCACCACTGCAGTGTACATG
CTCTACCTGCTGAGTCTGATGCAACCCAAGCCGGGGGCCCCGCGCCTCCA
GCCCCCACCCAACCAGAGAGGGTTGTGCTCCTTGGCGGCAGATGGGCTCT
GGAATCAGAAAATCCTATTTGAGGAGCAGGACCTCCGGAAGCACGGCCTA
GACGGGGAAGACGTCTCTGCCTTCCTCAACATGAACATCTTCCAGAAGGA
CATCAACTGTGAGAGGTACTACAGCTTCATCCACTTGAGTTTCCAGGAAT
TCTTTGCAGCTATGTACTATATCCTGGACGAGGGGGAGGGCGGGGCAGGC
CCAGACCAGGACGTGACCAGGCTGTTGACCGAGTACGCGTTTTCTGAAAG
GAGCTTCCTGGCACTCACCAGCCGCTTCCTGTTTGGACTCCTGAACGAGG
AGACCAGGAGCCACCTGGAGAAGAGTCTCTGCTGGAAGGTCTCGCCGCAC
ATCAAGATGGACCTGTTGCAGTGGATCCAAAGCAAAGCTCAGAGCGACGG
CTCCACCCTGCAGCAGGGCTCCTTGGAGTTCTTCAGCTGCTTGTACGAGA
TCCAGGAGGAGGAGTTTATCCAGCAGGCCCTGAGCCACTTCCAGGTGATC
GTGGTCAGCAACATTGCCTCCAAGATGGAGCACATGGTCTCCTCGTTCTG
TCTGAAGCGCTGCAGGAGCGCCCAGGTGCTGCACTTGTATGGCGCCACCT
```

FIGURE 13A

```
ACAGCGCGGACGGGGAAGACCGCGCGAGGTGCTCCGCAGGAGCGCACACG
CTGTTGGTGCAGCTCAGACCAGAGAGGACCGTTCTGCTGGACGCCTACAG
TGAACATCTGGCAGCGGCCCTGTGCACCAATCCAAACCTGATAGAGCTGT
CTCTGTACCGAAATGCCCTGGGCAGCCGGGGGGTGAAGCTGCTCTGTCAA
GGACTCAGACACCCCAACTGCAAACTTCAGAACCTGAGGCTGAAGAGGTG
CCGCATCTCCAGCTCAGCCTGCGAGGACCTCTCTGCAGCTCTCATAGCCA
ATAAGAATTTGACAAGGATGGATCTCAGTGGCAACGGCGTTGGATTCCCA
GGCATGATGCTGCTTTGCGAGGGCCTGCGGCATCCCCAGTGCAGGCTGCA
GATGATTCAGTTGAGGAAGTGTCAGCTGGAGTCCGGGCTTGTCAGGAGA
TGGCTTCTGTGCTCGGCACCAACCCACATCTGGTTGAGTTGGACCTGACA
GGAAATGCACTGGAGGATTTGGGCCTGAGGTTACTATGCCAGGGACTGAG
GCACCCAGTCTGCAGACTACGGACTTTGTGGCTGAAGATCTGCCGCCTCA
CTGCTGCTGCCTGTGACGAGCTGGCCTCAACTCTCAGTGTGAACCAGAGC
CTGAGAGAGCTGGACCTGAGCCTGAATGAGCTGGGGGACCTCGGGGTGCT
GCTGCTGTGTGAGGGCCTCAGGCATCCCACGTGCAAGCTCCAGACCCTGC
GGTTGGGCATCTGCCGGCTGGGCTCTGCCGCCTGTGAGGGTCTTTCTGTG
GTGCTCCAGGCCAACCACAACCTCCGGGAGCTGGACTTGAGTTTCAACGA
CCTGGGAGACTGGGGCCTGTGGTTGCTGGCTGAGGGGCTGCAACATCCCG
CCTGCAGACTCCAGAAACTGTGGCTGGATAGCTGTGGCCTCACAGCCAAG
GCTTGTGAGAATCTTTACTTCACCCTGGGGATCAACCAGACCTTGACCGA
CCTTTACCTGACCAACAACGCCCTAGGGGACACAGGTGTCCGACTGCTTT
GCAAGCGGCTGAGCCATCCTGGCTGCAAACTCCGAGTCCTCTG
```

FIGURE 13B

PAN 6

Amino Acid Sequence: SEQ ID NO:68

MLRTAGRDGLC
RLSTYLEELEAVELKKFKLYLGTATELGEGKIPWGSMEKAGPLEMAQLLI
THFGPEEAWRLALSTFERINRKDLWERGQREDLVRDTPPGGPSSLGNQST
CLLEVSLVTPRKDPQETYRDYVRRKFRLMEDRNARLGECVNLSHRYTRLL
LVKEHSNPMQVQQQLLDTGRGHARTVGHQASPIKIETLFEPDEERPEPPR
TVVMQGAAGIGKSMLAHKVMLDWADGKLFQGRFDYLFYINCREMNQSATE
CSMQDLIFSCWPEPSAPLQELIRVPERLLFIIDGFDELKPSFHDPQGPWC
LCWEEKRPTELLLNSLIRKKLLPELSLLITTRPTALEKLHRLLEHPRHVE
ILGFSEAERKEYFYKYFHNAEQAGQVFNYVRDNEPLFTMCFVPLVCWVVC
TCLQQQLEGGGLLRQTSRTTTAVYMLYLLSLMQPKPGAPRLQPPPNQRGL
CSLAADGLWNQKILFEEQDLRKHGLDGEDVSAFLNMNIFQKDINCERYYS
FIHLSFQEFFAAMYYILDEGEGGAGPDQDVTRLLTEYAFSERSFLALTSR
FLFGLLNEETRSHLEKSLCWKVSPHIKMDLLQWIQSKAQSDGSTLQQGSL
EFFSCLYEIQEEEFIQQALSHFQVIVVSNIASKMEHMVSSFCLKRCRSAQ
VLHLYGATYSADGEDRARCSAGAHTLLVQLRPERTVLLDAYSEHLAAALC
TNPNLIELSLYRNALGSRGVKLLCQGLRHPNCKLQNLRLKRCRISSSACE
DLSAALIANKNLTRMDLSGNGVGFPGMMLLCEGLRHPQCRLQMIQLRKCQ
LESGACQEMASVLGTNPHLVELDLTGNALEDLGLRLLCQGLRHPVCRLRT
LWLKICRLTAAACDELASTLSVNQSLRELDLSLNELGDLGVLLLCEGLRH
PTCKLQTLRLGICRLGSAACEGLSVVLQANHNLRELDLSFNDLGDWGLWL
LAEGLQHPACRLQKLWLDSCGLTAKACENLYFTLGINQTLTDLYLTNNAL
GDTGVRLLCKRLSHPG

FIGURE 13C

PAN 7

Nucleotide Sequence: SEQ ID NO:69 atgacatcgccccagctagagtggactctgcagacccttctggagcagctgaacgaggat
gaattaaagagtttcaaatccttttatgggcttttcccctcgaagacgtgctacagaag
accccatggtctgaggtggaagaggctgatggcaagaaactggcagaaattctggtcaac
acctcctcagaaaattggataaggaatgcgactgtgaacatcttggaagagatgaatctc
acggaattgtgtaagatggcaaaggctgagatgatggaggacggacaggtgcaagaaata
gataatcctgagctgggagatgcagaagaagactcggagttagcaaagccaggtgaaaag
gaaggatggagaaattcaatggagaaacagtctttggtctggaagaaccttttggcaa
ggagacattgacaatttccatgacgacgtcactctgagaaaccaacggttcattccattc
ttgaatcccagaacacccaggaagctaacaccttacacggtggtgctgcacggccccgca
ggcgtggggaaaaccacgctggccaaaagtgtatgctggactggacagactgcaacctc
agcccgacgctcagatacgcgttctacctcagctgcaaggagctcagccgcatgggcccc
tgcagttttgcagagctgatctccaaagactggcctgaattgcaggatgacattccaagc
atcctagcccaagcacagagaatcctgttcgtggtcgatggccttgatgagctgaaagtc
ccacctggggcgctgatccaggacatctgcggggactgggagaagaagaagccggtgccc
gtcctcctggggagtttgctgaagaggaagatgttacccagggcagccttgctggtcacc
acgcggcccagggcactgagggacctccagctcctggcgcagcagccgatctacgtaagg
gtggagggcttcctggaggaggacaggagggcctatttcctgagacactttggagacgag
gaccaagccatgcgtgcctttgagctaatgaggagcaacgcggccctgttccagctgggc
tcggccccgcggtgtgctggattgtgtgcacgactctgaagctgcagatggagaagggg
gaggacccggtccccacctgcctcacccgcacggggctgttcctgcgtttcctctgcagc
cggttcccgcagggcgcacagctgcggggcgcgctgcggacgctgagcctcctggccgcg
cagggcctgtgggcgcagatgtccgtgttccaccgagaggacctggaaaggctcggggtg
caggagtccgacctccgtctgttcctggacggagacatcctccgccaggacagagtctcc
aaaggctgctactccttcatccacctcagcttccagcagtttctcactgccctgttctac
gccctggagaaggaggaggggggaggacagggacggccacgcctgggacatcggggacgta
cagaagctgctttccggagaagaaagactcaagaaccccgacctgattcaagtaggacac
ttcttattcggcctcgctaacgagaagagagccaaggagttggaggccacttttggctgc
cggatgtcaccggacatcaaacaggaattgctgcaatgcaaagcacatcttcatgcaaat
aagcccttatccgtgaccgacctgaaggaggtcttgggctgcctgtatgagtctcaggag
gaggagctggcgaaggtggtggtggccccgttcaaggaaatttctattcacctgacaaat
acttctgaagtgatgcattgttccttcagcctgaagcattgtcaagacttgcagaaactc
tcactgcaggtagcaaaggggtgttcctggagaattacatggattttgaactggacatt
gaatttgaaagctcaaacagcaacctcaagtttctggaagtgaaacaaagcttcctgagt
gactcttctgtgcggattctttgtgaccacgtaacccgtagcacctgtcatctgcagaaa
gtggagattaaaaacgtcacccctgacaccgcgtaccgggacttctgtcttgctttcatt
gggaagaagaccctcacgcacctgaccctggcagggcacatcgagtgggaacgcacgatg
atgctgatgctgtgacctgctcagaaatcataaatgcaacctgcagtacctgaggttg
ggaggtcactgtgccaccccggagcagtgggctgaattcttctatgtcctcaaagccaac
cagtccctgaagcacctgcgtctctcagccaatgtgctcctggatgagggtgccatgttg
ctgtacaagaccatgacacgcccaaaacacttcctgcagatgttgtcgttggaaaactgt
cgtcttacagaagccagttgcaaggaccttgctgctgtcttggttgtcagcaagaagctg
acacctgtgcttggccaagaacccattggggatacaggggtgaagtttctgtgtgag
ggcttgagttaccctgattgtaaactgcagaccttggtgttacagcaatgcagcataacc
aagcttggctgtagatacctctcagaggcgctccaagaagcctgcagcctcacaaacctg
gacttgagtatcaaccagatagctcgtggattgtggattctctgtcaggcgttagagaat
ccaaactgtaacctaaaacacctacggttgaagacctatgaaactaatttggaaatcaag
aagctgttggaggaagtgaaagaaaagaatcccaagctgactattgattgcaatgcttcc
ggggcaacggcacctccgtgctgtgacttttttgctga

FIGURE 14A

PAN 7

Amino Acid Sequence: SEQ ID NO:70

MTSPQLEWTLQTLLEQLNEDELKSFKSLLWAFPLEDVLQKTPWSEVEEADGKKLAEILVN
TSSENWIRNATVNILEEMNLTELCKMAKAEMMEDGQVQEIDNPELGDAEEDSELAKPGEK
EGWRNSMEKQSLVWKNTFWQGDIDNFHDDVTLRNQRFIPFLNPRTPRKLTPYTVVLHGPA
GVGKTTLAKKCMLDWTDCNLSPTLRYAFYLSCKELSRMGPCSFAELISKDWPELQDDIPS
ILAQAQRILFVVDGLDELKVPPGALIQDICGDWEKKKPVPVLLGSLLKRKMLPRAALLVT
TRPRALRDLQLLAQQPIYVRVEGFLEEDRRAYFLRHFGDEDQAMRAFELMRSNAALFQLG
SAPAVCWIVCTTLKLQMEKGEDPVPTCLTRTGLFLRFLCSRFPQGAQLRGALRTLSLLAA
QGLWAQMSVFHREDLERLGVQESDLRLFLDGDILRQDRVSKGCYSFIHLSFQQFLTALFY
ALEKEEGEDRDGHAWDIGDVQKLLSGEERLKNPDLIQVGHFLFGLANEKRAKELEATFGC
RMSPDIKQELLQCKAHLHANKPLSVTDLKEVLGCLYESQEEELAKVVVAPFKEISIHLTN
TSEVMHCSFSLKHCQDLQKLSLQVAKGVFLENYMDFELDIEFESSNSNLKFLEVKQSFLS
DSSVRILCDHVTRSTCHLQKVEIKNVTPDTAYRDFCLAFIGKKTLTHLTLAGHIEWERTM
MLMLCDLLRNHKCNLQYLRLGGHCATPEQWAEFFYVLKANQSLKHLRLSANVLLDEGAML
LYKTMTRPKHFLQMLSLENCRLTEASCKDLAAVLVVSKKLTHLCLAKNPIGDTGVKFLCE
GLSYPDCKLQTLVLQQCSITKLGCRYLSEALQEACSLTNLDLSINQIARGLWILCQALEN
PNCNLKHLRLKTYETNLEIKKLLEEVKEKNPKLTIDCNASGATAPPCCDFFC

FIGURE 14B

PAN 8

Nucleotide Sequence: SEQ ID NO:71

```
atggcagattcatcatcatcttctttctttcctgattttgggctgctattgtatttggag
gagctaaacaaagaggaattaaatacattcaagttattcctaaaggagaccatggaacct
gagcatggcctgacaccctggaatgaagtgaagaaggccaggcgggaggacctggccaat
ttgatgaagaaatattatccaggagagaaagcctggagtgtgtctctcaaaatctttggc
aagatgaacctgaaggatctgtgtgagagagcgaagaagagatcaactggtcggcccag
actataggaccagatgatgccaaggctggagagacacaagaagatcaggaggcagtgctg
gtcatagttaacacaggggtccccaactcctgggccacagacccctactggtcggcggcc
cctcgggaatcaggtcgcatagcaggaggtgatggaacagaatacagaaatagaataaag
gaaaaattttgcatcacttgggacaagaagtctttggctggaaagcctgaagatttccat
catggaattgcagagaaagatagaaaactgttggaacacttgttcgatgtggatgtcaaa
accggtgcacagccacagatcgtggtgcttcagggagctgctggagttgggaaaacaacc
ttggtgagaaaggcaatgttagattgggcagagggcagtctctaccagcagaggtttaag
tatgttttttatctcaatgggagagaaattaaccagctgaaagagagaagctttgctcaa
ttgatatcaaaggactggcccagcacagaaggccccattgaagaaatcatgtaccagcca
agtagcctcttgtttattattgacagtttcgatgaactgaactttgcctttgaagaacct
gagtttgcactgtgcgaagactggacccaagaacacccagtgtccttcctcatgagtagt
ttgctgaggaaagtgatgctccctgaggcatccttattggtgacaacaagactcacaact
tctaagagactaaagcagttgttgaagaatcaccattatgtagagctactaggaatgtct
gaggatgcaagagaggagtatatttaccagttttttgaagataagaggtgggccatgaaa
gtattcagttcactaaaaagcaatgagatgctgtttagcatgtgccaagtcccctagtg
tgctgggccgcttgtacttgtctgaagcagcaaatggagaagggtggtgatgtcacattg
acctgccaaacaaccacagctctgtttacctgctatatttctagcttgttcacaccagta
gatggaggctctcctagtctacccaaccaagcccagctgagaagactgtgccaagtcgct
gccaaggaatatggactatgacttacgtgttttacagagaaaatctcagaaggcttggg
ttaactcaatctgatgtctctagttttatggacagcaatattattcagaaggacgcagag
tatgaaaactgctatgtgttcacccaccttcatgttcaggagttttttgcagctatgttc
tatatgttgaaaggcagttgggaagctgggaacccttcctgccagccttttgaagatttg
aagtcattacttcaaagcacaagttataaagaccccatttgacacagatgaagtgctttt
ttgtttggccttttgaatgaagatcgagtaaaacaactggagaggacttttaactgtaaa
atgtcactgaagataaaatcaaagttacttcagtgtatggaagtattaggaaacagtgac
tattctccatcacagctgggatttctggagttgtttcactgtctgtatgagactcaagat
aaagcgtttataagccaggcaatgagatgtttcccaaaggttgccattaatatttgtgag
aaaatacatttgcttgtatcttctttctgccttaagcactgccggtgtttgcggaccatc
aggctgtctgtaactgtggtatttgaagaagaagatattaaaaacaagcctcccaactaac
acttggggagtggatgggaaacgggagagctattggacaaataagacctctggagtgccca
gaggaagacttcctggtggactgtgcccacggtggagctgcactggatgctcttgcctt
ccaaagtacacttacttttactccaatactatcctctga
```

FIGURE 15A

PAN 8

Amino Acid Sequence: SEQ ID NO:72

MADSSSSSFFPDFGLLLYLEELNKEELNTFKLFLKETMEPEHGLTPWNEVKKARREDLAN
LMKKYYPGEKAWSVSLKIFGKMNLKDLCERAKEEINWSAQTIGPDDAKAGETQEDQEAVL
VIVNTGVPNSWATDPYWSAAPRESGRIAGGDGTEYRNRIKEKFCITWDKKSLAGKPEDFH
HGIAEKDRKLLEHLFDVDVKTGAQPQIVVLQGAAGVGKTTLVRKAMLDWAEGSLYQQRFK
YVFYLNGREINQLKERSFAQLISKDWPSTEGPIEEIMYQPSSLLFIIDSFDELNFAFEEP
EFALCEDWTQEHPVSFLMSSLLRKVMLPEASLLVTTRLTTSKRLKQLLKNHHYVELLGMS
EDAREEYIYQFFEDKRWAMKVFSSLKSNEMLFSMCQVPLVCWAACTCLKQQMEKGGDVTL
TCQTTTALFTCYISSLFTPVDGGSPSLPNQAQLRRLCQVAAKGIWTMTYVFYRENLRRLG
LTQSDVSSFMDSNIIQKDAEYENCYVFTHLHVQEFFAAMFYMLKGSWEAGNPSCQPFEDL
KSLLQSTSYKDPHLTQMKCFLFGLLNEDRVKQLERTFNCKMSLKIKSKLLQCMEVLGNSD
YSPSQLGFLELFHCLYETQDKAFISQAMRCFPKVAINICEKIHLLVSSFCLKHCRCLRTI
RLSVTVVFEKKILKTSLPTNTWEWMGNGRAIGQIRPLECPEEDFLVDCAHGGAALDALAF
PKYTYFYSNTIL

FIGURE 15B

PAN 9

Nucleotide Sequence: SEQ ID NO:73 atgtatgagtttttatattcacaaaggttatgatgatgtgtcttcagacaacagcagagag
aaaatcaaaggtgaaccctctgaatgtgagttggggcacttcccgcgtatcccctgggca
aacttgagagctgccgaccctttgaatctgtcctttctttggatgaacacttcccaaaa
ggtcaggcatggaaagtggtcctcggcatcttccagacaatgaatctgacctcactgtgt
gagaaagttagagccgagatgaaagagaatgtgcagacccaagagctgcaagatccaacc
caggaagatctagagatgctagaagcagcagcagggaatatgcagacccagggatgccaa
gatccaaaccaagaagaactagacgagctagaagaagaaacagggaatgtacaggcccag
ggatgccaagatccaaaccaagaagaaccagagatgctagaggaagcagaccacagaaga
aaatacagagagaacatgaaggctgaactactggagacatgggacaacatcagttggcct
aaagaccacgtatatatccgtaatacatcaaaggacgaacatgaggaactgcagcgccta
ctggatcctaataggactagagcccaggcccagacgatagtcttggtggggagggcaggg
gttgggaagaccaccttggcaatgcgggctatgctgcactgggcaaatggagttctcttt
cagcaaaggttctcctatgttttctatctcagctgccataaaataaggtacatgaaggaa
actacctttgctgaattgatttctttggattggcccgattttgatgccccattgaagag
ttcatgtctcaaccagagaagctcctgtttattattgatggctttgaggaaataatcata
tctgagtcacgctctgagagcttggatgatggctcgccatgtacagactggtaccaggag
ctcccagtgaccaaaatcctacacagcttgttgaagaagaattggttcccctggctacc
ttactgatcacgatcaagacctggtttgtgagagatcttaaggcctcattagtgaatcca
tgctttgtacaaattacagggttcacaggggacgacctacgggtatatttcatgagacac
tttgatgactcaagtgaagttgagaaaatcctgcagcagctaagaaaaaacgaaactctc
tttcattcctgcagtgcccccatggtgtgttggactgtatgttcctgtctgaagcagccg
aaggtgaggtattacgatctccagtcaatcactcagactaccaccagtctgtatgcctat
ttttctccaacttgttctccacagcagaggtagatttggcagatgacagctggccagga
caatggagggccctctgcagcctggccatagaagggctgtggtctatgaacttcacattt
aacaagaagacactgagattgagggcctggaagtgcctttcattgattctctctacgag
ttcaatattcttcaaaagatcaatgactgtggggttgcactactttcacccacctaagt
ttccaggagttttttgcagccatgtcctttgtgctagaggaacctagagaattccctccc
cattccacaaagccacaagagatgaagatgttactgcaacacgtcttgcttgacaaagaa
gcctactggactccagtggttctgttcttctttggtcttttaaataaaaacatagcaaga
gaactggaagatacttgcattgtaaaatatctcccagggtaatggaggaattattaaag
tggggagaagagttag

FIGURE 16A

PAN 9

Amino Acid Sequence: SEQ ID NO:74

MYEFYIHKGYDDVSSDNSREKIKGEPSECELGHFPRIPWANLRAADPLNLSFLLDEHFPK
GQAWKVVLGIFQTMNLTSLCEKVRAEMKENVQTQELQDPTQEDLEMLEAAAGNMQTQGCQ
DPNQEELDELEEETGNVQAQGCQDPNQEEPEMLEEADHRRKYRENMKAELLETWDNISWP
KDHVYIRNTSKDEHEELQRLLDPNRTRAQAQTIVLVGRAGVGKTTLAMRAMLHWANGVLF
QQRFSYVFYLSCHKIRYMKETTFAELISLDWPDFDAPIEEFMSQPEKLLFIIDGFEEIII
SESRSESLDDGSPCTDWYQELPVTKILHSLLKKELVPLATLLITIKTWFVRDLKASLVNP
CFVQITGFTGDDLRVYFMRHFDDSSEVEKILQQLRKNETLFHSCSAPMVCWTVCSCLKQP
KVRYYDLQSITQTTTSLYAYFFSNLFSTAEVDLADDSWPGQWRALCSLAIEGLWSMNFTF
NKEDTEIEGLEVPFIDSLYEFNILQKINDCGGCTTFTHLSFQEFFAAMSFVLEEPREFPP
HSTKPQEMKMLLQHVLLDKEAYWTPVVLFFFGLLNKNIARELEDTLHCKISPRVMEELLK
WGEEL

FIGURE 16B

PAN 10

Nucleotide Sequence: SEQ ID NO:75

```
GATCTCATATTTCTTGTGCCTCAAAATCCCTTCTCTGAAGTCTGCCTTCCCTGGAGAAGCAAG
ATGGCAGAATCGGATTCTACTGACTTTGACCTGCTGTGGTATCTAGAGAATCTCAGTGACAAG
GAATTTCAGAGTTTTAAGAAGTATCTGGCACGCAAGATTCTTGATTTCAAACTGCCACAGTTT
CCACTGATACAGATGACAAAAGAAGAACTGGCTAACGTGTTGCCAATCTCTTATGAGGGACAG
TATATATGGAATATGCTCTTCAGCATATTTTCAATGATGCGTAAGGAAGATCTTTGTAGGAAG
ATCATTGGCAGACGAAACCGCAATCAGGAGGCATGCAAAGCTGTCATGAGGAGAAAATTCATG
CTGCAATGGGAAAGTCACACTTTTGGAAAATTTCATTATAAATTTTTCGTGACGTTTCGTCA
GATGTGTTCTACATACTTCAATTAGCCTATGATTCTACCAGCTATTATTCAGCAAACAATCTC
AATGTGTTCCTGATGGGAGAGAGAGCATCTGGAAAAACTATTGTTATAAATCTGGCTGTGTTG
AGGTGGATCAAGGGTGAGATGTGGCAGAACATGATCTCGTACGTCGTTCACCTCACTGCTCAC
GAAATAAACCAGATGACCAACAGCAGCTTGGCTGAGCTAATCGCCAAGGACTGGCCTGACGGC
CAGGCTCCCATTGCAGACATCCTGTCTGATCCCAAGAAACTCCTTTTCATCCTCGAGGACTTG
GACAACATAAGATTCGAGTTAAATGTCAATGAAAGTGCTTTGTGTAGTAACAGCACCCAGAAA
GTTCCCATTCCAGTTCTCCTGGTCAGTTTGCTGAAGAGAAAAATGGCTCCAGGCTGCTGGTTC
CTCATCTCCTCAAGGCCCACACGTGGGAATAATGTAAAAACGTTCTTGAAAGAGGTAGATTGC
TGCACGACCTTGCAGCTGTCGAATGGGAAGAGGGAGATATATTTTAACTCTTTCTTTAAAGAC
CGCCAGAGGGCGTCGGCAGCCCTCCAGCTTGTACATGAGGATGAAATACTCGTGGGTCTGTGC
CGAGTCGCCATCTTATGCTGGATCACGTGTACTGTCCTGAAGCGGCAGATGGACAAGGGGCGT
GACTTCCAGCTCTGCTGCCAAACACCCACTGATCTACATGCCCACTTTCTTGCTGATGCGTTG
ACATCAGAGGCTGGACTTACTGCCAATCAGTATCACCTAGGTCTCCTAAAACGTCTGTGTTTG
CTGGCTGCAGGAGGACTGTTTCTGAGCACCCTGAATTTCAGTGGTGAAGACCTCAGATGTGTT
GGGTTTACTGAGGCTGATGTCTCTGTGTTGCAGGCCGCGAATATTCTTTTGCCGAGCAACACT
CATAAAGACCGTTACAAGTTCATACACTTGAACGTCCAGGAGTTTTGTACAGCCATTGCATTT
CTGATGGCAGTACCCAACTATCTGATCCCCTCAGGCAGCAGAGAGTATAAAGAGAAGAGAGAA
CAATACTCTGACTTTAATCAAGTGTTTACTTTCATTTTTGGTCTTCTAAATGCAAACAGGAGA
AAGATTCTTGAGACATCCTTTGGATACCAGCTACCGATGGTAGACAGCTTCAAGTGGTACTCG
GTGGGATACATGAAACATTTGGACCGTGACCCGGAAAAGTTGACGCACCATATGCCTTTGTTT
TACTGTCTCTATGAGAATCGGGAAGAAGAATTTGTGAAGACGATTGTGGATGCTCTCATGGAG
GTTACAGTTTACCTTCAATCAGACAAGGATATGATGGTCTCATTATACTGTCTGGATTACTGC
TGTCACCTGAGGACACTTAAGTTGAGTGTTCAGCGCATCTTTCAAAACAAAGAGCCACTTATA
AGGCCAACTGCTAGGTTGTCCTATGTCTCGACTGCTTCTGGTTTTGAAGACTTACTCAAGGCT
TTGGCTCGTAATCGGAGCCTGACATACCTGAGTATCAACTGTACGTCCATTTCCCTAAATATG
TTTTCACTTCTGCATGACATCCTGCACGAGCCCACATGCCAAATAAGTCATCTGAGCTTGATG
AAATGTGATTTGCGAGCCAGCGAATGCGAAGAAATCGCCTCTCCTCATCAGTGGCGGGAGT
CTGAGAAAACTGACCTTATCCAGCAATCCGCTGAGGAGCGACGGGATGAACATACTGTGTGAT
GCCTTGCTTCATCCCAACTGCACTCTTATATCACTGGTGTTAGTCTTCTGCTGTCTCACTGAA
AATTGCTGCAGCGCCCTTGGAAGAGTGCTTCTGTTCAGCCCAACTCTAAGACAACTAGACCTG
TGTGTGAATCGCTTAAAAAATTACG
```

FIGURE 17A

PAN 10

Amino Acid Sequence: SEQ ID NO:76

MAESDSTDFDLLWYLENLSDKEFQSFKKY
LARKILDFKLPQFPLIQMTKEELANVLPISYEGQYIWNMLFSIFSMMRKE
DLCRKIIGRRNRNQEACKAVMRRKFMLQWESHTFGKFHYKFFRDVSSDVF
YILQLAYDSTSYYSANNLNVFLMGERASGKTIVINLAVLRWIKGEMWQNM
ISYVVHLTAHEINQMTNSSLAELIAKDWPDGQAPIADILSDPKKLLFILE
DLDNIRFELNVNESALCSNSTQKVPIPVLLVSLLKRKMAPGCWFLISSRP
TRGNNVKTFLKEVDCCTTLQLSNGKREIYFNSFFKDRQRASAALQLVHED
EILVGLCRVAILCWITCTVLKRQMDKGRDFQLCCQTPTDLHAHFLADALT
SEAGLTANQYHLGLLKRLCLLAAGGLFLSTLNFSGEDLRCVGFTEADVSV
LQAANILLPSNTHKDRYKFIHLNVQEFCTAIAFLMAVPNYLIPSGSREYK
EKREQYSDFNQVFTFIFGLLNANRRKILETSFGYQLPMVDSFKWYSVGYM
KHLDRDPEKLTHHMPLFYCLYENREEEFVKTIVDALMEVTVYLQSDKDMM
VSLYCLDYCCHLRTLKLSVQRIFQNKEPLIRPTARLSYVSTASGFEDLLK
ALARNRSLTYLSINCTSISLNMFSLLHDILHEPTCQISHLSLMKCDLRAS
ECEEIASLLISGGSLRKLTLSSNPLRSDGMNILCDALLHPNCTLISLVLV
FCCLTENCCSALGRVLLFSPTLRQLDLCVNRLKNY

FIGURE 17B

PAN 5

Nucleotide Sequence: SEQ ID NO: 83 atggccatggccaaggccagaaagccccgggaggcattgctctgggccttgagtgacctt
gaggagaacgatttcaagaagttaaagttctacttacgggatatgaccctgtctgagggc
cagcccccactggccagaggggagttggagggcctgattccggtggacctggcagaatta
ctgatttcaaagtatggagaaaaggaggctgtgaagttgtcctcaagggcttgaaggtc
atgaacctgttggaacttgtggaccagctcagccatatttgtctgcatgattacagagaa
gtataccgagagcatgtgcgctgcctagaggaatggcaggaagcaggagtcaatggcaga
tacaaccaggtgctcctggtggccaagcccagctcagagagcccagaatcacttgcctgc
cccttcccggagcaggagctggagtctgtcacggtggaggctctatttgattcaggggaa
aagccctcactggccccatccttagttgtgctacaggggtcggctggcactggaaagaca
actctcgccagaaaaatggtgttggactgggccaccggtactctgtacccaggccggttt
gattatgtcttttatgtaagctgcaaagaagtggtcctgctgctggagagcaaactggag
cagctccttttctggtgctgcggggacaatcaagcccctgtcacagagattctgaggcag
ccagagcggctcctgttcatcctggatggctttgatgagctgcagaggccctttgaagaa
aagttgaagaagaggggtttgagtcccaaggagagcctgctgcaccttctaattaggaga
catacactccccacgtgctcccttctcatcaccacccggccctggctttgaggaatctg
gagcccttgctgaaacaagcacgtcatgtccatatcctaggcttctctgaggaggagagg
gcgaggtacttcagctcctatttcacggatgagaagcaagctgaccgtgccttcgacatt
gtacagaaaaatgacattctctacaaagcgtgtcaggttccaggcatttgctgggtggtc
tgctcctggctgcaggggcagatggagagaggcaaagttgtcttagagacacctagaaac
agcactgacatcttcatggcttacgtctccacctttctgccgcccgatgatgatggggc
tgctccgagctttcccggcacagggtcctgaggagtctgtgctccctagcagctgaaggg
attcagcaccagaggttcctatttgaagaagctgagctcaggaaacataatttagatggc
cccaggcttgccgcttttcctgagtagtaacgactaccaattgggacttgccatcaagaag
ttctacagcttccgccacatcagcttccaggacttttttcatgccatgtcttacctggtg
aaagaggaccaaagccggctggggaaggagtcccgcagagaagtgcaaaggctgctggag
gtaaaggagcaggaagggaatgatgagatgaccctcactatgcagttttactggacatc
tcgaaaaagacagcttctcgaacttggagctcaagttctgcttcagaatttctccctgt
ttagcgcaggatctgaagcattttaaagaacagatggaatctatgaagcacaacaggacc
tgggatttggaattctccctgtatgaagctaaaataaagaatctggtaaaaggtattcag
atgaacaatgtatcattcaagataaaacattcaaatgaaaagaaatcacagagccagaat
ttattttctgtcaaaagcagcttgagtcatggacctaaggaggagcaaaaatgtccttct
gtccatggacagaaggagggcaaagataatatagcaggaacacaaaaggaagcttctact
ggaaaaggcagagggacagaggaaacaccaaaaaatacttacatataa

FIGURE 18A

PAN 5

Amino Acid Sequence: SEQ ID NO: 84

MAMAKARKPREALLWALSDLEENDFKKLKFYLRDMTLSEGQPPLARGELEGLIPVDLAEL
LISKYGEKEAVKVVLKGLKVMNLLELVDQLSHICLHDYREVYREHVRCLEEWQEAGVNGR
YNQVLLVAKPSSESPESLACPFPEQELESVTVEALFDSGEKPSLAPSLVVLQGSAGTGKT
TLARKMVLDWATGTLYPGRFDYVFYVSCKEVVLLLESKLEQLLFWCCGDNQAPVTEILRQ
PERLLFILDGFDELQRPFEEKLKKRGLSPKESLLHLLIRRHTLPTCSLLITTRPLALRNL
EPLLKQARHVHILGFSEEERARYFSSYFTDEKQADRAFDIVQKNDILYKACQVPGICWVV
CSWLQGQMERGKVVLETPRNSTDIFMAYVSTFLPPDDDGGCSELSRHRVLRSLCSLAAEG
IQHQRFLFEEAELRKHNLDGPRLAAFLSSNDYQLGLAIKKFYSFRHISFQDFFHAMSYLV
KEDQSRLGKESRREVQRLLEVKEQEGNDEMTLTMQFLLDISKKDSFSNLELKFCFRISPC
LAQDLKHFKEQMESMKHNRTWDLEFSLYEAKIKNLVKGIQMNNVSFKIKHSNEKKSQSQN
LFSVKSSLSHGPKEEQKCPSVHGQKEGKDNIAGTQKEASTGKGRGTEETPKNTYI

PAAD DOMAIN-CONTAINING POLYPEPTIDES, ENCODING NUCLEIC ACIDS, AND METHODS OF USE

This application is a divisional of U.S. Ser. No. 10/407,866, filed Apr. 04, 2003, now abandoned which claims benefit of priority of U.S. Provisional Application No. 60/370,538, filed Apr. 4, 2002, each of which the entire contents are incorporated herein by reference.

This invention was made in part with United States Government support under grant number NIH GM60049 awarded by the National Institutes of Health and NSF DBI-0078731 awarded by the National Science Foundation. The U.S. Government has certain rights in this invention.

BACKGROUND OF THE INVENTION

1. Field of the Invention

This invention relates generally to the fields of molecular biology and molecular medicine and more specifically to the identification of proteins involved in innate immunity, programmed cell death, NFκB induction, cytokine processing and inflammation, and associations of these proteins.

2. Background Information

Proteins containing the death domain fold (DDF) play pivotal roles in programmed cell death (apoptosis) and inflammatory responses. The DDF represents a protein interaction motif consisting of a bundle of (usually) six antiparallel α-helices. This core structure is found in at least three families of evolutionarily conserved and closely related domain families, including Death Domain (DD), Death Effector Domain (DED) and Caspase Recruitment Domain (CARD) families.

CARD- and DED-family proteins have been implicated in activation of Caspase-family proteases. Though many of these intracellular cysteine proteases are involved in apoptosis induction, some of these proteases, such as Caspase-1, are chiefly responsible for proteolytic processing and activation of pro-inflammatory cytokines, such as Interleukin-1β. Homotypic interactions among CARD- and DED-containing adapter proteins occur with the inactive proforms of those Caspases which possess N-terminal prodomains containing complementary CARDs or DEDs, respectively. The resulting formation of multi-protein complexes leads to protease cleavage and activation by an induced proximity mechanism in which pro-proteases are clustered together, permitting trans-proteolytic cleavage events necessary for generation of active Caspases.

Besides regulating Caspase activation, some DDF proteins are also known to participate in activation of transcription factor NF-κB, a family of dimeric transcription factors containing the Rel-homology domain (RHD). In mammals, NF-κB family members play critical roles in regulating expression of genes involved in inflammatory and immune responses, including certain cytokines, lymphokines, immunoglobulins, and leukocyte adhesion proteins. Among the DDF proteins, DD- and CARD-containing proteins have been shown to participate in NF-κB induction, with certain DD-family proteins linking cytokine receptors to downstream adapter proteins implicated in IKK activation and specific CARD-family proteins linking to adapter proteins that connect to the IKK complex.

The identification of proteins with folds that structurally resemble the Death Domain Fold, determination of molecules with which they interact, and elucidation of their biological function, can form the basis for strategies designed to alter apoptosis, NFκB inductions, immune and inflammatory responses, cytokine production, and other cellular processes mediated by these proteins. Thus, a need exists to identify proteins with structural resemblance to DDF proteins, and to identify functional domains within these proteins. The present invention satisfies this need and provides additional advantages as well.

SUMMARY OF THE INVENTION

The invention provides isolated nucleic acid molecules encoding PAAD-domain containing polypeptides and functional fragments thereof, including fragments containing PAAD domains, NB-ARC (NACHT) domains and LRR domains. Also provided are vectors containing such nucleic acid molecules and host cells containing the vectors. Further provided are oligonucleotides therefrom and methods of identifying nucleic acid molecules encoding a PAAD-containing polypeptide in a sample using such oligonucleotides.

Also provided are isolated PAAD-domain containing polypeptides and functional fragments thereof, including fragments containing PAAD domains, NB-ARC (NACHT) domains and LRR domains, and peptides therefrom.

The invention further provides antibodies that can specifically bind to PAAD-domain containing polypeptides, and methods of detecting PAAD-domain containing polypeptides in a sample using such antibodies.

Also provided is a method of identifying a polypeptide that associates with a PAAD-domain containing polypeptide or fragment thereof, including fragments containing PAAD domains, NB-ARC (NACHT) domains and LRR domains. The method is practiced by contacting a PAAD domain-containing polypeptide or fragment with a candidate PAAD domain-containing polypeptide-associated polypeptide (PAP), and detecting association of the PAAD domain-containing polypeptide or fragment with the candidate PAP, wherein a candidate PAP that associates with the polypeptide is identified as a PAP.

The invention also provides a method of identifying an effective agent that alters the association of a PAAD domain-containing polypeptide or fragment with a PAP. The method is practiced by contacting a PAAD domain-containing polypeptide, or a PAAD, NB-ARC (NACHT) or LRR domain therefrom, and the PAP under conditions that allow the PAAD domain-containing polypeptide or fragment and the PAP to associate, with a candidate agent, and detecting the altered association of the PAAD domain-containing polypeptide or domain with the PAP, wherein an agent that alters the association is identified as an effective agent.

Further provided is a method for identifying an agent that associates with a PAAD-domain containing polypeptide or fragment therefrom, including a fragment containing a PAAD domain, NB-ARC (NACHT) domain or LRR domains. The method is practiced by contacting the PAAD domain-containing polypeptide or fragment with a candidate agent and detecting association of the PAAD domain-containing polypeptide with the agent.

Also provided is a method of identifying an agent that modulates PAAD domain-mediated inhibition of NFκB activity. The method is practiced by contacting a cell that recombinantly expresses a PAAD domain-containing polypeptide with a candidate agent and detecting NFκB activity in the cell. Increased or decreased NFκB activity in the cell compared to a control cell indicates that the candidate agent is an agent that modulates PAAD domain-mediated inhibition of NFκB activity.

Further provided is a method of identifying an agent that modulates an activity of a NB-ARC (NACHT) domain of a PAAD domain-containing polypeptide. The method is practiced by contacting an NB-ARC (NACHT) domain-containing polypeptide with a candidate agent and detecting an activity of the NB-ARC (NACHT) domain, wherein an increase or decrease of the activity identifies the agent as an agent that modulates the activity of the NB-ARC (NACHT) domain. The detected activity of the NB-ARC (NACHT) domain can be selected from homo-oligomerization, hetero-oligomerization, nucleotide hydrolysis, and nucleotide binding.

Further provided is a method of modulating NFκB transcriptional activity in a cell. The method is practiced by introducing a nucleic acid molecule encoding a PAAD domain-containing polypeptide into a cell and expressing the nucleic acid molecule in the cell, wherein the expression of the nucleic acid modulates NFκB transcriptional activity in the cell.

The invention also provides a method of decreasing expression of a PAAD domain-containing polypeptide in a cell, by introducing an antisense or dsRNA nucleic molecule into a cell, wherein the antisense or dsRNA nucleic molecule binds to a nucleic acid molecule encoding a PAAD domain-containing polypeptide.

BRIEF DESCRIPTION OF THE FIGURES

FIG. 1 shows that multiple alignment using the CLUSTAL W program (Higgins et al. *Nuc. Acid Res.* 22:4673-4680 (1995)) of the aligned part of selected members of the PAAD family from humans. NCBI gi accession numbers are included. The "sec_str" line shows secondary structure prediction made for pyrin using the PHD program (Rost et al., *Comput. Appl. Biosci.* 10:53-60 (1994)).

FIG. 6 shows a protein interaction assay in which vectors expressing Myc-tagged PAN2, or Myc-tagged domains of PAN2 as indicated, and either Flag-tagged IkBα or Flag-tagged empty vector, were co-transfected into 293T cells. The lysates were immunoprecipitated with an anti-Flag antibody and blotted with either an anti-Myc or an anti-Flag antibody.

Figure 11A:
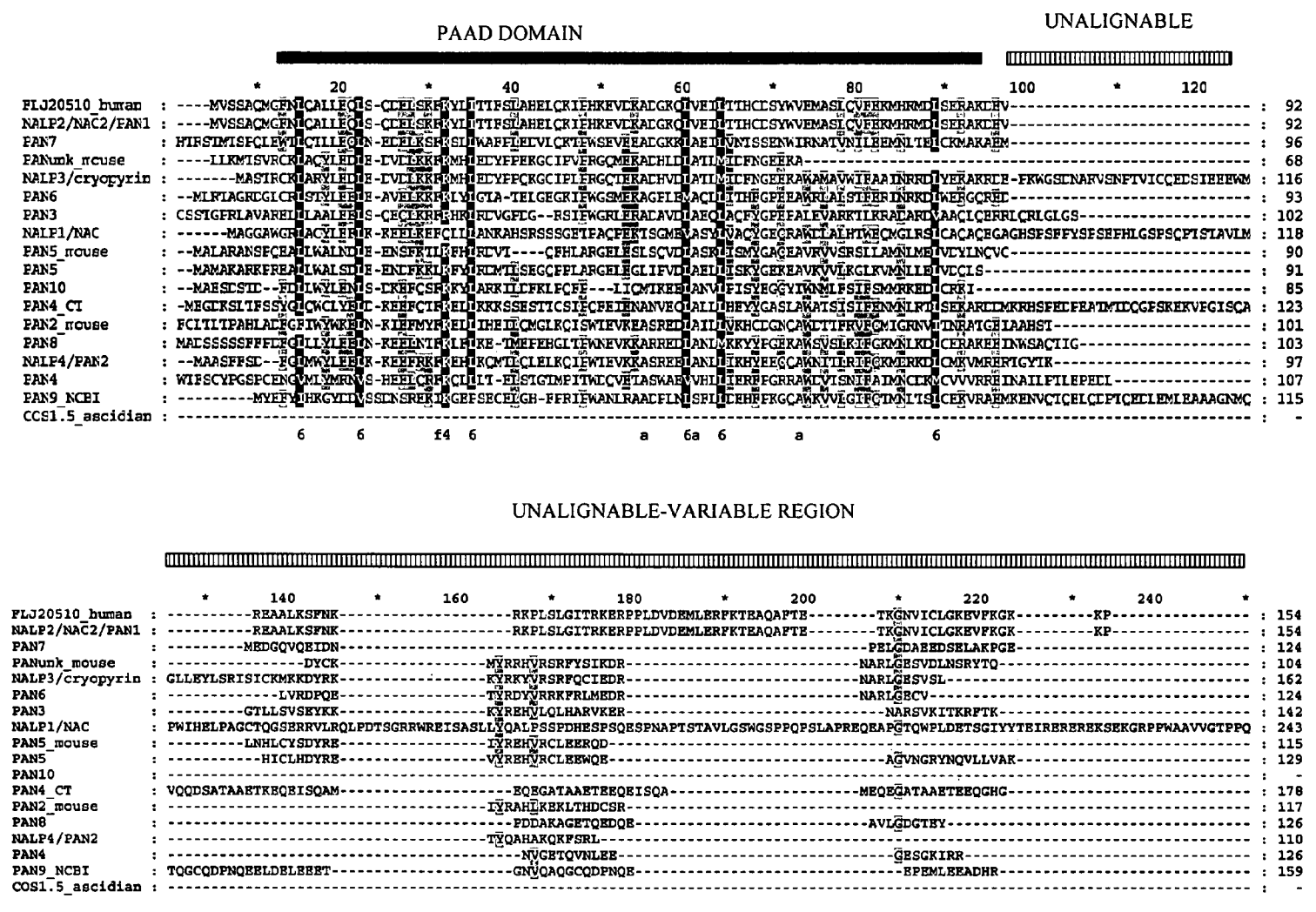
Figure 11B:
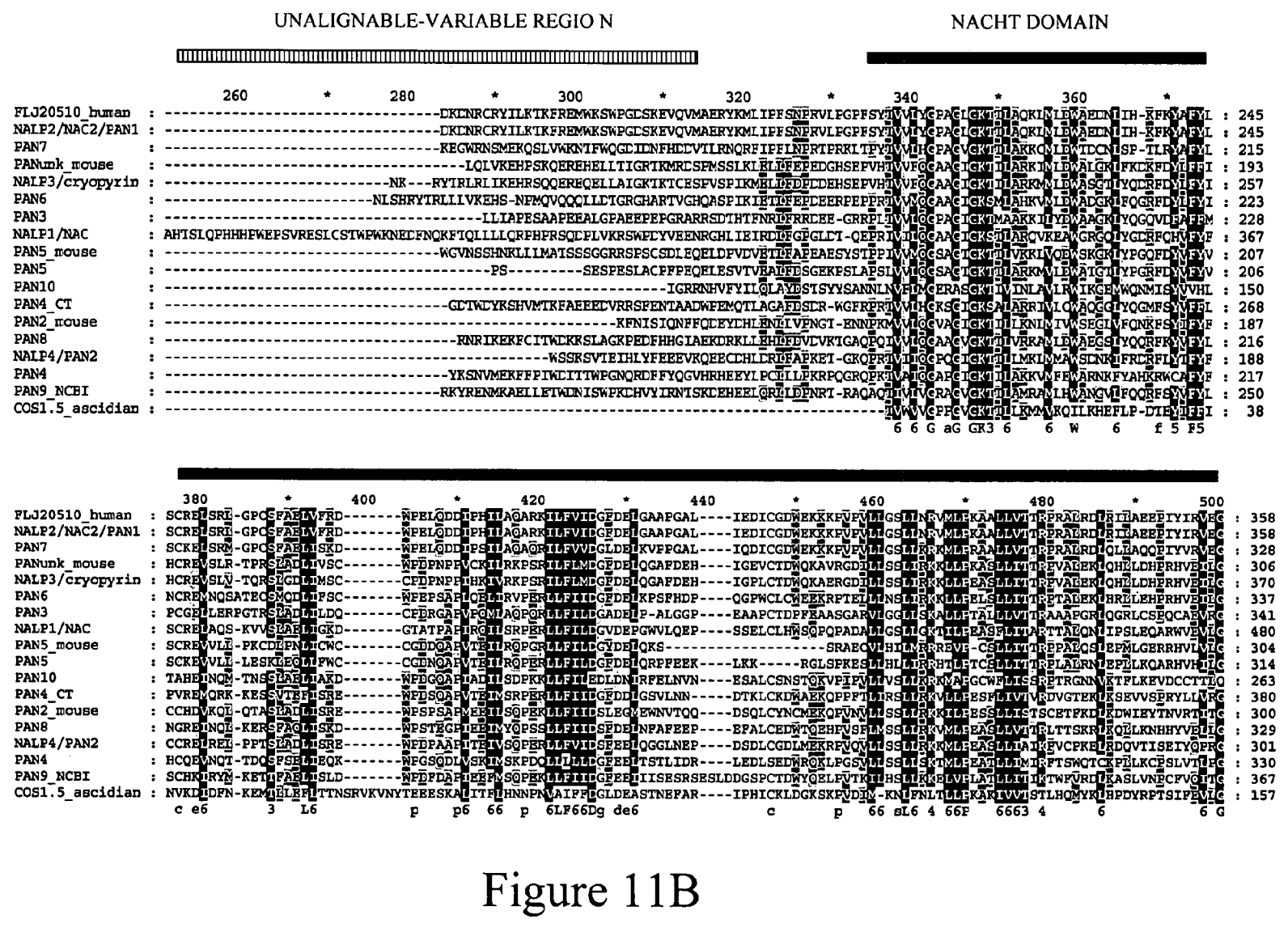
Figure 11C:
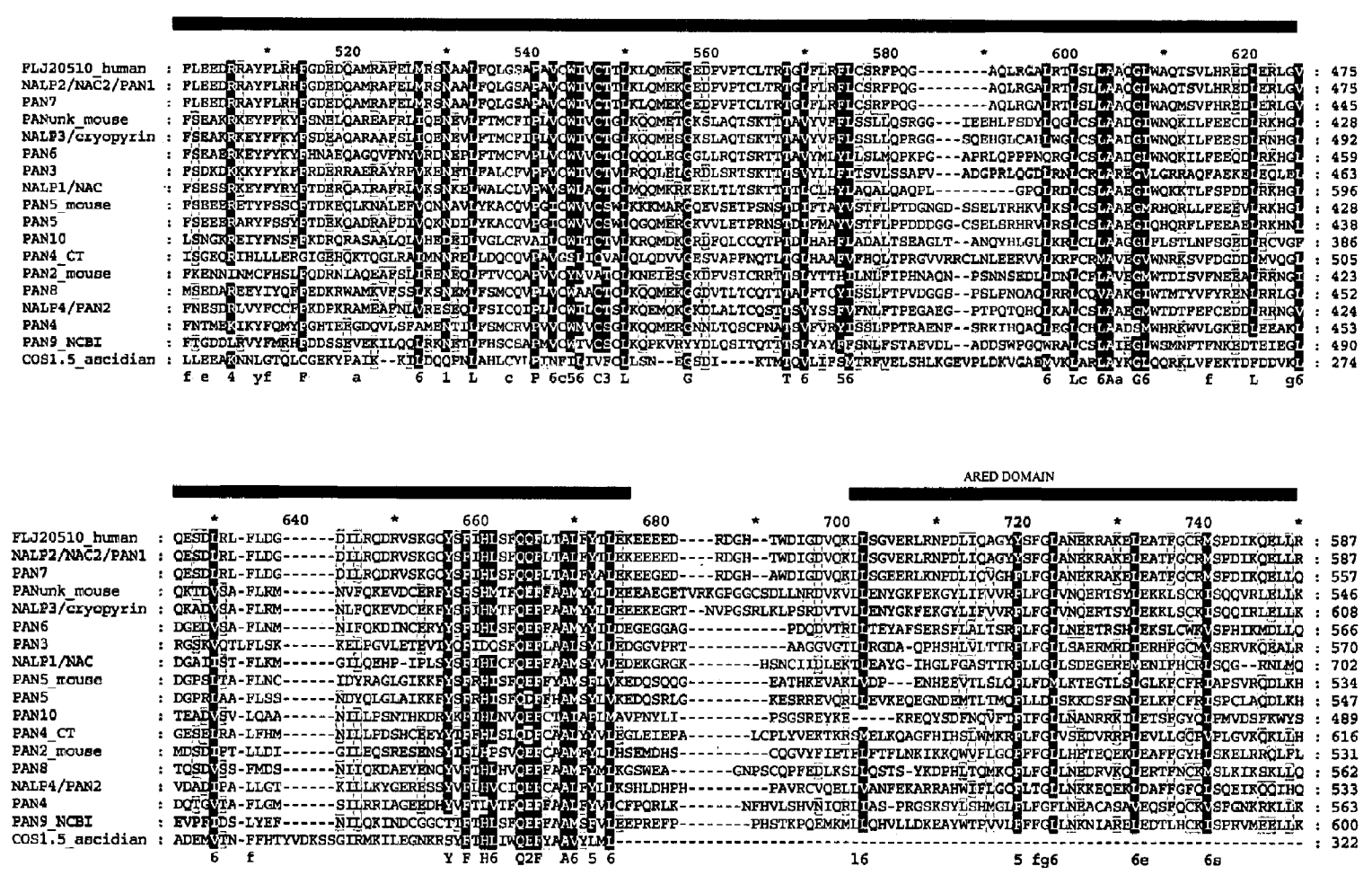
Figure 11D:
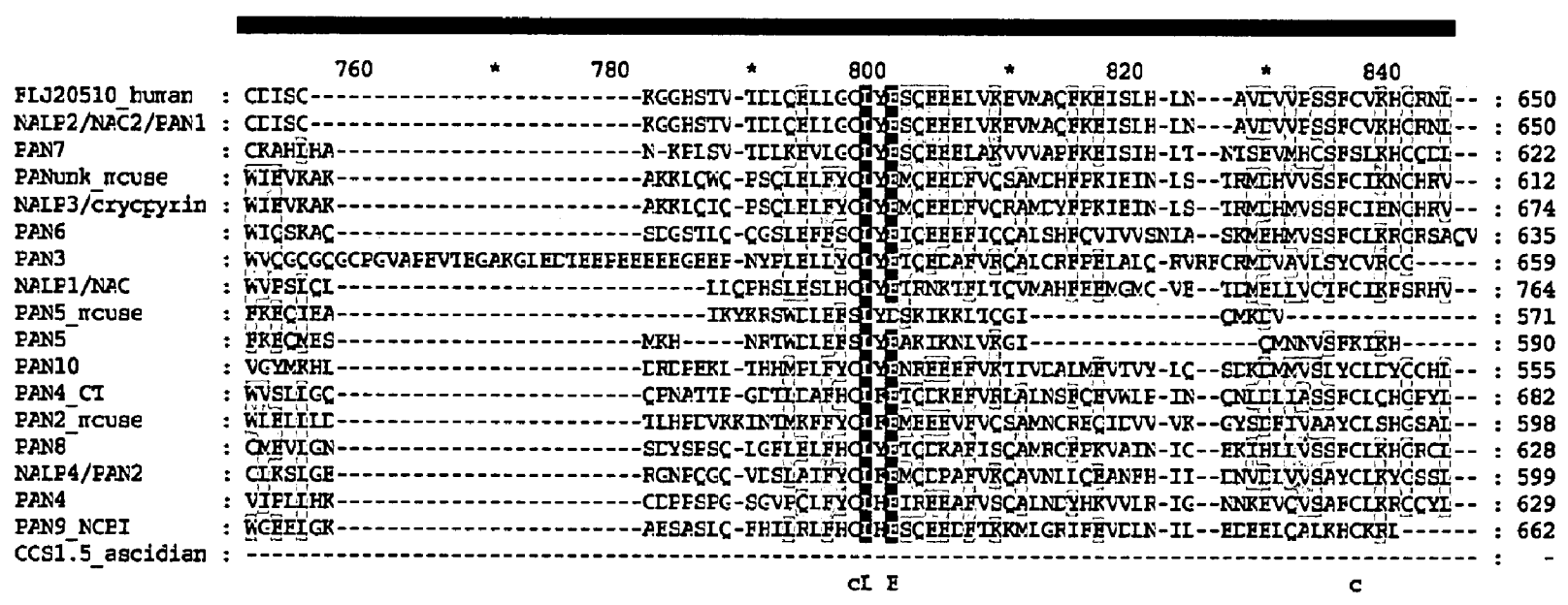

FIG. 11 shows an alignment of the PAAD, NACHT and ARED domains of the indicated proteins (SEQ ID NOS:85-102), and intervening variable sequences. Residues shown in white on a black background are conserved in at least 90% of the proteins; residues boxed in pale grey are conserved in at least 70% of the proteins; residues boxed in dark grey are conserved in at least 50% of the proteins. The PAAD domain, NACHT domain and ARED domain boundaries are shown by overlining.

FIG. 12 shows the PAN3 nucleotide sequence designated SEQ ID NO:65, and the PAN3 amino acid sequence designated SEQ ID NO:66.

FIG. 13 shows the PAN6 nucleotide sequence designated SEQ ID NO:67, and the PAN6 amino acid sequence designated SEQ ID NO:68.

FIG. 14 shows the PAN7 nucleotide sequence designated SEQ ID NO:69, and the PAN7 amino acid sequence designated SEQ ID NO:70.

FIG. 15 shows the PAN8 nucleotide sequence designated SEQ ID NO:71, and the PAN8 amino acid sequence designated SEQ ID NO:72.

FIG. 16 shows the PAN9 nucleotide sequence designated SEQ ID NO:73, and the PAN9 amino acid sequence designated SEQ ID NO:74.

FIG. 17 shows the PAN10 nucleotide sequence designated SEQ ID NO:75, and the PAN10 amino acid sequence designated SEQ ID NO:76.

FIG. 18 shows the PAN5 nucleotide sequence designated SEQ ID NO:83, and the PAN5 amino acid sequence designated SEQ ID NO:84.

DETAILED DESCRIPTION OF THE INVENTION

In accordance with the present invention, there are provided PAAD domain-containing polypeptides and functional fragments thereof, encoding nucleic acid molecules, and related compositions and methods. The "PAAD domain" is an 80-100 residue domain named after the protein families in which it was first identified: pyrin, AIM (Absent-in-melanoma), ASC (apoptosis-associated speck-like protein containing a caspase recruitment domain), and death domain (DD)-like. The terms "PAAD" and "PACS" (for identified in Pyrin, AIM, Caspase, and Speck-like protein) are synonymous.

Figure 1:
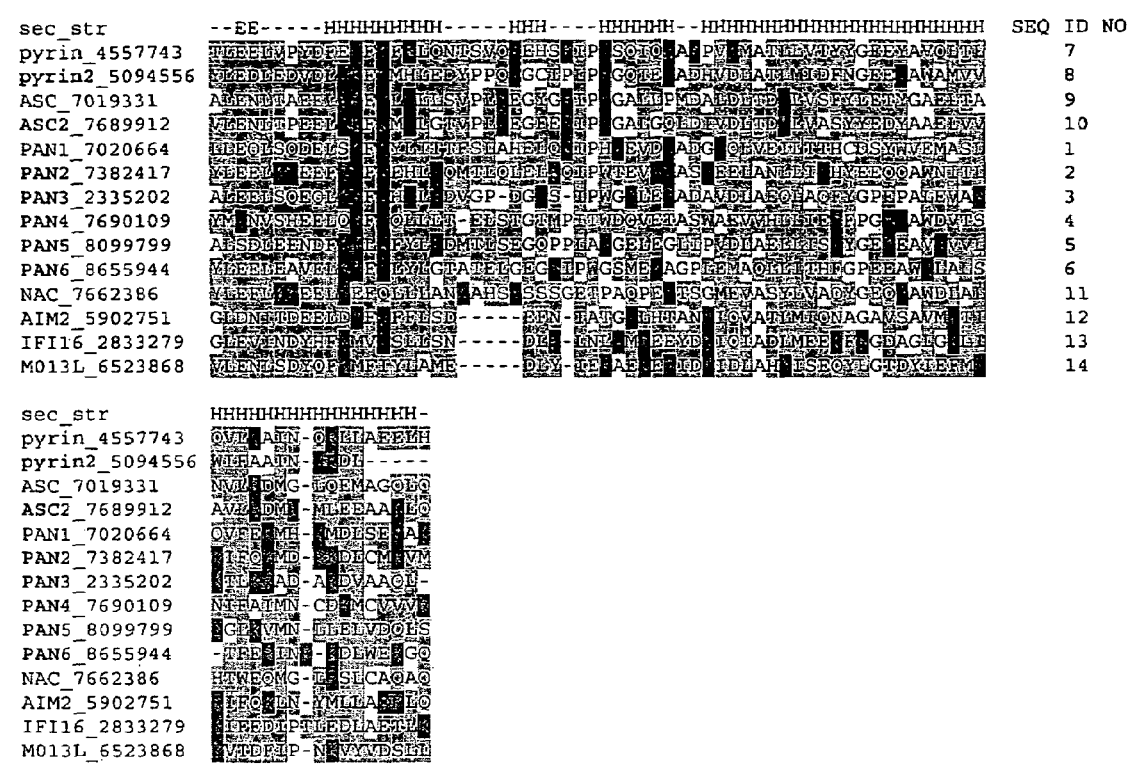
Figure 4:
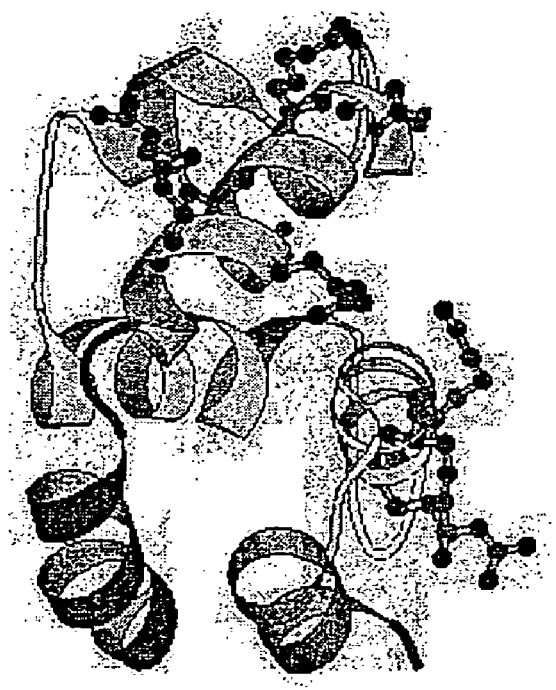
FIG. 4 shows a model of the PAAD domain built on the template of the Death Effector Domain from FADD protein (PDB code: 1a1z), using the FFAS alignment and the Modeller program (Sali et al, *J. Mol. Biol.* 234:779-815 (1993)). Some motifs identified in the sequence analyses of the PAAD family stand out as surface features that may be responsible for biological activity of these domains. A notable feature is the conserved Lys-Phe-Lys motif, that according to this model, is found on the protein surface, in helix 2. Positively charged residues from this motif, together with other charged residues from another, less conserved motif in helix 5, form a positively charged surface of the predicted protein that may be important for inter-molecule interaction. These residues are shown in the ball-and-stick representation.

Secondary structural predictions identify the PAAD domain as mostly helical (see FIG. 1). The PAAD domain has the predicted tertiary structure shown in FIG. 4, identifying PAAD as a member of the Death Domain Fold (DDF) family, whose members include Death Domain (DD), Death Effector Domain (DED) and Caspase Recruitment Domain (CARD) proteins. Structural properties of the PAAD domain, which is also known as PYRIN or DAPIN, are described, for example, in Pawlowski et al., *Trends Biochem. Sci.* 26:85-87 (2001); Bertin et al., *Cell Death Differ.* 7:1273-1274 (2000); Fairbrother et al., *Protein Sci.* 10:1911-1918 (2001); Martinon et al., *Curr. Biol.* 11:R118-120 (2001); and Staub et al., *Trends Biochem. Sci.* 26:83-85 (2001).

PAAD domains have been identified at the N-terminus of several different proteins involved in apoptosis, cancer, inflammation and immune responses, as described herein (see FIG. 1). The founding member of the PAAD domain family, Pyrin, is mutated in families with Familial Mediterranean Fever (FMF), a hereditary hyper-inflammatory response syndrome. Mutant alleles of a gene encoding another PAAD family protein, Cryopyrin, have been associated with familial cold auto-inflammatory syndrome and Muckle-Wells syndrome.

Protein-protein interactions influence the activity of various proteins involved in apoptosis and immune response. Several protein interaction domains have been implicated in interactions among these proteins. The PAAD domain has been identified at the N-terminus of the recently identified caspase-homologous gene from zebrafish (Inohara et al., *Cell Death Differ,* 7:509-510 (2000)), suggesting the involvement of the PAAD domain in apoptosis. In this protein, the PAAD domain occupies a position corresponding to the prodomain, which in other caspase genes is occupied by a CARD (caspase recruitment domain) or a DED (death effector domain) domain. Thus, it is contemplated herein that the PAAD domain functions as a death domain in apoptosis. Accordingly, methods are provided herein for identifying PAAD domain binding agents that modulate apoptotic activity.

As disclosed herein, PAAD domain-containing polypeptides bind proteins through their PAAD domains, including other PAAD domain-containing polypeptides, IKAP, Nod1, Cardiak, NIK, IKK-i, IKKα and IKKβ.

Accordingly, methods are provided herein for identifying PAAD domain-associating proteins, and for identifying compounds that disrupt the interaction between the PAAD domain and PAAD domain-associating proteins.

As disclosed herein, expression of the PAAD domain of PAAD domain-containing polypeptides is able to specifically modulate the induction of NFκB activity by various stimuli. NFκB is the collective name for inducible dimeric transcription factors composed of members of the Rel family of DNA-binding proteins that recognize a common sequence motif. NFκB is sequestered in the cytoplasm of resting cells through its association with an inhibitory protein called IκB. When stimulated by a variety of extracellular modulators, including the proinflammatory cytokines TNFα and IL-1, T- and B-cell mitogens, bacteria, bacterial lipopolysaccharide (LPS), viruses, viral proteins, double stranded RNA, and physical and chemical stresses, a cascade of adaptor proteins and protein kinases is activated, leading to phosphorylation of IκB by the IκB kinases α and β (IKKα/β). IκB phosphorylation leads to its ubiquitination, which targets the protein for rapid degradation by the 26S proteasome. The degradation of IκB exposes the nuclear localization signal (NLS) of NFκB, resulting in NFκB translocation to the nucleus and activation.

Active NFκB regulates the transcription of a large number of genes, including those involved in immune and inflammatory responses such as immunoreceptors, cell adhesion molecules, cytokines and chemokines. NFκB also plays an important role in the antiviral response through interferon gene induction. Through adaptation, many viruses that do not cause interferon induction exploit NFκB to activate their own genes and to stimulate the survival and proliferation of lymphoid cells in which they replicate.

NFκB can have either positive and negative effects on cellular apoptosis depending on the cell type, apoptotic stimulus, and timing of NFκB activation. NFκB regulates the transcription of a variety of genes involved in blocking apoptosis, including cellular inhibitor of apoptosis (cIAP)-1, cIAP-2, TRAF1, TRAF2, superoxide dismutase (SOD), A20, and the Bcl-2 homolog Bfl-1/A1.

Inappropriate regulation of NFκB is involved in a wide range of human disorders, including cancers, neurodegenerative disorders, ataxia-telangiectasia, arthritis, asthma, inflammatory bowel disease and numerous other inflammatory conditions (see Karin et al., *Ann. Rev. Immunol.* 18:621-663 (2000), and references therein). Activation of NFκB also correlates with resistance to apoptosis induced by cancer therapeutic agents.

As disclosed herein, gene-transfer-mediated increases in the level of PAAD domain-containing proteins such as PAN2 and ASC can suppress NFκB transcriptional activity and NFκB DNA-binding activity in response to TNFα and IL-1β, implicating PAAD domain-containing proteins at the point of convergence of these cytokine signal transduction pathways. PAAD domain-containing proteins can also suppress NFκB induction resulting from over-expression of several adapter proteins and protein kinases involved in the TNFα and IL-1β receptor signal transduction pathway, and suppress the cytokine-mediated activation of IKKα and IKKβ. PAAD domain-containing proteins also can associate with IKKα, indicating a direct effect on the IKK complex.

The PANs of the invention are contemplated to function in a negative feedback mechanism that ensures that NFκB activity is produced in short bursts that limit inflammatory responses. The hereditary mutations associated with the PAN family proteins Cryopyrin and the PAAD-containing protein Pyrin may alter the functions of these proteins so that they are no longer capable of properly suppressing NFκB, thereby explaining the hyperinflammatory syndromes associated with mutations in the genes encoding these proteins. Likewise, mutations in genes encoding PANs of the invention, or altered regulation of such PANs, may be associated with inflammatory syndromes.

Under certain circumstances, it is contemplated that PANs function as stimulators rather than inhibitors of NFκB. Homotypic interactions between PAAD domains of suppressors and activators can thus set thresholds within cells for NFκB induction and inflammatory responses.

Accordingly, methods are provided herein to identify agents that modulate, either positively or negatively, the PAAD domain-mediated modulation of NFκB activation. Such agents can thus be used to regulate inflammatory responses, immune responses (including autoimmune responses), apoptosis, and other processes mediated at least in part by NFκB activity.

Further, PAAD domain-containing polypeptides are contemplated herein as influencing a variety of cellular and biochemical processes beyond apoptosis, including cell adhesion, inflammation and cytokine receptor signaling, and responses to viruses and infectious agents.

Exemplary invention PAAD domain-containing polypeptides include a family of proteins that in addition to a PAAD domain, contain a domain similar to the recently identified NB-ARC NTP-ase family (Koonin et al., *Trends Biochem Sci,* 25:223-224 (2000)) (see FIG. 3), as well as ARED domains and variable numbers of Leucine-Rich Repeat (LRR) domains. The NB-ARC, or "NACHT" domain has been implicated in nucleotide binding, oligomerization, and nucleotide (e.g. ATP and/or GTP) hydrolysis. This family of proteins is referred to herein as PAAD and Nucleotide-binding ("PAN") proteins. The topological organisation of domains in PANs is reminiscent of proteins previously implicated in NF-κB induction or Caspase activation, such as Nod1 (CARD4), Nod2 (Inflammatory bowel disease protein 1), and CLAN (Ipaf1; CARD12), which contain a CARD followed by NACHT and LRR domains (Inohara et al., *J. Biol. Chem.* 274:14560-14567 (1999); Ogura et al., *J. Biol. Chem.* 276: 4812-4818 (2001); and Damiano et al., *Genomics* 75:77-83 (2001)). In those proteins, the N-terminal CARD is essential for the effector functions of these proteins as inducers of NF-κB or activators of Caspases. As disclosed herein, the PAAD domain of invention PAN proteins also modulates NF-κB induction.

The amino acid sequence of the PAAD domains of PAN1 through PAN6 are set forth in FIG. 1 and as SEQ ID NOS:1-6, respectively. Alternatively, the PAAD domains of PAN2-6 can have the boundaries set forth by overlining in FIG. 11, corresponding to SEQ ID NO:103 (PAAD domain of PAN2), SEQ ID NO:106 (PAAD domain of PAN3), SEQ ID NO:109 (PAAD domain of PAN4), SEQ ID NO:112 (PAAD domain of PAN5) and SEQ ID NO:115 (PAAD domain of PAN6).

The sequences of PAN2-6 cDNAs and encoded polypeptides are set forth as follows: PAN2: SEQ ID NOS:15 and 16; PAN3: SEQ ID NOS:17 and 18; PAN4: SEQ ID NOS:19 and 20; PAN5: SEQ ID NOS:21 and 22; PAN6: SEQ ID NOS:23 and 24.

Alternatively, PAN3-6 cDNAs and encoded polypeptides can have sequences set forth in FIG. 12 (PAN 3; SEQ ID NOS:65 and 66), FIG. 18 (PAN 5; SEQ ID NOS:83 and 84) and FIG. 13 (PAN 6; SEQ ID NOS:67 and 68).

Other invention PAAD domain-containing polypeptides are designated PAN7, PAN8, PAN9 and PAN10. The amino acid sequence of the PAAD domains of PAN7, PAN8, PAN9 and PAN10 are shown by overlining in FIG. 11, corresponding to SEQ ID NO:118 (PAAD domain of PAN7), SEQ ID NO:121 (PAAD domain of PAN8), SEQ ID NO:124 (PAAD domain of PAN9) an d SEQ ID NO:127 (PAAD domain of PAN10).

The cDNA and encoded polypeptide sequences of PAN7, PAN8, PAN9 and PAN10 are set forth in FIG. 14 (PAN7; SEQ ID NOS:69 and 70), FIG. 15 (PAN8; SEQ ID NOS:71 and 72), FIG. 16 (PAN9; SEQ ID NOS:73 and 74) and FIG. 17 (PAN10; SEQ ID NOS:75 and 76).

Other PAAD domain-containing polypeptides include pyrin2 and human ASC2, whose PAAD domain sequences are set forth in FIG. 1 and as SEQ ID NOS:8 and 10, respectively, and the proteins aligned in FIG. 11 designated FLJ20510_human (SEQ ID NO:85), PANunk_mouse (SEQ ID NO:88), NALP3/cryopyrin (SEQ ID NO:89), NALP1/NAC (SEQ ID NO:92), PAN5_mouse (SEQ ID NO:93), PAN4_CT (SEQ ID NO:6) and PAN2_mouse (SEQ. ID NO:97). The sequences of pyrin2 cDNA and encoded polypeptide are set forth as SEQ ID NOS:25 and 26. A 719 residue open reading frame from chromosome 1, which is identical over the N-terminal 41 amino acids with SEQ ID NO:26, has been identified and deposited as gi:14731966 (SEQ ID NOS:58 and 59). Accordingly, a PAAD domain-containing polypeptide can contain the first 41 amino acids of SEQ ID NO:26, and can optionally further comprise the amino acid sequence designated SEQ ID NO:59.

The sequences of ASC2 cDNA and encoded polypeptide are set forth as SEQ ID NOS:27 and 28. ASC2 is an 89-residue protein containing only the PAAD domain.

The PAAD domain has also been identified in the N-terminal part of "Absent in Melanoma-2" (AIM2) and several closely homologous human and murine proteins, such as interferon-inducible genes IFI16 and MNDA (DeYoung et al., *Oncogene,* 15:453-457 (1997) (see FIG. 1; SEQ ID NOS: 12 and 13). Proteins from this family were characterized as containing one or more copies of a conserved 200-residue domain, implicated in transcription repression (Johnstone et al., *J Biol Chem.* 273:17172-17177 (1998). The N-terminal part of AIM2 and related homologous proteins, containing the invention PAAD domain was not functionally analyzed, with two exceptions. In MNDA protein, it was shown that the N-terminal domain is partly responsible for homodimerization (Xie et al., *FEBS Lett.* 408:151-155 (1997). In IFI16, DNA-binding was attributed to a 159-residue long N-terminal segment (Dawson et al. *Biochem Biophys Res Commun,* 214:152-162 (1995)). There are also two viral proteins homologous to the interferon-inducible MNDA/IFI16 family, (M013L from myxoma virus and gp013L from rabbit fibroma virus), that contain an invention PAAD domain. The PAAD domain of M013L is shown in FIG. 1 (SEQ ID NO:14).

A PAAD domain has also been identified in the N-terminus of the ASC protein (apoptosis-associated speck-like protein containing a CARD) (Masumoto et al., *J Biol Chem,* 274: 33835-33838 (1999)) (see FIG. 1; SEQ ID NO:9). The ASC protein was identified by characteristic dot-like aggregates (specks) which were present in cells during apoptosis triggered by retinolic acid and other anti-cancer drugs (Masumoto et al., supra (1999)). The C-terminal half of the speck protein contains an easily recognizable CARD domain, while the N-terminal half has now been found to be occupied by an invention PAAD domain.

One of the PAAD domain-containing polypeptides, PAN6 (SEQ ID NO:24), allowed an independent and unambigous connection between the pyrin/ASC/caspase and the AIM2/IFI16 branches of the family. Three iterations of a standard PSI-BLAST search against the NCBI nr database starting from this putative domain pulled out, among others, pyrin and AIM2, with E-values of 1e-23 and 1e-18, respectively.

The average sequence similarity between different branches of the PAAD domain protein family is approximately 25% of sequence identity (see FIG. 1). However, clear amino acid regions of strong sequence similarity are conserved throughout the PAAD domain family of proteins, as shown in FIG. 11.

Accordingly, in one embodiment, invention PAAD domains comprise the following amino acid consensus sequence motif -KFKX$_1$X$_2$L- (SEQ ID NO:29), where X$_1$ and X$_2$ can be any amino acid. Preferably, X$_1$ is selected from amino acids F, M, L, Y, E, H, Q and S, and X$_2$ is preferably selected from amino acids K, H, L, Y and F. This motif has been found to be present in the N-terminal half of the majority of invention PAAD domains (see, e.g., FIG. 1).

In another embodiment, invention PAAD domains are also contemplated herein comprising the following amino acid consensus sequence motif -KLKX$_1$X$_2$L- (SEQ ID NO:30), where X$_1$ and X$_2$ can be any amino acid. Preferably, X$_1$ is selected from amino acids F, M, L, Y, E, H, Q and S, and X$_2$ is preferably selected from amino acids K, H, L, Y and F.

In yet another embodiment, invention PAAD domains are also contemplated herein comprising the following amino acid consensus sequence motif -RFRX$_1$X$_2$L- (SEQ ID NO:31), where X$_1$ and X$_2$ can be any amino acid. Preferably, X$_1$ is selected from amino acids F, M, L, Y, E, H, Q and S, and X$_2$ is preferably selected from amino acids K, H, L, Y and F.

In yet another embodiment, invention PAAD domains are also contemplated herein comprising the following amino acid consensus sequence motif -RFKX$_1$X$_2$L- (SEQ ID NO:32), where X$_1$ and X$_2$ can be any amino acid. Preferably, X$_1$ is selected from amino acids F, M, L, Y, E, H, Q and S, and X$_2$ is preferably selected from amino acids K, H, L, Y and F.

In yet another embodiment, invention PAAD domains are also contemplated herein comprising the following amino acid consensus sequence motif -KFRX$_1$X$_2$L- (SEQ ID NO:33), where X$_1$ and X$_2$ can be any amino acid. Preferably, X$_1$ is selected from amino acids F, M, L, Y, E, H, Q and S, and X$_2$ is preferably selected from amino acids K, H, L, Y and F.

In still another embodiment, invention PAAD domains are also contemplated herein comprising the following amino acid consensus sequence motif -KFKX$_1$X$_2$I- (SEQ ID NO:34), where X$_1$ and X$_2$ can be any amino acid. Preferably, X$_1$ is selected from amino acids F, M, L, Y, E, H, Q and S, and X$_2$ is preferably selected from amino acids K, H, L, Y and F.

Accordingly, there are provided PAAD domain-containing polypeptides comprising an amino acid consensus sequence selected from the group consisting of:

| | |
|---|---|
| -KFKX$_1$X$_2$L-; | (SEQ ID NO: 29) |
| -KLKX$_1$X$_2$L-; | (SEQ ID NO: 30) |
| -RFRX$_1$X$_2$L-; | (SEQ ID NO: 31) |
| -RFKX$_1$X$_2$L-; | (SEQ ID NO: 32) |
| -KFRX$_1$X$_2$L-; and | (SEQ ID NO: 33) |
| -KFKX$_1$X$_2$I-; | (SEQ ID NO: 34) | where X$_1$ and X$_2$ can be any amino acid. Preferably, X$_1$ is selected from amino acids F, M, L, Y, E, H, Q and S, and X$_2$ is preferably selected from amino acids K, H, L, Y and F.

PAAD domains can be present in an invention polypeptide fragment or chimeric protein in conjunction with other types of functional domains, thus providing a mechanism for bringing one or more functional domains into close proximity or contact with a target protein via PAAD:PAAD associations involving two PAAD-containing polypeptides. For example, the PAAD domains of invention PAN proteins (e.g., PAN1 through PAN6, PAN7, PAN8, PAN9 and PAN10) allows invention PAN proteins to self-associate forming homo- or hetero-oligimers, thereby forming an oligomeric complex which brings proteins associated with PAN proteins into close proximity to each other. Because some PAAD domain-containing proteins also contain a CARD domain, exemplary proteins that are contemplated for association with invention PAN proteins are pro-caspases. Because most pro-caspases possess at least a small amount of protease activity even in their unprocessed form, the assembly of a complex that brings the proforms of caspase into juxtaposition can result in trans-processing of zymogens, producing the proteolytically processed and active caspase. Thus, invention PAN proteins can employ a PAAD domain for self-oligomerization and a CARD domain for binding a pro-caspase, resulting in caspase clustering, proteolytic processing and activation. In addition to the ability to activate caspases, PAAD domains are contemplated herein as being able to inhibit caspases.

In addition to their role in regulation of cell death and cell proliferation, PAAD domains can regulate other cellular processes. A PAAD domain-containing polypeptide can, for example, induce activation of the transcription factor NF-κB. Though caspase activation resulting from PAAD domain interactions can be involved in inducing apoptosis, other caspases can be primarily involved in proteolytic processing and activation of inflammatory cytokines (such as pro-IL-1β and pro-IL-18). Thus, PAAD domain-containing polypeptides can also be involved in cytokine receptor signaling, cytokine production and cJun N-terminal kinase activation, and, therefore, can be involved in regulation of immune and inflammatory responses.

In view of the function of the PAAD domain within the invention PAAD domain-containing polypeptides or functional fragments thereof, polypeptides of the invention are contemplated herein for use in methods to alter cellular and biochemical processes such as apoptosis, NF-κB induction, cytokine processing, cytokine receptor signaling, caspase-mediated proteolysis, or cJun N-terminal kinase activation, thus having modulating effects on cell life and death (i.e., apoptosis), inflammation, cell adhesion, or other cellular or biochemical processes.

Invention PAAD domain-containing polypeptides or functional fragments thereof are also contemplated in methods to identify PAAD domain binding agents and PAAD-associated polypeptides (PAPs) that alter apoptosis, NF-kB induction, cytokine processing, cytokine receptor signaling, caspase-mediated proteolysis, or cJun N-terminal kinase activation, thus having modulating effects on cell life and death (i.e., apoptosis), inflammation, cell adhesion, or other cellular or biochemical processes.

It is also contemplated herein that invention PAAD domain-containing polypeptides can associate with other PAAD domain-containing polypeptides to form invention hetero-oligomers or homo-oligomers, such as heterodimers or homodimers. In particular, the association of the PAAD domain of invention polypeptides with another PAAD domain-containing polypeptide, such as those identified herein, including homo-oligomerization, is sufficiently specific such that the bound complex can form in vivo in a cell or in vitro under suitable conditions. Similarly therefore, an invention PAAD domain-containing polypeptide can associate with another PAAD domain-containing polypeptide by PAAD:PAAD interaction to form invention hetero-oligomers or homo-oligomers, such as heterodimers or homodimers.

Figure 3:
FIG. 3 shows a schematic (not to scale) representation of domain arrangement in proteins containing a PAAD domain.
Figure 3:
Figure 3:
Figure 3:
Figure 3:
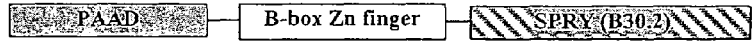
Figure 3:
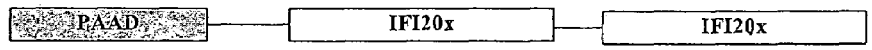
Figure 3:
Figure 3:

In addition to PAAD domains, an invention PAAD domain-containing polypeptide can contain a variety of additional domains including a CARD domain, a NACHT domain, a LRR domain, an ARED (ANGIO-R) domain, a caspase protease domain, or other recognized domains (see FIG. 3 and FIG. 11). Accordingly, PAAD domain-containing polypeptides can exhibit one or more of the biological activities characteristic of known CARD domain-, NACHT domain-, LRR domain-, ARED (ANGIO-R) domain or caspase domain-containing polypeptides.

A PAAD domain-containing polypeptide that contains a caspase recruitment domain, or CARD domain (e.g. ASC; FIG. 3), can associate with pro-caspases, caspases or with caspase-associated proteins, thereby altering caspase proteolytic activity.

A PAAD domain-containing polypeptide that contains a caspase protease domain (e.g. zebrafish caspase; FIG. 3) can hydrolyze amide bonds, particularly the amide bond of a peptide or polypeptide backbone. Typically, a caspase protease domain contains a P20/P10 domain in the active site region of the caspase protease domain. Thus, a caspase protease domain has proteolytic activity.

Caspase proteolytic activity is associated with apoptosis of cells, and additionally with cytokine production. As used herein a "caspase" is any member of the cysteine aspartyl proteases. A "pro-caspase" is an inactive or less-active precursor form of a caspase, which is typically converted to the more active caspase form by a proteolytic event, often a preceded by a protein:protein interaction, such as an interaction with a PAAD domain-containing polypeptide.

A PAAD domain-containing polypeptide that contains a NACHT domain (such as a PAN, or NAC; FIG. 3) can associate with other polypeptides, particularly with polypeptides comprising NACHT domains. Thus, a NACHT domain of an invention PAN associates with NACHT domain-containing polypeptides by way of NACHT:NACHT association. Further, a NACHT domain demonstrates both nucleotide-binding (e.g., ATP-binding) and hydrolytic activities, which is typically required for its ability to associate with NACHT domain-containing polypeptides. Thus, a NACHT domain of an invention PAN protein comprises one or more nucleotide binding sites. As used herein, a nucleotide binding site is a portion of a polypeptide that specifically binds a nucleotide such as, e.g., ADP, ATP, and the like. Typically, the nucleotide binding site of NACHT-will comprise a P-loop, a kinase 2 motif, or a kinase 3a motif of the invention PAAD domain-containing polypeptide (these motifs are defined, for example, in van der Biezen and Jones, Curr. Biol. 8:R226-R227 (1998)). Preferably, the nucleotide binding site of the NACHT of an invention PAN protein comprises a P-loop. The NACHT domain of the an invention PAN, therefore, is capable of associating with other NACHT domains in homo- or hetero-oligormerization. Additionally, the NACHT domain is characterized by nucleotide hydrolysis activity, which can influence the ability of a NACHT domain to associate with another NACHT domain. In accordance with the present invention, functional fragments of PAN proteins comprising NACHT domains are provided.

The amino acid sequences of NB-ARC (NACHT) domains of PAN2, 3, 5 and 6 are set forth as follows: PAN2, SEQ ID NO:37, corresponding to amino acids 147-465 of SEQ ID NO:16; PAN3, SEQ ID NO:60, corresponding to amino acids 196-512 of SEQ ID NO:18; PAN5, SEQ ID NO:62, corresponding to amino acids 93-273 of SEQ ID NO:22; and PAN6, SEQ ID NO:63, corresponding to amino acids 183-372 of SEQ ID NO:24. Alternatively, the NACHT domains of PAN2, 3, 5 and 6 can have the boundaries shown in FIG. 11, corresponding to SEQ ID NO:104 (NACHT domain of PAN2), SEQ ID NO:107 (NACHT domain of PAN3), SEQ ID NO:113 (NACHT domain of PAN5) and SEQ ID NO:116 (NACHT domain of PAN6).

The amino acid sequences of the NACHT domains of PAN4, PAN7, PAN8, PAN9 and PAN10 are shown in FIG. 11, and correspond to SEQ ID NO:110 (NACHT domain of PAN4), SEQ ID NO:119 (NACHT domain of PAN7), SEQ ID NO:122 (NACHT domain of PAN8), SEQ ID NO:125 (NACHT domain of PAN9) and SEQ ID-NO:128 (NACHT domain of PAN10).

The skilled person can readily determine the NACHT domain amino acid sequences from other invention PAN polypeptides.

Interestingly, several residues within highly conserved regions of the NACHT domain of PAN10 differ with respect to other NACHT domain-containing proteins. For example, as shown in FIG. 11, the P loop at the N-terminus of the NACHT domain (positions 338 to 351 of the aligned sequences; also called the "kinase 1a motif" in van der Biezen et al., supra (1998)) contains a substitution of an Ala (A) for a completely conserved Gly (G).

An invention PAAD domain-containing polypeptide, such as a PAN, therefore, is capable of PAAD:PAAD association and/or NACHT:NACHT association, resulting in a multifunctional polypeptide capable of one or more specific associations with other polypeptides.

As used herein, the term "associate" or "association" refers to binding that is sufficiently specific such that a bound complex can form in vivo in a cell or in vitro under suitable conditions.

A PAAD domain-containing polypeptide can also contain a Leucine-Rich Repeat (LRR) domain-(e.g. PAN2, PAN3, PAN6, NAC; see FIG. 3). Leucine-rich repeats (LRRs) are 22-28 amino acid-long leucine rich sequence motifs found in cytoplasmic, membrane and extracellular proteins, including the mammalian Ced4 proteins Nod1 (Inohara et al., J. Biol. Chem. 274:14560-14567 (1999)) and DEFCAP, Hlaing et al., J. Biol. Chem. 276:9230-9238 (2001), NAC (Chu et al., J. Biol. Chem. 276:9239-9245 (2001), and Toll-like receptors (Takeuchi et al., Gene 231:59-65 (1999)). The biological activities of LRR domains can include, for example, protein-protein interactions that regulate signal transduction and cell adhesion; assisting in formation of large, multiprotein complexes; and binding molecules produced by pathogens (e.g. lipids, RNA, proteins, DNA). For example, other. LRR-containing proteins are known to bind bacterial lipopolysaccharide (e.g. TLR4 and Nod1/2), CpG DNA (e.g. TLR9), the bacterial protein flagellin (e.g. TLR5), and steroids (e.g. plant LRRs) (see, for example, Fumitaka et al., Nature 410:1099-1103 (2001); Aderem et al., Nature 406:782-787 (2000); and Beutler, Immunity 15;5-14 (2001)). One model for how LRR-domain-containing proteins become activated is that the unliganded LRRs function as negative regulatory domains that suppress activitation of the NB-domains until appropriate stimulatory ligands bind, relieving this auto-repression. Thus, the LRRs of the invention PANs are contemplated to recognize pathogen products, changing the activation state of these proteins. In accordance with the present invention, functional fragments of PAN proteins comprising LRR domains are provided.

The amino acid sequences of the LRR domains of PAN2, 3 and 6 are set forth as follows: PAN2, SEQ ID NO:39, corresponding to amino acids 620-995 of SEQ ID NO:16; PAN3, SEQ ID NO:61, corresponding to amino acids 658 through the C-terminus of SEQ ID NO:18; and PAN6, SEQ ID NO:64, corresponding to amino acids 429-1031 of SEQ ID NO:24. The skilled person can readily determine the LRR domain amino acid sequences from other invention PAN polypeptides.

A PAAD domain-containing polypeptide can also contain an "ANGIO-R" or "ARED" domain. An ANGIO-R (ARED) domain is a region of a polypeptide chain that bears substantial similarity (e.g. 25, 30, 40% or higher sequence identity) to a portion of the 514-residue long protein "angiotensin II/vasopressin receptor" (described in Ruiz-Opazo et al., Nature Med. 1:1074-1081 (1995)). In an invention PAN, generally a single exon encodes both the NACHT domain and the ARED domain.

The amino acid sequence of the ANGIO-R (ARED) domain of PAN2 is set forth as SEQ ID NO:38, corresponding to amino acids 336-605 of SEQ ID NO:16. Alternatively, the ARED domain of PAN2 can have the boundaries set forth-by overlining in FIG. 11, corresponding to SEQ ID NO:105.

The amino acid sequences of the ARED domains of PAN3-6 and PAN7-10 are shown by overlining in FIG. 11, corresponding to SEQ ID NO:108 (ARED domain of PAN3), SEQ ID NO:111 (ARED domain of PAN4), SEQ ID NO:114 (ARED domain of PAN5), SEQ ID NO:117 (ARED domain of PAN6), SEQ ID NO:120 (ARED domain of PAN7), SEQ ID NO:123 (ARED domain of PAN8), SEQ ID NO:126 (ARED domain of PAN9) and SEQ ID NO:129 (ARED domain of PAN10)

An invention PAAD domain-containing polypeptide can alter cell processes such as apoptosis. For example, it is contemplated herein that an invention PAAD domain-containing polypeptide can increase apoptosis in a cell. It is also contemplated herein that an invention PAAD domain-containing polypeptide can decrease the level of apoptosis in a cell. For example, a PAAD domain-containing polypeptide which does not induce apoptosis may form hetero-oligomers with a PAAD domain-containing polypeptide which is apoptotic, thus interfering with its apoptosis-inducing activity.

In one embodiment, the invention provides PAAD domain-containing polypeptides comprising substantially the same, or the same, amino acid sequence as set forth in any of SEQ ID NOS:16, 18, 20, 22, 24, 26 and 28, and fragments therefrom, including PAAD, NB-ARC (NACHT) and LRR domain-containing fragments.

The invention also provides PAAD domain-containing polypeptides comprising substantially the same, or the same, amino acid sequence as set forth in any of SEQ ID NOS:66, 68, 70, 72, 74, 76 and 84, and fragments therefrom, including PAAD, NACHT and ARED domain-containing fragments;

As employed herein, the term "substantially the same amino acid sequence" refers to amino acid sequences having at least about 70% or 75% identity with respect to the reference amino acid sequence and retaining comparable functional and biological activity characteristic of the polypeptide defined by the reference amino acid sequence. Preferably, polypeptides having "substantially the same amino acid sequence" will have at least about 80%, 82%, 84%, 86% or 88%, more preferably 90%, 91%, 92%, 93% or 94% amino acid identity with respect to the reference amino acid sequence; with greater than about 95%, 96%, 97%, 98% or 99% amino acid sequence identity being especially preferred. It is recognized, however, that polypeptides containing less than the described levels of sequence identity arising as splice variants or that are modified by conservative amino acid substitutions, or by substitution of degenerate codons are also encompassed within the scope of the present invention.

The term "biologically active" or "functional", when used herein as a modifier of invention PAAD domain-containing polypeptide, functional fragments thereof, or chimeric proteins, refers to a polypeptide that exhibits functional characteristics similar to at least a portion of a naturally occurring PAAD domain-containing protein. Biological activities of a naturally occurring PAAD domain-containing protein include, for example, the ability to bind, preferably in vivo, to a nucleotide, to a PAAD domain-containing polypeptide, to a CARD-containing polypeptide, to a NB-ARC (NACHT)-containing polypeptide, to a LRR-containing polypeptide or to homo-oligomerize, or to alter protease activation, particularly caspase activation, or to catalyze reactions such as proteolysis or nucleotide hydrolysis, or to alter NF-κB activity, or to alter cJun N-terminal kinase activity, or to alter apoptosis, cytokine processing, cytokine receptor signaling, inflammation, immune response, or other biological activities described herein. Another biological activity of a PAAD domain-containing polypeptide is the ability to act as an immunogen for the production of polyclonal and monoclonal antibodies that bind specifically to an invention PAAD domain-containing polypeptide.

A further biological activity of a PAAD domain-containing polypeptide is the ability to modulate the NFκB transcriptional activity induced by a variety of stimuli, including activators of the TNFα and IL-1β signaling pathways (see Examples). The PAAD domain is sufficient for this activity.

The ability of a PAAD domain-containing polypeptide to bind another polypeptide such as a PAAD-associated polypeptide can be assayed using in vitro or in vivo methods. For example, methods well known in the art such as yeast two-hybrid assays, co-immunoprecipitation, GST fusion co-purification, GST pull-down assays, and other methods provided in standard technique manuals such as Sambrook et al., *Molecular Cloning: A Laboratory Manual*, 2nd ed., Cold Spring Harbor Press, Plainview, N.Y. (1989) and, Ausubel et al., *Current Protocols in Molecular Biology*, John Wiley & Sons, New York (2000) can be used.

As used herein, the term "substantially purified" means a polypeptide that is in a form that is relatively free from contaminating lipids, polypeptides, nucleic acids or other cellular material normally associated with the polypeptide. A substantially purified PAAD domain-containing polypeptide can be obtained by a variety of methods well-known in the art, e.g., recombinant expression systems described herein, precipitation, gel filtration, ion-exchange, reverse-phase and affinity chromatography, and the like. Other well-known methods are described in Deutscher et al., "Guide to Protein Purification" *Methods in Enzymology* Vol. 182, (Academic Press, (1990)). The methods and conditions for biochemical purification of a polypeptide of the invention can be chosen by those skilled in the art, and purification monitored, for example, by an immunological assay, binding assay, or a functional assay.

In addition to the ability of invention PAAD domain-containing polypeptides, or functional fragments thereof, to interact with other, heterologous proteins (e.g. other PAAD domain-, LRR domain-, or NB-ARC (NACHT) domain-containing polypeptides), invention PAAD-containing polypeptides have the ability to self-associate to form invention homo-oligomers such as homodimers. This self-association is possible through interactions between PAAD domains, and also through. interactions between CARD domains or NACHT domains. Further, self-association can take place as a result of interactions between LRR domains.

In accordance with the invention, there are also provided mutations of PAAD domain-containing polypeptides which have activity different than a predominant naturally occurring PAAD domain-containing polypeptide activity. As used herein, a "mutation" can be any deletion, insertion, or change of one or more amino acids within the predominant naturally occurring protein sequence (e.g., wild-type), and a "fragment" is any truncated form, either carboxy-terminal, amino-terminal, or both, of the predominant naturally occurring protein. Preferably, the different activity of the mutation or fragment is a result of the mutant polypeptide or fragment maintaining some but not all of the activities of the respective predominant naturally occurring PAAD domain-containing polypeptide.

For example, a functional fragment of an invention protein can contain one or more of the following: a PAAD domain, a NACHT domain, a LRR domain or an ANGIO-R (ARED) domain. In a specific example, a functional fragment of a PAAD domain-containing polypeptide such as a PAN can contain a PAAD domain and LRR domain, or only a PAAD domain, but lack a functional NACHT domain. Such a fragment will maintain a portion of the predominant naturally occurring PAN activity (e.g., PAAD domain functionality), but not all such activities (e.g., lacking an active NACHT domain). The resultant fragment will therefore have an activity different than the predominant naturally occurring PAN activity. In another example, a functional fragment of a PAN protein might have only the NACHT domain, allowing it to interact with other NACHT domain proteins in forming homo-oligomers or hetero-oligomers. Thus, a functional fragment of a PAAD domain-containing protein or polypeptide is not required to contain a functional PAAD domain, but only to contain a functional domain from a naturally occurring PAAD domain-containing protein. In one embodiment, the activity of the fragment will be "dominant-negative." A dominant-negative activity will allow the fragment to reduce or inactivate the activity of one or more isoforms of a predominant naturally occurring PAAD domain-containing polypeptide.

Methods to identify additional invention PAAD domain-containing polypeptides and functional fragments thereof are well known in the art and are disclosed herein. For example, genomic or cDNA libraries, including universal cDNA libraries can be probed according to methods disclosed herein or other methods known in the art. Full-length polypeptide-encoding nucleic acids such as full-length cDNAs can be obtained by a variety of methods well-known in the art. For example, 5' and 3' RACE, methodology is well known in the art and described in Ausubel et al., supra, and the like.

In another embodiment of the invention, chimeric proteins are provided comprising a PAAD domain-containing polypeptide, or a functional fragment thereof, fused with another protein or functional fragment thereof. Functional fragments of a PAAD domain-containing polypeptide include, for example, PAAD, NACHT, LRR, and ANGIO-R (ARED) domains or other fragments that retain a biological activity of an invention containing polypeptide. Polypeptides with which the PAAD domain-containing polypeptide or functional fragment thereof are fused can include, for example, glutathione-S-transferase, an antibody, or other proteins or functional fragments thereof which facilitate recovery of the chimera. Further polypeptides with which a PAAD domain-containing polypeptide or functional fragment thereof are fused can include, for example, luciferase, green fluorescent protein, an antibody, or other proteins or functional fragments thereof which facilitate identification of the chimera. Still further polypeptides with which a PAAD-containing polypeptide or functional fragment thereof are fused will include, for example, the LexA DNA binding domain, ricin, α-sarcin, an antibody or fragment thereof, or other polypeptides which have therapeutic properties or other biological activity.

Further invention chimeric proteins contemplated herein are chimeric proteins wherein a functional fragment of a PAAD domain-containing polypeptide is fused with a catalytic domain or a protein interaction domain from a heterologous polypeptide. For example, chimeric proteins can contain a functional fragment of a PAAD domain-containing polypeptide of the invention fused with a domain of a protein known in the art, such as CED-4, Apaf-1, caspase-1, and the like. For example, the NACHT domain of an invention PAN can be replaced by the NACHT domain of CED-4 and the like. Another example of such a chimera is a polypeptide wherein the CARD domain of an invention PAN is replaced by the CARD domain from CED-4, and the like. In a further example, a NACHT domain can be fused with a P20/P10 domain to form a novel chimera with caspase activity. In another embodiment, a chimeric protein can be formed which contains functional domains of 2 or more PAAD domain-containing polypeptides of the invention.

As used herein, the term "polypeptide" when used in reference to a PAAD domain-containing polypeptide is intended to refer to a peptide or polypeptide of two or more amino acids. The term "polypeptide analog" includes any polypeptide having an amino acid residue sequence substantially the same as a sequence specifically described herein in which one or more residues have been conservatively substituted with a functionally similar residue and which displays the ability to functionally mimic a PAAD domain-containing polypeptide as described herein. A "modification" of an invention polypeptide also encompasses conservative substitutions of an invention polypeptide amino acid sequence. Conservative substitutions of encoded amino acids include, for example, amino acids that belong within the following groups: (1) non-polar amino acids (Gly, Ala, Val, Leu, and Ile); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Trp, Tyr, and His). Other groupings of amino acids can be found, for example in Taylor, *J. Theor. Biol.* 119:205-218 (1986), which is incorporated herein by reference. Other minor modifications are included within invention polypeptides so long as the polypeptide retains some or all of its function as described herein.

The amino acid length of functional fragments or polypeptide analogs of the present invention can range from about 5 amino acids up to the full-length protein sequence of an invention PAAD domain-containing polypeptide. In certain embodiments, the amino acid lengths include, for example, at least about 10 amino acids, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 125, at least about 150, at least about 175, at least about 200, at least about 250 or more amino acids in length up to no more than 1 residue less than a full-length naturally occurring PAAD domain-containing protein. In a particular embodiment of the invention, PAAD domain-containing functional fragments comprise an amino acid consensus sequence selected from the group consisting of:

| | |
|---|---|
| -KFKX$_1$X$_2$L-; | (SEQ ID NO: 29) |
| -KLKX$_1$X$_2$L-; | (SEQ ID NO: 30) |
| -RFRX$_1$X$_2$L-; | (SEQ ID NO: 31) |
| -RFKX$_1$X$_2$L-; | (SEQ ID NO: 32) |
| -KFRX$_1$X$_2$L-; and | (SEQ ID NO: 33) |
| -KFKX$_1$X$_2$I-; | (SEQ ID NO: 34) | where $X_1$ and $X_2$ can be any amino acid. Preferably, PAAD domain-containing functional fragments comprise 15 or more contiguous amino acids selected from the group consisting of SEQ ID NOS:1-14.

A modification of a polypeptide can also include derivatives, analogues and functional mimetics thereof, provided that such polypeptide displays a PAAD domain-containing polypeptide biological activity. For example, derivatives can include chemical modifications of the polypeptide such as alkylation, acylation, carbamylation, iodination, or any modification that derivatizes the polypeptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by peptide bonds. Polypeptides of the present invention also include any polypeptide having one or more additions and/or deletions of residues, relative to the sequence of a polypeptide whose sequence is shown herein, so long as PAAD domain-containing polypeptide activity is maintained.

A modification of an invention polypeptide includes functional mimetics thereof. Mimetics encompass chemicals containing chemical moieties that mimic the function of the polypeptide. For example, if a polypeptide contains two charged chemical moieties having functional activity, a mimetic places two charged chemical moieties in a spatial orientation and constrained structure so that the charged chemical function is maintained in three-dimensional space. Thus, a mimetic, which orients functional groups that provide a function of a PAAD domain-containing polypeptide, are included within the meaning of a PAAD domain-containing polypeptide derivative. All of these modifications are included within the term "polypeptide" so long as the invention polypeptide or functional fragment retains its function. Exemplary mimetics are peptidomimetics, peptoids, or other peptide-like polymers such as poly(b-amino acids), and also non-polymeric compounds upon which functional groups that mimic a peptide are positioned.

Another embodiment of the invention provides a PAAD domain-containing polypeptide, or a functional fragment thereof, fused with a moiety to form a conjugate. As used herein, a "moiety" can be a physical, chemical or biological entity which contributes functionality to a PAAD domain-containing polypeptide or a functional fragment thereof. Functionalities contributed by a moiety include therapeutic or other biological activity, or the ability to facilitate identification or recovery of a PAAD domain-containing polypeptide. Therefore, a moiety will include molecules known in the art to be useful for detection of the conjugate by, for example, by fluorescence, magnetic imaging, detection of radioactive emission. A moiety may also be useful for recovery of the conjugate, for example a His tag or other known tags used for protein isolation and/or purification, or a physical substance such as a bead. A moiety can be a therapeutic compound, for example, a cytotoxic drug which can be useful to effect a biological change in cells to which the conjugate localizes.

An example of the methods for preparing the invention polypeptide(s) is to express nucleic acids encoding a PAAD domain-containing polypeptide in a suitable host cell, such as a bacterial cell, a yeast cell, an amphibian cell such as an oocyte, or a mammalian cell, using methods well known in the art, and recovering the expressed polypeptide, again using well-known purification methods. Invention polypeptides can be isolated directly from cells that have been transformed with expression vectors as known in the art. Recombinantly expressed polypeptides of the invention can also be expressed as fusion proteins with appropriate affinity tags, such as glutathione S transferase (GST) or poly His, and affinity purified. The invention polypeptide, biologically functional fragments, and functional equivalents thereof can also be produced by in vitro transcription/translation methods known in the art, such as using reticulocyte lysates, as used for example, in the TNT system (Promega). The invention polypeptide, biologically functional fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

The present invention also provides compositions containing an acceptable carrier and any of an isolated, purified PAAD domain-containing mature protein, such as an invention PAN protein, or functional polypeptide fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil/water or water/oil emulsion, and various types of wetting agents.

The invention thus provides a therapeutic composition comprising a pharmaceutically acceptable carrier and a compound selected from the group consisting of a PAAD domain-containing fragment polypeptide, a PAAD domain-containing chimeric protein, a PAAD domain-containing polypeptide modulating compound, and an anti-PAAD antibody. The invention additionally provides a method of treating a pathologies characterized by abnormal cell proliferation, abnormal cell death, or inflammation by administering an effective amount of the composition containing a pharmaceutically acceptable carrier and a compound selected from the group consisting of a PAAD domain-containing polypeptide, a functional fragment thereof, a PAAD domain-containing polypeptide modulating compound, and an anti-PAAD antibody.

PAAD domain-containing polypeptides can be administered to an individual to increase an activity associated with a PAAD domain-containing polypeptide, including induction of apoptosis, functioning as a tumor suppressor, modulation of inflammation or cell adhesion, and the like. For example, a PAAD domain-containing polypeptide can be administered therapeutically to an individual using expression vectors containing nucleic acids encoding PAAD domain-containing polypeptides, as described below. In addition, PAAD domain-containing polypeptides, or a functional portion thereof, can be directly administered to an individual. Methods of administering therapeutic polypeptides are well known to those skilled in the art, for example, in the form of a pharmaceutical composition.

In accordance with another embodiment of the invention, there are provided isolated nucleic acids encoding a PAAD domain-containing polypeptide fragment or chimeric protein comprising a PAAD domain-containing polypeptide. The isolated nucleic acids can be selected from:

(a) DNA encoding a polypeptide containing the amino acid sequence set forth in SEQ ID NOs: 16, 18, 20, 22, 24, 26 or 28; or DNA encoding a polypeptide containing the amino acid sequence set forth in SEQ ID NOs: 66, 68, 70, 72, 74, 76 or 84;

(b) DNA that hybridizes to the DNA of (a) under moderately stringent conditions, where the DNA encodes a biologically active PAAD domain-containing polypeptide.

The nucleic acid molecules described herein are useful for producing invention polypeptides, when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of an invention PAAD domain encoding gene or mRNA transcript in a given sample. The nucleic acid molecules described herein, and fragments thereof, are also useful as primers and/or templates in a PCR reaction for amplifying genes, encoding invention polypeptides described herein.

The term "nucleic acid" or "nucleic acid molecule" (also referred to as polynucleotides) encompasses ribonucleic acid (RNA) or deoxyribonucleic acid (DNA), probes, oligonucleotides, and primers and can be single stranded or double stranded. DNA can be either, complementary DNA (cDNA) or genomic DNA, e.g. a PAAD domain-encoding gene, and can represent the sense strand, the anti-sense strand, or both. Examples of nucleic acids are RNA, cDNA, or isolated genomic DNA encoding a PAAD domain-containing polypeptide. One means of isolating a PAAD domain encoding nucleic acid polypeptide is to probe a mammalian genomic or cDNA library with a natural or artificially designed DNA probe using methods well known in the art. DNA probes derived from the PAAD domain encoding gene are particularly useful for this purpose. DNA and cDNA molecules that encode PAAD domain-containing polypeptides can be used to obtain complementary genomic DNA, cDNA or RNA from mammalian (e.g., human, mouse, rat, rabbit, pig, and the like), or other animal sources, or to isolate related cDNA or genomic clones by screening cDNA or genomic libraries, using methods described in more detail below.

In one embodiment, invention nucleic acids comprise substantially the same or the same nucleotide sequence as set forth in SEQ ID NOs:15 (PAN2), 17 (PAN3), 19 (PAN4), 21 (PANS), 23 (PAN6), 25 (pyrin2), or 27 (ASC2). The invention also provides nucleic acids that comprise substantially the same or the same nucleotide sequence as set forth in SEQ ID NOs:65, 67, 69, 71, 73, 75 or 83.

Thus a PAAD domain encoding nucleic acid as used herein refers to a nucleic acid encoding a polypeptide containing a PAAD domain-containing polypeptide fragment of the invention, or a PAAD domain-containing chimeric protein.

Use of the terms "isolated" and/or "purified" and/or "substantially purified" in the present specification and claims as a modifier of DNA, RNA, polypeptides or proteins means that the DNA, RNA, polypeptides or proteins so designated have been produced in such form by the hand of man, and thus are separated from their native in vivo cellular environment, and are substantially free of any other species of nucleic acid or protein. As a result of this human intervention, the recombinant DNAs, RNAs, polypeptides and proteins of the invention are useful in ways described herein that the DNAs, RNAs, polypeptides or proteins as they naturally occur are not.

Invention nucleic acids encoding PAAD domain-containing polypeptides and invention PAAD domain-containing polypeptides can be obtained from any species of organism, such as prokaryotes, eukaryotes, plants, fungi, vertebrates, invertebrates, and the like. A particular species can be mammalian, e.g., human, rat, mouse, rabbit, monkey, baboon, bovine, porcine, ovine, canine, feline, and the like. A preferred PAAD domain encoding nucleic acid herein, is human PAAD domain encoding nucleic acid.

As employed herein, the term "substantially the same nucleotide sequence" refers to DNA having sufficient identity to the reference polynucleotide, such that it will hybridize to the reference nucleotide under moderately or highly stringent hybridization conditions. In one embodiment, DNA having substantially the same nucleotide sequence as the reference nucleotide sequence encodes substantially the same amino acid sequence as that set forth in any of SEQ ID NOs:16, 18, 20, 22, 24, 26 or 28, or in SEQ ID NOs:65, 67, 69, 71, 73, 75 or 83. In another embodiment, DNA having "substantially the same nucleotide sequence" as the reference nucleotide sequence has at least 60%, or at least 65% identity with respect to the reference nucleotide sequence. DNA having at least 70%, 72%, 74%, 76%, 78%, 80%, 82%, 84%, 86% or 88%, more preferably at least 90%, 91%, 92%, 93% or 94% yet more preferably at least 95%, 96%, 97%, 98% or 99% identity to the reference nucleotide sequence is preferred.

As used herein, a "modification" of a nucleic acid can also include one or several nucleotide additions, deletions, or substitutions with respect to a reference sequence. A modification of a nucleic acid can include substitutions that do not change the encoded amino acid sequence due to the degeneracy of the genetic code. Such modifications can correspond to variations that are made deliberately, or which occur as mutations during nucleic acid replication.

Exemplary modifications of the recited nucleotide sequences include sequences that correspond to homologs of other species, including mammalian species such as mouse, primates, including monkey and baboon, rat, rabbit, bovine, porcine, ovine, canine, feline, or other animal species. The corresponding nucleotide sequences of non-human species can be determined by methods known in the art, such as by PCR or by screening genomic, cDNA or expression libraries.

Another exemplary modification of the invention PAAD domain encoding nucleic acid or PAAD domain-containing polypeptide can correspond to mutant or splice variant forms of the PAAD domain encoding nucleotide sequence. Additionally, a modification of a nucleotide sequence can include one or more non-native nucleotides, having, for example, modifications to the base, the sugar, or the phosphate portion, or having a modified phosphodiester linkage. Such modifications can be advantageous in increasing the stability of the nucleic acid molecule.

Furthermore, a modification of a nucleotide sequence can include, for example, a detectable moiety, such as a radiolabel, a fluorochrome, a ferromagnetic substance, a luminescent tag or a detectable binding agent such as biotin. Such modifications can be advantageous in applications where detection of a PAAD domain encoding nucleic acid molecule is desired.

This invention also encompasses nucleic acids which differ from the nucleic acids shown in SEQ ID NOs:15, 17, 19, 21, 23, 25 or 27, or in SEQ ID NOs:65, 67, 69, 71, 73, 75 or 83, but which have the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same polypeptide product(s) as the nucleic acids disclosed herein. In particular, functionally equivalent nucleic acids encode polypeptides that are the same as those encoded by the nucleic acids disclosed herein or that have conservative amino acid variations. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding invention PAAD domain-containing polypeptides that, by virtue of the degeneracy of the genetic code, do not necessarily hybridize to the invention nucleic acids under specified hybridization conditions. Preferred nucleic acids encoding the invention PAAD domain-containing polypeptides are comprised of nucleotides that encode substantially the same amino acid sequence as set forth in SEQ ID NOs:16, 18, 20, 22, 24, 26 or 28, or SEQ ID NOs:65, 67, 69, 71, 73, 75 or 83.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature (Tm) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-nucleic acid to bind a complementary nucleic acid. The hybridized nucleic acids will generally have at least about 60% identity, at least about 75% identity, more at least about 85% identity; or at least about 90% identity. Moderately stringent conditions are conditions-equivalent to hybridization in 50% formamide, 5× Denhart's solution, 5× SSPE, 0.2% SDS at 42° C., followed by washing in 0.2× SSPE, 0.2% SDS, at 42° C.

The phrase "high stringency hybridization" refers to conditions that permit hybridization of only those nucleic acid sequences that form stable hybrids in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5× Denhart's solution, 5× SSPE, 0.2% SDS at 42° C., followed by washing in 0.1× SSPE, and 0.1% SDS at 65° C.

The phrase "low stringency hybridization" refers to conditions equivalent to hybridization in 10% formamide, 5× Denhart's solution, 6× SSPE, 0.2% SDS at 22° C., followed by washing in 1× SSPE, 0.2% SDS, at 37° C. Denhart's solution contains 1% Ficoll, 1% polyvinylpyrolidone, and 1% bovine serum albumin (BSA). 20× SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency Hybridization buffers and conditions are well known to those of skill in the art and are described, for example, in Sambrook et al., supra (1989); and Ausubel et al., supra (2000).

Nucleic acids encoding polypeptides hybridize under moderately stringent or high stringency conditions to substantially the entire sequence, or substantial portions, for example, typically at least 15, 17, 21, 25, 30, 40, 50 or more nucleotides of the recited nucleic acid sequences.

As used herein, the term "degenerate" refers to codons that differ in at least one nucleotide from a reference nucleic acid, but encode the same amino acids as the reference nucleic acid. For example, codons specified by the triplets "UCU", "UCC", "UCA", and "UCG" are degenerate with respect to each other since all four of these codons encode the amino acid serine.

The invention also provides a modification of a nucleotide sequence that hybridizes to a PAAD domain encoding nucleic acid molecule under moderately stringent conditions. Modifications of nucleotide sequences, where the modification has at least 60% identity to a PAAD domain encoding nucleotide sequence, are also provided. The invention also provides modification of a PAAD domain encoding nucleotide sequence having at least 65% identity, at least 70% identity, at least 72% identity, at least 74% identity, at least 76% identity, at least 78% identity, at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity or at least 99% identity to a recited sequence.

Identity of any two nucleic acid or amino acid sequences can be determined by those skilled in the art based, for example, on known computer alignments such as BLAST 2.0, ClustalW and the like, which can be adjusted manually, if appropriate, to insert gaps to optimize the alignment according to standard practice in the art.

One means of isolating a nucleic acid encoding a PAAD domain-containing polypeptide is to probe a cDNA library or genomic library with a natural or artificially designed nucleic acid probe using methods well known in the art. Nucleic acid probes derived from a PAAD domain encoding gene are particularly useful for this purpose. DNA and cDNA molecules that encode PAAD domain-containing polypeptides can be used to obtain complementary genomic DNA, cDNA or RNA from mammals, for example, human, mouse, rat, rabbit, pig, and the like, or other animal sources, or to isolate related cDNA or genomic clones by the screening of cDNA or genomic libraries, by methods well known in the art (see, for example, Sambrook et al., supra (1989); Ausubel et al., supra (2000)).

The invention additionally provides a nucleic acid that hybridizes under high stringency conditions to the PAAD domain coding portion of any of SEQ ID NOs:15, 17, 19, 21, 23, 25 or 27, or SEQ ID NOs:65, 67, 69, 71, 73, 75 or 83. The invention also provides a nucleic acid having a nucleotide sequence substantially the same as set that forth in any of SEQ ID NOs:15, 17, 19, 21, 23, 25 or 27, or SEQ ID NOs:65, 67, 69, 71, 73, 75 or 83.

The invention also provides a method for identifying nucleic acids encoding a mammalian PAAD domain-containing polypeptide by contacting a sample containing nucleic acids with one or more invention oligonucleotides, wherein the contacting is effected under high stringency hybridization conditions, and identifying a nucleic acid that hybridizes to the oligonucleotide. The invention additionally provides a method of detecting a PAAD domain encoding nucleic acid molecule in a sample by contacting the sample with two or more invention oligonucleotides, amplifying a nucleic acid molecule, and detecting the amplification. The amplification can be performed, for example, using PCR. The invention further provides oligonucleotides that function as single stranded nucleic acid primers for amplification of a PAAD domain encoding nucleic acid, wherein the primers comprise a nucleic acid sequence derived from the nucleic acid sequences set forth as SEQ ID NOS:SEQ ID NOs:15, 17, 19, 21, 23, 25 or 27, or SEQ ID NOs:65, 67, 69; 71, 73, 75 or 83.

In accordance with a further embodiment of the present invention, optionally labeled PAAD-encoding cDNAs, or fragments thereof, can be employed to probe library(ies) such as cDNA, genomic, BAC, and the like for predominant nucleic acid sequences or additional nucleic acid sequences encoding novel PAAD domain-containing polypeptides. Construction and screening of suitable mammalian cDNA-libraries, including human cDNA libraries, is well-known in the art, as demonstrated, for example, in Ausubel et al., supra. Screening of such a cDNA library is initially carried out under low-stringency conditions, which comprise a temperature of less than about 42° C., a formamide concentration of less than about 50%, and a moderate to low salt concentration.

Presently preferred probe-based screening conditions comprise a temperature of about 37° C., a formamide concentration of about 20%, and a salt concentration of about 5× standard saline citrate (SSC; 20×SSC contains 3M sodium chloride, 0.3M sodium citrate, pH 7.0). Such conditions will allow the identification of sequences which have a substantial degree of similarity with the probe sequence, without requiring perfect homology. The phrase "substantial similarity" refers to sequences which share at least 50% homology. Hybridization conditions are selected which allow the identification of sequences having at least 70% homology with the probe, while discriminating against sequences which have a lower degree of homology with the probe. As a result, nucleic acids having substantially the same nucleotide sequence as SEQ ID NOs:15, 17, 19, 21, 23, 25 or 27, or SEQ ID NOs:65, 67, 69, 71, 73, 75 or 83, are obtained.

As used herein, a nucleic acid "probe" is single-stranded nucleic acid, or analog thereof, that has a sequence of nucleotides that includes at least 15, at least at least 17, at least 20, at least 22, at least 25, at least 30, at least 40, at least 50, at least 75, at least 100, at least 200, at least 300, at least 400, or at least 500 contiguous bases that are substantially the same as, or the complement of, any contiguous bases set forth in any of SEQ ID NOs:15, 17, 19, 21, 23, 25 or 27, or SEQ ID NOs:65, 67, 69, 71, 73, 75 or 83. Preferred regions from which to construct probes include 5' and/or 3' coding regions of SEQ ID NOs:15, 17, 19, 21, 23, 25 or 27. In addition, the entire cDNA encoding region of an invention PAAD domain-containing polypeptide, or an entire sequence substantially the same as SEQ ID NOs:15, 17, 19, 21, 23, 25 or 27, may be used as a probe, or SEQ ID NOs:65, 67, 69, 71, 73, 75 or 83. Probes can be labeled by methods well-known in the art, as described hereinafter, and used in various diagnostic kits.

The invention additionally provides an oligonucleotide comprising at least 15 contiguous nucleotides of SEQ ID NOs:15, 17, 19, 21, 23, 25 or 27, or SEQ ID NOs:69, 71, 73, 75, or the anti-sense strand thereof. As used herein, the term "oligonucleotide" refers to a nucleic acid molecule that includes at least 15 contiguous nucleotides from a reference nucleotide sequence, can include at least 16, 17, 18, 19, 20 21, 22, or at least 25 contiguous nucleotides, and often includes at least 30, 40, 50, 60, 70, 80, 90, 100, 125, 150, 175, 200, 225, 250, 275, 300, 325, 350, 400, 500, 600, 700 or more contiguous nucleotides from the reference nucleotide sequence. The reference nucleotide sequence can be the sense strand or the anti-sense strand.

In some embodiments, the oligonucleotides comprise, or consist of, sequences from those portions of SEQ ID NOs:65, 67, 69, 71, 73, 75 or 83 that are not also present in SEQ ID NOs:15, 17, 19, 21, 23, 25 or 27.

The oligonucleotides of the invention that contain at least 15 contiguous nucleotides of a reference PAAD domain encoding nucleotide sequence are able to hybridize to PAAD domain encoding nucleotide sequences under moderately stringent hybridization conditions and thus can be advantageously used, for example, as probes to detect PAAD domain encoding DNA or RNA in a sample, and to detect splice variants thereof; as sequencing or PCR primers; as antisense reagents to block transcription of PAAD domain encoding RNA in cells; or in other applications known to those skilled in the art in which hybridization to a PAAD domain encoding nucleic acid molecule is desirable.

In accordance with another embodiment of the invention, a method is provided for identifying nucleic acids encoding a PAAD-containing polypeptide, comprising, contacting a sample containing nucleic acids with an invention probe or an invention oligonucleotide, wherein said contacting is effected under high stringency hybridization conditions, and identifying nucleic acids which hybridize thereto. Methods for identification of nucleic acids encoding a PAAD domain-containing polypeptide are disclosed herein.

Also provided in accordance with present invention is a method for identifying a PAAD domain encoding nucleotide sequence comprising the steps of using a PAAD domain encoding nucleotide sequence selected from SEQ ID NOS: 15, 17, 19, 21, 23, 25 or 27, or SEQ ID NOs:65, 67, 69, 71, 73, 75 or 83, to identify a candidate PAAD domain encoding nucleotide sequence and verifying the candidate PAAD domain encoding nucleotide sequence by aligning the candidate sequence with known PAAD domain encoding nucleotide sequences, where a conserved PAAD domain sequence or a predicted three dimensional polypeptide structure similar to a known PAAD domain three dimensional structure confirms the candidate sequence as a PAAD domain encoding sequence. Methods for identifying PAAD-encoding sequences are provided herein (See Examples 1.0, 2.0, 3.0 and 4.0).

It is understood that a PAAD domain encoding nucleic acid molecule of the invention, as used herein, specifically excludes previously known nucleic acid molecules consisting of nucleotide sequences having exact sequence identity with the PAAD domain encoding nucleotide sequence, such as Expressed Sequence Tags (ESTs), Sequence Tagged Sites (STSs) and genomic fragments, deposited in public databases such as the nr, dbest, dbsts, gss and htgs databases, which are available for searching at ncbi.nlm.nih.gov/blast/.

In particular, invention PAAD domain encoding nucleic acid molecules, and PAAD domain-containing polypeptides, excludes the exact, specific and complete nucleic acid and/or amino acid sequences corresponding to any of the nucleotide and/or amino acid sequences having the Genbank (gb), NCBI, EMBL (emb) or DDBJ (dbj) accession numbers described below. Accession numbers specifically excluded include NCBI Accession Nos: GI 4557743, 5094556, 7019331, 7689912, 7020664, 7382417, 2335202, 7690109, 8099799, 8655944, 7662386, 5902751, 2833279, 6523868, 3483677, 10440263, 14731965, 2335202, 15488764, 202805, 9211204, 3483677, 15488878, 14779455, 14779445, 14488058, 11096298, 9802275, 9863861, 9863863, 10835255, 10801601, 7020146, 14779447, 13325315, 15215377, 11230601, 9937751, 14758026, 15193291, 13182796, 14731965, 14731967, 4757727, 3341995, 10440263, 14253110, 9153913, 1383656, 19387135, 15193292, 18448932, 17461450, 17483016, 17483018, 17483020, 17472936, 4081482, 17483013 and EST clones BE018433, AA421452 and AI204456.

Since one of skill in the art will realize that the above-recited excluded sequences may be revised at a later date, the skilled artisan will recognize that the above-recited sequences are excluded as they stand on the priority date of this application.

The isolated nucleic acid molecules of the invention can be used in a variety of diagnostic and therapeutic applications. For example, the isolated nucleic acid molecules of the invention can be used as probes, as described above; as templates for the recombinant expression of PAAD domain-containing polypeptides; or in screening assays such as two-hybrid assays to identify cellular molecules that bind PAAD domain-containing polypeptides.

Another useful method for producing a PAAD domain encoding nucleic acid molecule or fragment of the invention involves amplification of the nucleic acid molecule using PCR and invention oligonucleotides and, optionally, purification of the resulting product by gel electrophoresis. Either PCR or RT-PCR can be used to produce a nucleic acid molecule having any desired nucleotide boundaries. Desired modifications to the nucleic acid sequence can also be introduced by choosing an appropriate oligonucleotide primer with one or more additions, deletions or substitutions. Such nucleic acid molecules can be amplified exponentially starting from as little as a single gene or mRNA copy, from any cell, tissue or species of interest.

The invention thus provides methods for detecting a PAAD domain encoding nucleic acid or fragment in a sample. The methods of detecting a PAAD domain encoding nucleic acid in a sample can be either qualitative or quantitative, as desired. For example, the presence, abundance, integrity or structure of a PAAD domain encoding nucleic acid can be determined, as desired, depending on the assay format and the probe used for hybridization or primer pair chosen for application.

Useful assays for detecting a PAAD domain-containing nucleic acid based on specific hybridization with an isolated invention oligonucleotide are well known in the art and include, for example, in situ hybridization, which can be used to detect altered chromosomal location of the nucleic acid molecule, altered gene copy number, and RNA abundance, depending on the assay format used. Other hybridization assays include, for example, Northern blots and RNase protection assays, which can be used to determine the abundance and integrity of different RNA splice variants, and Southern blots, which can be used to determine the copy number and integrity of DNA. A hybridization probe can be labeled with any suitable detectable moiety, such as a radioisotope, fluorochrome, chemiluminescent marker, biotin, or other detectable moiety known in the art that is detectable by analytical methods.

Useful assays for detecting a PAAD domain encoding nucleic acid in a sample based on amplifying a PAAD domain encoding nucleic acid with two or more invention oligonucleotides are also well known in the art, and include, for example, qualitative or quantitative polymerase chain reaction (PCR); reverse-transcription PCR (RT-PCR); single strand conformational polymorphism (SSCP) analysis, which can readily identify a single point mutation in DNA based on differences in the secondary structure of single-strand DNA that produce an altered electrophoretic mobility upon non-denaturing gel electrophoresis; and coupled PCR, transcription and translation assays, such as a protein truncation test, in which a mutation in DNA is determined by an altered protein product on an electrophoresis gel. Additionally, the amplified PAAD domain encoding nucleic acid can be sequenced to detect mutations and mutational hot-spots, and specific assays for large-scale screening of samples to identify such mutations can be developed.

In a particular embodiment, a PAAD domain-containing polypeptide, or functional fragment thereof, can be administered to an individual so that the PAAD domain-containing polypeptide or functional fragment is targeted to a tumor to induce apoptosis, inhibit cell proliferation, or otherwise function as a tumor suppressor. One method of delivering a PAAD domain-containing polypeptide to an intracellular target is to fuse a PAAD domain-containing polypeptide or functional fragment to an intracellular-targeting peptide that can penetrate the cell membrane or otherwise deliver a polypeptide to the intracellular environment such as via internalization, thereby causing the fused PAAD domain-containing polypeptide to enter the cell. One example of such an intracellular-targeting peptides is a fusion to the transduction domain of HIV TAT, which allows transduction of up to 100% of cells (Schwarze et al., Science 285:1569-1572 (1999); Vocero-Akbani et al., Nature Med. 5:29-33 (1999)).

Another example of such an intracellular-targeting peptide is the Antennapeida homeoprotein internalization domain (Holinger et al., J. Biol. Chem. 274:13298-13304 (1999)). Still another intracellular-targeting peptide is a peptide that is specific for a cell surface receptor, which allows binding and internalization of a fusion polypeptide via receptor-mediated endocytosis (Ellerby et al., Nature Med. 5:1032-1038 (1999)). Such intracellular-targeting peptides that mediate specific receptor interactions can be advantageously used to target a tumor (see Ellerby et al., supra, 1999). Alternatively, a PAAD domain-containing polypeptide of the invention can be incorporated, if desired, into liposomes, microspheres or other polymer matrices (Gregoriadis, Liposome Technology, Vols. I to III, 2nd ed., CRC Press, Boca Raton Fla. (1993)).

Also provided are antisense-nucleic acids having a sequence capable of binding specifically with full-length or any portion of an mRNA that encodes PAAD domain-containing polypeptides so as to prevent translation of the mRNA. The antisense-nucleic acid can have a sequence capable of binding specifically with any portion of the sequence of the cDNA encoding PAAD domain-containing polypeptides. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense-nucleic acid is an antisense-nucleic acid comprising chemical analogs of nucleotides.

Also provided are double-stranded RNA molecules for use in RNA interference methods. RNA interference (RNAi) is a process of sequence-specific gene silencing by post-transcriptional RNA degradation, which is initiated by double-stranded RNA (dsRNA) homologous in sequence to the silenced gene. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end (Elbashir et al., Nature 411:494-498 (2001); Bass, Nature 411:428-429 (2001); Zamore, Nat. Struct. Biol. 8:746-750 (2001)). dsRNAs of about 25-30 nucleotides have also been used successfully for RNAi (Karabinos et al., Proc. Natl. Acad. Sci. 98:7863-7868 (2001). dsRNA can be synthesized in vitro and introduced into a cell by methods known in the art. By such methods, translation of the target polypeptide can be decreased.

The present invention provides a method of reducing levels of expression of PAAD domain-containing polypeptides by introducing into a cell anti-sense nucleic acids that inhibit translation or degrade mRNA encoding these polypeptides. Such nucleic acid molecules are designed to recognize and selectively bind to mRNA, such as to mRNA comprising SEQ ID NOs:15, 17, 19, 21, 23, 25 or 27, or SEQ ID NOs:65, 67, 69, 71, 73, 75 or 83, and are complementary to portions thereof.

The present invention also provides a method of reducing levels of expression of PAAD domain-containing polypeptides by introducing into a cell dsRNA that degrades mRNA encoding such polyepeptides. Such dsRNA contains short contiguous sequences of about 21-30 nucleotides of SEQ ID NOs:15, 17, 19, 21, 23, 25 or 27, or SEQ ID NOs:65, 67, 69, 71, 73, 75 or 83, and about 21-30 nucleotides complementary thereto, designed such that there is about a 2 base overhang at each 3' end of the double-stranded sequence.

Compositions comprising an amount of the antisense-nucleic acid or dsRNA effective to reduce expression of PAAD domain-containing polypeptides can further contain an acceptable hydrophobic carrier capable of passing through a cell membrane are also provided herein. Suitable hydrophobic carriers are described, for example, in U.S. Pat. Nos. 5,334,761; 4,889,953; 4,897,355, and the like. The acceptable hydrophobic carrier capable of passing through cell membranes may also comprise a structure which binds to a receptor specific for a selected cell type and is thereby taken up by cells of the selected cell type. For example, the structure can be part of a protein known to bind to a cell-type specific receptor.

The invention also provides a method for expression of a PAAD domain-containing polypeptide by culturing cells containing a PAAD domain encoding nucleic acid under conditions suitable for expression of a PAAD domain-containing polypeptide. Thus, there is provided a method for the recombinant production of a PAAD domain-containing polypeptide of the invention by expressing the PAAD domain encoding nucleic acid sequences in suitable host cells. Recombinant DNA expression systems that are suitable to produce a PAAD domain-containing polypeptide described herein are well-known in the art (see, for example, Ausubel et al., supra (2000)). For example, the above-described nucleotide sequences can be incorporated into vectors for further manipulation. As used herein, a vector refers to a recombinant DNA or RNA plasmid or virus containing discrete elements that are used to introduce heterologous DNA into cells for either expression or replication thereof.

The invention also provides vectors containing the PAAD domain encoding nucleic acids of the invention. Suitable expression vectors are well-known in the art and include vectors capable of expressing nucleic acid operatively linked to a regulatory sequence or element such as a promoter region or enhancer region that is capable of regulating expression of such nucleic acid. Appropriate expression vectors include those that are replicable in eukaryotic cells and/or prokaryotic cells and those that remain episomal or those which integrate into the host cell genome.

Promoters or enhancers, depending upon the nature of the regulation, can be constitutive or regulated. The regulatory sequences or regulatory elements are operatively linked to a nucleic acid of the invention such that the physical and functional relationship between the nucleic acid and the regulatory sequence allows transcription of the nucleic acid.

Suitable vectors for expression in prokaryotic or eukaryotic cells are well known to those skilled in the art (see, for example, Ausubel et al., supra (2000)). Vectors useful for expression in eukaryotic cells can include, for example, regulatory elements including the SV40 early promoter, the cytomegalovirus (CMV) promoter, the mouse mammary tumor virus (MMTV) steroid-inducible promoter, Moloney murine leukemia virus (MMLV) promoter, and the like. The vectors of the invention are useful for subcloning and amplifying a PAAD domain encoding nucleic acid molecule and for recombinantly expressing a PAAD domain-containing polypeptide. A vector of the invention can include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art. One skilled in the art will know or can readily determine an appropriate promoter for expression in a particular host cell.

The invention additionally provides recombinant cells containing PAAD domain encoding nucleic acids of the invention. The recombinant cells are generated by introducing into a host cell a vector containing a PAAD domain encoding nucleic acid molecule. The recombinant cells are transducted, transfected or otherwise genetically modified. Exemplary host cells that can be used to express recombinant PAAD molecules include mammalian primary cells; established mammalian cell lines, such as COS, CHO, HeLa, NIH3T3, HEK 293 and PC12 cells; amphibian cells, such as *Xenopus* embryos and oocytes and other vertebrate cells. Exemplary host cells also include insect cells such as *Drosophila,* yeast cells such as *Saccharomyces cerevisiae, Saccharomyces pombe,* or *Pichia pastoris,* and prokaryotic cells such as *Escherichia coli.* Additional host cells can be obtained, for example, from ATCC (Manassas, Va.)

In one embodiment, PAAD domain encoding nucleic acids can be delivered into mammalian cells, either in vivo or in vitro using suitable vectors well-known in the art. Suitable vectors for delivering a PAAD domain-containing polypeptide, or a functional fragment thereof to a mammalian cell, include viral vectors such as retroviral vectors, adenovirus, adeno-associated virus, lentivirus, herpesvirus, as well as non-viral vectors such as plasmid vectors. Such vectors are useful for providing therapeutic amounts of a PAAD domain-containing polypeptide (see, for example, U.S. Pat. No. 5,399,346, issued Mar. 21, 1995). Delivery of PAAD polypeptides or nucleic acids therapeutically can be particularly useful when targeted to a tumor cell, thereby inducing apoptosis in tumor cells. In addition, where it is desirable to limit or reduce the in vivo expression of a PAAD domain-containing polypeptide, the introduction of the antisense strand of the invention nucleic acid is contemplated.

The invention additionally provides an isolated anti-PAAD domain antibody (also referred to herein as an anti-PAAD antibody) having specific reactivity with a invention PAAD domain-containing polypeptide. The anti-PAAD antibody can be a monoclonal antibody or a polyclonal antibody. The invention further provides cell lines producing monoclonal antibodies having specific reactivity with an invention PAAD domain-containing protien.

The invention thus provides antibodies that specifically bind a PAAD domain-containing polypeptide. As used herein, the term "antibody" is used in its broadest sense to include polyclonal and monoclonal antibodies, as well as antigen binding fragments of such antibodies. With regard to an anti-PAAD antibody of the invention, the term "antigen" means a native or synthesized PAAD domain-containing polypeptide or fragment thereof. An anti-PAAD antibody, or antigen binding fragment of such an antibody, is characterized by having specific binding activity for a PAAD polypeptide or a peptide portion thereof of at least about $1 \times 10^5$ M$^{-1}$. Thus, Fab, F(ab')$_2$, Fd and Fv fragments of an anti-PAAD antibody, which retain specific binding activity for a PAAD domain-containing polypeptide, are included within the definition of an antibody. Specific binding activity of a PAAD domain-containing polypeptide can be readily determined by one skilled in the art, for example, by comparing the binding activity of an anti-PAAD antibody to a PAAD domain-containing polypeptide versus a reference polypeptide that is not a PAAD domain-containing polypeptide. Methods of preparing polyclonal or monoclonal antibodies are well known to those skilled in the art (see, for example, Harlow and Lane, *Antibodies: A Laboratory Manual,* Cold Spring Harbor Laboratory Press (1988)).

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275-1281 (1989)). These and other methods of making, for example, chimeric, humanized, CDR-grafted, single chain, and bifunctional antibodies are well known to those skilled in the art (Winter and Harris, *Immunol. Today* 14:243-246 (1993); Ward et al., *Nature* 341:544-546 (1989) ; Harlow and Lane, supra, 1988); Hilyard et al., *Protein Engineering: A practical approach* (IRL Press 1992); Borrabeck, *Antibody Engineering*, 2d ed. (Oxford University Press 1995)).

Anti-PAAD antibodies can be raised using a PAAD immunogen such as an isolated PAAD domain-containing functional fragment cromprising an amino acid consensus sequence selected from the group consisting of:

| | |
|---|---|
| -KFKX$_1$X$_2$L-; | (SEQ ID NO: 29) |
| -KLKX$_1$X$_2$L-; | (SEQ ID NO: 30) |
| -RFRX$_1$X$_2$L-; | (SEQ ID NO: 31) |
| -RFKX$_1$X$_2$L-; | (SEQ ID NO: 32) |
| -KFRX$_1$X$_2$L-; and | (SEQ ID NO: 33) |
| -KFKX$_1$X$_2$I-; | (SEQ ID NO: 34) | where $X_1$ and $X_2$ can be any amino acid; or PAAD domain-containing protein having substantially the same amino acid sequence as SEQ ID NOS:16, 18, 20, 22, 24, 26 or 28, or SEQ ID NOs: 66, 68, 70, 72, 74, 76 or 84, or a portion thereof, which can be prepared from natural sources or produced recombinantly. Such a portion of a PAAD domain-containing polypeptide is a functional antigenic portion if the antigenic peptides can be used to generate a PAAD domain-containing polypeptide-specific antibody.

Thus, the invention provides isolated peptides comprising at least 10 contiguous amino acids of any of SEQ ID NOS:70, 72, 74 or 76, which can be used, for example, as antigens to generate antibodies against the polypeptides of the invention. In some embodiments, the isolated peptides consist of or comprise contiguous sequences of any of SEQ ID NOS:66, 68, 70, 72, 74, 76 or 84 that are not also present in any of SEQ ID NOS:16, 18, 20, 22, 24, 26 or 28.

The invention further provides a method for detecting the presence of a human PAAD domain-containing polypeptide in a sample by contacting a sample with a PAAD domain specific antibody, and detecting the presence of specific binding of the antibody to the sample, thereby detecting the presence of a human PAAD domain-containing polypeptide in the sample. PAAD domain specific antibodies can be used in diagnostic methods and systems to detect the level of PAAD domain-containing polypeptide present in a sample. As used herein, the term "sample" is intended to mean any biological fluid, cell, tissue, organ or portion thereof, that includes or potentially includes PAAD domain encoding nucleic acids or PAAD domain-containing polypeptides. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid or polypeptide preparation.

PAAD domain specific antibodies can also be used for the immunoaffinity or affinity chromatography purification of an invention PAAD domain-containing polypeptide. In addition, methods are contemplated herein for detecting the presence of an invention PAAD domain-containing polypeptide in a cell, comprising contacting the cell with an antibody that specifically binds to PAAD domain-containing polypeptides under conditions permitting binding of the antibody to the PAAD domain-containing polypeptides, detecting the presence of the antibody bound to the PAAD domain-containing polypeptide, and thereby detecting the presence of invention polypeptides in a cell. With respect to the detection of such polypeptides, the antibodies can be used for in vitro diagnostic or in vivo imaging methods.

Immunological procedures useful for in vitro detection of target PAAD domain-containing polypeptides in a sample include immunoassays that employ a detectable antibody. Such immunoassays include, for example, immunohistochemistry, immunofluorescence, ELISA assays, radioimmunoassay, FACS analysis, immunoprecipitation, immunoblot analysis, Pandex microfluorimetric assay, agglutination assays, flow cytometry and serum diagnostic assays, which are well known in the art (Harlow and Lane, supra (1988); Harlow and Lane, *Using Antibodies: A Laboratory Manual*, Cold Spring Harbor Press (1999)).

An antibody can be made detectable by various means well known in the art. For example, a detectable marker can be directly attached to the antibody or indirectly attached using, for example, a secondary agent that recognizes the PAAD specific antibody. Useful markers include, for example, radionucleotides, enzymes, binding proteins such as biotin, fluorogens, chromogens, fluorescent labels and chemiluminescent labels. A description of immunofluorescent analytic techniques is found in DeLuca, "Immunofluorescence Analysis", in *Antibody As a Tool*, Marchalonis et al., eds., John Wiley & Sons, Ltd., pp. 189-231 (1982), which is incorporated herein by reference.

In addition to detecting the presence of a PAAD domain-containing polypeptide, invention anti-PAAD antibodies are contemplated for use herein to alter the activity of the PAAD domain-containing polypeptide in living animals, in humans, or in biological tissues or fluids isolated therefrom. The term "alter" refers to the ability of a compound such as a PAAD domain-containing polypeptide, a PAAD domain encoding nucleic acid, an agent or other compound to increase or decrease biological activity which is modulated by the compound, by functioning as an agonist or antagonist of the compound. Accordingly, compositions comprising a carrier and an amount of an antibody having specificity for PAAD domain-containing polypeptides effective to block naturally occurring ligands or other PAAD-associated polypeptides from binding to invention PAAD domain-containing polypeptides are contemplated herein. For example, a monoclonal antibody directed to an epitope of an invention PAAD domain-containing polypeptide, including an amino acid sequence substantially the same as SEQ ID NOS:16, 18, 20, 22, 24, 26 or 28, or SEQ ID NOs: 66, 68, 70, 72, 74, 76 or 84, can be useful for this purpose.

The present invention further provides transgenic non-human mammals that are capable of expressing exogenous nucleic acids encoding PAAD domain-containing polypeptides. As employed herein, the phrase "exogenous nucleic acid" refers to nucleic acid sequence which is not native to the host, or which is present in the host in other than its native environment, for example, as part of a genetically engineered DNA construct. In addition to naturally occurring PAAD domain-containing polypeptide levels, a PAAD domain-containing polypeptide of the invention can either be overexpressed or underexpressed in transgenic mammals, for example, underexpressed in a knock-out animal.

Animal model systems useful for elucidating the physiological and behavioral roles of PAAD domain-containing polypeptides are also provided, and are produced by creating transgenic animals in which the expression of the PAAD domain-containing polypeptide is altered using a variety of techniques. Examples of such techniques include the insertion of normal or mutant versions of nucleic acids encoding a PAAD domain-containing polypeptide by microinjection, retroviral infection or other means well known to those skilled in the art, into appropriate fertilized embryos to produce a transgenic animal, see, for example, Hogan et al., *Manipulating the Mouse Embryo: A Laboratory Manual* (Cold Spring Harbor Laboratory, (1986)). Transgenic animal model systems are useful for in vivo screening of compounds for identification of specific ligands, such as agonists or antagonists, which activate or inhibit a biological activity.

In accordance with another embodiment of the invention, a method is provided for identifying a PAAD-associated polypeptide (PAP). The method is carried out by contacting an invention PAAD domain-containing polypeptide with a candidate PAP and detecting association of the PAAD domain-containing polypeptide with the PAP.

As used herein, the term "PAAD-associated polypeptide" or "PAP" means a polypeptide that can specifically bind to the PAAD domain-containing polypeptides of the invention, or to any functional fragment of a PAAD domain-containing polypeptide of the invention. Because PAAD domain-containing polypeptides of the invention contain domains which can self-associate, PAAD domain-containing polypeptides are encompassed by the term PAP. An exemplary PAP is a protein or a polypeptide portion of a protein that can bind a PAAD, NACHT, LRR or ANGIO-R (ARED) domain of an invention PAAD domain-containing polypeptide. A PAP can be identified, for example, using in vitro or in vivo protein-interaction assays and methods known in the art, including yeast two-hybrid assays, co-immunoprecipitation, GST fusion co-purification, GST pull-down assays and the like (see, for example, Ausubel et al., supra (2000)). Additional methods include, for example, scintillation proximity assay (SPA) (Alouani, Methods Mol. Biol. 138:135-41 (2000)), UV or chemical cross-linking (Fancy, *Curr. Opin. Chem. Biol.* 4:28-33 (2000)), competition binding assays (Yamamura et al., *Methods in Neurotransmitter Receptor Analysis*, Raven Press, New York, 1990), biomolecular interaction analysis (BIA) such as surface plasmon resonance (SPR) (Weinberger et al., *Pharmacogenomics* 1:395-416 (2000)), mass spectrometry (MS) (McLafferty et al., *Science* 284:1289-1290 (1999) and Degterev, et al., *Nature Cell Biology* 3:173-182 (2001)), nuclear magnetic resonance (NMR) (Shuker etal., *Science* 274:1531-1534 (1996), Hajduk et al., *J. Med. Chem.* 42:2315-2317 (1999), and Chen and Shapiro, *Anal. Chem.* 71:669A-675A (1999)), and fluorescence polarization assays (FPA) (Degterev et al., supra, 2001).

Exemplary PAPs contemplated herein can include a protein involved in regulating apoptosis, caspase activation or NFκB induction, and other PAAD domain-containing polypeptides, selected from: Apaf-1, CED4, Nod1/CARD4, ASC-1, CARDX1, pro-Casp1, pro-Casp2, pro-Casp4, pro-Casp5, pro-Casp7, pro-Casp11, pro-Casp12, pro-Casp14, CED3, Dronc, Raidd/CRADD, Cardiak (RIP2, Rick), Bcl-1/CIPER, ARC, NOP30, cIAP-1, cIAP-2, Fadd/mort1, pro-Casp8, pro-Casp10, Dredd, c-Flip/flame, KSV/V-Flip, MCV, DEDD/DEFT, PEA-15, Flash, BAP31, BAR, RIP, IRAK-1, IRAK-2, IRAK-M, My D88, NMP-84, Ankyrin-1, Ankyrin-3, TNFR1, NGFR, Fas, DR3, DR4, DR5, DR6, Tradd, Fadd, Raidd2, DAP Kinase, NIK, IKKα, IKKβ, IκB, p65, p50, IKAP, pyrin, pyrin2, PAN1, PAN2, PAN3, PAN4, PANS, PAN6, PAN7, PAN8, PAN9, PAN10, FLJ20510_human, PANunk_mouse, NALP3/cryopyrin, NALP1/NAC, PAN5_mouse, PAN4_CT, PAN2_mouse, ASC, ASC2, NAC, AIM2, IFI16, MO13L, p52, p1000, p105, ParaCaspase (MALT1) and all members of the NFκB/IκB families. The naturally occurring sequences of these molecules from a variety of species, including human and rodent, are well known in the art. The skilled person can readily determine fragments and modifications of naturally occurring PAP sequences that retain their ability to associate with a PAAD domain-containing polypeptide, or domain therefrom, in the assays described herein.

As disclosed herein, exemplary PAPs that associate with ASC include ASC, ASC2, Caspase-1, Card10, Nod1, Cardiak, NIK and IKK-i. An exemplary PAP that associates with PAN2 is IκBα. An exemplary PAP that associates with PAN6 is IKAP.

The normal association between a PAAD domain-containing polypeptide and a PAP polypeptide in a cell can be altered due, for example, to the expression in the cell of a variant PAP or PAAD domain-containing polypeptide, respectively, either of which can compete with the normal binding function of a PAAD domain-containing polypeptide and, therefore, can decrease the association of PAP and PAAD domain-containing polypeptides in a cell. The term "variant" is used generally herein to mean a polypeptide that is different from the PAP or PAAD domain-containing polypeptide that normally is found in a particular cell type. Thus, a variant can include a mutated protein or a naturally occurring protein, such as an isoform, that is not normally found in a particular cell type.

PAAD domain-containing-polypeptides and PAAD-associated polypeptides of the invention can be characterized, for example, using in vitro binding assays or the yeast two hybrid system. An in vivo transcription activation assay such as the yeast two hybrid system is particularly useful for identifying and manipulating the association of proteins. In addition, the results observed in such an assay likely mirror the events that naturally occur in a cell. Thus, the results obtained in such an in vivo assay can be predictive of results that can occur in a cell in a subject such as a human subject.

A transcription activation assay such as the yeast two hybrid system is based on the modular nature of transcription factors, which consist of functionally separable DNA-binding and trans-activation domains. When expressed as separate proteins, these two domains fail to mediate gene transcription. However, transcription activation activity can be restored if the DNA-binding domain and the trans-activation domain are bridged together due, for example, to the association of two proteins. The DNA-binding domain and trans-activation domain can be bridged, for example, by expressing the DNA-binding domain and trans-activation domain as fusion proteins (hybrids), provided that the proteins that are fused to the domains can associate with each other. The non-covalent bridging of the two hybrids brings the DNA-binding and trans-activation domains together and creates a transcriptionally competent complex. The association of the proteins is determined by observing transcriptional activation of a reporter gene.

The yeast two hybrid systems exemplified herein use various strains of *S. cerevisiae* as host cells for vectors that express the hybrid proteins. A transcription activation assay also can be performed using, for example, mammalian cells. However, the yeast two hybrid system is particularly useful due to the ease of working with yeast and the speed with which the assay can be performed. For example, yeast host cells containing a lacZ reporter gene linked to a LexA operator sequence can be used to demonstrate that a PAAD domain of an invention PAAD domain-containing polypeptide can interact with itself or other PAAD domain-containing polypeptides. For example, the DNA-binding domain can consist of the LexA DNA-binding domain, which binds the LexA promoter, fused to the PAAD domain of a PAAD domain-containing polypeptide of the invention and the trans-activation domain can consist of the B42 acidic region separately fused to several cDNA sequences which encode known PAAD domain-containing polypeptides. When the LexA domain is non-covalently bridged to a trans-activation domain fused to a PAAD domain-containing polypeptide, the association can activate transcription of the reporter gene.

A PAP, for example, a PAAD domain-containing polypeptide, a CARD-containing polypeptide, an NACHT-containing polypeptide or a LRR-containing polypeptide, also can be identified using well known in vitro assays, for example, an assay utilizing a glutathione-S-transferase (GST) fusion protein. Such an in vitro assay provides a simple, rapid and inexpensive method for identifying and isolating a PAP. Such an in vitro assay is particularly useful in confirming results obtained in vivo and can be used to characterize specific binding domains of a PAP. For example, a GST can be fused to a PAAD domain-containing polypeptide of the invention, and expressed and purified by binding to an affinity matrix containing immobilized glutathione. If desired, a sample that can contains a PAP or active fragments of a PAP can be passed over an affinity column containing bound GST/PAAD and a PAP that binds to a PAAD domain-containing polypeptide can be obtained. In addition, GST/PAAD can be used to screen a cDNA expression library, wherein binding of the GST/PAAD fusion protein to a clone indicates that the clone contains a cDNA encoding a PAP.

Thus, one of skill in the art will recognize that using the PAAD domain-containing polypeptides described herein, a variety of methods, such as protein purification, protein interaction cloning, or protein mass-spectrometry, can be used to identify a PAP.

Although the term "PAP" is used generally, it should be recognized that a PAP that is identified using the novel polypeptides described herein can be a fragment of a protein. Thus, as used herein, a PAP also includes a polypeptide that specifically associates to a portion of an invention PAAD domain-containing polypeptide that does not include a PAAD domain. For example, a PAP can associate with the NACHT domain of an invention PAN. As used herein, a "candidate PAP" refers to a polypeptide containing a polypeptide sequence know or suspected of binding one or more PAAD domain-containing polypeptides of the invention. Thus, a PAP can represent a full-length protein or a PAAD-associating fragment thereof. Since a PAP polypeptide can be a full-length protein or a PAAD-associating fragment thereof, one of skill in the art will recognize that a PAP-encoding nucleic acid, such as the genomic sequence, an mRNA sequence or a cDNA sequence need not encode the full-length protein. Thus, a cDNA can encode a polypeptide that is a fragment of a full-length PAP which, nevertheless, binds one or more invention PAAD domain-containing polypeptides. It is also within the scope of the invention that a full-length PAP can assume a conformation that does not, absent some post-translational modification, bind a PAAD domain-containing polypeptide of the invention, due, for example, to steric blocking of the binding site. Thus, a PAP can be a protein or a polypeptide portion of a protein that can bind one of the PAAD domain-containing polypeptides of the invention.

Also, it should be recognized that a PAP can be identified by using a minimal polypeptide derived from the sequences of the PAAD domain-containing polypeptides of the invention, and does not necessarily require that the full-length molecules be employed for identifying such PAPs.

Since PAAD domain-containing polypeptides can be involved in apoptosis, the association of a PAP with a PAAD domain-containing polypeptide can affect the sensitivity or resistance of a cell to apoptosis or can induce or block apoptosis induced by external or internal stimuli. The identification of various PAPs by use of known methods can be used to determine the function of these PAPs in cell death or signal transduction pathways controlled by PAAD domain-containing polypeptides, allowing for the development of assays that are useful for identifying agents that effectively alter the association of a PAP with a PAAD domain-containing polypeptide. Such agents can be useful for providing effective therapy for conditions caused, at least in part, by insufficient apoptosis, such as cancer, autoimmune disease or certain viral infections. Such agents can also be useful for providing an effective therapy for diseases where excessive apoptosis is known to occur, such as stroke, heart failure, or AIDS; as well as inflammatory diseases, such as inflammatory bowel diseases (e.g. Crohn's disease and ulcerative colitus); rheumatoid arthritis, sepsis, trauma, allograft rejection and graft-versus-host disease.

Since PAAD domain-containing polypeptides are also involved in regulating NFκB activity, the association of a PAP with a PAAD domain-containing polypeptide can also affect responses of cells to stimuli that activate NFκB transcription, including TNFα and IL-1 and other proinflammatory cytokines, T- and B-cell mitogens, bacteria, bacterial lipopolysaccharide (LPS), viruses, viral proteins, double stranded RNA, and physical and chemical stresses. The identification of various PAPs as described herein and agents that effectively alter the association of a PAP with a PAAD domain-containing polypeptide can be used to provide effective therapy for conditions mediated, at least in part, by NFκB, including, for example, inflammatory conditions, infections, cancers, neurodegenerative disorders, arthritis and asthma.

Assays of the invention can be used for identification of agents that alter the self-association of the PAAD domain-containing polypeptides of the invention. Thus, the methods of the invention can be used to identify agents that alter the self-association of invention PAAD domains, such as SEQ ID NOS:1-14 and PAAD domain-containing proteins, such as SEQ ID NOs:16, 18, 20, 22, 24, 26 and 28, or SEQ ID NOs: 66, 68, 70, 72, 74, 76 or 84, via their PAAD domains, NB-ARC (NACHT) domains, LRR domains, ANGIO-R (ARED) domains or other domains within these polypeptides.

The ATP-binding and hydrolysis of the NACHT domains can be critical for function of a PAAD domain-containing polypeptide, for example, by altering the oligomerization of the PAAD domain-containing polypeptide. Thus, agents that interfere with or enhance ATP or nucleotide binding and/or hydrolysis by the NACHT domain of a PAAD domain-containing polypeptide of the invention, such as invention PAN proteins, can also be useful for altering the activity of these polypeptides in cells.

A further embodiment of the invention provides a method to identify agents that can effectively alter PAAD domain-containing polypeptide activity, for example the ability of PAAD domain-containing polypeptides to associate with one or more heterologous proteins. Thus, the present invention provides a screening assay useful for identifying an effective agent, which can alter the association of a PAAD domain-containing polypeptide, such as a PAN, with a PAAD-associated polypeptide (PAP), such as a heterologous PAAD domain-containing polypeptide.

Effective agents can be useful to alter a biochemical process modulated by a PAAD domain-containing polypeptide of the invention. Additional biochemical processes (also referred to herein as "cell activities") modulated by PAAD domain-containing polypeptide include, for example, apoptosis, regulation of NFκB induction, cytokine processing, cytokine receptor signaling, cJUN N-terminal kinase induction, caspase-mediated proteolytic activation/inhibition, transcription, inflammation and cell adhesion.

As used herein, the term "agent" means a chemical or biological molecule such as a simple or complex organic molecule, a peptide, a peptido-mimetic, a polypeptide, a protein or an oligonucleotide that has the potential for altering the association of a PAAD domain-containing polypeptide with a heterologous protein or altering the ability of a PAAD domain-containing polypeptide to self-associate or altering the ligand binding or biological activity of a PAAD domain-containing polypeptide. An exemplary ligand binding activity is nucleotide binding activity, such as ADP or ATP binding activity; and exemplary catalytic activities are nucleotide hydrolytic activity and proteolytic activity. In addition, the term "effective agent" is used herein to mean an agent that is confirmed as capable of altering the association of a PAAD domain-containing polypeptide with a heterologous protein or altering the ability of a PAAD domain-containing polypeptide to self-associate or altering the ligand binding or catalytic activity of a PAAD domain-containing polypeptide. For example, an effective agent may be an anti-PAAD antibody, a PAAD-associated polypeptide and the like.

As used herein, the term "alter the association" means that the association between two specifically interacting polypeptides either is increased or decreased due to the presence of an effective agent. As a result of an altered association of PAAD domain-containing polypeptide with another polypeptide in a cell, the activity of the PAAD domain-containing polypeptide or the PAP can be increased or decreased, thereby altering a biochemical process, for example, the level of apoptosis or NFκB transcriptional activity in the cell. As used herein, the term "alter the activity" means that the agent can increase or decrease the activity of a PAAD domain-containing polypeptide in a cell, thereby modulating a biochemical process in a cell, for example, the level of apoptosis or NFκB transcriptional activity in the cell. Similarly, the term "alter the level" of a biological process modulated by a PAAD domain-containing polypeptide refers to an increase or decrease a biochemical process which occurs upon altering the activity of a PAAD domain-containing polypeptide. For example, an effective agent can increase or decrease the PAAD:PAAD-associating activity of a PAAD domain-containing polypeptide, which can result in altered apoptosis or increased or decreased NFκB transcriptional activity. In another example, alteration of the ATP hydrolysis activity can modulate the ability of the NACHT domain of a PAAD domain-containing polypeptide to associate with other NACHT-containing polypeptides, such as Apaf-1, thereby altering any process effected by such association between a PAAD domain-containing polypeptide and a NACHT-containing polypeptide.

An effective agent can act by interfering with the ability of a PAAD domain-containing polypeptide to associate with another polypeptide, or can act by causing the dissociation of a PAAD domain-containing polypeptide from a complex with a PAAD-associated polypeptide, wherein the ratio of bound PAAD domain-containing polypeptide to free PAAD domain-containing polypeptide is related to the level of a biochemical process, such as apoptosis or NFκB transcriptional activity, in a cell. For example, binding of a ligand to a PAP can allow the PAP, in turn, to bind a specific PAAD domain-containing polypeptide such that all of the specific PAAD domain-containing polypeptide is bound to a PAP.

An effective agent can be useful, for example, to increase the level of apoptosis in a cell such as a cancer cell, which is characterized by having a decreased level of apoptosis as compared to its normal cell counterpart. An effective agent also can be useful, for example, to decrease the level of apoptosis in a cell such as a T lymphocyte in a subject having a viral disease such as acquired immunodeficiency syndrome, which is characterized by an increased level of apoptosis in an infected T cell as compared to a normal T cell. Thus, an effective agent can be useful as a medicament for altering the level of apoptosis in a subject having a pathology characterized by increased or decreased apoptosis. In addition, an effective agent can be used, for example, to decrease the level of apoptosis and, therefore, increase the survival time of a cell such as a hybridoma cell in culture. The use of an effective agent to prolong the survival of a cell in vitro can significantly improve bioproduction yields in industrial tissue culture applications.

An effective agent can also be useful to increase or decrease NFκB transcriptional activity, and thus can be used to provide effective therapy for conditions mediated, at least in part, by NFκB, including, for example, inflammatory conditions (e.g. inflammatory bowel diseases, such as Crohn's disease and ulcerative colitus), infections, cancers, neurodegenerative disorders, arthritis, asthma, stroke, heart failure, AIDS, sepsis, trauma, allograft rejection and graft-versus-host disease.

A PAAD domain-containing polypeptide that lacks the ability to bind the CARD domain, NACHT domain or LRR domain of another polypeptide but retains the ability to self-associate via its PAAD domain or to bind to other PAAD domain-containing polypeptides is an example of an effective agent, since the expression of a non-NACHT-associating or non-catalytically active PAAD domain-containing polypeptide in a cell can alter the association of a the endogenous PAAD-domain-containing polypeptide with itself or with PAPs.

Thus, it should be recognized that a mutation of a PAAD domain-containing polypeptide can be an effective agent, depending, for example, on the normal levels of PAAD domain-containing polypeptide and PAAD-associated polypeptide that occur in a particular cell type. In addition, an active fragment of a PAAD domain-containing polypeptide can be an effective agent, provided the active fragment can alter the association of a PAAD domain-containing polypeptide and another polypeptide in a cell. Such active fragments, which can be peptides as small as about five amino acids, can be identified, for example, by screening a peptide library (see, for example, Ladner et al., U.S. Pat. No: 5,223,409, which is incorporated herein by reference) to identify peptides that can bind a PAAD-associated polypeptide.

Similarly, a peptide or polypeptide portion of a PAAD-associated polypeptide also can be an effective agent. A peptide of PAAD-associated polypeptide can be useful, for example, for decreasing the association of a PAAD domain-containing polypeptide with a PAP in a cell by competing for binding to the PAAD domain-containing polypeptide. A non-naturally occurring peptido-mimetic also can be useful as an effective agent. Such a peptido-mimetic can include, for example, a peptoid, which is peptide-like sequence containing N-substituted glycines, or an oligocarbamate. A peptido-mimetic can be particularly useful as an effective agent due, for example, to having an increased stability to enzymatic degradation in vivo.

In accordance with another embodiment of the present invention, there is provided a method of identifying an effective agent that alters the association of an invention PAAD domain-containing polypeptide with a PAAD-associated polypeptide (PAP), by the steps of:

(a) contacting the PAAD domain-containing polypeptide and PAP polypeptides, under conditions that allow the PAAD domain-containing polypeptide and PAP polypeptides to associate, with an agent suspected of being able to alter the association of the PAAD domain-containing polypeptide and PAP polypeptides; and (b) detecting the altered association of the PAAD domain-containing polypeptide and PAP polypeptides, where the altered association identifies an effective agent.

Methods well-known in the art for detecting the altered association of the PAAD domain-containing polypeptide and PAP polypeptides, for example, measuring protein:protein binding, protein degradation or apoptotic activity can be employed in bioassays described herein to identify agents as agonists or antagonists of PAAD domain-containing polypeptides. As described herein, PAAD domain-containing polypeptides have the ability to self-associate. Thus, methods for identifying effective agents that alter the association of a PAAD domain-containing polypeptide with a PAP are useful for identifying effective agents that alter the ability of a PAAD domain-containing polypeptide to self-associate.

As used herein, "conditions that allow said PAAD domain-containing polypeptide and PAP polypeptides to associate" refers to environmental conditions in which a PAAD domain-containing polypeptide and PAP specifically associate. Such conditions will typically be aqueous conditions, with a pH between 3.0 and 11.0, and temperature below 100° C. Preferably, the conditions will be aqueous conditions with salt concentrations below the equivalent of 1 M NaCl, and pH between 5.0 and 9.0, and temperatures between 0° C. and 50° C. Most preferably, the conditions will range from physiological conditions of normal yeast or mammalian cells, or conditions favorable for carrying out in vitro assays such as immunoprecipitation and GST protein:protein association assays, and the like.

In another embodiment of the invention, a method is provided for identifying agents that modulate a biological activity of an invention PAAD domain-containing polypeptide, such as ligand interaction or catalytic activity. The method contains the steps of contacting an invention PAAD domain-containing polypeptide with an agent suspected of modulating a ligand binding or biological activity of the PAAD domain-containing polypeptide and measuring a biological activity of the PAAD domain-containing polypeptide, where modulated biological activity identifies the agent as an agent that alters the biological activity of a PAAD domain-containing polypeptide.

As used herein in regard to biological activity, "modulate" refers to an increase or decrease in the measured biological activity. Thus, modulation encompasses inhibition of biological activity as well as activation or enhancement of biological activity. Exemplary biological activities include nucleotide binding, nucleotide hydrolysis and modulation of NFκB activation.

Methods for measuring ligand binding and other biological activities are well known in the art, as disclosed herein. For example, an agent known or suspected of modulating a biological activity can be contacted with an invention PAAD domain-containing polypeptide in vivo or in vitro, and the activity can be measured using known methods. Exemplary agents that can modulate a biological activity include peptides, peptidomimetics and other peptide analogs, non-peptide organic molecules such as naturally occuring protease inhibitors and derviatives thereof, nucleotides and nucleotide analogs, and the like. Such inhibitors can be either reversible or irreversible, as is well known in the art.

Agents that modulate a biological activity of a PAAD domain-containing polypeptide identified using the invention methods can be used to modulate the activity of a PAAD domain-containing polypeptide. For example, an agent can modulate the nucleotide binding or nucleotide hydrolytic activity of an NACHT domain of a PAAD domain-containing polypeptide. In another example, an agent can modulate the NFκB regulatory activity of the PAAD domain. Methods of modulating a biological activity of invention PAAD domain-containing proteins can be used in methods of altering biochemical processes modulated by PAAD domain-containing proteins, such as the biochemical processes disclosed herein.

In yet another embodiment of the present invention, there are provided methods for altering a bioloigcal activity of a PAAD domain-containing polypeptide of the invention, the method comprising:

contacting an PAAD domain-containing polypeptide with an effective amount of an agent identified by the herein-described bioassays.

The present invention also provides in vitro screening assays. Such screening assays are particularly useful in that they can be automated, which allows for high through-put screening, for example, of randomly or rationally designed agents such as drugs, peptidomimetics or peptides in order to identify those agents that effectively alter the association of a PAAD domain-containing polypeptide and a PAP or the catalytic or ligand binding activity of a PAAD domain-containing polypeptide and, thereby, alter a biochemical process modulated by a PAAD domain-containing polypeptide such as apoptosis. An in vitro screening assay can utilize, for example, a PAAD domain-containing polypeptide including a PAAD domain-containing fusion protein such as a PAAD-glutathione-S-transferase fusion protein. For use in the in vitro screening assay, the PAAD domain-containing polypeptide should have an affinity for a solid substrate as well as the ability to associate with a PAAD-associated polypeptide. For example, when a PAAD domain-containing polypeptide is used in the assay, the solid substrate can contain a covalently attached anti-PAAD antibody. Alternatively, a GST/PAAD fusion protein can be used in the assay and the solid substrate can contain covalently attached glutathione, which is bound by the GST component of the GST/PAAD fusion protein. Similarly, a PAAD-associated polypeptide can be used in any of a variety of in vitro enzymatic or in vitro binding assays known in the art and described in texts such as Ausubel et al., supra, 2000.

An in vitro screening assay can be performed by allowing a PAAD domain-containing polypeptide or fragment thereof to bind to the solid support, then adding a PAAD-associated polypeptide and an agent to be tested. Reference reactions, which do not contain an agent, can be performed in parallel. Following incubation under suitable conditions, which include, for example, an appropriate buffer concentration and pH and time and temperature that permit binding of the particular PAAD domain-containing polypeptide and PAAD-associated polypeptide, the amount of protein that has associated in the absence of an agent and in the presence of an agent can be determined. The association of a PAAD-associated polypeptide with a PAAD domain-containing polypeptide can be detected, for example, by attaching a detectable moiety such as a radionuclide or a fluorescent label to a PAAD-associated polypeptide and measuring the amount of label that is associated with the solid support, wherein the amount of label detected indicates the amount of association of the PAAD-associated polypeptide with a PAAD domain-containing polypeptide. An effective agent is determined by comparing the amount of specific binding in the presence of an agent as compared to a reference level of binding, wherein an effective agent alters the association of PAAD domain-containing polypeptide with the PAAD-associated polypeptide. Such an assay is particularly useful for screening a panel of agents such as a peptide library in order to detect an effective agent.

Additionally, a PAAD domain-containing polypeptide or domain thereof, such as a PAAD domain or NACHT domain, can be contacted with a candidate agent and association between the polypeptide and the candidate agent determined. Agents that bind in such assays can further be tested for their ability to alter a biological activity of a PAAD domain-containing polypeptide or for their ability to alter associations between a PAAD domain-containing polypeptide and a PAP.

Various binding assays described above, such as the two hybrid assay, co-immunoprecipitation assay, co-localization assay, scintillation proximity assay (SPA), UV or chemical cross-linking, biomolecular interaction analysis (BIA), mass spectrometry (MS), nuclear magnetic resonance (NMR), and fluorescence polarization assays (FPA) can be used to identify an effective agent.

Another assay for screening of agents that alter the activity of a PAAD domain-containing polypeptide is based on altering the phenotype of yeast by expressing a PAAD domain-containing polypeptide. In one embodiment, expression of a PAAD domain-containing polypeptide can be inducible (Tao et al., *J. Biol. Chem.* 273:23704-23708 (1998), and the compounds can be screened when PAAD domain-containing polypeptide expression is induced. PAAD domain-containing polypeptides of the invention can also be co-expressed in yeast with PAP polypeptides used to screen for compounds that antagonize the activity of the PAAD domain-containing polypeptide.

A biological activity that can potentially be altered by an agent is PAAD domain-mediated modulation of NFκB activity. An agent that increases or decreases PAAD domain-mediated inhibition of NFκB activity with correspondingly decrease or increase NFκB activity. Such agents can be useful for treating conditions associated with decreased or increased NFκB activity as described herein, including, for example, inflammation, autoimmune diseases, neurodegenerative diseases, cancer and infectious disorders.

The invention thus provides methods of identifying agents that modulate PAAD domain-mediated inhibition or stimulation of NFκB activity. In one embodiment, a cell that recombinantly expresses a PAAD domain-containing polypeptide is contacted with a candidate agent and altered NFκB activity, such as increased or decreased activity, is detected in the cell. As NFκB activity in an unstimulated cell is normally low, such methods can be practiced by contacting the cell with an NFκB inducer, such as TNFα or IL1β, or recombinantly expressing within the cell an NFκB inducer, such as Bcl10, TRAF2, TRAF6, NIK, RIP2, p65, IRAK2, IRAK3, MyD88, RIP, IL-1R, Nod1, IKKα, IKKβ, TNFR1, and the like, such that the PAAD domain-containing polypeptide inhibits the induced level of NFκB activity.

The skilled person can employ appropriate controls to confirm that the effect of the candidate agent is specific for the PAAD domain-containing polypeptide. For example, the effect on NFκB activation of the candidate agent can be compared to the effect in a control cell that does not express nucleic acid molecule encoding a PAAD domain-containing polypeptide. Additionally, the effect of the candidate agent on NFκB activation can be compared with the effect of a vehicle control not containing the agent.

Various methods of determining the amount of NFκB activity in a cell are well known in the art. For example, binding assays have been developed that take advantage of the observation that active NFκB, but not inactive NFκB, binds to DNA. Therefore, the binding of a test cell extract to a labeled oligonucleotide containing an NFκB consensus binding site can be assayed. Active NFκB in the cell extract is evidenced by retardation of the mobility of the oligonucleotide band on a gel (Schreck et al., *Nucleic Acids Res.* 18:6497-6502 (1990); Rusher et al., *J. Biotech.* 78:163-170 (2000)). An alternative method is to attach an oligonucleotide containing an NFκB consensus binding site to a multiwell plate and detect bound, active NFκB in an ELISA-type assay using NFκB antibodies (Renard et al., *Nucleic Acids Res.* 29:E21 (2001)).

An alternative assay for determining the amount of NFκB activity in a cell monitors the cleavage of the NFκB precursors p100 or p105 to the active p50 or p55 subunits (see, for example, Lin et al., *Mol. Cell. Biol.* 16:2248-2254 (1996); Morgan et al., *Cancer Res.* 59:6205-6213 (1999); Uren et al., *Mol. Cell* 6:961-967 (2000)).

Activity assays can also be used to determine the amount of NFκB activity in a cell. For example, a reporter gene such as the luciferase, β-galactosidase or secretory alkaline phosphatase gene can be placed under the control of a promoter containing the NFκB consensus site. NFκB activity in cells transfected with the reporter construct is evidenced by expression of the product of the reporter gene (Moon et al., *Anal. Biochem.* 292:17-21 (2001); see Examples).

Additional methods of monitoring NFκB activation include, for example, monitoring cytoplasmic IκB degradation using antibodies directed against IκB (Sun et al., *Proc. Natl. Acad. Sci. USA* 91:1346-1350 (1994), and monitoring exposure of the nuclear localization signal (NLS) of active NFκB using NLS-specific antibodies (Zabel et al., *EMBO J.* 12:201-211 (1993)).

Also provided with the present invention are assays to identify agents that alter PAAD domain-containing polypeptide expression. Methods to determine PAAD domain-containing polypeptide expression can involve detecting a change in PAAD domain-containing polypeptide abundance in response to contacting the cell with an agent that modulates PAAD domain-containing polypeptide expression. Assays for detecting changes in polypeptide expression include, for example, immunoassays with PAAD domain specific antibodies, such as immunoblotting, immunofluorescence, immunohistochemistry and immunoprecipitation assays, as described herein.

As understood by those of skill in the art, assay methods for identifying agents that alter PAAD domain-containing polypeptide activity generally require comparison to a reference. One type of a "reference" is a cell or culture that is treated substantially the same as the test cell or test culture exposed to the agent, with the distinction that the "reference" cell or culture is not exposed to the agent. Another type of "reference" cell or culture can be a cell or culture that is identical to the test cells, with the exception that the "reference" cells or culture do not express a PAAD domain-containing polypeptide. Accordingly, the response of the transfected cell to an agent is compared to the response, or lack thereof, of the "reference" cell or culture to the same agent under the same reaction conditions.

Methods for producing pluralities of agents to use in screening for compounds that alter the activity of a PAAD domain-containing polypeptide, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422-428 (1998); Tietze et al., *Curr. Biol.,* 2:363-371 (1998); Sofia, *Mol. Divers.* 3:75-94 (1998); Eichler et al., *Med. Res. Rev.* 15:481-496 (1995); and the like. Libraries containing large numbers of natural and synthetic agents also can be obtained from commercial sources. Combinatorial libraries of molecules can be prepared using well known combinatorial chemistry methods (Gordon et al., *J. Med. Chem.* 37: 1233-1251 (1994); Gordon et al., *J. Med. Chem.* 37: 1385-1401 (1994); Gordon et al., *Acc. Chem. Res.* 2-9:144-154 (1996); Wilson and Czarnik, eds., *Combinatorial Chemistry: Synthesis and Application,* John Wiley & Sons, New York (1997)).

The invention further provides a method of diagnosing or predicting clinical prognosis of a pathology characterized by an increased or decreased level of a PAAD domain-containing polypeptide in a subject. The method includes the steps of (a) obtaining a test sample from the subject; (b) contacting the sample with an agent that can bind a PAAD domain-containing polypeptide of the invention under suitable conditions, wherein the conditions allow specific binding of the agent to the PAAD domain-containing polypeptide; and (c) comparing the amount of the specific binding in the test sample with the amount of specific binding in a reference sample, wherein an increased or decreased amount of the specific binding in the test sample as compared to the reference sample is diagnostic of, or predictive of the clinical prognosis of, a pathology. The agent can be, for example, an anti-PAAD antibody, a PAAD-associated-polypeptide (PAP), or a PAAD domain encoding nucleic acid.

Exemplary pathologies for diagnosis or the prediction of clinical prognosis include any of the pathologies described herein, such as neoplastic pathologies (e.g. cancer), autoimmune diseases, and other pathologies related to abnormal cell proliferation or abnormal cell death (e.g. apoptosis), as disclosed herein.

The invention also provides a method of diagnosing cancer or monitoring cancer therapy by contacting a test sample from a patient with a PAAD domain specific antibody. The invention additionally provides a method of assessing prognosis (e.g., predicting the clinical prognosis) of patients with cancer comprising contacting a test sample from a patient with a PAAD domain specific antibody.

The invention additionally provides a method of diagnosing cancer or monitoring cancer therapy by contacting a test sample from a patient with a oligonucleotide that selectively hybridizes to a PAAD domain encoding nucleic acid molecule. The invention further provides a method of assessing prognosis (e.g., predicting the clinical prognosis) of patients with cancer by contacting a test sample from a patient with a oligonucleotide that selectively hybridizes to a PAAD domain encoding nucleic acid molecule.

The methods of the invention for diagnosing cancer or monitoring cancer therapy using a PAAD domain specific antibody or oligonucleotide or nucleic acid that selectively hybridizes to a PAAD domain encoding nucleic acid molecule can be used, for example, to segregate patients into a high risk group or a low risk group for diagnosing cancer or predicting risk of metastasis or risk of failure to respond to therapy. Therefore, the methods of the invention can be advantageously used to determine, for example, the risk of metastasis in a cancer patient, or the risk of an autoimmune disease of a patient, or as a prognostic indicator of survival or disease progression in a cancer patient or patient with an autoimmune disease. One of ordinary skill in the art would appreciate that the prognostic indicators of survival for cancer patients suffering from stage I cancer can be different from those for cancer patients suffering from stage IV cancer. For example, prognosis for stage I cancer patients can be oriented toward the likelihood of continued growth and/or metastasis of the cancer, whereas prognosis for stage IV cancer patients can be oriented toward the likely effectiveness of therapeutic methods for treating the cancer. Accordingly, the methods of the invention directed to measuring the level of or determining the presence of a PAAD domain-containing polypeptide or PAAD domain encoding nucleic acid can be used advantageously as a prognostic indicator for the presence or progression of a cancer or response to therapy.

The invention further provides methods for introducing a PAAD domain encoding nucleic acid into a cell in a subject, for example, for gene therapy. Viruses are specialized infectious agents that can elude host defense mechanisms and can infect and propagate in specific cell types. Viral based systems provide the advantage of being able to introduce relatively high levels of the heterologous nucleic acid into a variety of cells. Suitable viral vectors for introducing an invention PAAD domain encoding nucleic acid into mammalian cells (e.g., vascular tissue segments) are well known in the art.

The present invention also provides therapeutic compositions useful for practicing the therapeutic methods described herein. Therapeutic compositions of the present invention, such as pharmaceutical compositions, contain a physiologically compatible carrier together with an invention PAAD domain-containing polypeptide (or functional fragment thereof), an invention PAAD domain encoding nucleic acid, an agent that alters PAAD activity or expression identified by the methods described herein, or an anti-PAAD antibody, as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically compatible" and grammatical variations thereof, as they refer to compositions, carriers, diluents and reagents, are used interchangeably and represent that the materials are capable of administration to a mammal without the production of undesirable physiological effects such as nausea, dizziness, gastric upset, and the like.

The preparation of a pharmacological composition that contains active ingredients dissolved or dispersed therein is well known in the art. Typically such compositions are prepared as injectables either as liquid solutions or suspensions; however, solid forms suitable for solution, or suspension, in liquid prior to use can also be prepared. The preparation can also be emulsified.

The active ingredient can be mixed with excipients which are pharmaceutically acceptable and compatible with the active ingredient in amounts suitable for use in the therapeutic methods described herein. Suitable excipients are, for example, water, saline, dextrose, glycerol, ethanol, or the like, as well as combinations of any two or more thereof. In addition, if desired, the composition can contain minor amounts of auxiliary substances such as wetting or emulsifying agents, pH buffering agents, and the like, which enhance the effectiveness of the active ingredient.

Physiologically tolerable carriers are well known in the art. Exemplary liquid carriers are sterile aqueous solutions that contain no materials in addition to the active ingredients and water; or contain a buffer such as sodium phosphate at physiological pH, physiological saline or both, such as phosphate-buffered saline. Still further, aqueous carriers can contain more than one buffer salt, as well as salts such as sodium and potassium chlorides, dextrose, polyethylene glycol and other solutes.

As described herein, an "effective amount" is a predetermined amount calculated to achieve the desired therapeutic effect, i.e., to alter the protein binding activity of a PAAD domain-containing polypeptide or the catalytic activity of a PAAD domain-containing polypeptide, resulting in altered biochemical process modulated by a PAAD domain-containing polypeptide. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such agents in depot or long-lasting form as discussed herein. A therapeutically effective amount is typically an amount of an agent identified herein that, when administered in a physiologically acceptable composition, is sufficient to achieve a plasma concentration of from about 0.1 µg/ml to about 100 µg/ml, preferably from about 1.0 µg/ml to about 50 µg/ml, more preferably at least about 2 µg/ml and usually 5 to 10 µg/ml. Therapeutic invention anti-PAAD antibodies can be administered in proportionately appropriate amounts in accordance with known practices in this art.

Also provided herein are methods of treating pathologies characterized by abnormal cell proliferation, abnormal cell death, or inflammation said method comprising administering an effective amount of an invention therapeutic composition. Such compositions are typically administered in a physiologically compatible composition.

Exemplary abnormal cell proliferation diseases associated with PAAD domain-containing polypeptides contemplated herein for treatment according to the present invention include cancer pathologies, keratinocyte hyperplasia, neoplasia, keloid, benign prostatic hypertrophy, inflammatory hyperplasia, fibrosis, smooth muscle cell proliferation in arteries following balloon angioplasty (restenosis), and the like. Exemplary cancer pathologies contemplated herein for treatment include, gliomas, carcinomas, adenocarcinomas, sarcomas, melanomas, hamartomas, leukemias, lymphomas, and the like. Further diseases associated with PAAD domain-containing polypeptides contemplated herein for treatment according to the present invention include inflammatory diseases and diseases of cell loss. Such diseases include allergies, inflammatory diseases including arthritis, lupus, Schrogen's syndrome, Crohn's disease, ulcerative colitis, as well as allograft rejection, such as graft-versus-host disease, and the like. PAAD domain-containing polypeptides can also be useful in design of strategies for preventing diseases related to abnormal cell death in conditions such as stroke, myopyrinial infarction, heart failure, neurodegenerative diseases such as Parkinson's and Alzheimer's diseases, and for immunodeficiency associated diseases such as HIV infection, HIV-related disease, and the like.

Methods of treating pathologies can include methods of modulating the activity of one or more oncogenic proteins, wherein the oncogenic proteins specifically interact with a PAAD domain-containing polypeptide of the invention. Methods of modulating the activity of such oncogenic proteins will include contacting the oncogenic protein with a substantially pure PAAD domain-containing polypeptide or an active fragment (i.e., oncogenic protein-binding fragment) thereof. This contacting will alter the activity of the oncogenic protein, thereby providing a method of treating a pathology caused by the oncogenic protein. Further methods of modulating the activity of oncogenic proteins will include contacting the oncogenic protein with an agent, wherein the agent alters interaction between a PAAD domain-containing polypeptide and an oncogenic protein.

Also contemplated herein, are therapeutic methods using invention pharmaceutical compositions for the treatment of pathological disorders in which there is too little cell division, such as, for example, bone marrow aplasias, immunodeficiencies due to a decreased number of lymphocytes, and the like. Methods of treating a variety of inflammatory diseases with invention therapeutic compositions are also contemplated herein, such as treatment of sepsis, fibrosis (e.g., scarring), arthritis, graft versus host disease, and the like.

The present invention also provides methods for diagnosing a pathology that is characterized by an increased or decreased level of a biochemical process to determine whether the increased or decreased level of the biochemical process is due, for example, to increased or decreased expression of a PAAD domain-containing polypeptide or to expression of a variant PAAD domain-containing polypeptide. As disclosed herein, such biochemical processes include apoptosis, NFκB induction, cytokine processing, caspase-mediated proteolysis, transcription, inflammation, cell adhesion, and the like. The identification of such a pathology, which can be due to altered association of a PAAD domain-containing polypeptide with a PAAD-associated polypeptide in a cell, or altered ligand binding or catalytic activity of a PAAD domain-containing polypeptide, can allow for intervention therapy using an effective agent or a nucleic acid molecule or an antisense or dsRNA nucleotide sequence as described herein. In general, a test sample can be obtained from a subject having a pathology characterized by having or suspected of having increased or decreased apoptosis and can be compared to a reference sample from a normal subject to determine whether a cell in the test sample has, for example, increased or decreased expression of a PAAD domain encoding gene. The level of a PAAD domain-containing polypeptide in a cell can be determined by contacting a sample with a reagent such as an anti-PAAD antibody or a PAAD-associated polypeptide, either of which can specifically bind a PAAD domain-containing polypeptide. For example, the level of a PAAD domain-containing polypeptide in a cell can determined by well known immunoassay or immunohistochemical methods using an anti-PAAD antibody (see, for example, Reed and Godzik et al., *Anal. Biochem.* 205:70-76 (1992); see, HCXalso, Harlow and Lane, supra, (1988)). As used herein, the term "reagent" means a chemical or biological molecule that can specifically bind to a PAAD domain-containing polypeptide or to a bound PAAD/PAAD-associated polypeptide complex. For example, either an anti-PAAD antibody or a PAAD-associated polypeptide can be a reagent for a PAAD domain-containing polypeptide, whereas either an anti-PAAD antibody or an anti-PAAD-associated polypeptide antibody can be a reagent for a PAAD:PAAD-associated polypeptide complex.

As used herein, the term "test sample" means a cell or tissue specimen that is obtained from a subject and is to be examined for expression of a PAAD domain-encoding gene in a cell in the sample. A test sample can be obtained, for example, during surgery or by needle biopsy and can be examined using the methods described herein to diagnose a pathology characterized by increased or decreased apoptosis.

Increased or decreased expression of a PAAD domain encoding gene in a cell in a test sample can be determined, for example, by comparison to an expected normal level of PAAD domain-containing polypeptide or PAAD domain encoding mRNA in a particular cell type. A normal range of PAAD domain-containing polypeptide or PAAD domain encoding mRNA levels in various cell types can be determined by sampling a statistically significant number of normal subjects. In addition, a reference sample can be evaluated in parallel with a test sample in order to determine whether a pathology characterized by increased or decreased apoptosis is due to increased or decreased expression of a PAAD domain encoding gene. The test sample can be examined using, for example, immunohistochemical methods as described above or the sample can be further processed and examined. For example, an extract of a test sample can be prepared and examined to determine whether a PAAD domain-containing polypeptide in the sample can associate with a PAAD-associated polypeptide in the same manner as a PAAD domaincontaining polypeptide from a reference cell or whether, instead, a variant PAAD domain-containing polypeptide is expressed in the cell.

In accordance with another embodiment of the present invention, there are provided diagnostic systems, preferably in kit form, comprising at least one invention PAAD domain encoding nucleic acid, PAAD domain-containing polypeptide, and/or anti-PAAD antibody described herein, in a suitable packaging material. In one embodiment, for example, the diagnostic nucleic acids are derived from any of SEQ ID NOs:15, 17, 19, 21, 23, 25 or 27, or SEQ ID NOs:65, 67, 69, 71, 73, 75 or 83, or their complements. Invention diagnostic systems are useful for assaying for the presence or absence of PAAD domain encoding nucleic acid in either genomic DNA or in transcribed PAAD domain encoding nucleic acid, such as mRNA or cDNA.

A suitable diagnostic system includes at least one invention PAAD domain encoding nucleic acid, PAAD domain-containing polypeptide, and/or anti-PAAD antibody, preferably two or more invention nucleic acids, proteins and/or antibodies, as a separately packaged chemical reagent(s) in an amount sufficient for at least one assay. Instructions for use of the packaged reagent are also typically included. Those of skill in the art can readily incorporate invention nucleic acid probes and/or primers into kit form in combination with appropriate buffers and solutions for the practice of the invention methods as described herein.

As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment. The packaging material has a label which indicates that the invention nucleic acids can be used for detecting a particular PAAD domain encoding sequence including the nucleotide sequences set forth in SEQ ID NOs:15, 17, 19, 21, 23, 25 or 27, or in SEQ ID NOs:65, 67, 69, 71, 73, 75 or 83, or the complement thereof, or mutations or deletions therein, thereby diagnosing the presence of, or a predisposition for a pathology such as cancer or an autoimmune disease. In addition, the packaging material contains instructions indicating how the materials within the kit are employed both to detect a particular sequence and diagnose the presence of, or a predisposition for a pathology such as cancer or an autoimmune disease.

The packaging materials employed herein in relation to diagnostic systems are those customarily utilized in nucleic acid-based diagnostic systems. As used herein, the term "package" refers to a solid matrix or material such as glass, plastic, paper, foil, and the like, capable of holding within fixed limits an isolated nucleic acid, oligonucleotide, or primer of the present invention. Thus, for example, a package can be a glass vial used to contain milligram quantities of a contemplated nucleic acid, oligonucleotide or primer, or it can be a microtiter plate well to which microgram quantities of a contemplated nucleic acid probe have been operatively affixed. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

A diagnostic assay should include a simple method for detecting the amount of a PAAD domain-containing polypeptide or PAAD domain encoding nucleic acid in a sample that is bound to the reagent. Detection can be performed by labeling the reagent and detecting the presence of the label using well known methods (see, for example, Harlow and Lane, supra, 1988; chap. 9, for labeling an antibody). A reagent can be labeled with various detectable moieties including a radiolabel, an enzyme, biotin or a fluorochrome. Materials for labeling the reagent can be included in the diagnostic kit or can be purchased separately from a commercial source. Following contact of a labeled reagent with a test sample and, if desired, a control sample, specifically bound reagent can be identified by detecting the particular moiety.

A labeled antibody that can specifically bind the reagent also can be used to identify specific binding of an unlabeled reagent. For example, if the reagent is an anti-PAAD antibody, a second antibody can be used to detect(specific binding of the anti-PAAD antibody. A second antibody generally will be specific for the particular class of the first antibody. For example, if an anti-PAAD antibody is of the IgG class, a second antibody will be an anti-IgG antibody. Such second antibodies are readily available from commercial sources. The second antibody can be labeled using a detectable moiety as described above. When a sample is labeled using a second antibody, the sample is first contacted with a first antibody, then the sample is contacted with the labeled second antibody, which specifically binds to the first antibody and results in a labeled sample.

All patents, publications and database sequences mentioned herein are incorporated in; their entirety by reference thereto. The invention will now be described in greater detail by reference to the following non-limiting examples.

EXAMPLES 1.0 Identification of PAAD domain-containing polypeptides.

Figure 2:
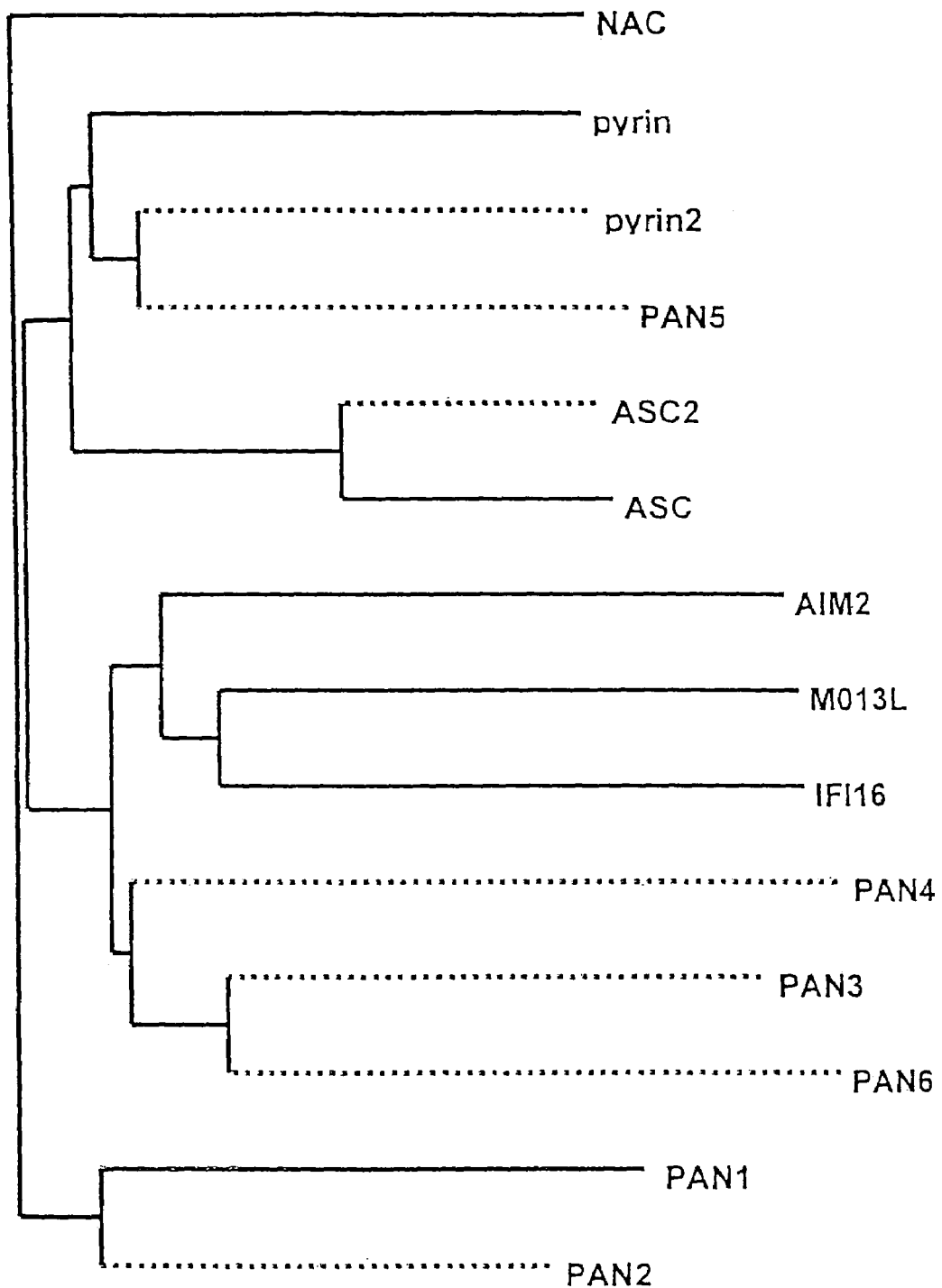
FIG. 2 shows the evolutionary tree showing the relationship between selected members of the PAAD family of proteins from humans and viruses. The tree was built using the CLUSTALW program. Proteins containing NB-ARC (NACHT) NTP-ase domains as well as PAAD domains (NAC and PAN1-6) are shown in grey.

The sequence of the N-terminal 100 amino acid fragment of the pyrin protein (Genbank Accession # NP00234; Pras, 1998, *Scand. J. Rheumatol.*, 27:92-97) was used to perform a cascade of PSI-BLAST searches until no new hits were found. Lower significance hits from this procedure (called Saturated BLAST) were confirmed using the profile-to-profile alignment algorithm FFAS (Rychlewski et al., 2000, *Protein Science* 9:232-241) against a library of apoptosis-related domains. Proteins suspected of having a PAAD domain were added to the Saturated BLAST and FFAS databases and the FFAS similarity score was used to accept or reject the putative PAAD domains. Most of the proteins identified in FIGS. 1 and 2 could be connected with each other with PSI-BLAST significance better than 0.001 and/or the FFAS Z-score better than 10. The weakest link in the chain is the connection between the AIM2/IFI16 branch and the rest of the family (pyrin/ASC/caspase/NAC), with 0.05 PSI-BLAST E-value and FFAS Z-score of 8. The latter value was independently verified on a protein structure benchmark to give a correct match in more than 99% of cases (Rychlewski et al. supra). The same link was also confirmed by independent application of the Gibbs sampling algorithm (Lawrence, C. et al. (1993) *Science* 262:208-14), where sequence patterns identified in the pyrin/ASC/caspase branch of the family could be consistently used to find the AIM2/IFI16 group, albeit with low significance. In accordance with the present invention, this Saturated BLAST procedure resulted in the identification of several putative PAAD homologues in the unfinished nucleotide databases.

The process of gene identification and assembling include the following steps:

A) Identification of new candidate PAAD containing polypeptides. A iterative database search was performed using the TBLASTN program with the PAAD domain of pyrin and all other identified PAAD domains as the query in the following NCBI databases: high throughput genome sequence (HTGS), genomic survey sequence (GSS) and expressed sequence tag (EST) databases.

B) Verification that the new candidate PAAD domain-containing polypeptide is novel. Using PSI-BLAST, each new candidate PAAD domain gene was queried in the annotated non-redundant (NR) database at NCBI. When the new candidate gene showed significant but not identical homology with other known PAAD domain-containing polypeptides during this search, the PAAD domain-containing polypeptide candidate was kept for further analysis.

C) 3-D-Model Building of new candidate PAAD domain polypeptide: When the sequence homology was low (<25% identity), three-dimensional criteria was added to characterization of new PAAD domain-containing polypeptides. The candidate PAAD domain fragment was analyzed by a profile-profile sequence comparison method which aligns the candidate PAAD domain with a database of sequences of known three-dimensional structure. From this analysis, a sequence alignment was produced and a model three-dimensional structure was built using DD, DED and CARD domains as templates. In most cases, the best score was produced using PAAD domain sequences having known three-dimensional structures. The quality of the three-dimensional model obtained from the alignments confirmed that novel PAAD domain-containing polypeptides had been identified.

D) Identification of additional domains in the full length protein. Full length protein sequences were obtained using the new PAAD domain identified in step B as query. TBLASTN searches of the sequences containing the newly identified PAAD domains were performed. Longer aligned fragments or multiple aligned fragments in the accession number corresponding to the newly identified PAAD domain-containing polypeptides indicated a longer PAAD domain-containing protein.

E) These additional domains were assembled using the following gene building procedure:

Genomic DNA fragments identified by T-BLAST-N analysis were extended and identified using intron/exon prediction programs, such as Genescan, GRAIL, ORF-find, and the like; searching in both directions until start and stop codons were identified.

2.0 Identification of PAAD domain-containing polypeptides PAN2-6, Pyrin2 and ASC2.

Nucleic acids encoding PAAD domain-containing proteins corresponding to PAN2, PAN3, PAN4, PAN5, PAN6, Pyrin2, ASC2, PAN7, PAN8, PAN9 and PAN10 were identified from different. PAAD domain queries using tblastn and systematically scanning gss, htgs, and all EST databases at NCBI. Further analysis using translated genomic fragments containing PAAD domains, which fragments were larger than the PAAD domain itself as query, were performed to identify additional domains. Genomic DNA were translated in all reading frames and examined for additional domains using psi-blast and nr database. Using this strategy, additional domains of PAAD domain-containing polypeptides, including a NB-ARC (NACHT) domain, LRR repeat and ANGIO-R (ARED) domain, were identified.

3.0 Cloning and sequencing of large cDNA.

For cDNA larger than 1500 bp, cloning is accomplished by amplification of multiple fragments of the cDNA. Jurkat total RNA is reverse-transcribed to complementary DNAs using MMLV reverse transcriptase (Stratagene) and random hexanucleotide primers. Overlapping cDNA fragments of a PAAD domain-containing polypeptide are amplified from the Jurkat complementary DNAs with Turbo Pfu DNA polymerase (Stratagene) using an oligonucleotide primer set for every 1500 bp of cDNA, where the amplified cDNA fragment contains a unique restriction site near the end that is to be ligated with an adjacent amplified cDNA fragment.

The resultant cDNA fragments are ligated into mammalian expression vector pcDNA-myc (Invitrogen, modified as described in Roy et al., *EMBO J.* 16:6914-6925 (1997)) and assembled to full-length cDNA by consecutively ligating adjacent fragments at the unique endonuclease sites form the full-length cDNA. Sequencing analysis of the assembled full-length cDNA is carried out, and splice isoforms of PAAD domain-containing polypeptides can be identified.

4.0 Plasmid Constructions.

Complementary DNA encoding a PAAD domain-containing polypeptide, or a functional fragment thereof is amplified from Jurkat cDNAs with Turbo Pfu DNA polymerase (Stratagene) and desired primers, such as those described above. The resultant PCR fragments are digested with restriction enzymes such as EcoRI and Xho I and ligated into pGEX-4T1 (Pharmacia) and pcDNA-myc vectors.

5.0 In vitro Protein Binding Assays.

PAAD domain-containing or fragments thereof encoded in pGEX-4T1 are expressed in XL-1 blue *E. coli* cells (Stratagene), and affinity-purified using glutathione (GSH)-sepharose according to known methods, such as those in *Current Protocols in Molecular Biology,* Ausubel et al. eds., John Wiley and Sons (1999). For GST pull-down assays, purified PAAD domain GST fusion proteins and GST alone (0.1-0.5 µg immobilized on 10-15 µl GSH-sepharose beads) are incubated with 1 mg/ml of BSA in 100 µl Co-IP buffer [142.4 mM KCl, 5 mM $M_gCl_2$, 10 mM HEPES (pH 7.4), 0.5 mM EGTA, 0.2% NP-40, 1 mM DTT, and 1 mM PMSF] for 30 min. at room temperature. The beads are then incubated with 1 µl of rat reticulocyte lysates (TnT-lysate; Promega, Inc.) containing $^{35}$S-labeled, in vitro translated PAAD domain-containing or control protein Skp-1 in 100 µl Co-IP buffer supplemented with 0.5 mg/ml BSA for overnight at 4° C. The beads are washed four times in 500 µl Co-IP buffer, followed by boiling in 20 µl Laemmli-SDS sample buffer. The eluted proteins are analyzed by SDS-PAGE. The bands of SDS-PAGE gels are detected by fluorography.

The resultant oligomerization pattern will reveal that PAAD:PAAD and other protein:protein interactions occur with invention PAAD domain-containing polypeptides (e.g., PAN2 through PAN6, PAN7, PAN8, PAN9 and PAN10 and the like) or fragments thereof.

In vitro translated candidate PAAD-associated polypeptides, along with a control, are subjected to GST pull-down assay using GSH-sepharose beads conjugated with GST and GST-PAAD domain-containing polypeptides as described above. Lanes containing GST-PAAD domain yield positive binding signals when incubated with a PAAD-associated polypeptide selected from Apaf-1, CED4, Nod1/CARD4, ASC-1, CARDX1, pro-Casp1, pro-Casp2, pro-Casp4, pro-Casp5, pro-Casp7, pro-Casp11, pro-Casp12, pro-Casp14, CED3, Dronc, Raidd/CRADD, Cardiak (RIP2, Rick), Bcl-1/CIPER, ARC, NOP30, cIAP-1, cIAP-2, Fadd/mort1, pro-Casp8, pro-Casp10, Dredd, c-Flip/flame, KSV/V-Flip, MCV, DEDD/DEFT, PEA-15, Flash, BAP31, BAR, RIP, IRAK-1, IRAK-2, IRAK-M, My D88, NMP-84, Ankyrin-1, Ankyrin-3, TNFR1, NGFR, Fas, DR3, DR4, DR5, DR6, Tradd, Fadd, Raidd2, DAP Kinase, NIK, IKKα, IKKβ, IκB, p65, p50, IKAP, pyrin, pyrin2, PAN1, PAN2, PAN3, PAN4, PAN5, PAN6, PAN7, PAN8, PAN9, PAN10, FLJ20510_human, PANunk_mouse, NALP3/cryopyrin, NALP1/NAC, PAN5_mouse, PAN4_CT, PAN2_mouse, ASC, ASC2, NAC, AIM2, IFI16, MO13L, p52, p100, p105, ParaCaspase (MALT1), and all members of the NFκB/IκB families, whereas, the controls GST alone and Skp-1 yield negligible signals.

6.0 Self-Association of NB-ARC (NACHT) domain of PAAD domain-containing polypeptides.

In vitro translated, $^{35}$S-labeled rabbit reticulocyte lysates (1 μl) containing an NB-ARC (NACHT) domain of an invention PAN protein or a control protein, such as SKP-1, are incubated with GSH-sepharose beads conjugated with purified GST-NB-ARC or GST alone for GST pull-down assay, resolved on SDS-PAGE and visualized by fluorography as described above. One tenth of input is loaded for NB-ARC (NACHT) or Skp-1 as controls. The results indicate that the NB-ARC (NACHT) domains of invention proteins can self-associate by binding through the NB-ARC (NACHT) domains.

7.0 Protein-Protein Interactions of PAAD domain-containing polypeptides.

Transient transfections of 293T, a human embryonic kidney fibroblast cell line, are conducted using SuperFect reagents (Qiagen) according to manufacturer's instructions. 293T cells are transiently transfected with an expression plasmid (2 μg) encoding HA-tagged Apaf-1, CED4, Nod1/CARD4, ASC-1, CARDX1, pro-Casp1, pro-Casp2, pro-Casp4, pro-Casp5, pro-Casp7, pro-Casp11, pro-Casp12, pro-Casp14, CED3, Dronc, Raidd/CRADD, Cardiak (RIP2, Rick), Bcl-1/CIPER, ARC, NOP30, cIAP-1, cIAP-2, Fadd/mort1, pro-Casp8, pro-Casp10, Dredd, c-Flip/flame, KSV/V-Flip, MCV, DEDD/DEFT, PEA-15, Flash, BAP31, BAR, RIP, IRAK-1, IRAK-2, IRAK-M, My D88, NMP-84, Ankyrin-1, Ankyrin-3, TNFR1, NGFR, Fas, DR3, DR4, DR5, DR6, Tradd, Fadd, Raidd2, DAP Kinase, NIK, IKKα, IKKβ, IκB, p65, p50, IKAP, pyrin, pyrin2, PAN1, PAN2, PAN3, PAN4, PAN5, PAN6, PAN7, PAN8, PAN9, PAN10, FLJ20510_human, PANunk_mouse, NALP3/cryopyrin, NALP1/NAC, PAN5_mouse, PAN4_CT, PAN2_mouse, ASC, ASC2, NAC, AIM2, IFI16, MO13L, p52, p100, p105, ParaCaspase (MALT1), and all members of the NFκB/IκB families, or the like, in the presence or absence of a plasmid (2 μg) encoding a myc-tagged PAAD domain-containing polypeptide. After 24 hr growth in culture, transfected cells are collected and lysed in Co-IP buffer [142.4 mM KCl, 5 mM $MgCl_2$, 10 mM HEPES (pH 7.4), 0.5 mM EGTA, 0.1% NP-40, and 1 mM DTT] supplemented with 12.5 mM β-glycerolphosphate, 2 mM NaF, 1 mM $Na_3VO_4$, 1 mM PMSF, and 1× protenase inhibitor mix (Boehringer Mannheim). Cell lysates are clarified by microcentrifugation and subjected to immunoprecipitation using either a mouse monoclonal antibody to myc (Santa Cruz Biotechnologies, Inc) or a control mouse IgG. Proteins from the immune complexes are resolved by SDS-PAGE, transferred to nitrocellulose membranes, and subjected to immunoblot analysis using anti-HA antibodies followed by anti-myc antibodies using a standard Western blotting procedure and ECL reagents from Amersham-Pharmacia Biotechnologies, Inc. (Krajewski et al., *Proc. Natl. Acad. Sci. USA* 96:5752-5757 (1999)).

The results indicate that invention PAAD domain-containing polypeptides can bind to themselves (e.g., homodimers, and the like) and to one or more polypeptides selected from Apaf-1, CED4, Nod1/CARD4, ASC-1, CARDX1, pro-Casp1, pro-Casp2, pro-Casp4, pro-Casp5, pro-Casp7, pro-Casp11, pro-Casp12, pro-Casp14, CED3, Dronc, Raidd/CRADD, Cardiak (RIP2, Rick), Bcl-1/CIPER, ARC, NOP30, cIAP-1, cIAP-2, Fadd/mort1, pro-Casp8, pro-Casp10, Dredd, c-Flip/flame, KSV/V-Flip, MCV, DEDD/DEFT, PEA-15, Flash, BAP31, BAR, RIP, IRAK-1, IRAK-2, IRAK-M, My D88, NMP-84, Ankyrin-1, Ankyrin-3, TNFR1, NGFR, Fas, DR3, DR4, DR5, DR6, Tradd, Fadd, Raidd2, DAP Kinase, NIK, IKKα, IKKβ, IκB, p65, p50, IKAP, pyrin, pyrin2, PAN1, PAN2, PAN3, PAN4, PAN5, PAN6, PAN7, PAN8, PAN9, PAN10, FLJ20510_human, PANunk_mouse, NALP3/cryopyrin, NALP1/NAC, PAN5_mouse, PAN4_CT, PAN2_mouse, ASC, ASC2, NAC, AIM2, IFI16, MO13L, p52, p100, p105, ParaCaspase (MALT1), and all members of the NFκB/IκB families.

8.0 Cloning and Characterization of PAN2

As a first step in cloning PAN2 cDNA, RT-PCR was performed on total RNA from HeLa cells using oligo dT to prime the first-strand synthesis and then 2 PAN2-specific primers designated Pan2/5': 5'-CCGGAATTCACCATGGCAGC-CTCTTTCTTCTCTGATTTT-3' (SEQ ID NO:35) and Pan2/3': 5'-CCGCTCGAGTCACGTAGAGCTGTGT-TCATCCTCTTTCTTAA-3' (SEQ ID NO:36). These primers were designed based on the predicted PAN2 open reading frame identified in the genomic sequence AC022066 on chromosome 19, as described in Example 2.0. The ATG of PAN2 and an artificial stop codon inserted after amino acid 620 are underlined in SEQ ID NOS:35 and 36, respectively. EcoRI and XhoI restriction sites are shown in italics in SEQ ID NOS:35 and 36, respectively. The resulting PCR product was cloned into a pcDNA3Myc expression-vector at the EcoRI (5') and XhoI(3'), and sequenced.

A BLAST search of the human EST database was then performed using the partial PAN2 sequence. Several EST clones were identified, and several corresponding I.M.A.G.E. Consortium cDNA clones (Lennon et al., *Genomics* 33;151-152 (1996)) were obtained. I.M.A.G.E. Consortium CloneID 3139498, corresponding to EST GenBank Accession Number BE278926, was sequenced and determined to contain full-length PAN2 cDNA, including the stop codon, the 3' UTR of the gene and the poly-A tail.

The complete coding sequence of PAN2 was cloned by PCR from I.M.A.G.E. Consortium CloneID 3139498 by PCR, using as the 5' primer SEQ ID NO:35 and as the 3' primer Pan2STOP4: 5'-CCTCTCGAGTCAGATCTCTAC-CCTTGTGATTGTGTCAC-3' (SEQ ID NO:40). The PAN2 cDNA was independently amplified from HeLa cells using overlapping primers to confirm that the I.M.A.G.E. clone contained an intact, single cDNA. The PAN2 cDNA coding sequence (SEQ ID NO:15) is 2985 nucleotides and encodes an amino acid sequence (SEQ ID NO:16) of 995 amino acids.

The PAN2 gene spans 30 kbp on chromosome 19, and contains at least 10 exons, including 9 coding and at least 1 non-coding exon.

Several domains within PAN2 were identified, based on homology with known proteins. The PAAD domain (SEQ ID NO:2) corresponds to amino acids 14-89 of SEQ ID NO:16. The nucleotide-binding domain (NB-ARC) (SEQ ID NO:37) corresponds to amino acids 147-336 of SEQ ID NO:16. The Angiotensin receptor-like domain (AR-like or ARED domain) (SEQ ID NO:38) corresponds to amino acids 465-605 of SEQ ID NO:16. The Leucine rich region (LRR) (SEQ ID NO:39) corresponds to amino acids 620-995 of SEQ ID NO:16, or alternatively amino acids 604-995.

Expression of PAN2 in human tissues was determined using a panel of Clontech (Palo Alto, Calif.) first-strand cDNAs to amplify a region of PAN2 corresponding to the NB-ARC (NACHT) domain (amino acids 147-465), following manufacturer's recommended procedures. PAN2 was found to be expressed in several human tissues, including placenta, lung, liver, muscle, kidney, pancreas, spleen, thymus, prostate, testis and ovary.

In order to determine whether the PAAD domain of PAN2 is able to self-associate, fusions of the PAN2 PAAD domain (amino acids 1-89 of SEQ ID NO:16) and PAN2(1-620) (amino acids 1-620 of SEQ ID NO:16) with glutathione-S-transferase (GST) were constructed, expressed in bacteria and attached to glutathione beads. The GST fusion proteins were used to pull down in vitro-translated PAN2 PAAD or PAN2(1-620). GST alone and GST-CD40 were used as controls. The PAAD domain of PAN2 was determined not to self-associate or to associate with PAN2. However, PAN2(1-620) was determined to self-associate, likely through its NB-ARC (NACHT) domain. Therefore, the PAAD domain is likely not involved in PAN2/PAN2 interactions.

The effect of expression of the PAN2 PAAD domain on NF-κB activation by the TNFα pathway and the IL-1β pathway were assessed as follows. 10,000 293N cells were seeded into 96-well plates and cells were transfected the following day using SuperFect™ transfection reagent (Qiagen, Venlo, The Netherlands) with 10 ng of pNFκB-luc and 2.5 ng of thymidine kinase promoter-Renilla luciferase (pRL-TK) reporter vectors (Stratagene, San Diego, Calif.), together with 100 ng of plasmids encoding proteins in the TNF-α pathway (pCMV TNFR1, pcDNA3 Traf2 or pcDNA3HA RIP) or in the IL-1β pathway (pCMVFlag IL-1R, pcDNA3His MyD88, pcDNA3HA IRAK3 or pcDNA3HA Traf6), and either 400 ng of pcDNA3Myc ("Empty") or 400 ng of pcDNA3Myc PAAD 1-89 ("PAAD"). After 36 hours, cells were harvested and luciferase activities were determined using the Dual Luciferase System (Promega, Madison, Wis.).

The results of the luciferase assays for cells transfected with molecules in the TNFα pathway are shown in Table 1, below. For the "TNFα" condition, cells were stimulated with 10 ng TNFα for 6-8 hours prior to lysis. The numbers indicate the fold induction of NFκB activity.

TABLE 1

|  | TNFR1 | TNFα | TRAF2 | RIP |
|---|---|---|---|---|
| EMPTY | 20.04 | 21.05 | 33.53 | 53.93 |
| PAAD2 | 19.62 | 7.14 | 15.75 | 23.51 |

The results of the luciferase assays for cells transfected with molecules in the IL-1β pathway are shown in Table 2, below. The numbers indicate the fold induction of NFκB activity.

TABLE 2

|  | IL1R | MyD88 | IRAK2 | TRAF6 |
|---|---|---|---|---|
| EMPTY | 6 | 28.16 | 10.27 | 28.17 |
| PAAD2 | 4.27 | 21.23 | 4.58 | 20.41 |

The results of the NFκB activation assays shown in Tables 1 and 2 indicate that expression of the PAAD domain of PAN2 significantly inhibits NFκB activation by either the TNFα or the IL-1β pathway.

Expression of full-length PAN2 was also demonstrated to inhibit NFκB activation by either the TNFα or the IL-1β pathway. At the same DNA concentration, the inhibition of NFκB activation following transfection with pcDNA3Myc PAN2 was almost the same as the extent of inhibition following transfection with pcDNA3Myc PAAD 1-89. It was concluded that inhibition of NFκB activation by PAN2 was mediated by the PAAD domain.

To determine whether the observed reduction in NFκB activity correlated with reduced NFκB DNA-binding activity in PAN2 over-expressing cells, an electro-mobility shift assay (EMSA) was performed using a $^{32}$P-labeled double strand DNA oligonucleotide encompassing NFκB binding sites. Nuclear extracts were prepared from cells that had been stably transfected with either control or PAN2-encoding plasmids, then stimulated with TNFα. Incubation of the nuclear extracts with $^{32}$P-labeled NFκB probe then permitted measurements of the relative levels of the NFκB DNA binding activity. The results indicated that TNFα stimulated increases in NFκB DNA-binding activity in control transfected cells. In contrast, NFκB DNA-binding activity,was markedly reducer in cells stably over-expressing PAN2. Incubating the protein/DNA complexes with antibodies recognizing various members of the Rel/NFκB family of transcription factors provided evidence that p50 and p65 subunits of NFκB are included in the DNA/protein complexes, producing a super-shift effect in EMSAs. From these experiments it was concluded that PAN2 inhibits the induction NFκB DNA-binding activity by TNFα.

Figure 5:
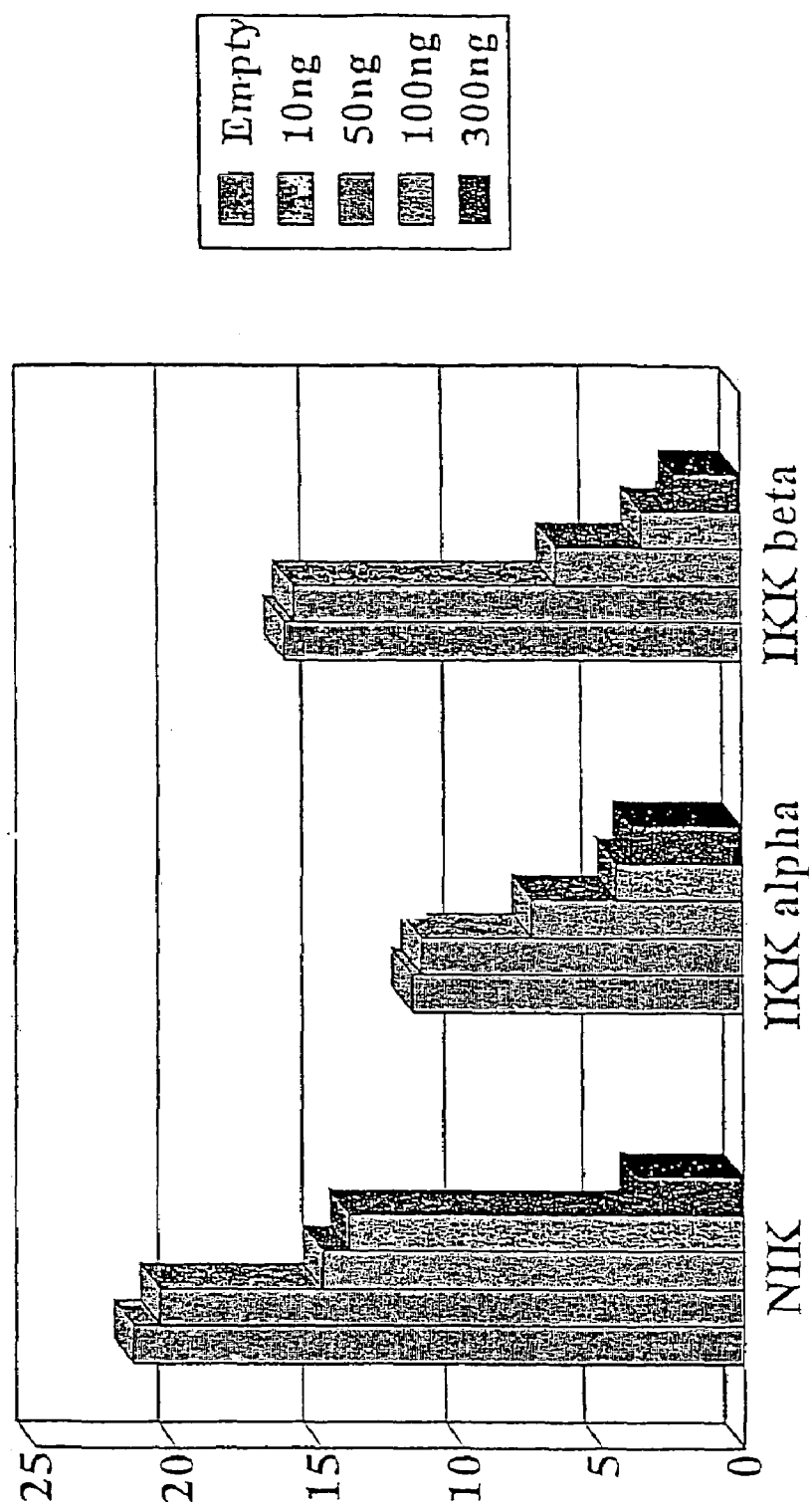
FIG. 5 shows a luciferase reporter assay in which NFκB transcription activity was determined in cells transfected with NIK, IKKα or IKKβ and either an empty vector or the indicated amounts of a vector expressing PAN2.

In order to determine whether PAN2 affects activation of NFκB mediated by upstream components in the NFκB activation pathway, plasmids encoding either NIK (pCMV-NIK), IKKα (pRE-HA-IKKα) or IKKβ (pRE-HA-IKKβ) were co-transfected into 293N cells as described above with from 10 ng to 300 ng of pcDNA3Myc PAN2 or with empty vector, together with 10 ng of pNFκB-luc and 2.5 ng of pTK-RL. Luciferase activities determined as described above. As shown in FIG. 5, PAN2 expression dose-dependently blocked the activation of NFκB mediated by either NIK, IKKα or IKKβ. Therefore, PAN2 acts downstream of the IκB kinase complex.

The effect of PAN2 on the activity of IKKα was also assessed, using in vitro kinase assays. For these experiments, HEK293 cells were transiently transfected with plasmids encoding epitope-tagged either IKKα or IKKβ together with either a control or various amounts of a PAN2-encoding plasmid. After 36 h, cells were left untreated or stimulated with TNFα for 15 minutes, then cell lysates were prepared and either IKKα or IKKβ was immunoprecipitated. The resulting immunoprecipitates were then employed for in vitro kinase assays, where they were incubated with the exogenous substrate (GST-IκB 1-54) in the presence of $^{32}$P γ-ATP. The kinase reaction products were then analyzed by SDS-PAGE, examining phosphorylation of GST-IκB substrate as well as phosphorylation of the kinases. Furthermore, the immunoprecipitates were subjected to SDS-PAGE/immunoblot analysis to verify loading of equivalent amounts of proteins.

The results showed that TNFα induced increases in both the phosphorylation and kinase activity of IKKα in control-transfected cells. In contrast, TNFα-inducible IKKα activity and phosphorylation were suppressed in a concentration-dependent manner by PAN2. Similar results were obtained for IKKβ, where PAN2 over-expression potentially suppressed IKKβ activity below baseline levels in TNFα-stimulated HEK293 cells.

NFκB is normally sequestered into the cytoplasm of non-stimulated cells by a family of inhibitory proteins, called IκB (α, β, γ and ε). Exposure of cells to various stimuli leads to the rapid phosphorylation, ubiquitination and proteolytic degradation of IκB, which frees NFκB to translocate to the nucleus where it regulates gene expression. Accordingly, it was hypothesized that the PAN2 inhibitory effect on NFκB activation could be related to IκB. To test this hypothesis, the in vivo interactions between PAN2 and IκBα were determined.

For co-immunoprecipitation experiments, HEK293T cells were seeded at $3 \times 10^6$ cells per well in 100 mm dishes and transfected with 6-8 µg plasmid DNA using Lipofectamine Plus™ transfection reagent (GIBCO) 24 hours later. After culturing for 36 hours, cells were collected, washed in PBS and lysed in isotonic lysis buffer [150 or 500 mM NaCl, 20 mM Tris/HCl (pH 7.4), 1% NP-40, 12.5 mM β-glycerophosphate, 2 mM NaF, 1 mM $Na_3VO_4$, 1 mM PMSF, and 1× protease inhibitor mix (Roche)]. Lysates were clarified by centrifugation and subjected to immunoprecipitation using agarose-conjugated anti-c-Myc antibodies (Santa Cruz) or anti-FlagM2 antibodies (Sigma) or non-specific control antibodies and Protein G-agarose for 2-4 hours at 4° C. Immune-complexes were washed 3-5 times with lysis buffer and once with PBS, boiled in 1.5× Laemmli buffer, and separated by 12-15% PAGE. Immune-complexes were then transferred to PVDF membranes (Millipore) and immunoblotted with anti-c-Myc (Santa Cruz) or anti-Flag (Sigma) antibodies in 5% dry milk in TBS-T. Membranes were washed, incubated with HRP-conjugated secondary antibodies, and reactive proteins were detected using ECL.

Figure 6:
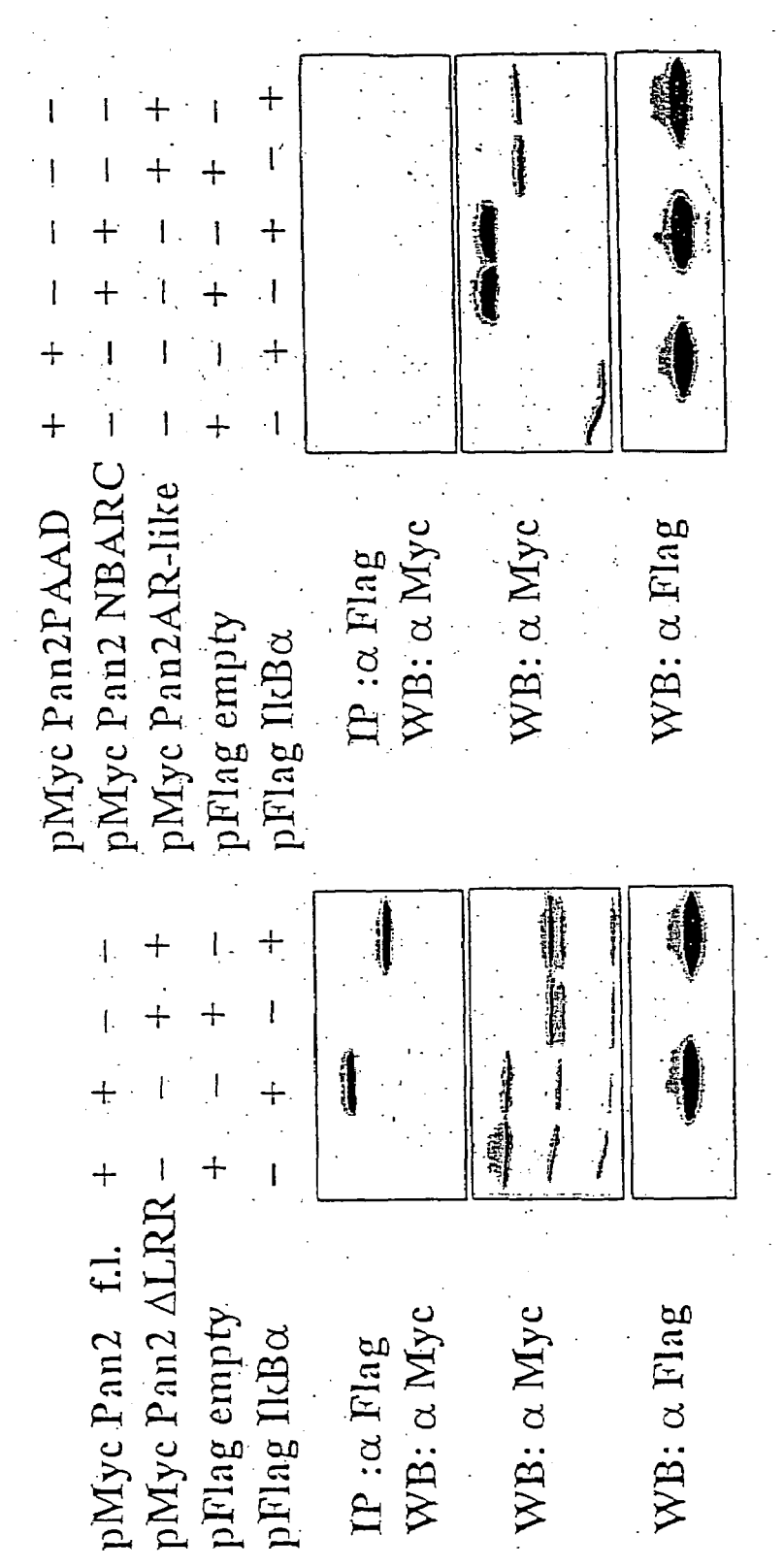

As shown in FIG. 6, Flag-tagged IκBα co-immunoprecipitated with Myc-tagged PAN2 ("f.l.") when both plasmids were expressed in 293T cells. Under similar conditions, associations of PAN2 with IKKβ, IKKγ, p105 or Nik were not detected.

In order to determine which domain of PAN2 is responsible for association with IκB, the following constructs were co-expressed in 293T cells with Flag-tagged IκBα or an empty Flag-tagged vector: Myc-tagged full-length PAN2, Myc-tagged PAN2 ΔLRR (amino acids 1-619 of PAN2), Myc-tagged PAN2PAAD (amino acids 1-89 of PAN2), Myc-tagged PAN2NBARC (amino acids 147-465 of PAN2), or Myc-tagged PAN2AR-like (amino acids 336-605 of PAN2). Immunoprecipitation and immunoblot assays were performed as described above.

As shown in FIG. 6, Flag-tagged IκBα co-immunoprecipitated with Myc-tagged full-length PAN2 ("f.l."), Myc-tagged PAN2 ΔLRR, and Myc-tagged PAN2NBARC, each of which contained the NBARC domain, but not with Myc-tagged PAN2PAAD or Myc-tagged PAN2AR-like.

These results indicate that the NBARC (NACHT) domain of PAN2 is responsible for association with IκBα, whereas the PAAD domain of PAN2 is responsible for inhibition of NFκB interaction.

9.0 Cloning and Characterization of PAN5

In order to clone PAN5 cDNA, first strand cDNA was synthesized at 42° C. for 1 hour from HeLa total RNA (1 µg) using the PAN5 specific primer (300 ng): L1515 (reverse): TTGCTCGAGTCATCTGAATAC (SEQ ID NO:53), and the ProStart Ultra HF RT-PCR system (Stratagene) as described by the manufacturer. A control mRNA and primers provided in the kit were also used (positive control). The completed first-strand cDNA was used for PCR amplification using Pfu DNA polymerase (2.5 units) and PAN5-specific primers (100 ng each), U1(forward): ATGGCCATGGCCAAGGC CAGAAAGC (SEQ ID NO:54) and L1515 (reverse): TTGCTCGAGTCATCTGAATAC (SEQ ID NO:55). The following PCR conditions were used: 4' hot start at 94° C., 35 cycles of 94° C. denaturation for 1 minute, 44° C. annealing for 1 minute and extension at 72° C. for 2 minutes and a final 10 minute extension at 72° C. A 1515 bp PCR product corresponding to PAN5 was observed on an agarose gel. The resultant PCR product was cloned into pcDNA4-His/Max Topo (Invitrogen) following the recommendations of the manufacturer.

The PAAD domain of PAN5 ("PAAD5"), corresponding to bp34-271 of PAN5 cDNA (SEQ ID NO:21), encoding amino acids 12-90 of SEQ ID NO:22, was amplified by PCR from a HeLa cDNA library using the primer set EA-PAC5-Eco-U34: GAATTCCTCTGGGCCTTGAGTGACCTTGAG (SEQ ID NO:51) and EA-PAC5-Xho-St-L271: CCAGCCGACCTC-GAGCAGTCAAATATGGC (SEQ ID NO:52). PCR reactions contained in a total volume of 50 µl: 10× PCR buffer, 20 mM each dNTPs, amplitaq polymerase (0.5 U), 100 ng HeLa cDNA, 50 ng of each primer and 10% DMSO. The same mixture lacking DNA was used as a negative control. The PCR conditions used were as follows: the DNA was first denatured for 3 minutes (hot start). The primer mixture was then added and for 30 subsequent cycles of PCR, the samples were denatured at 94° C. for 30 seconds, annealed at 44° C. for 30 seconds and extended at 72° C. for 1 minute. The 30 cycles of PCR were followed by a 10 minute extension at 72° C.

The PAAD5 domain was first cloned into pCR-II-Topo, sequence-verified and then digested with EcoR1/Xho1. The digest was then analyzed by gel electrophoresis and the 238 bp band containing the PAAD5 domain gel purified for subcloning into pcDNA3-Myc at the EcoR1/XhoI sites for expression in mammalian cells.

In order to determine the effect of PAN5 or the PAAD5 domain on NFκB activation, HEK293 cells were transiently transfected using SuperFect™ transfection reagent (1.5 µl/well) with pNFκB-Luc (50 ng) and pRL-TK (10 ng) luciferase reporter constructs, pcDNA3-PAAD5 or pcDNA4-PAN5 (390 ng) and 50 ng each of different components of the TNF, LPS or IL signaling pathways, as indicated in Table 3. After incubation for 3 hours, the transfection reagent was removed, fresh serum-containing media was added and cells were then incubated for 36 hours. After 36 hours, cells were lysed with Passive lysis buffer (1×; Promega) and then the effect of PAAD5 domain or PAN5 on NFκB activaty was measured with a luminometer. Co-transfection of pToF-Flash/β-catenin was used as a control for stickiness.

The results of the luciferase assays are shown in Table 3, below.

TABLE 3

| Construct | NFκB Activity (fold induction) |
|---|---|
| Control | 1 |
| TNFα | 24 |
| PAAD5 | 3 |
| PAN5 | 4 |
| TNFR1 | 23 |
| TNFR1/PAAD5 | 21 |
| TNFR1/PAN5 | 24 |
| NIK | 30 |
| NIK/PAAD5 | 5 |
| NIK/PAN5 | 3 |
| IKKβ | 45 |
| IKKβ/PAAD5 | 6 |
| IKKβ/PAN5 | 8 |
| p65 | 55 |
| p65/PAAD5 | 13 |
| p65/PAN5 | 46 |
| ToF-Flash + β-catenin | 16 |
| ToF-Flash + β-catenin/PAAD5 | 15 |
| ToF-Flash + β-catenin/PAN5 | 17 |

As evidenced by the data shown in Table 3, overexpression of either PAN5, or the PAAD domain of PAN5, inhibits NFκB activation by a variety of proteins in the TNF, LPS or IL signaling pathways. Therefore, the PAAD domain of PAN5, like the PAAD domain of other PAN proteins described herein, is responsible for the inhibition of NFκB activation.

In order to determine the expression of PAN5 in human tissues, a commercially available Northern membrane (Stratagene) was prehybridized with QuikHyb hybridization solution (Stratagene) containing single stranded sperm DNA for 1-2 hours at 68° C. $^{32}$P-primer labeling of the DNA probe (the 1.5 kb fragment corresponding to the PAN5 ORF) was performed at 37° C. for 30 minutes, using the RTS radprime DNA labeling kit (Life Technologies), as described by the manufacturer. The $^{32}$P primer labeling reaction contained 25 ng of denatured DNA, dATP, dAGTP, dTTP, random octamer primers, 50 μCi [$^{32}$P] dCTP and Klenow fragment. The prehybridization solution was removed, and the denatured radiolabeled probe was added to the hybridization solution (same as prehybridization buffer) and the membrane was hybridized overnight at 68° C. The membrane was washed three times for 40' with 2× SSC/0.05% SDS at room temperature, washed twice for 40' at 50° C., and exposed to Kodak XAR-5 film with intensifying screens at −70° C. C for 1-3 days.

Two transcripts, of 1.8 kb and 1.35 kb, were found to be expressed at varying levels in most human tissues tested. Thymus, spleen, placental and lung had the highest expression of PAD5 transcripts. In thymus and spleen, the 1.35 kb transcript was more abundant than the 1.8 kb transcript, whereas in placenta the 1.8 kb transcript was more abundant than the 1.35 kb transcript.

10.0 Cloning and Characterization of PAN6

The PAN6 gene was determined to share certain LRR-encoding exons with a gene designated RNO2 (GenBank. Accession Number NP_15039 (gi:15193292)). The RNO2 cDNA is expressed in hematopoietic cells and is upregulated in leukemia cells by nitric oxide. It is contemplated that the RNO2 gene product and PAN6 can compete for ligands that bind the LRR domain.

The PAAD domain of PAN6 ("PAAD6") corresponding to bp34-271 of PAN6 cDNA (SEQ ID NO:23), encoding amino acids 12-90 of SEQ ID NO:24, was amplified by PCR from HeLa cDNA library using the primer set EA-PAAD6-U22: GACGGATCCTGTGGCATGGCCACCTACTTGG (SEQ ID NO:56) and EA-PAAD6-L291: ATCCCTCACGAATTC-CCCTCACTGTCCTC (SEQ ID NO:57), essentially as described for PAAD5. The PAAD 6 domain was first cloned into pCR-II-Topo, sequence-verified and then digested with BamH1 and Xho1. The 270 bp band containing the PAAD 6 domain was gel puffified and ligated into pcDNA3-Myc for expression in mammalian cells, into pGEX-4T.3 for GST-fusion protein production and into pGilda for yeast two-hybrid studies, at the BamH1/Xho1 sites of the relevant vector.

In order to determine the effect of PAAD6 expression on NFκB activation, HEK293 cells were transiently transfected with pNFκB-Luc (50 ng) and pRL-TK (10 ng) luciferase reporter constructs, pcDNA3-PAAD6(390 ng) and 50 ng each of different components of the TNF, LPS or IL signaling pathways, as indicated in Table 4, as described above for PAAD5.

The results of the luciferase assays are shown in Table 4, below.

TABLE 4

| Construct | NFκB Activity (fold induction) |
|---|---|
| Control | 1 |
| TNFα | 20 |
| PAAD6 | 4 |
| IRAK2 | 18 |
| IRAK2/PAAD6 | 2 |
| TRAF2 | 44 |
| TRAF2/PAAD6 | 5 |
| TRAF6 | 45 |
| TRAF6/PAAD6 | 6 |
| NIK | 29 |
| NIK/PAAD6 | 3 |
| RIP | 45 |
| RIP/PAAD6 | 2 |
| p65 | 50 |
| p65/PAAD6 | 11 |
| IKKβ | 42 |
| IKKβ/PAAD6 | 2 |
| Bcl10 | 10 |
| Bcl10/PAAD6 | 1 |
| Nod1 | 17 |
| Nod1/PAAD6 | 18 |
| TNFR1 | 25 |
| TNFR1/PAAD6 | 19 |
| ToF-Flash + β-catenin | 18 |
| ToF-Flash + β-catenin/PAAD6 | 17 |

As evidenced by the data shown in Table 4, overexpression of the PAAD domain of PAN6 inhibits NFκB activation by a variety of proteins in the TNF, LPS or IL signaling pathways. Therefore, the PAAD domain of PAN6, like the PAAD domain of other PAN proteins described herein, is responsible for the inhibition of NFκB activation.

In order to identify proteins that associate with PAN6 in vivo, the pGilda plasmid was used to express as a "bait" protein the PAAD domain of PAN6 (nucleotides 22-291 of PAN6 cDNA, corresponding to amino acids 8-97 of SEQ ID NO:24). The plasmid expressing the LexA-PAAD6 bait protein was then used to transform the yeast strain EGY48 (MAT, trp1, ura3, his, his leu2::6LexAop-LEU2. The ability of the LexA-PAAD6 bait protein alone to activate LEU2 or LacZ reporter genes was also tested. The LexA-PAAD6 bait protein was used to screen a human fetal brain and Jurkat T cell pJG4-5 cDNA libraries. Briefly, cells were grown in either YPD medium with 1% yeast extract, 2% polypeptone and 2% glucose, or in Burkholder's minimal medium (BMM) supplemented with appropriate amino acids. Transformations were performed by a LiCl method using 0.1 mg of pJG4-5 cDNA library DNA and 5 mg denatured salmon sperm DNA. The potential positive transformants that grew on Leu deficient BMM plates containing 2% galactose were transferred to BMM plates containing leucine and 2% glucose. Filter assays were then performed to measure β-galactosidase activity as described in Sato et al. *Proc. Natl. Acad. Sci USA* 91:9238-9242 (1994). As a result of the screening, 7 β-galactosidase positive clones out of 11 clones from the Jurkat T cell cDNA library were obtained that transactivated the LEU2 reporter gene (based on the ability to grow on leu deficient media). The screening of a fetal brain cDNA library gave 430 positive clones for the transactivation of the LEU2 reporter gene. Of those, 42 colonies were also positive in the β-galactosidase assay.

Two of the clones identified as encoding PAAD6-interacting proteins by yeast two hybrid analysis encoded IKAP, which is an IKβ kinase complex associated protein. The region of IKAP that interacted with PAAD6 was within amino acids 1089-1232. IKAP is known in the art and described, for example, in Cohen et al., *Nature* 395:292-296 (1998).

In order to determine the expression of PAN6 in human tissues, a commercially available Northern membrane (Stratagene) was hybridized as described above in regard to PAN5 expression, using the EST I.M.A.G.E. clone 2900568, corresponding to nucleotides 892-2331 of PAN6 as the radiolabeled probe.

A PAN6 transcript of 3.3 kb was observed at highest levels in thymus, spleen and skeletal muscle, with lower levels in other tissues.

11.0 Cloning and characterization of ASC and ASC2

ASC and ASC2 were cloned as following. The ASC or ASC2 (SEQ ID NO:27) open reading frames, or the ASC CARD or PAAD domains, were amplified by high fidelity PCR using primers containing EcoRI and XhoI sites and sub cloned into pcDNA3 vectors containing Myc, Flag or HA epitope tags on the N- or C-terminal end. As template either the ASC cDNA described in Masumoto et al., *J. Biol. Chem.* 274:33835-33838 (1999) or the 619 bp EST with GenBank Accession No. W73523 (gi:1383656) were used. Authenticity of all constructs was confirmed by DNA sequencing. The primers used were as follows:

```
ASC:
5'-GAATTCGATCCTGGAGCCATGGGG-3'      (SEQ ID NO: 41)

5'-CTCGAGCCGGAGTGTTGCTGGGAA-3'      (SEQ ID NO: 42)

ASC-PAAD:
5'-GAATTCGATCCTGGAGCCATGGGG-3'      (SEQ ID NO: 43)

5'-CTCGAGTCAGCTTGGCTGCCGACT-3'      (SEQ ID NO: 44)
or

5'-CCCCCTCGAGGGCCTGGCTTGGCTGCCGA    (SEQ ID NO: 45)
CT-3';

ASC-CARD:
5'-GAATTCCCTCAGTCGGCAGCCAAG-3'      (SEQ ID NO: 46)

5'-CTCGAGCCGGAGTGTTGCTGGGAA-3'      (SEQ ID NO: 47)

ASC2:
5'-GAATTCGAGGCGCAGGGCTGTG-3'        (SEQ ID NO: 48)
```

```
5'-CTCGAGGCTTCACAGGCGTTGCAT-3'      (SEQ ID NO: 49)
or

5'-CTCGAGGCTACACAGGCGTTGCAT-3'.     (SEQ ID NO: 50)
```

ASC contains a PAAD domain at the N-terminus followed by a CARD domain. ASC2 contains only a PAAD domain, which shares extensive sequence homology with the PAAD domain of ASC. The ASC gene is localized at chromosome 16p12-11.2, whereas the ASC2 gene is localized at chromosome 16.p13.

To determine associations between various domains of ASC and ASC2, GST pull-down assays and yeast two-hybrid assays were performed. For GST pull-down assays, ASC-PAAD and ASC2 were subcloned into pGEX4-T1 (Pharmacia) and affinity purified as GST-fusion proteins from *E. coli* XL-1 blue (Stratagene) using GSH-Sepharose. Purified GST-fusion proteins (0.1 µg) immobilized on 10-15 µl of GSH-Sepharose beads were incubated with 1 mg/ml bovine serum albumin in 1001 µl buffer A [142.4 mM KCl, 5 mM MgCl$_2$, 10 mM HEPES (pH 7.4), 0.5 mM EGTA, 1 mM EDTA, and 0.2% Nonidet P-40, supplemented with 1 mM dithiothreitol, 12.5 mM β-glycerol phosphate, 1 βM Na$_3$V0$_4$, 1 mM phenylmethylsulfonyl fluoride, and 1× protease inhibitor mix (Roche)] for 30 min at 25° C. The beads were washed twice and incubated overnight at 4° C. with 1 µl of rabbit reticulocyte lysate (Quick-TNT-lysate, Promega) containing $^{35}$S-labeled, in vitro-translated proteins in 100 µl of buffer A supplemented with 0.5 mg/ml bovine serum albumin. Bound proteins were washed four times in 500 µl of buffer A, followed by boiling in 20 µl of Laemmli-SDS sample buffer, SDS-PAGE and detected by fluorography.

By the GST pull-down assays, the PAAD domain of ASC did not associate with the CARD domain of ASC, but weakly associated with full-length ASC and with ASC2, suggesting that the PAAD domain of ASC self-associates and also associates with ASC2.

For the yeast two-hybrid assays, the yeast EGY-48 strain was transformed with various combinations of ASC, ASC-CARD, ASC-PAAD, and ASC2 in the plasmids pGilda and pJG 4-5, together with the β-galactosidase expression plasmid pSH-18-34 (Invitrogen). Colonies were plated on both LEU+ and LEU– media and also used for a β-Gal-assay. The results of the yeast interaction assays are shown in Table 5, below.

TABLE 5

| pJG 4-5 | pGilda | Leu | β-Gal |
|---|---|---|---|
| ASC-CARD | ASC-CARD | + | + |
| ASC-CARD | empty | – | – |
| ASC-CARD | ASC | + | + |
| ASC-CARD | ASC-PAAD | – | – |
| ASC-CARD | ASC2 | – | – |
| ASC-PAAD | empty | – | – |
| ASC-PAAD | ASC-PAAD | + | + |
| ASC2 | empty | – | – |
| ASC2 | ASC2 | + | – |
| ASC2 | ASC | + | + |
| ASC | empty | – | – |

As shown in Table 5, the CARD domain of ASC self associates. In this in vivo assay, the PAAD domain of ASC was shown to self-associate, and also to associate with ASC2.

For co-immunoprecipitation experiments, HEK293T cells were seeded at 5×10$^5$ cells per well in six-well plates (35 mm wells) and transfected with 2 µg plasmid DNA using Superfect (Qiagen) 24 hours later. After culturing for 36 hours, cells were collected, washed in PBS and lysed in isotonic lysis buffer [150 or 500 mM NaCl, 20 mM Tris/HCl (pH 7.4), 0.2% NP-40, 12.5 mM β-glycerophosphate, 2 mM NaF, 1 mM $Na_3VO_4$, 1 mM PMSF, and 1× protease inhibitor mix (Roche). Lysates were clarified by centrifugation and subjected to immunoprecipitation using agarose-conjugated anti-c-Myc antibodies (Santa Cruz), anti-HA antibodies (Santa Cruz, Roche) anti-FlagM2 antibodies (Sigma) or non-specific control antibodies and Protein G-agarose for 2-4 hours at 4° C. Immune-complexes were washed 3-5 times with lysis buffer and once with PBS, boiled in 1.5× Laemmli buffer, and separated by 12-15% PAGE next to 10% of the total lysate. Immune-complexes were then transferred to PVDF membranes (Millipore) and immunoblotted with anti-c-Myc (Santa Cruz), anti-HA (Roche), or anti-Flag (Sigma) antibodies in 5% dry milk in TBS-T. Membranes were washed, incubated with HRP-conjugated secondary antibodies, and reactive proteins were detected using ECL.

The results of the co-immunoprecipitation assays are shown in Table 6, below, with a "+" sign indicating co-immunoprecipititation.

TABLE 6

| Myc-ASC | HA-ASC | + |
| Myc-Caspase-1 | HA-ASC | + |
| Myc-Card10 | HA-ASC | + |
| Flag-Nod1 | HA-ASC | + |
| Flag-Cardiak | HA-ASC | + |
| Myc-ASC2 | HA-ASC-PAAD | + |
| Flag-Nod1 | HA-ASC-PAAD | + |
| Flag-Cardiak | HA-ASC-PAAD | + |
| Myc-NIK | HA-ASC-PAAD | + |
| Flag-IKK-i | HA-ASC-PAAD | + |
| Flag-IκBα | HA-ASC-PAAD | − |
| HA-IKKβ | Myc-ASC-PAAD | − |

The results shown in Table 6 indicate that ASC associates with ASC, ASC2, Caspase-1, Card10, Nod1, Cardiak, NIK and IKK-i.

GST pull-down assays, as described above, were used to determine whether the CARD domain of ASC is able to associate with other proteins, including other CARD domain-containing proteins. The results of these assays are shown in Table 7, with a "+" indicating a detectable interaction between the GST-ASC-CARD domain and the indicated in vitro-translated (IVT) test protein.

TABLE 7

| GST-ASC-CARD/IVT Caspase-8 | − |
| GST-ASC-CARD/IVT Caspase-9 | − |
| GST-ASC-CARD/IVT Caspase-10 | − |
| GST-ASC-CARD/IVT Bcl-10 | − |
| GST-ASC-CARD/IVT RAIDD | − |
| GST-ASC-CARD/IVT ASC-2 | − |
| GST-ASC-CARD/IVT ASC | + |
| GST-ASC-CARD/IVT Xiap | − |
| GST-ASC-CARD/IVT cIAP-1 | − |
| GST-ASC-CARD/IVT cIAP-2 | − |

As shown in Table 7, the CARD domain of ASC, while self-associating, does not associate with several other CARD domain-containing proteins.

In order to determine the localization of ASC and ASC2, Cos-7 cells were seeded onto 12-well plates and transfected with 1.5 µq total fusion plasmid DNA (either EGFP-ASC, EGFP-ASC2 or EGFP-ASC in combination with RFP-ASC2) (Clontech) using Lipofectamine plus (Life Technologies) 24 hours later. The next day cells were trypsinized and seeded onto 4- or 8-well chamber slides (LabTec) and fixed with 4% paraformaldehyde and mounted (Vectashield). Confocal laser scanning microscopy was then performed.

The microscopy results indicated that ASC, when expressed alone, was localized to characteristic "speckles." ASC2, when expressed alone, exhibited a diffuse pattern of cytoplasmic and nuclear localization. However, when expressed together, ASC and ASC2 co-localized in ASC speckles. Therefore, ASC is apparently able to recruit ASC2 into ASC "speckles." This co-localization is further evidence that ASC and ASC2 associate in vivo.

In order to determine the effect of ASC, ASC-CARD, ASC-PAAD and ASC2-on NFκB induction in response to TNFα, IL-1β, Bcl10, Nod1 or Cardiak, reporter assays were performed using the Dual-Luciferase assay system (Promega). In brief, HEK293N cells were seeded onto 24-well plates and transfected with 1 µg total plasmid DNA including 6 ng of pRL-TK and 150 ng pRL-NF-κB or pRL-p53 (all Promega) using SuperFect™ transfection reagent (Qiagen) 24 hours later. After culturing for 48 hours, cells were lysed in 100 µl passive lysis buffer (Promega) and frozen at −80° C. Subsequently, 5-10 µl of lysate were transferred to 96-well plates and analyzed using a Luminometer (Wallach, Perkin Elmer). If indicated, cells were treated with 10 ng TNF-α or IL-1β 6-8 hours prior to lysis. All experiments were performed in triplicate and repeated at least twice.

Figure 7A:
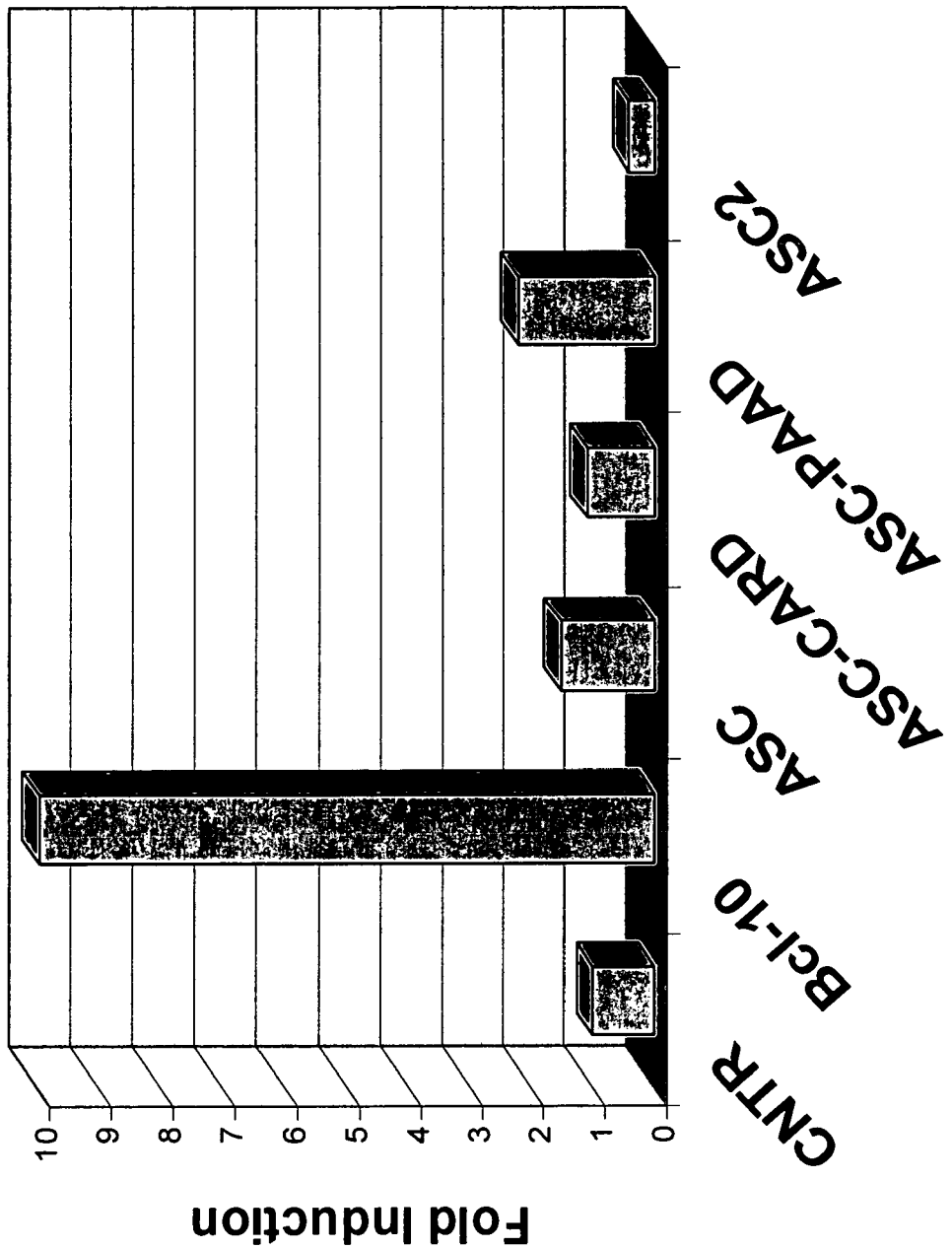
FIG. 7 shows a luciferase reporter assay in which NFκB transcriptional activity was determined in cells transfected with Bcl10 (A), contacted with TNFα (B), contacted with IL-1β (C), or transfected with Bcl10, Nod1 or Cardiak (D), and further transfected with either an empty vector (CNTR), or vectors expressing ASC, domains therefrom, or ASC2, as indicated.
Figure 7B:
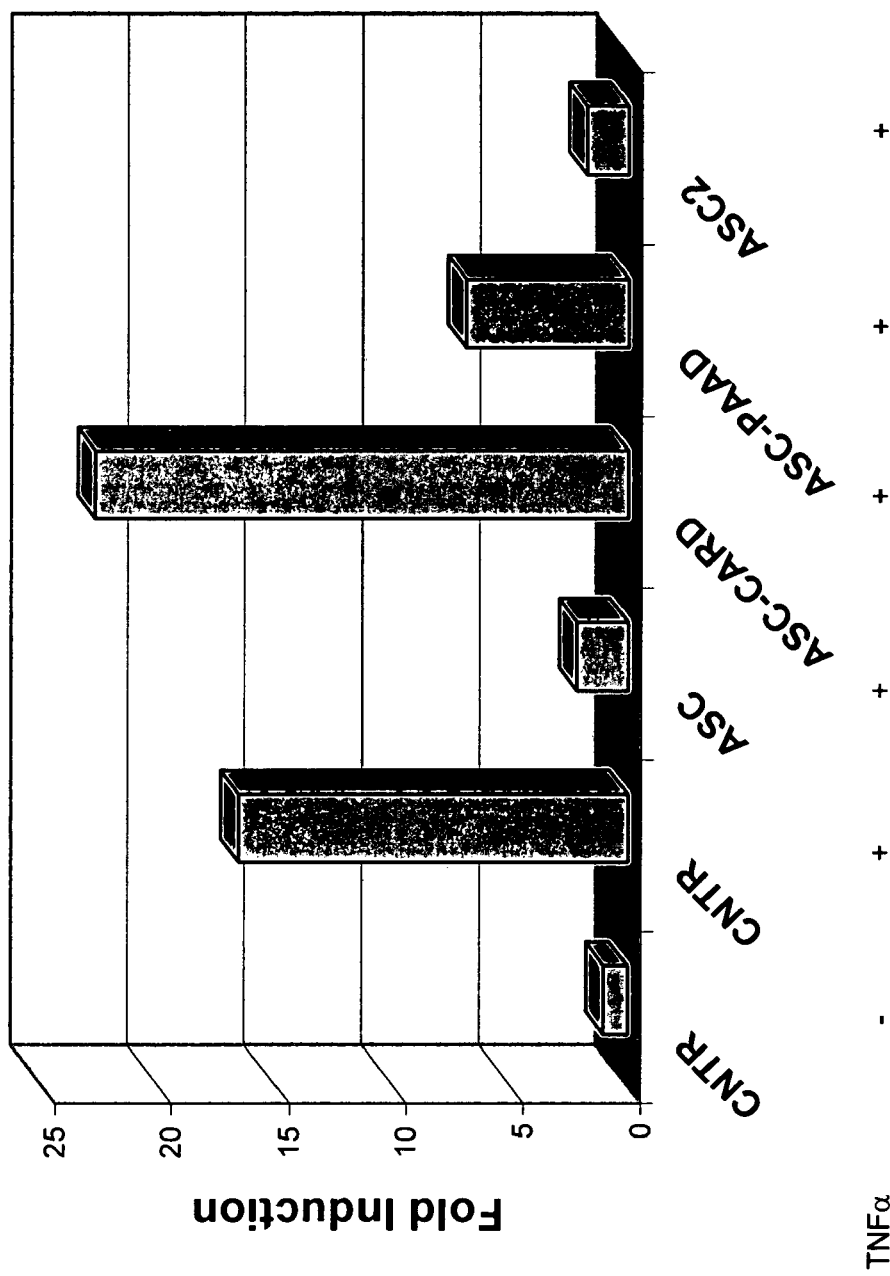
Figure 7C:
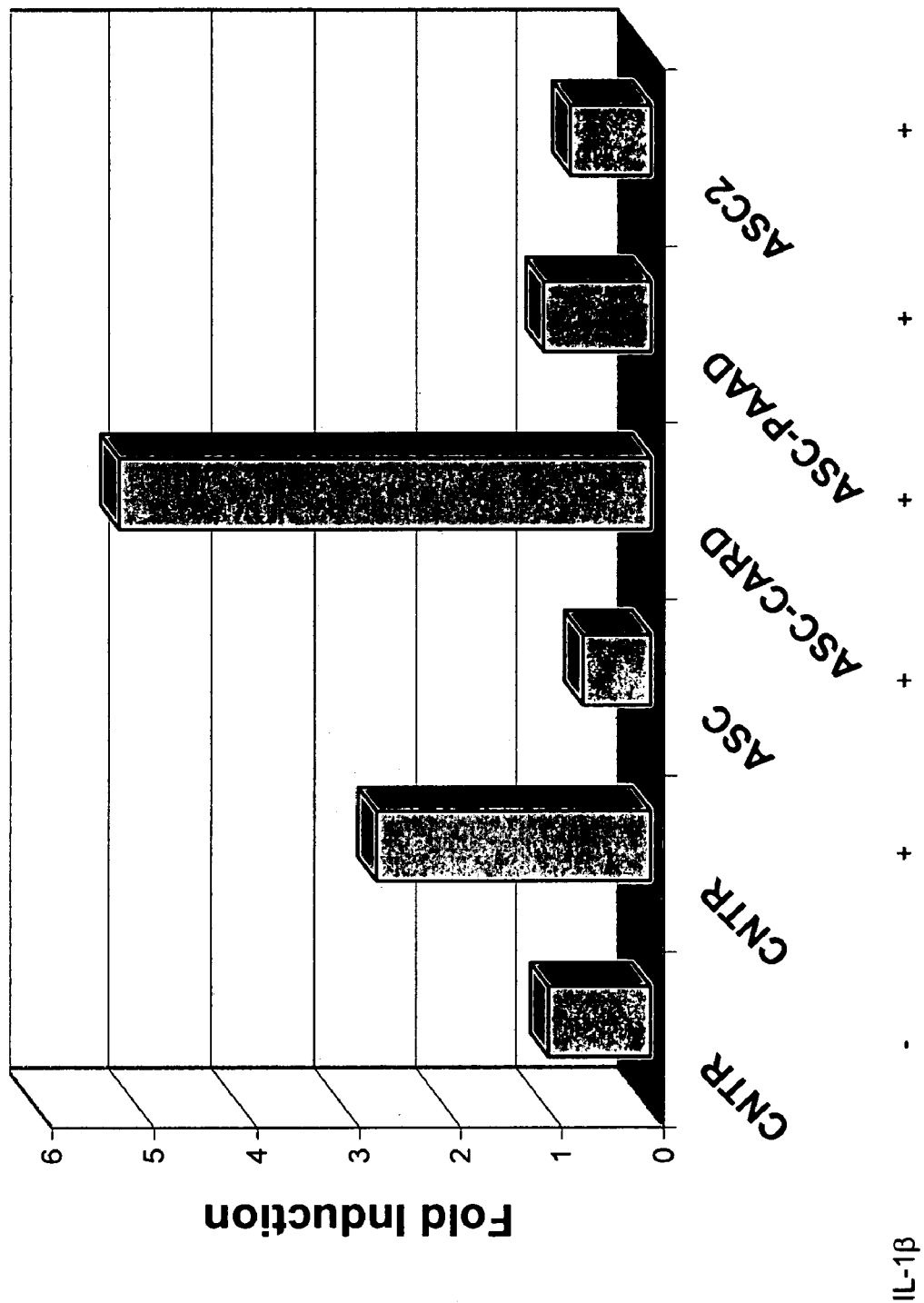
Figure 7D:
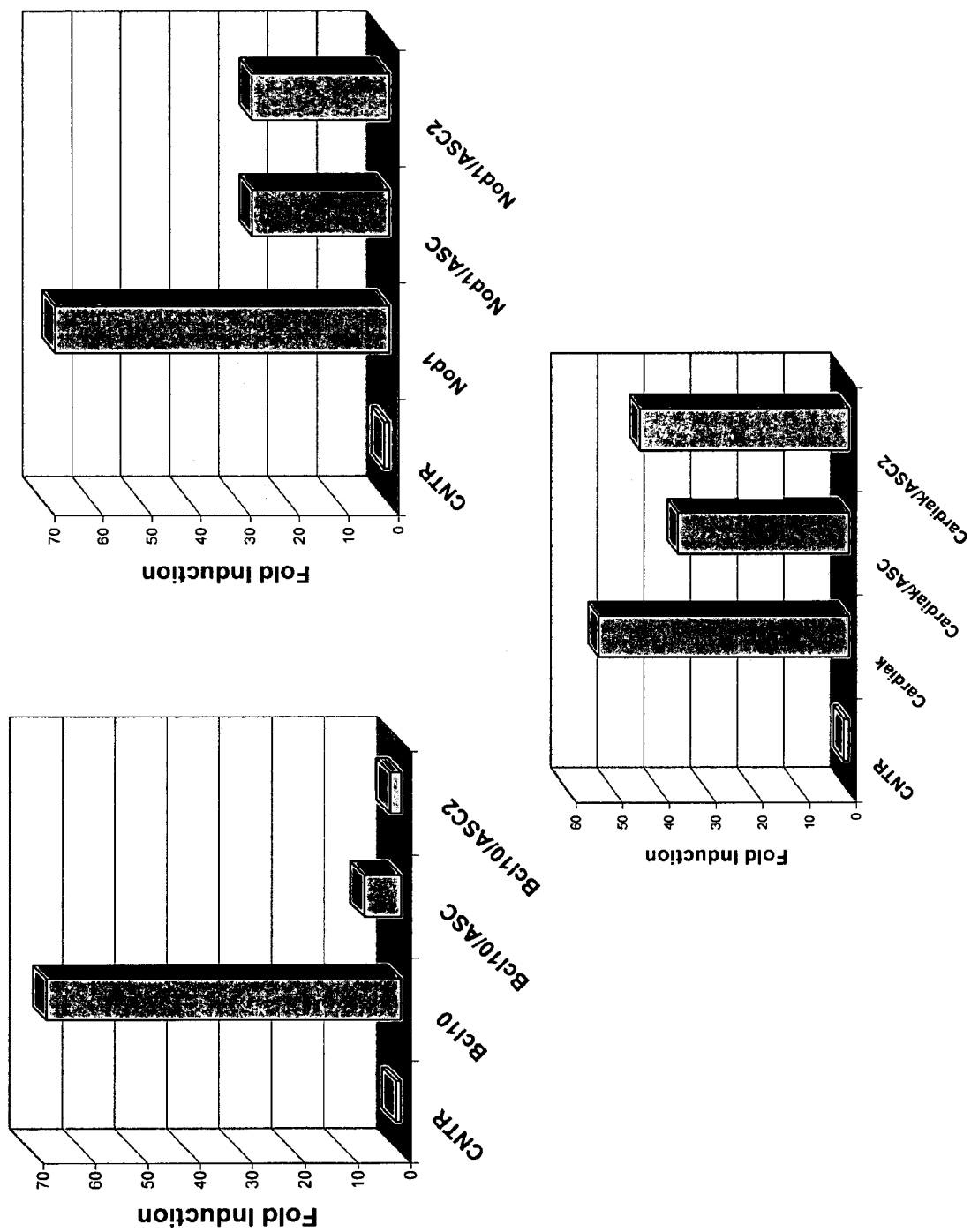

As shown in FIG. 7A-7C, ASC, ASC2 and the PAAD domain of ASC are each able to inhibit NFκB induction by Bcl-10, TNFα and IL-1β. As shown in FIG. 7D, ASC and ASC2 also inhibited NFκB induction by Nod1 and, to a lesser extent, by Cardiak. In other experiments, the inhibition of TNFα-induced NFκB activation was shown to be dependent on the amount of either ASC or ASC2 transfected, and also to be specific for NFκB, as no inhibition of adriamycin-induced p53 activation by ASC was observed.

Figure 8:
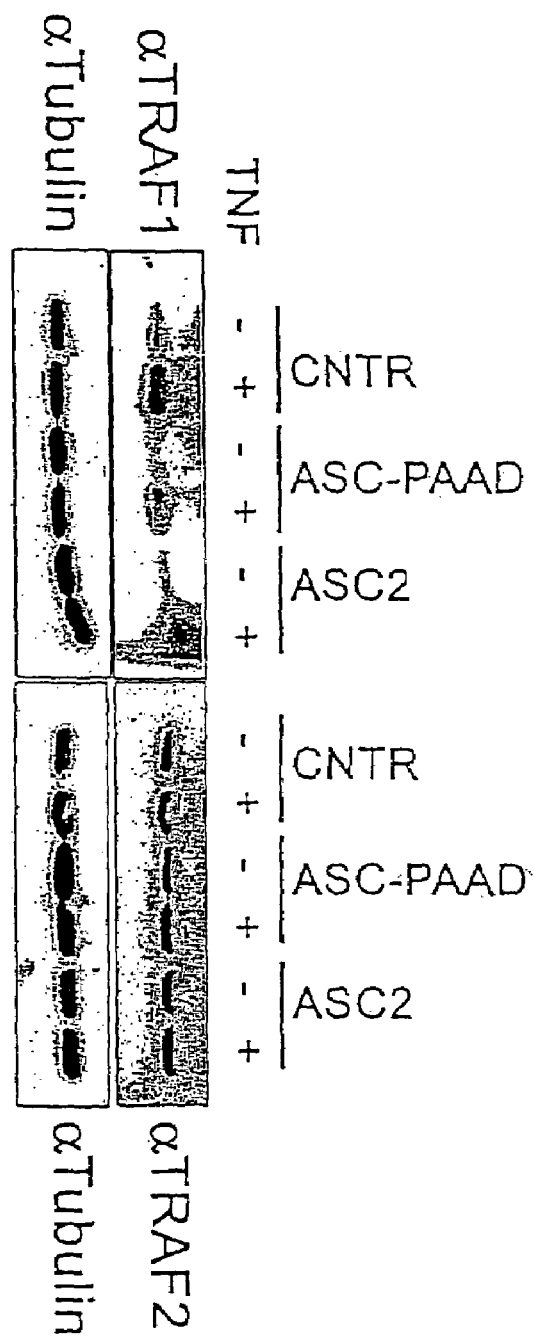
FIG. 8 shows an immunoblot in which the expression of TRAF1 and TRAF2 was examined in cells transfected with the indicated expression vectors and either stimulated with TNF or unstimulated. The expression of Tubulin was determined as a control.

Certain genes are induced by NFκB, including TRAF1 (Carpentier et al., *FEBS Lett.* 460:246-250 (1999). TNFα is a potent inducer of NFκB activation. In order to examine the effect of ASC-PAAD and ASC2 on TNFα-induced expression of the endogenous NFκB target gene TRAF1, HEK 293N cells were transiently transfected with expression plasmids for ASC-PAAD or ASC2, and either treated for 4-hours with TNFα or left untreated. Cleared lysates were immunoblotted with anti-TRAF1 or anti-TRAF2 antibodies. Equal loading was confirmed by re-blotting with an anti-Tubulin antibody. As shown in FIG. 8, treatment with TNF normally causes an increase in expression of TRAF1 but not TRAF2 protein (see lanes marked CNTR, compare − and +TNF). Expression of either ASC-PAAD or ASC2 decreased both basal and TNF-induced expression of TRAF1, without affecting expression of TRAF2. Because increased TRAF1 expression in response to TNF stimulation is mediated by NFκB activation, this result is consistent with the determination (see FIG. 7) that ASC-PAAD or ASC2 inhibit NFκB activation.

Active caspase-1 cleaves pro-IL-1β, resulting in the generation of bioactive IL-1β which is secreted from cells. In order to determine whether ASC or ASC2 affected caspase-1-induced pro-IL-1β processing, COS-7 cells and HEK293N cells were grown in 24 well plates (14 mm wells) and transfected with lug plasmid DNA (Myc-tagged pro-caspase-1, pro-IL-1β (Lee et al., J. Biol. Chem. 276:34495-34500 (2001); Damiano et al., *Genomics* 75:77-83 (2001)), HA-tagged ASC and HA-tagged ASC2 in various combinations) using Lipofectamine plus (Gibco BRL, Grand Island, N.Y.) or Superfect (Qiagen, Valencia, Calif.) 24 hours later. After culturing for 36 hours at 37° C. and 5% $CO_2$ in Dulbecco's modified Eagle medium (DMEM) supplemented with either 20% or 10% heat-inactivated fetal bovine serum (FBS), 1 mM L-glutamine, and antibiotics, supernatants were collected, volume adjusted and stored at −80° C. or used immediately for an IL-1β ELISA assay (R&D Systems, Minneapolis, Minn.) according to the manufacturer's instructions. Cells were washed in PBS, lysed in isotonic lysis buffer, and directly analyzed by immunoblotting using anti-Myc and anti-HA antibodies. Results from one representative experiment of at least three experiments are shown in FIG. 9.

Figure 9:
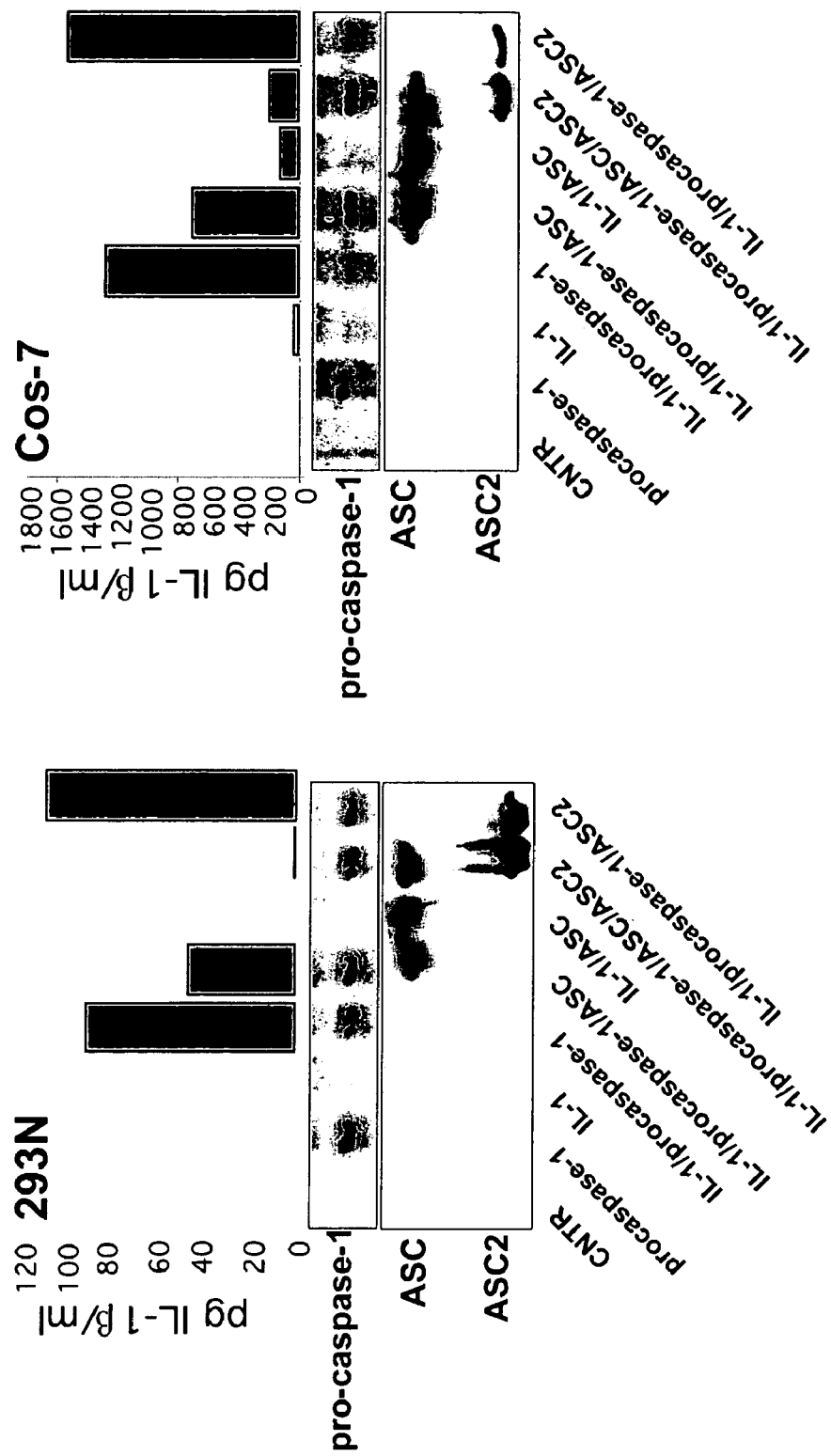
FIG. 9 shows the amount of interleukin-1β secreted from 293N or Cos-7 cells transfected with the indicated expression vectors.

As shown in FIG. 9, co-expression of procaspase-1 and pro-IL-1β ("IL-1") resulted in a high level of secretion of active IL-1β. This IL-1β secretion was inhibited by about 50% by co-expression of ASC, and almost completely inhibited by co-expression of both ASC and ASC2, but was not inhibited by expression of ASC2 alone. Therefore, ASC interferes with activation of a CARD-containing caspase, caspase-1. The association between Cardiak and ASC (see Table 6) may be involved in the inhibition of caspase-1 activation.

Figure 10A:
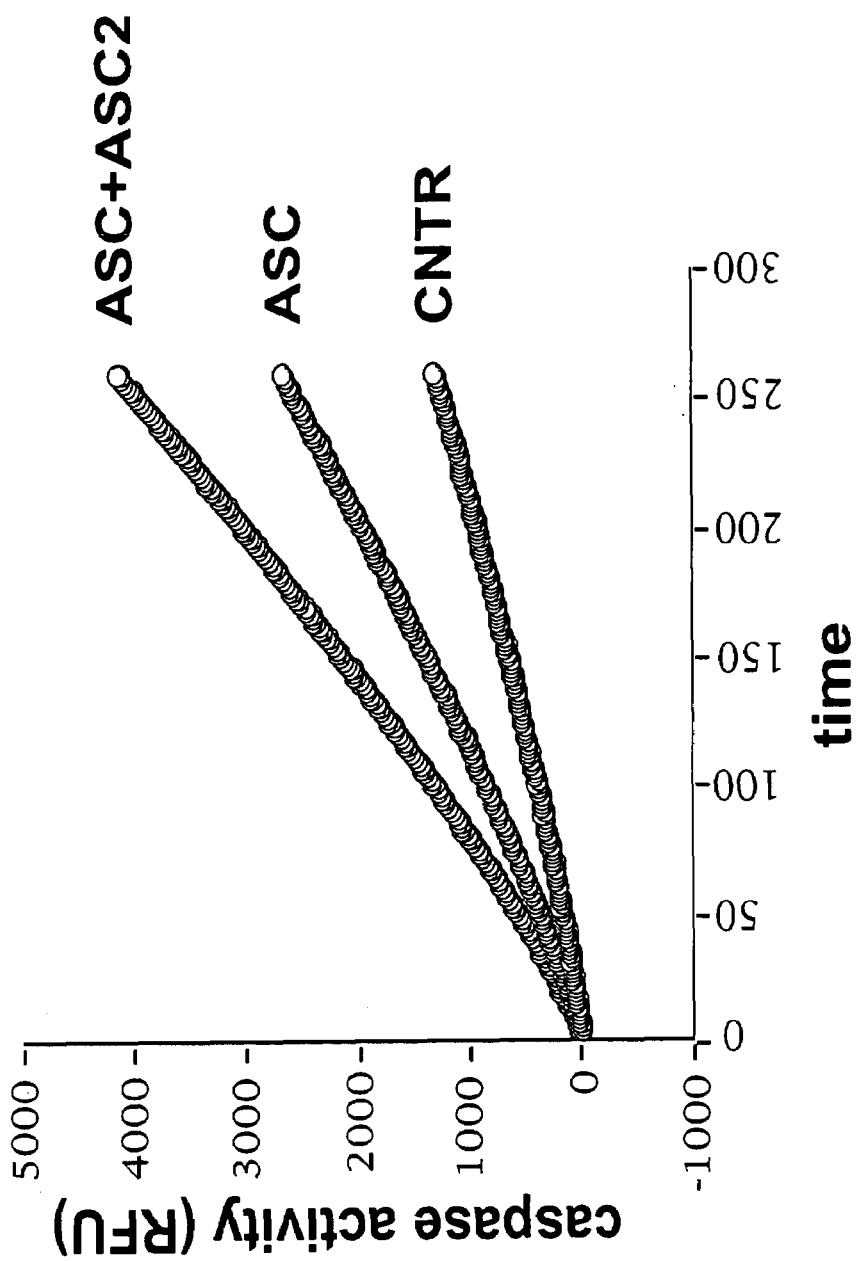
FIG. 10 shows caspase activity, indicated by the cleavage of the fluorogenic substrate Ac-DEVD-AFC over time in cells transfected with the indicated expression vectors. c/a indicates that the caspase is an active site mutant.
Figure 10B:
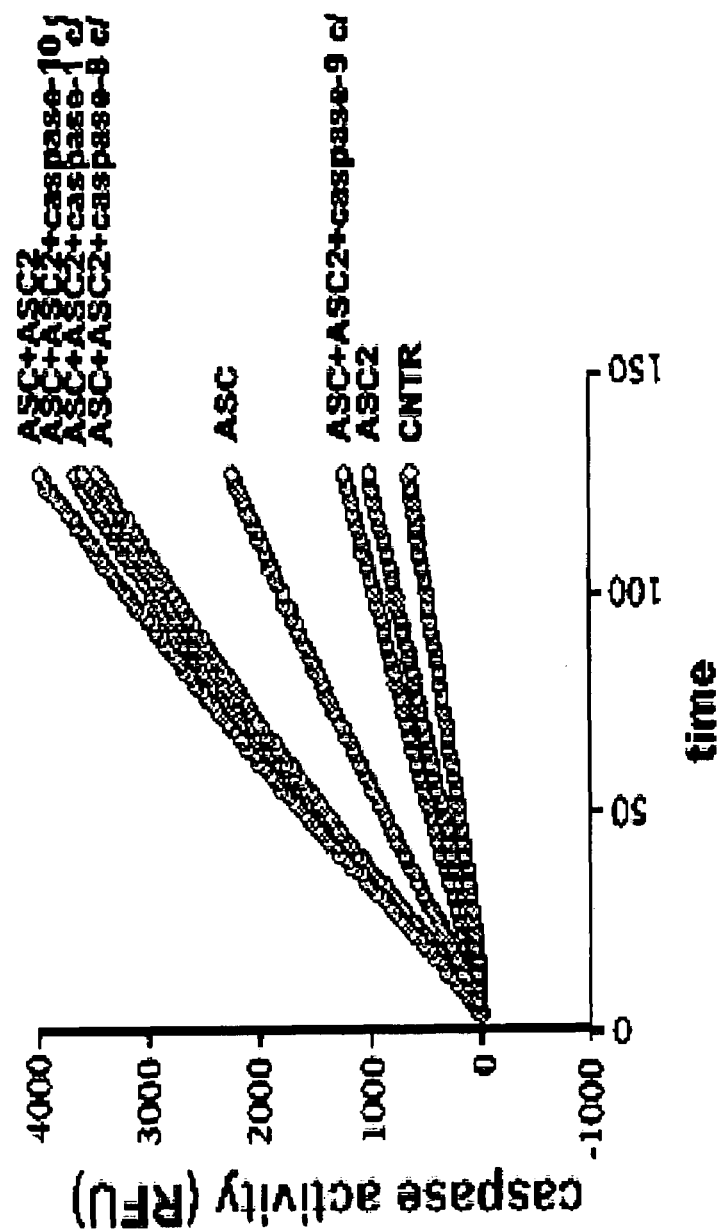

Caspases that cleave the tetrapeptide substrate DEVD-AFC are directly involved in apoptosis, and thus DEDVase activity serves as a surrogate marker of apoptosis. In order to determine the effect of ASC and ASC2 on caspase activation, HEK293N cells were transiently transfected with expression plasmids for ASC; or ASC in combination with ASC2 alone or further in combination with active site mutants of caspase-1, caspase-8, caspase-9 or caspase-10. Transfected HEK293N cells were directly lysed in caspase lysis buffer (10 mM HEPES (pH 7.4), 25 mM NaCl, 0.25% Triton X-100, and 1 mM EDTA), normalized for protein content, and protease activity was measured continuously by monitoring the release of fluorigenic Ac-DEVD-AFC (Bachem, Philadelphia, Pa.) at 37□ C. As shown in FIG. 10, caspase activity was increased by expression of ASC (A and B), and further increased by expression of ASC and ASC2 in combination (A and B). Caspase activity was only slightly increased by expression of ASC2 alone (B). Expression of catalytic site mutants of caspase-1, caspase-8 or caspase-10 (c/a) only slightly decreased ASC+ASC2-mediated caspase activity (B), whereas expression of a catalytic site mutant of caspase-9 (c/a) strongly inhibited ASC+ASC2-mediated caspase activity (B). Therefore, ASC and ASC2 activate a caspase-9-dependent pathway for apoptosis.

Experiments were also performed using stable transfectants of HEK293N expressing the PAAD domain of ASC. The PAAD of ASC was chosen for expression to exclude any contribution from the CARD and to focus on the role of the PAAD in NFκB regulation. Clones of HEK293N stably expressing ASC-PAAD demonstrated reduced activation of a transfected NFκB reporter gene in response to TNFα, consistent with the transient transfection experiments. Moreover, this effect on NfκB activity in HEK293N-ASC-PAAD cells was confirmed to be ASC-dependent by introduction of an ASC-antisense plasmid, in which a cDNA fragment corresponding to the ASC-PAAD was subcloned in reverse orientation downstream of the GFP open reading frame in pEGFP (Clontech), positioning it into the 3' untranslated region of this plasmid. Transfection of various amounts of this ASC-antisense plasmid induced concentration-dependent decreases in the amounts of Myc-ASC-PAAD protein, correlating with dose-dependent restoration of NFκB activity following TNFα-stimulation.

Next, it was evaluated whether stable expression of the ASC-PAAD protein in HEK293N cells interfered with TNFα-induced expression of an endogenous NFκB target gene, TRAF1, which contains several NFκB binding sites in its promoter. Whereas TNFα stimulated marked increases in TRAF1 protein levels in HEK293N-Neo control cells, this response was markedly blunted in ASC-PAAD-expressing cells. The specificity of these results was confirmed by re-probing the same blot with antibodies recognizing TRAF2 or α-Tubulin, showing that the levels of these proteins did not change in response to TNFα.

To extend these studies to another cell line, THP-1 monocytic cells were infected with retrovirus encoding either GFP or GFP fused to the PAAD of ASC. The effects of LPS on expression of the NFκB-inducible gene, ICAM-1, were then studied in these cells by immunoblotting (Chen et al., *J. Biol. Chem.* 276:30724-30728 (2001)). Compared to control GFP-expressing THP-1 cells in which LPS induced >20-fold increases in the levels of ICAM protein within 10 hrs after stimulation, LPS-mediated induction of ICAM-I expression was markedly reduced in ASC-PAAD-expressing cells. Reprobing the same blot with antibodies recognizing GFP confirmed production of the GFP-ASC-PAAD and GFP proteins at comparable levels, while reprobing with anti-β-Actin antibody confirmed loading of equivalent amounts of protein for all samples. Taken together, the data derived from stable transfectants of HEK293N and THP-1 cells indicate that ASC is capable of suppressing TNFα- and LPS-inducible expression of endogenous NFκB target genes through its PAAD domain.

To map where ASC-PAAD affects pathways leading to NFκB induction, NFκB activity in cells was assessed by transient transfection of plasmids encoding various intracellular signal-transducing proteins that operate within cytokine receptor pathways leading to phosphorylation of IκB, a key event required for NFκB release. Co-expression of ASC-encoding plasmids with these signal transducers revealed that ASC blocks induction of NFκB activity by the adapter proteins TRAF2 and TRAF6, the TRAF-binding kinases TBK1 and NIK, the IKK complex constituents IKKα and IKKβ, and by the related kinase IKKi. In contrast, co-expression of ASC did not suppress reporter gene activation induced by over-expression of the p65 subunit of NFκB These functional mapping studies thus suggest that ASC blocks upstream of NFκB, apparently at the level of the IKK complex.

Next, in vitro kinase assays were performed to directly evaluate the effects of ASC on IKK activity. For initial experiments, either HA-epitope tagged IKKα or IKKβ was expressed in cells alone or in combination with ASC-encoding or kinase dead IKK expressing plasmids, then either HA-IKKα or HA-IKKβ was immunoprecipitated from transfected cells, and its phosphorylation in vitro of GST-IκBα substrate was measured. In some cases, in vitro phosphorylation of IKKα as well as phosphorylation of associated endogenous IκBα was also measured in the kinase assays. In unstimulated cells, low levels of IKKα and IKKβ activity were detected, which increased about 5-10-fold in response to TNFα stimulation. Co-expression of kinase-dead IKKα or IKKβ mutants blocked this response, serving as a control. TNFα-induced activation of IKKα and IKKβ was suppressed to essentially baseline levels by co-expression of either full-length ASC or its PAAD. This inhibitory effect of ASC and ASC-PAAD on IKKα and IKKβ activity was not attributable to a difference in the total levels of the IKKα or IKKβ proteins, as determined by immunoblot analysis, thus confirming that ASC suppresses activation of the IKK complex. Similar results were obtained when IKKα or IKKβ was activated in cells by transient transfection of plasmids encoding intracellular signaling proteins such as TRAF2 and TRAF6.

To extend these studies involving expression of epitope-tagged proteins by transient transfection, the activity of endogenous IKKα was evaluated in HEK293 cells that had been stably transfected with either control or Myc-ASC-PAAD-encoding plasmids. ASC-PAAD potently suppressed TNFα-induced activation of endogenous IKKα in these cells, as determined by kinase assays where immunoprecipitated IKKα was tested for ability to phosphorylate GST-IκBα substrate in vitro. The in vitro phosphorylation of IKKα and of endogenous IκBα that was associated with these immune-complexes was also suppressed in ASC-PAAD-expressing cells. These differences in IKKα activity were not due to differences in the total levels of IKKα protein, as determined by immunoblotting.

Since IKK phosphorylates IκB-family proteins, causing their ubiquitination and proteasome-dependent degradation, the effects of the PAAD domain of ASC on levels of endogenous IκBα in these stably transfected cells were also evaluated, before and at various times after TNFα stimulation. Immunoblot analysis of lysates from HEK293N-Neo cells using anti-IκBα antibody demonstrated the appearance of a doublet band indicative of phosphorylation of IκBα within 5 minutes after TNFα simulation, followed by disappearance of IκBα protein. In contrast, IκBα protein levels were sustained at detectable levels in HEK293N-ASC-PAAD cells despite TNFα treatment. Furthermore, the IκBα doublet band indicative of phosphorylation was not observed until much later, at 15-30 minutes post-stimulation, thus demonstrating a marked delay relative to control cells.

Having mapped the site of action of ASC to the IKK complex, experiments were performed to explore whether ASC associated with these protein kinases. In the course of these studies of ASC, it was observed that expression of ASC is induced in myeloid-lineage hematopoietic cells by LPS and TNFα. For example, in THP-1 monocytic cells, levels of ASC mRNA (as determined by RT-PCR) and ASC protein (as determined by immunoblot analysis of lysates using anti-ASC antiserum) increased after LPS stimulation, reaching maximum levels at 3 and 6 hrs, respectively, then declining. It was thus determined whether endogenous ASC protein could be found associated with endogenous IKK complex components after LPS- or TNFα-stimulation in these cells. Co-immunoprecipitation experiments provided evidence of association of ASC with both IKKα and IKKβ in LPS-stimulated THP-1 and TNFα-treated HL-60 cells. These protein interactions were reciprocally demonstrable, regardless of whether immune-complexes were prepared using anti-IKKα and anti-IKKβ antibodies (followed by immunoblotting with anti-ASC antiserum) or using anti-ASC antiserum (followed by immunoblotting with anti-IKKα and anti-IKKβ antibodies).

HEK293N transfectants stably expressing ASC-PAAD were also analyzed to determine whether the PAAD domain is sufficient for association with endogenous IKKα and IKKβ. Again, co-immunoprecipitation experiments demonstrated specific interaction of ASC-PAAD with both IKKα and IKKβ.

Finally, immunofluorescence microscopy was used to examine the intracellular location of IKKα and IKKβ in control HEK293N and ASC-PAAD-expressing cells. In control-transfected HEK293N cells, endogenous IKKα and IKKβ were diffusely distributed throughout the cytosol. In contrast, IKKα and IKKβ relocated to filament-like structures in HEK293N cells stably expressing ASC-PAAD, co-localizing with the ASC-PAAD proteins (as determined by two-color immunofluorescence microscopy). Treatment of these cells with TNFα did not affect the co-localization of ASC-PAAD with IKKs. It was thus concluded that the PAAD domain of ASC associates with endogenous IKKα and IKKβ containing protein complexes, altering their intracellular location and suppressing cytokine- and LPS-mediated activation of these protein kinases involved in NFκB induction.

Although the invention has been described with reference to the examples above, it should be understood that various modifications can be made without departing from the spirit of the invention. Accordingly, the invention is limited only by the following claims.

We claimed:

1. An isolated nucleic acid molecule consisting of a nucleic acid sequence selected from the group consisting of nucleotides 583-1545 of SEQ ID NO:65, nucleotides 607-1569 of SEQ ID NO:19, nucleotides 496-1446 of SEQ ID NO:83, nucleotides 745-1707 of SEQ ID NO:67, nucleotides 511-1452 of SEQ ID NO:69, nucleotides 613-1575 of SEQ ID NO:71, nucleotides 628-1602 of SEQ ID NO:73, nucleotides 499-1561 of SEQ ID NO:75, or a degenerate variant of any of said nucleic acid sequences, wherein said nucleic acid sequences encode the NACHT domain amino acid sequences SEQ ID NOS:107, 110, 113, 116, 119, 122, 125, 128, respectively.

2. The isolated nucleic acid molecule of claim 1, wherein said amino acid sequence is SEQ ID NO: 107.

3. The isolated nucleic acid molecule of claim 1, wherein said amino acid sequence is SEQ ID NO: 110.

4. The isolated nucleic acid molecule of claim 1, wherein said amino acid sequence is SEQ ID NO:113.

5. The isolated nucleic acid molecule of claim 1, wherein said amino acid sequence is SEQ ID NO:116.

6. The isolated nucleic acid molecule of claim 1, wherein said amino acid sequence is SEQ ID NO:119.

7. The isolated nucleic acid molecule of claim 1, wherein said amino acid sequence is SEQ ID NO: 122.

8. The isolated nucleic acid molecule of claim 1, wherein said amino acid sequence is SEQ ID NO: 125.

9. The isolated nucleic acid molecule of claim 1, wherein said amino acid sequence is SEQ ID NO: 128.

* * * * *

SEQUENCE LISTING

<160> NUMBER OF SEQ ID NOS: 129

<210> SEQ ID NO 1
<211> LENGTH: 76
<212> TYPE: PRT
<213> ORGANISM: Homo sapien

<400> SEQUENCE: 1

```
Leu Leu Glu Gln Leu Ser Gln Asp Glu Leu Ser Lys Phe Lys Tyr Leu
 1               5                  10                  15

Ile Thr Thr Phe Ser Leu Ala His Glu Leu Gln Lys Ile Pro His Lys
            20                  25                  30

Glu Val Asp Lys Ala Asp Gly Lys Gln Leu Val Glu Ile Leu Thr Thr
        35                  40                  45

His Cys Asp Ser Tyr Trp Val Glu Met Ala Ser Leu Gln Val Phe Glu
    50                  55                  60

Lys Met His Arg Met Asp Leu Ser Glu Arg Ala Lys
65                  70                  75
```

<210> SEQ ID NO 2
<211> LENGTH: 76
<212> TYPE: PRT
<213> ORGANISM: Homo sapien

-continued

```
<400> SEQUENCE: 2

Tyr Leu Glu Glu Leu Lys Lys Glu Phe Arg Lys Phe Lys Glu His
1               5                   10                  15

Leu Lys Gln Met Thr Leu Gln Leu Glu Leu Lys Gln Ile Pro Trp Thr
                20                  25                  30

Glu Val Lys Lys Ala Ser Arg Glu Glu Leu Ala Asn Leu Leu Ile Lys
            35                  40                  45

His Tyr Glu Glu Gln Gln Ala Trp Asn Ile Thr Leu Arg Ile Phe Gln
    50                  55                  60

Lys Met Asp Arg Lys Asp Leu Cys Met Lys Val Met
65                  70                  75

<210> SEQ ID NO 3
<211> LENGTH: 73
<212> TYPE: PRT
<213> ORGANISM: Homo sapien

<400> SEQUENCE: 3

Ala Leu Glu Glu Leu Ser Gln Glu Gln Leu Lys Arg Phe Arg His Lys
1               5                   10                  15

Leu Arg Asp Val Gly Pro Asp Gly Arg Ser Ile Pro Trp Gly Arg Leu
                20                  25                  30

Glu Arg Ala Asp Ala Val Asp Leu Ala Glu Gln Leu Ala Gln Phe Tyr
            35                  40                  45

Gly Pro Glu Pro Ala Leu Glu Val Ala Arg Lys Thr Leu Lys Arg Ala
    50                  55                  60

Asp Ala Arg Asp Val Ala Ala Gln Leu
65                  70

<210> SEQ ID NO 4
<211> LENGTH: 75
<212> TYPE: PRT
<213> ORGANISM: Homo sapien

<400> SEQUENCE: 4

Tyr Met Arg Asn Val Ser His Glu Glu Leu Gln Arg Phe Lys Gln Leu
1               5                   10                  15

Leu Leu Thr Glu Leu Ser Thr Gly Thr Met Pro Ile Thr Trp Asp Gln
                20                  25                  30

Val Glu Thr Ala Ser Trp Ala Glu Val Val His Leu Leu Ile Glu Arg
            35                  40                  45

Phe Pro Gly Arg Arg Ala Trp Asp Val Thr Ser Asn Ile Phe Ala Ile
    50                  55                  60

Met Asn Cys Asp Lys Met Cys Val Val Val Arg
65                  70                  75

<210> SEQ ID NO 5
<211> LENGTH: 76
<212> TYPE: PRT
<213> ORGANISM: Homo sapien

<400> SEQUENCE: 5

Ala Leu Ser Asp Leu Glu Glu Asn Asp Phe Lys Lys Leu Lys Phe Tyr
1               5                   10                  15

Leu Arg Asp Met Thr Leu Ser Glu Gly Gln Pro Pro Leu Ala Arg Gly
                20                  25                  30

Glu Leu Glu Gly Leu Ile Pro Val Asp Leu Ala Glu Leu Leu Ile Ser
```

```
                35                  40                  45
Lys Tyr Gly Glu Lys Glu Ala Val Lys Val Leu Lys Gly Leu Lys
 50                  55                  60

Val Met Asn Leu Leu Glu Leu Val Asp Gln Leu Ser
 65                  70                  75

<210> SEQ ID NO 6
<211> LENGTH: 75
<212> TYPE: PRT
<213> ORGANISM: Homo sapien

<400> SEQUENCE: 6

Tyr Leu Glu Glu Leu Glu Ala Val Glu Leu Lys Lys Phe Lys Leu Tyr
 1               5                  10                  15

Leu Gly Thr Ala Thr Glu Leu Gly Glu Gly Lys Ile Pro Trp Gly Ser
                20                  25                  30

Met Glu Lys Ala Gly Pro Leu Glu Met Ala Gln Leu Leu Ile Thr His
                35                  40                  45

Phe Gly Pro Glu Glu Ala Trp Arg Leu Ala Leu Ser Thr Phe Glu Arg
 50                  55                  60

Ile Asn Arg Lys Asp Leu Trp Glu Arg Gly Gln
 65                  70                  75

<210> SEQ ID NO 7
<211> LENGTH: 76
<212> TYPE: PRT
<213> ORGANISM: Homo sapien

<400> SEQUENCE: 7

Thr Leu Glu Glu Leu Val Pro Tyr Asp Phe Glu Lys Phe Lys Phe Lys
 1               5                  10                  15

Leu Gln Asn Thr Ser Val Gln Lys Glu His Ser Arg Ile Pro Arg Ser
                20                  25                  30

Gln Ile Gln Arg Ala Arg Pro Val Lys Met Ala Thr Leu Leu Val Thr
                35                  40                  45

Tyr Tyr Gly Glu Glu Tyr Ala Val Gln Leu Thr Leu Gln Val Leu Arg
 50                  55                  60

Ala Ile Asn Gln Arg Leu Leu Ala Glu Glu Leu His
 65                  70                  75

<210> SEQ ID NO 8
<211> LENGTH: 71
<212> TYPE: PRT
<213> ORGANISM: Homo sapien

<400> SEQUENCE: 8

Tyr Leu Glu Asp Leu Glu Asp Val Asp Leu Lys Lys Phe Lys Met His
 1               5                  10                  15

Leu Glu Asp Tyr Pro Pro Gln Lys Gly Cys Ile Pro Leu Pro Arg Gly
                20                  25                  30

Gln Thr Glu Lys Ala Asp His Val Asp Leu Ala Thr Leu Met Ile Asp
                35                  40                  45

Phe Asn Gly Glu Glu Lys Ala Trp Ala Met Val Val Trp Ile Phe Ala
 50                  55                  60

Ala Ile Asn Arg Arg Asp Leu
 65                  70

<210> SEQ ID NO 9
```

```
<211> LENGTH: 76
<212> TYPE: PRT
<213> ORGANISM: Homo sapien

<400> SEQUENCE: 9

Ala Leu Glu Asn Leu Thr Ala Glu Glu Leu Lys Lys Phe Lys Leu Lys
1               5                   10                  15

Leu Leu Ser Val Pro Leu Arg Glu Gly Tyr Gly Arg Ile Pro Arg Gly
            20                  25                  30

Ala Leu Leu Pro Met Asp Ala Leu Asp Leu Thr Asp Lys Leu Val Ser
        35                  40                  45

Phe Tyr Leu Glu Thr Tyr Gly Ala Glu Leu Thr Ala Asn Val Leu Arg
50                  55                  60

Asp Met Gly Leu Gln Glu Met Ala Gly Gln Leu Gln
65                  70                  75

<210> SEQ ID NO 10
<211> LENGTH: 76
<212> TYPE: PRT
<213> ORGANISM: Homo sapien

<400> SEQUENCE: 10

Val Leu Glu Asn Leu Thr Pro Glu Glu Leu Lys Lys Phe Lys Met Lys
1               5                   10                  15

Leu Gly Thr Val Pro Leu Arg Glu Gly Phe Glu Arg Ile Pro Arg Gly
            20                  25                  30

Ala Leu Gly Gln Leu Asp Ile Val Asp Leu Thr Asp Lys Leu Val Ala
        35                  40                  45

Ser Tyr Tyr Glu Asp Tyr Ala Ala Glu Leu Val Val Ala Val Leu Arg
50                  55                  60

Asp Met Arg Met Leu Glu Glu Ala Ala Arg Leu Gln
65                  70                  75

<210> SEQ ID NO 11
<211> LENGTH: 76
<212> TYPE: PRT
<213> ORGANISM: Homo sapien

<400> SEQUENCE: 11

Tyr Leu Glu Phe Leu Lys Lys Glu Glu Leu Lys Glu Phe Gln Leu Leu
1               5                   10                  15

Leu Ala Asn Lys Ala His Ser Arg Ser Ser Gly Glu Thr Pro Ala
            20                  25                  30

Gln Pro Glu Lys Thr Ser Gly Met Glu Val Ala Ser Tyr Leu Val Ala
        35                  40                  45

Gln Tyr Gly Glu Gln Arg Ala Trp Asp Leu Ala Leu His Thr Trp Glu
50                  55                  60

Gln Met Gly Leu Arg Ser Leu Cys Ala Gln Ala Gln
65                  70                  75

<210> SEQ ID NO 12
<211> LENGTH: 70
<212> TYPE: PRT
<213> ORGANISM: Homo sapien

<400> SEQUENCE: 12

Gly Leu Asp Asn Ile Thr Asp Glu Glu Leu Asp Arg Phe Lys Phe Phe
1               5                   10                  15

Leu Ser Asp Glu Phe Asn Ile Ala Thr Gly Lys Leu His Thr Ala Asn
```

-continued

```
            20                  25                  30

Arg Ile Gln Val Ala Thr Leu Met Ile Gln Asn Ala Gly Ala Val Ser
        35                  40                  45

Ala Val Met Lys Thr Ile Arg Ile Phe Gln Lys Leu Asn Tyr Met Leu
    50                  55                  60

Leu Ala Lys Arg Leu Gln
65                  70

<210> SEQ ID NO 13
<211> LENGTH: 71
<212> TYPE: PRT
<213> ORGANISM: Homo sapien

<400> SEQUENCE: 13

Gly Leu Glu Val Ile Asn Asp Tyr His Phe Arg Met Val Lys Ser Leu
 1               5                  10                  15

Leu Ser Asn Asp Leu Lys Leu Asn Leu Lys Met Arg Glu Glu Tyr Asp
            20                  25                  30

Lys Ile Gln Ile Ala Asp Leu Met Glu Glu Lys Phe Arg Gly Asp Ala
        35                  40                  45

Gly Leu Gly Lys Leu Ile Lys Ile Phe Glu Asp Ile Pro Thr Leu Glu
    50                  55                  60

Asp Leu Ala Glu Thr Leu Lys
65                  70

<210> SEQ ID NO 14
<211> LENGTH: 70
<212> TYPE: PRT
<213> ORGANISM: Myxoma virus

<400> SEQUENCE: 14

Val Leu Glu Asn Leu Ser Asp Tyr Gln Phe Lys Met Phe Ile Tyr Leu
 1               5                  10                  15

Ala Met Glu Asp Leu Tyr Ile Glu Arg Ala Glu Lys Glu Lys Ile Asp
            20                  25                  30

Arg Ile Asp Leu Ala His Lys Ile Ser Glu Gln Tyr Leu Gly Thr Asp
        35                  40                  45

Tyr Ile Glu Phe Met Lys Arg Val Thr Asp Phe Ile Pro Asn Lys Val
    50                  55                  60

Tyr Val Asp Ser Leu Leu
65                  70

<210> SEQ ID NO 15
<211> LENGTH: 2985
<212> TYPE: DNA
<213> ORGANISM: Homo sapien
<220> FEATURE:
<221> NAME/KEY: CDS
<222> LOCATION: (1)...(2985)
<220> FEATURE:
<221> NAME/KEY: misc_feature
<222> LOCATION: (1)...(1857)
<223> OTHER INFORMATION: n = A,T,C or G

<400> SEQUENCE: 15 atg gca gcc tct ttc ttc tct gat ttt ggt ctt atg tgg tat ctg gag       48
Met Ala Ala Ser Phe Phe Ser Asp Phe Gly Leu Met Trp Tyr Leu Glu
 1               5                   10                  15 gag ctc aaa aag gag gag ttc agg aaa ttt aaa gaa cat ctc aag caa       96
Glu Leu Lys Lys Glu Glu Phe Arg Lys Phe Lys Glu His Leu Lys Gln
             20                  25                  30
```

-continued

| | |
|---|---|
| atg act ttg cag ctt gaa ctc aag cag att ccc tgg act gag gtc aaa<br>Met Thr Leu Gln Leu Glu Leu Lys Gln Ile Pro Trp Thr Glu Val Lys<br>35                    40                    45 | 144 |
| aaa gca tcc cgg gaa gaa ctt gca aac ctc ttg atc aag cac tat gaa<br>Lys Ala Ser Arg Glu Glu Leu Ala Asn Leu Leu Ile Lys His Tyr Glu<br>50                    55                    60 | 192 |
| gaa caa caa gct tgg aac ata acc tta aga atc ttt caa aag atg gat<br>Glu Gln Gln Ala Trp Asn Ile Thr Leu Arg Ile Phe Gln Lys Met Asp<br>65                    70                    75                    80 | 240 |
| aga aag gat ctc tgc atg aag gtc atg agg gag aga aca gga tac aca<br>Arg Lys Asp Leu Cys Met Lys Val Met Arg Glu Arg Thr Gly Tyr Thr<br>                    85                    90                    95 | 288 |
| aag acc tat caa gct cac gca aag cag aaa ttc agc cgc tta tgg tcc<br>Lys Thr Tyr Gln Ala His Ala Lys Gln Lys Phe Ser Arg Leu Trp Ser<br>                  100                  105                110 | 336 |
| agc aag tct gtc act gag att cac cta tac ttt gag gag gaa gtc aag<br>Ser Lys Ser Val Thr Glu Ile His Leu Tyr Phe Glu Glu Glu Val Lys<br>115                    120                  125 | 384 |
| caa gaa gaa tgt gac cat ttg gac cgc ctt ttt gct ccc aag gaa act<br>Gln Glu Glu Cys Asp His Leu Asp Arg Leu Phe Ala Pro Lys Glu Thr<br>130                    135                  140 | 432 |
| ggg aaa cag cca cgt aca gtg att att caa gga cca caa gga att gga<br>Gly Lys Gln Pro Arg Thr Val Ile Ile Gln Gly Pro Gln Gly Ile Gly<br>145                    150                  155                160 | 480 |
| aaa acg aca ctc ctg atg aag ctg atg atg gcc tgg tcg gac aac aag<br>Lys Thr Thr Leu Leu Met Lys Leu Met Met Ala Trp Ser Asp Asn Lys<br>                  165                  170                175 | 528 |
| atc ttt cgg gat agg ttc ctg tac acg ttc tat ttc tgc tgc aga gaa<br>Ile Phe Arg Asp Arg Phe Leu Tyr Thr Phe Tyr Phe Cys Cys Arg Glu<br>                  180                  185                190 | 576 |
| ctg agg gag ttg ccg cca acg agt ttg gct gac ttg att tcc aga gag<br>Leu Arg Glu Leu Pro Pro Thr Ser Leu Ala Asp Leu Ile Ser Arg Glu<br>                  195                  200                205 | 624 |
| tgg cct gac ccc gct gct cct ata aca gag atc gtg tct caa ccg gag<br>Trp Pro Asp Pro Ala Ala Pro Ile Thr Glu Ile Val Ser Gln Pro Glu<br>210                    215                  220 | 672 |
| aga ctc ttg ttc gtc atc gac agc ttc gaa gag ctg cag ggc ggc ttg<br>Arg Leu Leu Phe Val Ile Asp Ser Phe Glu Glu Leu Gln Gly Gly Leu<br>225                    230                  235                240 | 720 |
| aac gaa ccc gat tcg gat ctg tgt ggt gac ttg atg gag aaa cgg ccg<br>Asn Glu Pro Asp Ser Asp Leu Cys Gly Asp Leu Met Glu Lys Arg Pro<br>                  245                  250                255 | 768 |
| gtg cag gtg ctt ctg agc agt ttg ctg agg aag aag atg ctc ccg gag<br>Val Gln Val Leu Leu Ser Ser Leu Leu Arg Lys Lys Met Leu Pro Glu<br>                  260                  265                270 | 816 |
| gcc tcc ctg ctc atc gcc atc aaa ccc gtg tgc ccg aag gag ctc cgg<br>Ala Ser Leu Leu Ile Ala Ile Lys Pro Val Cys Pro Lys Glu Leu Arg<br>                  275                  280                285 | 864 |
| gat cag gtg acg atc tca gaa atc tac cag ccc cgg gga ttc aac gag<br>Asp Gln Val Thr Ile Ser Glu Ile Tyr Gln Pro Arg Gly Phe Asn Glu<br>290                    295                  300 | 912 |
| agt gat agg tta gtg tat ttc tgc tgt ttc ttc aaa gac ccg aaa aga<br>Ser Asp Arg Leu Val Tyr Phe Cys Cys Phe Phe Lys Asp Pro Lys Arg<br>305                    310                  315                320 | 960 |
| gcc atg gaa gcc ttc aat ctt gta aga gaa agt gaa cag ctg ttt tcc<br>Ala Met Glu Ala Phe Asn Leu Val Arg Glu Ser Glu Gln Leu Phe Ser<br>                  325                  330                335 | 1008 |
| ata tgc caa atc ccg ctc ctc tgc tgg atc ctg tgt acc agt ctg aag<br>Ile Cys Gln Ile Pro Leu Leu Cys Trp Ile Leu Cys Thr Ser Leu Lys | 1056 |

-continued

```
                  340                 345                 350
caa gag atg cag aaa gga aaa gac ctg gcc ctg acc tgc cag agc act      1104
Gln Glu Met Gln Lys Gly Lys Asp Leu Ala Leu Thr Cys Gln Ser Thr
            355                 360                 365 acc tct gtg tac tcc tct ttc gtc ttt aac ctg ttc aca cct gag ggt      1152
Thr Ser Val Tyr Ser Ser Phe Val Phe Asn Leu Phe Thr Pro Glu Gly
        370                 375                 380 gcc gag ggc ccg act ccg caa acc cag cac cag ctg aag gcc ctg tgc      1200
Ala Glu Gly Pro Thr Pro Gln Thr Gln His Gln Leu Lys Ala Leu Cys
385                 390                 395                 400 tcc ctg gct gca gag ggt atg tgg aca gac aca ttt gag ttt tgt gaa      1248
Ser Leu Ala Ala Glu Gly Met Trp Thr Asp Thr Phe Glu Phe Cys Glu
                405                 410                 415 gac gac ctc cgg aga aat ggg gtt gtt gac gct gac atc cct gcg ctg      1296
Asp Asp Leu Arg Arg Asn Gly Val Val Asp Ala Asp Ile Pro Ala Leu
            420                 425                 430 ctg ggc acc aag ata ctt ctg aag tac ggg gag cgt gag agc tcc tac      1344
Leu Gly Thr Lys Ile Leu Leu Lys Tyr Gly Glu Arg Glu Ser Ser Tyr
        435                 440                 445 gtg ttc ctc cac gtg tgt atc cag gag ttc tgt gcc gcc ttg ttc tat      1392
Val Phe Leu His Val Cys Ile Gln Glu Phe Cys Ala Ala Leu Phe Tyr
450                 455                 460 ttg ctc aag agc cat ctt gat cat cct cac cca gct gtg aga tgt gta      1440
Leu Leu Lys Ser His Leu Asp His Pro His Pro Ala Val Arg Cys Val
465                 470                 475                 480 cag gaa ttg cta gtt gcc aat ttt gaa aaa gca agg aga gca cat tgg      1488
Gln Glu Leu Leu Val Ala Asn Phe Glu Lys Ala Arg Arg Ala His Trp
                485                 490                 495 att ttt ttg ggg tgt ttt cta act ggc ctt tta aat aaa aag gaa caa      1536
Ile Phe Leu Gly Cys Phe Leu Thr Gly Leu Leu Asn Lys Lys Glu Gln
            500                 505                 510 gaa aaa ctg gat gcg ttt ttt ggc ttc caa ctg tcc caa gag ata aag      1584
Glu Lys Leu Asp Ala Phe Phe Gly Phe Gln Leu Ser Gln Glu Ile Lys
        515                 520                 525 cag caa att cac cag tgc ctg aag agc tta ggg gag cgt ggc aat cct      1632
Gln Gln Ile His Gln Cys Leu Lys Ser Leu Gly Glu Arg Gly Asn Pro
530                 535                 540 cag gga cag gtg gat tcc ttg gcg ata ttt tac tgt ctc ttt gaa atg      1680
Gln Gly Gln Val Asp Ser Leu Ala Ile Phe Tyr Cys Leu Phe Glu Met
545                 550                 555                 560 cag gat cct gcc ttt gtg aag cag gca gtg aac ctc ctc caa gaa gct      1728
Gln Asp Pro Ala Phe Val Lys Gln Ala Val Asn Leu Leu Gln Glu Ala
                565                 570                 575 aac ttt cat att att gac aac gtg gac ttg gtg gtt tct gcc tac tgc      1776
Asn Phe His Ile Ile Asp Asn Val Asp Leu Val Val Ser Ala Tyr Cys
            580                 585                 590 tta aaa tac tgc tcc agc ttg agg aaa ctc tgt ttt tcc gtt caa aat      1824
Leu Lys Tyr Cys Ser Ser Leu Arg Lys Leu Cys Phe Ser Val Gln Asn
        595                 600                 605 gtc ttt aag aaa gag gat gaa cac agc tct acg tcg gat tac agc ctc      1872
Val Phe Lys Lys Glu Asp Glu His Ser Ser Thr Ser Asp Tyr Ser Leu
610                 615                 620 atc tgt tgg cat cac atc tgc tct gtg ctc acc acc agc ggg cac ctc      1920
Ile Cys Trp His His Ile Cys Ser Val Leu Thr Thr Ser Gly His Leu
625                 630                 635                 640 aga gag ctc cag gtg cag gac agc acc ctc agc gag tcg acc ttt gtg      1968
Arg Glu Leu Gln Val Gln Asp Ser Thr Leu Ser Glu Ser Thr Phe Val
                645                 650                 655 acc tgg tgt aac cag ctg agg cat ccc agc tgt cgc ctt cag aag ctt      2016
```

```
            Thr Trp Cys Asn Gln Leu Arg His Pro Ser Cys Arg Leu Gln Lys Leu
                            660                 665                 670 gga ata aat aac gtt tcc ttt tct ggc cag agt gtt ctg ctc ttt gag       2064
Gly Ile Asn Asn Val Ser Phe Ser Gly Gln Ser Val Leu Leu Phe Glu
            675                 680                 685 gtg ctc ttt tat cag cca gac ttg aaa tac ctg agc ttc acc ctc acg       2112
Val Leu Phe Tyr Gln Pro Asp Leu Lys Tyr Leu Ser Phe Thr Leu Thr
    690                 695                 700 aaa ctc tct cgt gat gac atc agg tcc ctc tgt gat gcc ttg aac tac       2160
Lys Leu Ser Arg Asp Asp Ile Arg Ser Leu Cys Asp Ala Leu Asn Tyr
705                 710                 715                 720 cca gca ggc aac gtc aaa gag cta gcg ctg gta aat tgt cac ctc tca       2208
Pro Ala Gly Asn Val Lys Glu Leu Ala Leu Val Asn Cys His Leu Ser
                725                 730                 735 ccc att gat tgt gaa gtc ctt gct ggc ctt cta acc aac aac aag aag       2256
Pro Ile Asp Cys Glu Val Leu Ala Gly Leu Leu Thr Asn Asn Lys Lys
            740                 745                 750 ctg acg tat ctg aat gta tcc tgc aac cag tta gac aca ggc gtg ccc       2304
Leu Thr Tyr Leu Asn Val Ser Cys Asn Gln Leu Asp Thr Gly Val Pro
        755                 760                 765 ctt ttg tgt gaa gcc ctg tgc agc cca gac acg gtc ctg gta tac ctg       2352
Leu Leu Cys Glu Ala Leu Cys Ser Pro Asp Thr Val Leu Val Tyr Leu
770                 775                 780 atg ttg gct ttc tgc cac ctc agc gag cag tgc tgc gaa tac atc tct       2400
Met Leu Ala Phe Cys His Leu Ser Glu Gln Cys Cys Glu Tyr Ile Ser
785                 790                 795                 800 gaa atg ctt ctg cgt aac aag agc gtg cgc tat cta gac ctc agt gcc       2448
Glu Met Leu Leu Arg Asn Lys Ser Val Arg Tyr Leu Asp Leu Ser Ala
                805                 810                 815 aat gtc ctg aag gac gaa gga ctg aaa act ctc tgc gag gcc ttg aaa       2496
Asn Val Leu Lys Asp Glu Gly Leu Lys Thr Leu Cys Glu Ala Leu Lys
            820                 825                 830 cat ccg gac tgc tgc ctg gat tca ctg tgt ttg gta aaa tgt ttt atc       2544
His Pro Asp Cys Cys Leu Asp Ser Leu Cys Leu Val Lys Cys Phe Ile
        835                 840                 845 act gct gct ggc tgt gaa gac ctc gcc tct gct ctc atc agc aat caa       2592
Thr Ala Ala Gly Cys Glu Asp Leu Ala Ser Ala Leu Ile Ser Asn Gln
850                 855                 860 aac ctg aag att ctg caa att ggg tgc aat gaa atc gga gat gtg ggt       2640
Asn Leu Lys Ile Leu Gln Ile Gly Cys Asn Glu Ile Gly Asp Val Gly
865                 870                 875                 880 gtg cag ctg ttg tgt cgg gct ctg acg cat acg gat tgc cgc tta gag       2688
Val Gln Leu Leu Cys Arg Ala Leu Thr His Thr Asp Cys Arg Leu Glu
                885                 890                 895 att ctt ggg ttg gaa gaa tgt ggg tta acg agc acc tgc tgt aag gat       2736
Ile Leu Gly Leu Glu Glu Cys Gly Leu Thr Ser Thr Cys Cys Lys Asp
            900                 905                 910 ctc gcg tct gtt ctc acc tgc agt aag acc ctg cag cag ctc aac ctg       2784
Leu Ala Ser Val Leu Thr Cys Ser Lys Thr Leu Gln Gln Leu Asn Leu
        915                 920                 925 acc ttg aac acc ttg gac cac aca ggg gtg gtt gta ctc tgt gag gcc       2832
Thr Leu Asn Thr Leu Asp His Thr Gly Val Val Val Leu Cys Glu Ala
930                 935                 940 ctg aga cac cca gag tgt gcc ctg cag gtg ctc ggg ctg aga aaa act       2880
Leu Arg His Pro Glu Cys Ala Leu Gln Val Leu Gly Leu Arg Lys Thr
945                 950                 955                 960 gat ttt gat gag gaa acc cag gca ctt ctg acg gct gag gaa gag aga       2928
Asp Phe Asp Glu Glu Thr Gln Ala Leu Leu Thr Ala Glu Glu Glu Arg
                965                 970                 975
```

```
aat cct aac ctg acc atc aca gac gac tgt gac aca atc aca agg gta    2976
Asn Pro Asn Leu Thr Ile Thr Asp Asp Cys Asp Thr Ile Thr Arg Val
            980                 985                 990 gag atc tga                                                         2985
Glu Ile *
```

<210> SEQ ID NO 16
<211> LENGTH: 994
<212> TYPE: PRT
<213> ORGANISM: Homo sapien

<400> SEQUENCE: 16

```
Met Ala Ala Ser Phe Phe Ser Asp Phe Gly Leu Met Trp Tyr Leu Glu
 1               5                  10                  15

Glu Leu Lys Lys Glu Glu Phe Arg Lys Phe Lys Glu His Leu Lys Gln
            20                  25                  30

Met Thr Leu Gln Leu Glu Leu Lys Gln Ile Pro Trp Thr Glu Val Lys
        35                  40                  45

Lys Ala Ser Arg Glu Glu Leu Ala Asn Leu Leu Ile Lys His Tyr Glu
    50                  55                  60

Glu Gln Gln Ala Trp Asn Ile Thr Leu Arg Ile Phe Gln Lys Met Asp
65                  70                  75                  80

Arg Lys Asp Leu Cys Met Lys Val Met Arg Glu Arg Thr Gly Tyr Thr
                85                  90                  95

Lys Thr Tyr Gln Ala His Ala Lys Gln Lys Phe Ser Arg Leu Trp Ser
            100                 105                 110

Ser Lys Ser Val Thr Glu Ile His Leu Tyr Phe Glu Glu Val Lys
        115                 120                 125

Gln Glu Glu Cys Asp His Leu Asp Arg Leu Phe Ala Pro Lys Glu Thr
    130                 135                 140

Gly Lys Gln Pro Arg Thr Val Ile Ile Gln Gly Pro Gln Gly Ile Gly
145                 150                 155                 160

Lys Thr Thr Leu Leu Met Lys Leu Met Met Ala Trp Ser Asp Asn Lys
                165                 170                 175

Ile Phe Arg Asp Arg Phe Leu Tyr Thr Phe Tyr Phe Cys Cys Arg Glu
            180                 185                 190

Leu Arg Glu Leu Pro Pro Thr Ser Leu Ala Asp Leu Ile Ser Arg Glu
        195                 200                 205

Trp Pro Asp Pro Ala Ala Pro Ile Thr Glu Ile Val Ser Gln Pro Glu
    210                 215                 220

Arg Leu Leu Phe Val Ile Asp Ser Phe Glu Glu Leu Gln Gly Gly Leu
225                 230                 235                 240

Asn Glu Pro Asp Ser Asp Leu Cys Gly Asp Leu Met Glu Lys Arg Pro
                245                 250                 255

Val Gln Val Leu Leu Ser Ser Leu Leu Arg Lys Lys Met Leu Pro Glu
            260                 265                 270

Ala Ser Leu Leu Ile Ala Ile Lys Pro Val Cys Pro Lys Glu Leu Arg
        275                 280                 285

Asp Gln Val Thr Ile Ser Glu Ile Tyr Gln Pro Arg Gly Phe Asn Glu
    290                 295                 300

Ser Asp Arg Leu Val Tyr Phe Cys Phe Phe Lys Asp Pro Lys Arg
305                 310                 315                 320

Ala Met Glu Ala Phe Asn Leu Val Arg Glu Ser Glu Gln Leu Phe Ser
                325                 330                 335

Ile Cys Gln Ile Pro Leu Leu Cys Trp Ile Leu Cys Thr Ser Leu Lys
```

-continued

```
                340                 345                 350
Gln Glu Met Gln Lys Gly Lys Asp Leu Ala Leu Thr Cys Gln Ser Thr
                355                 360                 365
Thr Ser Val Tyr Ser Ser Phe Val Phe Asn Leu Phe Thr Pro Glu Gly
            370                 375                 380
Ala Glu Gly Pro Thr Pro Gln Thr Gln His Gln Leu Lys Ala Leu Cys
385                 390                 395                 400
Ser Leu Ala Ala Glu Gly Met Trp Thr Asp Thr Phe Glu Phe Cys Glu
                405                 410                 415
Asp Asp Leu Arg Arg Asn Gly Val Val Asp Ala Asp Ile Pro Ala Leu
            420                 425                 430
Leu Gly Thr Lys Ile Leu Leu Lys Tyr Gly Glu Arg Glu Ser Ser Tyr
                435                 440                 445
Val Phe Leu His Val Cys Ile Gln Glu Phe Cys Ala Ala Leu Phe Tyr
            450                 455                 460
Leu Leu Lys Ser His Leu Asp His Pro His Pro Ala Val Arg Cys Val
465                 470                 475                 480
Gln Glu Leu Leu Val Ala Asn Phe Glu Lys Ala Arg Arg Ala His Trp
                485                 490                 495
Ile Phe Leu Gly Cys Phe Leu Thr Gly Leu Leu Asn Lys Lys Glu Gln
            500                 505                 510
Glu Lys Leu Asp Ala Phe Phe Gly Phe Gln Leu Ser Gln Glu Ile Lys
            515                 520                 525
Gln Gln Ile His Gln Cys Leu Lys Ser Leu Gly Glu Arg Gly Asn Pro
            530                 535                 540
Gln Gly Gln Val Asp Ser Leu Ala Ile Phe Tyr Cys Leu Phe Glu Met
545                 550                 555                 560
Gln Asp Pro Ala Phe Val Lys Gln Ala Val Asn Leu Leu Gln Glu Ala
                565                 570                 575
Asn Phe His Ile Ile Asp Asn Val Asp Leu Val Val Ser Ala Tyr Cys
            580                 585                 590
Leu Lys Tyr Cys Ser Ser Leu Arg Lys Leu Cys Phe Ser Val Gln Asn
        595                 600                 605
Val Phe Lys Lys Glu Asp Glu His Ser Ser Thr Ser Asp Tyr Ser Leu
        610                 615                 620
Ile Cys Trp His His Ile Cys Ser Val Leu Thr Thr Ser Gly His Leu
625                 630                 635                 640
Arg Glu Leu Gln Val Gln Asp Ser Thr Leu Ser Glu Ser Thr Phe Val
                645                 650                 655
Thr Trp Cys Asn Gln Leu Arg His Pro Ser Cys Arg Leu Gln Lys Leu
            660                 665                 670
Gly Ile Asn Asn Val Ser Phe Ser Gly Gln Ser Val Leu Leu Phe Glu
            675                 680                 685
Val Leu Phe Tyr Gln Pro Asp Leu Lys Tyr Leu Ser Phe Thr Leu Thr
            690                 695                 700
Lys Leu Ser Arg Asp Asp Ile Arg Ser Leu Cys Asp Ala Leu Asn Tyr
705                 710                 715                 720
Pro Ala Gly Asn Val Lys Glu Leu Ala Leu Val Asn Cys His Leu Ser
                725                 730                 735
Pro Ile Asp Cys Glu Val Leu Ala Gly Leu Leu Thr Asn Asn Lys Lys
            740                 745                 750
Leu Thr Tyr Leu Asn Val Ser Cys Asn Gln Leu Asp Thr Gly Val Pro
        755                 760                 765
```

```
Leu Leu Cys Glu Ala Leu Cys Ser Pro Asp Thr Val Leu Val Tyr Leu
    770                 775                 780
Met Leu Ala Phe Cys His Leu Ser Glu Gln Cys Cys Glu Tyr Ile Ser
785                 790                 795                 800
Glu Met Leu Leu Arg Asn Lys Ser Val Arg Tyr Leu Asp Leu Ser Ala
                805                 810                 815
Asn Val Leu Lys Asp Glu Gly Leu Lys Thr Leu Cys Glu Ala Leu Lys
            820                 825                 830
His Pro Asp Cys Cys Leu Asp Ser Leu Cys Leu Val Lys Cys Phe Ile
        835                 840                 845
Thr Ala Ala Gly Cys Glu Asp Leu Ala Ser Ala Leu Ile Ser Asn Gln
    850                 855                 860
Asn Leu Lys Ile Leu Gln Ile Gly Cys Asn Glu Ile Gly Asp Val Gly
865                 870                 875                 880
Val Gln Leu Leu Cys Arg Ala Leu Thr His Thr Asp Cys Arg Leu Glu
                885                 890                 895
Ile Leu Gly Leu Glu Glu Cys Gly Leu Thr Ser Thr Cys Cys Lys Asp
            900                 905                 910
Leu Ala Ser Val Leu Thr Cys Ser Lys Thr Leu Gln Gln Leu Asn Leu
        915                 920                 925
Thr Leu Asn Thr Leu Asp His Thr Gly Val Val Leu Cys Glu Ala
    930                 935                 940
Leu Arg His Pro Glu Cys Ala Leu Gln Val Leu Gly Leu Arg Lys Thr
945                 950                 955                 960
Asp Phe Asp Glu Glu Thr Gln Ala Leu Leu Thr Ala Glu Glu Arg
                965                 970                 975
Asn Pro Asn Leu Thr Ile Thr Asp Asp Cys Asp Thr Ile Thr Arg Val
            980                 985                 990
Glu Ile

<210> SEQ ID NO 17
<211> LENGTH: 2844
<212> TYPE: DNA
<213> ORGANISM: Homo sapien
<220> FEATURE:
<221> NAME/KEY: CDS
<222> LOCATION: (1)...(2841)

<400> SEQUENCE: 17 atg gac cag cca gag gcc ccc tgc tcc agc acg ggg ccg cgc ctc gcg        48
Met Asp Gln Pro Glu Ala Pro Cys Ser Ser Thr Gly Pro Arg Leu Ala
1               5                   10                  15 gtg gcc cgc gag ctg ctc ctg gct gcg ctg gag gaa ctg agc caa gag        96
Val Ala Arg Glu Leu Leu Leu Ala Ala Leu Glu Glu Leu Ser Gln Glu
            20                  25                  30 cag ctg aag cgc ttc cgc cac aag ctg cgc gac gtg ggc ccg gac gga       144
Gln Leu Lys Arg Phe Arg His Lys Leu Arg Asp Val Gly Pro Asp Gly
        35                  40                  45 cgc agc atc ccg tgg ggg cgg ctg gag cgc gcg gac gcc gtg gac ctc       192
Arg Ser Ile Pro Trp Gly Arg Leu Glu Arg Ala Asp Ala Val Asp Leu
    50                  55                  60 gcg gag cag ctg gcc cag ttc tac ggc ccg gag cct gcc ctg gag gtg       240
Ala Glu Gln Leu Ala Gln Phe Tyr Gly Pro Glu Pro Ala Leu Glu Val
65                  70                  75                  80 gcc cgc aag acc ctc aag agg gcg gac gcg cgc gac gtg gcg gcg cag       288
Ala Arg Lys Thr Leu Lys Arg Ala Asp Ala Arg Asp Val Ala Ala Gln
                85                  90                  95
```

-continued

| | |
|---|---|
| ctc cag gag cgg cgg ctg cag cgg ctc ggg ctc ggc tcc ggg acg ctg<br>Leu Gln Glu Arg Arg Leu Gln Arg Leu Gly Leu Gly Ser Gly Thr Leu<br>100                                105                         110 | 336 |
| ctc tcc gtg tcc gag tac aag aag aag tac cgg gag cac gtg ctg cag<br>Leu Ser Val Ser Glu Tyr Lys Lys Lys Tyr Arg Glu His Val Leu Gln<br>              115                       120                     125 | 384 |
| ctg cac gct cgg gtg aag gag agg aac gcc cgc tcc gtg aag atc acc<br>Leu His Ala Arg Val Lys Glu Arg Asn Ala Arg Ser Val Lys Ile Thr<br>130                                135                         140 | 432 |
| aag cgc ttc acc aag ctg ctc atc gcg ccc gag agc gcc gcc ccg gag<br>Lys Arg Phe Thr Lys Leu Leu Ile Ala Pro Glu Ser Ala Ala Pro Glu<br>145                                150                     155                     160 | 480 |
| gag gcg ctg ggg ccc gcg gaa gag cct gag ccg ggg cgc gcg cgg cgc<br>Glu Ala Leu Gly Pro Ala Glu Glu Pro Glu Pro Gly Arg Ala Arg Arg<br>                       165                       170                     175 | 528 |
| tcg gac acg cac act ttc aac cgc ctc ttc cgc cgc gac gag gag ggc<br>Ser Asp Thr His Thr Phe Asn Arg Leu Phe Arg Arg Asp Glu Glu Gly<br>                   180                       185                     190 | 576 |
| cgg cgg ccg ctg acc gtg gtg ctg cag ggc ccg gcg ggc atc ggc aag<br>Arg Arg Pro Leu Thr Val Val Leu Gln Gly Pro Ala Gly Ile Gly Lys<br>                       195                       200                     205 | 624 |
| acc atg gcg gcc aaa aag atc ctg tac gac tgg gcg gcg ggc aag ctg<br>Thr Met Ala Ala Lys Lys Ile Leu Tyr Asp Trp Ala Ala Gly Lys Leu<br>210                                215                     220 | 672 |
| tac cag ggc cag gtg gac ttc gcc ttc ttc atg ccc tgc ggc gag ctg<br>Tyr Gln Gly Gln Val Asp Phe Ala Phe Phe Met Pro Cys Gly Glu Leu<br>225                                230                     235                     240 | 720 |
| ctg gag agg ccg ggc acg cgc agc ctg gct gac ctg atc ctg gac cag<br>Leu Glu Arg Pro Gly Thr Arg Ser Leu Ala Asp Leu Ile Leu Asp Gln<br>                             245                     250                     255 | 768 |
| tgc ccc gac cgc ggc gcg ccg gtg ccg cag atg ctg gcc cag ccg cag<br>Cys Pro Asp Arg Gly Ala Pro Val Pro Gln Met Leu Ala Gln Pro Gln<br>                   260                       265                     270 | 816 |
| cgg ctg ctc ttc atc ctg gac ggc gcg gac gag ctg ccg gcg ctg ggg<br>Arg Leu Leu Phe Ile Leu Asp Gly Ala Asp Glu Leu Pro Ala Leu Gly<br>                       275                       280                     285 | 864 |
| ggc ccc gag gcc gcg ccc tgc aca gac ccc ttc gag gcg gcg agc ggc<br>Gly Pro Glu Ala Ala Pro Cys Thr Asp Pro Phe Glu Ala Ala Ser Gly<br>290                                295                     300 | 912 |
| gcg cgg gtg cta ggc ggg ctg ctg agc aag gcg ctg ctg ccc acg gcc<br>Ala Arg Val Leu Gly Gly Leu Leu Ser Lys Ala Leu Leu Pro Thr Ala<br>305                                310                     315                     320 | 960 |
| ctc ctg ctg gtg acc acg cgc gcc gcc gcc ccc ggg agg ctg cag ggc<br>Leu Leu Leu Val Thr Thr Arg Ala Ala Ala Pro Gly Arg Leu Gln Gly<br>                       325                       330                     335 | 1008 |
| cgc ctg tgt tcc ccg cag tgc gcc gag gtg cgc ggc ttc tcc gac aag<br>Arg Leu Cys Ser Pro Gln Cys Ala Glu Val Arg Gly Phe Ser Asp Lys<br>                       340                       345                     350 | 1056 |
| gac aag aag aag tat ttc tac aag ttc ttc cgg gat gag agg agg gcc<br>Asp Lys Lys Lys Tyr Phe Tyr Lys Phe Phe Arg Asp Glu Arg Arg Ala<br>                   355                       360                     365 | 1104 |
| gag cgc gcc tac cgc ttc gtg aag gag aac gag acg ctg ttc gcg ctg<br>Glu Arg Ala Tyr Arg Phe Val Lys Glu Asn Glu Thr Leu Phe Ala Leu<br>370                                375                     380 | 1152 |
| tgc ttc gtg ccc ttc gtg tgc tgg atc gtg tgc acc gtg ctg cgc cag<br>Cys Phe Val Pro Phe Val Cys Trp Ile Val Cys Thr Val Leu Arg Gln<br>385                                390                     395                     400 | 1200 |
| cag ctg gag ctc ggt cgg gac ctg tcg cgc acg tcc aag acc acc acg<br>Gln Leu Glu Leu Gly Arg Asp Leu Ser Arg Thr Ser Lys Thr Thr Thr | 1248 |

-continued

| | | | |
|---|---|---|---|
| | 405 | 410 | 415 |
| tca gtg tac ctg ctt ttc atc acc agc gtt ctg agc tcg gct ccg gta<br>Ser Val Tyr Leu Leu Phe Ile Thr Ser Val Leu Ser Ser Ala Pro Val<br>420         425         430 | | | 1296 |
| gcc gac ggg ccc cgg ttg cag ggc gac ctg cgc aat ctg tgc cgc ctg<br>Ala Asp Gly Pro Arg Leu Gln Gly Asp Leu Arg Asn Leu Cys Arg Leu<br>435         440         445 | | | 1344 |
| gcc cgc gag ggt gtc ctc gga cgc agg gcg cag ttt gcc gag aag gaa<br>Ala Arg Glu Gly Val Leu Gly Arg Arg Ala Gln Phe Ala Glu Lys Glu<br>450         455         460 | | | 1392 |
| ctg gag caa ctg gag ctt cgt ggc tcc aaa gtg cag acg ctg ttt ctc<br>Leu Glu Gln Leu Glu Leu Arg Gly Ser Lys Val Gln Thr Leu Phe Leu<br>465         470         475         480 | | | 1440 |
| agc aaa aag gag ctg ccg ggc gtg ctg gag aca gag gtc acc tac cag<br>Ser Lys Lys Glu Leu Pro Gly Val Leu Glu Thr Glu Val Thr Tyr Gln<br>485         490         495 | | | 1488 |
| ttc atc gac cag agc ttc cag gag ttc ctc gcg gca ctg tcc tac ctg<br>Phe Ile Asp Gln Ser Phe Gln Glu Phe Leu Ala Ala Leu Ser Tyr Leu<br>500         505         510 | | | 1536 |
| ctg gag gac ggc ggg gtg ccc agg acc gcg gct ggc ggc gtt ggg aca<br>Leu Glu Asp Gly Gly Val Pro Arg Thr Ala Ala Gly Gly Val Gly Thr<br>515         520         525 | | | 1584 |
| ctc ctg cgt ggg gac gcc cag ccg cac agc cac ttg gtg ctc acc acg<br>Leu Leu Arg Gly Asp Ala Gln Pro His Ser His Leu Val Leu Thr Thr<br>530         535         540 | | | 1632 |
| cgc ttc ctc ttc gga ctg ctg agc gcg gag cgg atg cgc gac atc gag<br>Arg Phe Leu Phe Gly Leu Leu Ser Ala Glu Arg Met Arg Asp Ile Glu<br>545         550         555         560 | | | 1680 |
| cgc cac ttc ggc tgc atg gtt tca gag cgt gtg aag cag gag gcc ctg<br>Arg His Phe Gly Cys Met Val Ser Glu Arg Val Lys Gln Glu Ala Leu<br>565         570         575 | | | 1728 |
| cgg tgg gtg cag gga cag gga cag ggc tgc ccc gga gtg gca cca gag<br>Arg Trp Val Gln Gly Gln Gly Gln Gly Cys Pro Gly Val Ala Pro Glu<br>580         585         590 | | | 1776 |
| gtg acc gag ggg gcc aaa ggg ctc gag gac acc gaa gag cca gag gag<br>Val Thr Glu Gly Ala Lys Gly Leu Glu Asp Thr Glu Glu Pro Glu Glu<br>595         600         605 | | | 1824 |
| gag gag gag gga gag gag ccc aac tac cca ctg gag ttg ctg tac tgc<br>Glu Glu Glu Gly Glu Glu Pro Asn Tyr Pro Leu Glu Leu Leu Tyr Cys<br>610         615         620 | | | 1872 |
| ctg tac gag acg cag gag gac gcg ttt gtg cgc caa gcc ctg tgc cgg<br>Leu Tyr Glu Thr Gln Glu Asp Ala Phe Val Arg Gln Ala Leu Cys Arg<br>625         630         635         640 | | | 1920 |
| ttc ccg gag ctg gcg ctg cag cga gtg cgc ttc tgc cgc atg gac gtg<br>Phe Pro Glu Leu Ala Leu Gln Arg Val Arg Phe Cys Arg Met Asp Val<br>645         650         655 | | | 1968 |
| gct gtt ctg agc tac tgc gtg agg tgc tgc cct gct gga cag gca ctg<br>Ala Val Leu Ser Tyr Cys Val Arg Cys Cys Pro Ala Gly Gln Ala Leu<br>660         665         670 | | | 2016 |
| cgg ctg atc agc tgc aga ttg gtt gct gcg cag gag aag aag aag aag<br>Arg Leu Ile Ser Cys Arg Leu Val Ala Ala Gln Glu Lys Lys Lys Lys<br>675         680         685 | | | 2064 |
| agc ctg ggg aag cgg ctc cag gcc agc ctg ggt ggc ggc agc tgg ctg<br>Ser Leu Gly Lys Arg Leu Gln Ala Ser Leu Gly Gly Gly Ser Trp Leu<br>690         695         700 | | | 2112 |
| ggg acc caa ctg gct cca gaa gta ccc ttt cga cca ccc tgc tgt gac<br>Gly Thr Gln Leu Ala Pro Glu Val Pro Phe Arg Pro Pro Cys Cys Asp<br>705         710         715         720 | | | 2160 |
| atc tgc ccc aca cct cca cca gac cct cgg ctc ctc cag ggc aag gct | | | 2208 |

```
Ile Cys Pro Thr Pro Pro Asp Pro Arg Leu Leu Gln Gly Lys Ala
            725             730             735 ttt gcc aga gtt cct ttg aat ata gct cca att cag ccc ctg ccc agg    2256
Phe Ala Arg Val Pro Leu Asn Ile Ala Pro Ile Gln Pro Leu Pro Arg
        740             745             750 ggc ttg gca tct gtt gag agg atg aat gtc acg gtg ttg gca ggg gct    2304
Gly Leu Ala Ser Val Glu Arg Met Asn Val Thr Val Leu Ala Gly Ala
            755             760             765 ggg cct ggg gac cca aag acc cat gca atg act gac cca ctg tgc cat    2352
Gly Pro Gly Asp Pro Lys Thr His Ala Met Thr Asp Pro Leu Cys His
        770             775             780 ctg agc agc ctc acg ctg tcc cac tgc aaa ctc cct gac gcg gtc tgc    2400
Leu Ser Ser Leu Thr Leu Ser His Cys Lys Leu Pro Asp Ala Val Cys
785             790             795             800 cga gac ctt tct gag gcc ctg agg gca gcc ccc gca ctg acg gag ctg    2448
Arg Asp Leu Ser Glu Ala Leu Arg Ala Ala Pro Ala Leu Thr Glu Leu
                805             810             815 ggc ctc ctc cac aac agg ctc agt gag gca gga ctg cgt atg ctg agt    2496
Gly Leu Leu His Asn Arg Leu Ser Glu Ala Gly Leu Arg Met Leu Ser
            820             825             830 gag ggc cta gcc tgg ccg cag tgc agg gtg cag acg gtc agg gta cag    2544
Glu Gly Leu Ala Trp Pro Gln Cys Arg Val Gln Thr Val Arg Val Gln
        835             840             845 ctg cct gac ccc cag cga ggg ctc cag tac ctg gtg ggt atg ctt cgg    2592
Leu Pro Asp Pro Gln Arg Gly Leu Gln Tyr Leu Val Gly Met Leu Arg
    850             855             860 cag agc cct gcc ctg acc acc ctg gat ctc agc ggc tgc caa ctg ccc    2640
Gln Ser Pro Ala Leu Thr Thr Leu Asp Leu Ser Gly Cys Gln Leu Pro
865             870             875             880 gcc ccc atg gtg acc tac ctg tgt gca gtc ctg cag cac cag gga tgc    2688
Ala Pro Met Val Thr Tyr Leu Cys Ala Val Leu Gln His Gln Gly Cys
                885             890             895 ggc ctg cag acc ctc agt ctg gcc tct gtg gag ctg agc gag cag tca    2736
Gly Leu Gln Thr Leu Ser Leu Ala Ser Val Glu Leu Ser Glu Gln Ser
            900             905             910 cta cag gag ctt cag gct gtg aag aga gca aag ccg gat ctg gtc atc    2784
Leu Gln Glu Leu Gln Ala Val Lys Arg Ala Lys Pro Asp Leu Val Ile
        915             920             925 aca cac cca gcg ctg gac ggc cac cca caa cct ccc aag gaa ctc atc    2832
Thr His Pro Ala Leu Asp Gly His Pro Gln Pro Pro Lys Glu Leu Ile
    930             935             940 tcg acc ttc tga                                                    2844
Ser Thr Phe
945

<210> SEQ ID NO 18
<211> LENGTH: 947
<212> TYPE: PRT
<213> ORGANISM: Homo sapien

<400> SEQUENCE: 18

Met Asp Gln Pro Glu Ala Pro Cys Ser Ser Thr Gly Pro Arg Leu Ala
1               5                   10                  15

Val Ala Arg Glu Leu Leu Leu Ala Ala Leu Glu Glu Leu Ser Gln Glu
            20                  25                  30

Gln Leu Lys Arg Phe Arg His Lys Leu Arg Asp Val Gly Pro Asp Gly
        35                  40                  45

Arg Ser Ile Pro Trp Gly Arg Leu Glu Arg Ala Asp Ala Val Asp Leu
    50                  55                  60
```

-continued

```
Ala Glu Gln Leu Ala Gln Phe Tyr Gly Pro Glu Pro Ala Leu Glu Val
 65                  70                  75                  80

Ala Arg Lys Thr Leu Lys Arg Ala Asp Ala Arg Asp Val Ala Ala Gln
                 85                  90                  95

Leu Gln Glu Arg Arg Leu Gln Arg Leu Gly Leu Gly Ser Gly Thr Leu
            100                 105                 110

Leu Ser Val Ser Glu Tyr Lys Lys Lys Tyr Arg Glu His Val Leu Gln
        115                 120                 125

Leu His Ala Arg Val Lys Glu Arg Asn Ala Arg Ser Val Lys Ile Thr
    130                 135                 140

Lys Arg Phe Thr Lys Leu Leu Ile Ala Pro Glu Ser Ala Ala Pro Glu
145                 150                 155                 160

Glu Ala Leu Gly Pro Ala Glu Glu Pro Glu Pro Gly Arg Ala Arg Arg
                165                 170                 175

Ser Asp Thr His Thr Phe Asn Arg Leu Phe Arg Arg Asp Glu Glu Gly
            180                 185                 190

Arg Arg Pro Leu Thr Val Val Leu Gln Gly Pro Ala Gly Ile Gly Lys
        195                 200                 205

Thr Met Ala Ala Lys Lys Ile Leu Tyr Asp Trp Ala Ala Gly Lys Leu
    210                 215                 220

Tyr Gln Gly Gln Val Asp Phe Ala Phe Phe Met Pro Cys Gly Glu Leu
225                 230                 235                 240

Leu Glu Arg Pro Gly Thr Arg Ser Leu Ala Asp Leu Ile Leu Asp Gln
                245                 250                 255

Cys Pro Asp Arg Gly Ala Pro Val Pro Gln Met Leu Ala Gln Pro Gln
            260                 265                 270

Arg Leu Leu Phe Ile Leu Asp Gly Ala Asp Glu Leu Pro Ala Leu Gly
        275                 280                 285

Gly Pro Glu Ala Ala Pro Cys Thr Asp Pro Phe Glu Ala Ala Ser Gly
    290                 295                 300

Ala Arg Val Leu Gly Gly Leu Leu Ser Lys Ala Leu Leu Pro Thr Ala
305                 310                 315                 320

Leu Leu Leu Val Thr Thr Arg Ala Ala Ala Pro Gly Arg Leu Gln Gly
                325                 330                 335

Arg Leu Cys Ser Pro Gln Cys Ala Glu Val Arg Gly Phe Ser Asp Lys
            340                 345                 350

Asp Lys Lys Lys Tyr Phe Tyr Lys Phe Phe Arg Asp Glu Arg Arg Ala
        355                 360                 365

Glu Arg Ala Tyr Arg Phe Val Lys Glu Asn Glu Thr Leu Phe Ala Leu
    370                 375                 380

Cys Phe Val Pro Phe Val Cys Trp Ile Val Cys Thr Val Leu Arg Gln
385                 390                 395                 400

Gln Leu Glu Leu Gly Arg Asp Leu Ser Arg Thr Ser Lys Thr Thr Thr
                405                 410                 415

Ser Val Tyr Leu Leu Phe Ile Thr Ser Val Leu Ser Ser Ala Pro Val
            420                 425                 430

Ala Asp Gly Pro Arg Leu Gln Gly Asp Leu Arg Asn Leu Cys Arg Leu
        435                 440                 445

Ala Arg Glu Gly Val Leu Gly Arg Arg Ala Gln Phe Ala Glu Lys Glu
    450                 455                 460

Leu Glu Gln Leu Glu Leu Arg Gly Ser Lys Val Gln Thr Leu Phe Leu
465                 470                 475                 480

Ser Lys Lys Glu Leu Pro Gly Val Leu Glu Thr Glu Val Thr Tyr Gln
```

```
                485                 490                 495
Phe Ile Asp Gln Ser Phe Gln Glu Phe Leu Ala Ala Leu Ser Tyr Leu
            500                 505                 510

Leu Glu Asp Gly Gly Val Pro Arg Thr Ala Ala Gly Gly Val Gly Thr
            515                 520                 525

Leu Leu Arg Gly Asp Ala Gln Pro His Ser His Leu Val Leu Thr Thr
            530                 535                 540

Arg Phe Leu Phe Gly Leu Leu Ser Ala Glu Arg Met Arg Asp Ile Glu
545                 550                 555                 560

Arg His Phe Gly Cys Met Val Ser Glu Arg Val Lys Gln Glu Ala Leu
            565                 570                 575

Arg Trp Val Gln Gly Gln Gly Gln Cys Pro Gly Val Ala Pro Glu
            580                 585                 590

Val Thr Glu Gly Ala Lys Gly Leu Glu Asp Thr Glu Glu Pro Glu Glu
            595                 600                 605

Glu Glu Glu Gly Glu Glu Pro Asn Tyr Pro Leu Glu Leu Leu Tyr Cys
            610                 615                 620

Leu Tyr Glu Thr Gln Glu Asp Ala Phe Val Arg Gln Ala Leu Cys Arg
625                 630                 635                 640

Phe Pro Glu Leu Ala Leu Gln Arg Val Arg Phe Cys Arg Met Asp Val
            645                 650                 655

Ala Val Leu Ser Tyr Cys Val Arg Cys Cys Pro Ala Gly Gln Ala Leu
            660                 665                 670

Arg Leu Ile Ser Cys Arg Leu Val Ala Ala Gln Glu Lys Lys Lys Lys
            675                 680                 685

Ser Leu Gly Lys Arg Leu Gln Ala Ser Leu Gly Gly Gly Ser Trp Leu
            690                 695                 700

Gly Thr Gln Leu Ala Pro Glu Val Pro Phe Arg Pro Pro Cys Cys Asp
705                 710                 715                 720

Ile Cys Pro Thr Pro Pro Asp Pro Arg Leu Leu Gln Gly Lys Ala
            725                 730                 735

Phe Ala Arg Val Pro Leu Asn Ile Ala Pro Ile Gln Pro Leu Pro Arg
            740                 745                 750

Gly Leu Ala Ser Val Glu Arg Met Asn Val Thr Val Leu Ala Gly Ala
            755                 760                 765

Gly Pro Gly Asp Pro Lys Thr His Ala Met Thr Asp Pro Leu Cys His
            770                 775                 780

Leu Ser Ser Leu Thr Leu Ser His Cys Lys Leu Pro Asp Ala Val Cys
785                 790                 795                 800

Arg Asp Leu Ser Glu Ala Leu Arg Ala Ala Pro Ala Leu Thr Glu Leu
            805                 810                 815

Gly Leu Leu His Asn Arg Leu Ser Glu Ala Gly Leu Arg Met Leu Ser
            820                 825                 830

Glu Gly Leu Ala Trp Pro Gln Cys Arg Val Gln Thr Val Arg Val Gln
            835                 840                 845

Leu Pro Asp Pro Gln Arg Gly Leu Gln Tyr Leu Val Gly Met Leu Arg
            850                 855                 860

Gln Ser Pro Ala Leu Thr Thr Leu Asp Leu Ser Gly Cys Gln Leu Pro
865                 870                 875                 880

Ala Pro Met Val Thr Tyr Leu Cys Ala Val Leu Gln His Gln Gly Cys
            885                 890                 895

Gly Leu Gln Thr Leu Ser Leu Ala Ser Val Glu Leu Ser Glu Gln Ser
            900                 905                 910
```

```
             Leu Gln Glu Leu Gln Ala Val Lys Arg Ala Lys Pro Asp Leu Val Ile
                         915                 920                 925

Thr His Pro Ala Leu Asp Gly His Pro Gln Pro Pro Lys Glu Leu Ile
             930                 935                 940

Ser Thr Phe
             945

<210> SEQ ID NO 19
<211> LENGTH: 2046
<212> TYPE: DNA
<213> ORGANISM: Homo sapien
<220> FEATURE:
<221> NAME/KEY: CDS
<222> LOCATION: (1)...(2043)

<400> SEQUENCE: 19 atg agt gac gtg aat cca ccc tct gac acc ccc att ccc ttt tca tcc      48
Met Ser Asp Val Asn Pro Pro Ser Asp Thr Pro Ile Pro Phe Ser Ser
 1               5                  10                  15 tcc tcc act cac agt tct cat att ccg ccc tgg aca ttc tct tgc tac      96
Ser Ser Thr His Ser Ser His Ile Pro Pro Trp Thr Phe Ser Cys Tyr
             20                  25                  30 ccc ggc tcc cca tgt gaa aat ggg gtc atg ctg tac atg aga aac gtg     144
Pro Gly Ser Pro Cys Glu Asn Gly Val Met Leu Tyr Met Arg Asn Val
         35                  40                  45 agc cat gag gag cta caa cgg ttc aag cag ctc tta ctg act gag ctc     192
Ser His Glu Glu Leu Gln Arg Phe Lys Gln Leu Leu Leu Thr Glu Leu
     50                  55                  60 agt act ggc acc atg ccc atc acc tgg gac cag gtc gag aca gcc agc     240
Ser Thr Gly Thr Met Pro Ile Thr Trp Asp Gln Val Glu Thr Ala Ser
 65                  70                  75                  80 tgg gca gag gtg gtt cat ctc ttg ata gag cgt ttc cct gga cga cgc     288
Trp Ala Glu Val Val His Leu Leu Ile Glu Arg Phe Pro Gly Arg Arg
                 85                  90                  95 gct tgg gat gtg act tcg aac atc ttt gcc att atg aac tgt gat aaa     336
Ala Trp Asp Val Thr Ser Asn Ile Phe Ala Ile Met Asn Cys Asp Lys
            100                 105                 110 atg tgt gtt gta gtc cgc aga gag ata aat gcc att ctg cct acc ttg     384
Met Cys Val Val Val Arg Arg Glu Ile Asn Ala Ile Leu Pro Thr Leu
        115                 120                 125 gaa cca gag gac ttg aat gtg gga gaa aca cag gtg aat ctg gag gaa     432
Glu Pro Glu Asp Leu Asn Val Gly Glu Thr Gln Val Asn Leu Glu Glu
    130                 135                 140 gga gaa tct ggt aaa ata cgg cgg tat aaa tcg aat gtg atg gaa aag     480
Gly Glu Ser Gly Lys Ile Arg Arg Tyr Lys Ser Asn Val Met Glu Lys
145                 150                 155                 160 ttt ttc ccc ata tgg gac att acg act tgg cct gga aac cag agg gac     528
Phe Phe Pro Ile Trp Asp Ile Thr Thr Trp Pro Gly Asn Gln Arg Asp
                165                 170                 175 ttc ttc tac caa ggt gta cac agg cac gag gag tac tta cca tgt ctg     576
Phe Phe Tyr Gln Gly Val His Arg His Glu Glu Tyr Leu Pro Cys Leu
            180                 185                 190 ctt ctg ccc aaa aga ccc cag ggt aga cag ccc aag acc gtg gcc ata     624
Leu Leu Pro Lys Arg Pro Gln Gly Arg Gln Pro Lys Thr Val Ala Ile
        195                 200                 205 cag gga gct cct ggg atc gga aaa aca atc ctg gcc aaa aag gtg atg     672
Gln Gly Ala Pro Gly Ile Gly Lys Thr Ile Leu Ala Lys Lys Val Met
    210                 215                 220 ttt gag tgg gcc aga aac aag ttc tac gcc cac aag cgc tgg tgt gct     720
Phe Glu Trp Ala Arg Asn Lys Phe Tyr Ala His Lys Arg Trp Cys Ala
```

-continued

```
                225                 230                 235                 240
ttc tac ttc cat tgc caa gag gtg aac cag acg aca gac cag agc ttc    768
Phe Tyr Phe His Cys Gln Glu Val Asn Gln Thr Thr Asp Gln Ser Phe
            245                 250                 255 tcc gag ctg att gag caa aag tgg cct gga tct cag gac ctc gtg tca    816
Ser Glu Leu Ile Glu Gln Lys Trp Pro Gly Ser Gln Asp Leu Val Ser
        260                 265                 270 aag att atg tcc aaa ccc gac caa ctt ctg ctg ctc ttg gat ggc ttt    864
Lys Ile Met Ser Lys Pro Asp Gln Leu Leu Leu Leu Leu Asp Gly Phe
    275                 280                 285 gag gag ctc aca tct acc ctc att gac aga ctg gag gac ctg agt gaa    912
Glu Glu Leu Thr Ser Thr Leu Ile Asp Arg Leu Glu Asp Leu Ser Glu
290                 295                 300 gac tgg agg cag aaa ttg cct ggg tct gtc cta ctg agc agt ttg ctg    960
Asp Trp Arg Gln Lys Leu Pro Gly Ser Val Leu Leu Ser Ser Leu Leu
305                 310                 315                 320 agc aaa acg atg ctt cca gag gcc acg cta ctg atc atg ata aga ttt   1008
Ser Lys Thr Met Leu Pro Glu Ala Thr Leu Leu Ile Met Ile Arg Phe
                325                 330                 335 acc tct tgg cag aca tgc aag ccc ttg ctg aaa tgt ccc tct ctc gta   1056
Thr Ser Trp Gln Thr Cys Lys Pro Leu Leu Lys Cys Pro Ser Leu Val
            340                 345                 350 acc ctt ccg ggg ttt aat acg atg gaa aaa atc aag tat ttc cag atg   1104
Thr Leu Pro Gly Phe Asn Thr Met Glu Lys Ile Lys Tyr Phe Gln Met
        355                 360                 365 tat ttt gga cac aca gag gag gga gac caa gtc ttg agt ttc gcc atg   1152
Tyr Phe Gly His Thr Glu Glu Gly Asp Gln Val Leu Ser Phe Ala Met
    370                 375                 380 gaa aac acc att ctc ttc tcc atg tgc cgg gtc cct gtg gtt tgc tgg   1200
Glu Asn Thr Ile Leu Phe Ser Met Cys Arg Val Pro Val Val Cys Trp
385                 390                 395                 400 atg gtc tgc tct ggt ctg aaa cag caa atg gag aga gga aac aat ctc   1248
Met Val Cys Ser Gly Leu Lys Gln Gln Met Glu Arg Gly Asn Asn Leu
                405                 410                 415 aca cag tca tgt cca aat gcc acc tct gtg ttc gtc cgg tat att tct   1296
Thr Gln Ser Cys Pro Asn Ala Thr Ser Val Phe Val Arg Tyr Ile Ser
            420                 425                 430 agc ttg ttt ccc acc aga gct gag aac ttt tcc aga aag atc cac caa   1344
Ser Leu Phe Pro Thr Arg Ala Glu Asn Phe Ser Arg Lys Ile His Gln
        435                 440                 445 gca caa ctg gaa ggt ctg tgt cac ttg gcc gca gac agc atg tgg cac   1392
Ala Gln Leu Glu Gly Leu Cys His Leu Ala Ala Asp Ser Met Trp His
    450                 455                 460 agg aaa tgg gtg tta ggt aaa gaa gat ctt gag gaa gcc aag ctg gat   1440
Arg Lys Trp Val Leu Gly Lys Glu Asp Leu Glu Glu Ala Lys Leu Asp
465                 470                 475                 480 cag acg gga gtc acc gcc ttc ctt ggc atg agt att ctt cgg aga att   1488
Gln Thr Gly Val Thr Ala Phe Leu Gly Met Ser Ile Leu Arg Arg Ile
                485                 490                 495 gca ggt gag gaa gac cac tat gtc ttt acc ctc gtg act ttt cag gaa   1536
Ala Gly Glu Glu Asp His Tyr Val Phe Thr Leu Val Thr Phe Gln Glu
            500                 505                 510 ttt ttt gcg gcc ttg ttt tat gtt ctc tgt ttc cca caa aga ctc aaa   1584
Phe Phe Ala Ala Leu Phe Tyr Val Leu Cys Phe Pro Gln Arg Leu Lys
        515                 520                 525 aat ttt cat gtg ttg agc cac gtg aat atc cag cgc ctg ata gcg agt   1632
Asn Phe His Val Leu Ser His Val Asn Ile Gln Arg Leu Ile Ala Ser
    530                 535                 540 ccc aga gga agc aaa agc tat ctc tct cac atg gga ctt ttc tta ttc   1680
```

```
Pro Arg Gly Ser Lys Ser Tyr Leu Ser His Met Gly Leu Phe Leu Phe
545                 550                 555                 560 ggt ttt ctg aac gag gcc tgc gct tcg gcc gtg gaa cag tca ttc caa       1728
Gly Phe Leu Asn Glu Ala Cys Ala Ser Ala Val Glu Gln Ser Phe Gln
                565                 570                 575 tgc aag gtg tct ttc ggt aat aag agg aaa ctg ctg aaa gtc ata cct       1776
Cys Lys Val Ser Phe Gly Asn Lys Arg Lys Leu Leu Lys Val Ile Pro
            580                 585                 590 ctg ttg cat aaa tgt gac cca cct tct ccg ggc agt ggg gtc ccg cag       1824
Leu Leu His Lys Cys Asp Pro Pro Ser Pro Gly Ser Gly Val Pro Gln
        595                 600                 605 tta ttc tac tgt ctg cat gaa atc cgg gag gaa gcc ttt gta agc caa       1872
Leu Phe Tyr Cys Leu His Glu Ile Arg Glu Glu Ala Phe Val Ser Gln
610                 615                 620 gcc cta aat gat tat cat aaa gtt gtc ttg aga att ggc aac aac aaa       1920
Ala Leu Asn Asp Tyr His Lys Val Val Leu Arg Ile Gly Asn Asn Lys
625                 630                 635                 640 gaa gtt caa gtg tct gct ttt tgc ctg aag cgg tgt caa tat ttg cat       1968
Glu Val Gln Val Ser Ala Phe Cys Leu Lys Arg Cys Gln Tyr Leu His
                645                 650                 655 gag gtg gaa ctg acc gtc acc ctg aac ttc atg aac gtg tgg aag ctc       2016
Glu Val Glu Leu Thr Val Thr Leu Asn Phe Met Asn Val Trp Lys Leu
            660                 665                 670 agc tcc agc tcc cat cct ggc tct gag taa                               2046
Ser Ser Ser Ser His Pro Gly Ser Glu
        675                 680

<210> SEQ ID NO 20
<211> LENGTH: 681
<212> TYPE: PRT
<213> ORGANISM: Homo sapien

<400> SEQUENCE: 20

Met Ser Asp Val Asn Pro Pro Ser Asp Thr Pro Ile Pro Phe Ser Ser
1               5                   10                  15

Ser Ser Thr His Ser Ser His Ile Pro Pro Trp Thr Phe Ser Cys Tyr
            20                  25                  30

Pro Gly Ser Pro Cys Glu Asn Gly Val Met Leu Tyr Met Arg Asn Val
        35                  40                  45

Ser His Glu Glu Leu Gln Arg Phe Lys Gln Leu Leu Thr Glu Leu
    50                  55                  60

Ser Thr Gly Thr Met Pro Ile Thr Trp Asp Gln Val Glu Thr Ala Ser
65              70                  75                  80

Trp Ala Glu Val Val His Leu Leu Ile Glu Arg Phe Pro Gly Arg Arg
                85                  90                  95

Ala Trp Asp Val Thr Ser Asn Ile Phe Ala Ile Met Asn Cys Asp Lys
            100                 105                 110

Met Cys Val Val Arg Arg Glu Ile Asn Ala Ile Leu Pro Thr Leu
        115                 120                 125

Glu Pro Glu Asp Leu Asn Val Gly Glu Thr Gln Val Asn Leu Glu Glu
    130                 135                 140

Gly Glu Ser Gly Lys Ile Arg Arg Tyr Lys Ser Asn Val Met Glu Lys
145                 150                 155                 160

Phe Phe Pro Ile Trp Asp Ile Thr Thr Trp Pro Gly Asn Gln Arg Asp
                165                 170                 175

Phe Phe Tyr Gln Gly Val His Arg His Glu Glu Tyr Leu Pro Cys Leu
            180                 185                 190
```

-continued

```
Leu Leu Pro Lys Arg Pro Gln Gly Arg Gln Pro Lys Thr Val Ala Ile
        195                 200                 205
Gln Gly Ala Pro Gly Ile Gly Lys Thr Ile Leu Ala Lys Lys Val Met
210                 215                 220
Phe Glu Trp Ala Arg Asn Lys Phe Tyr Ala His Lys Arg Trp Cys Ala
225                 230                 235                 240
Phe Tyr Phe His Cys Gln Glu Val Asn Gln Thr Thr Asp Gln Ser Phe
                245                 250                 255
Ser Glu Leu Ile Glu Gln Lys Trp Pro Gly Ser Gln Asp Leu Val Ser
            260                 265                 270
Lys Ile Met Ser Lys Pro Asp Gln Leu Leu Leu Leu Leu Asp Gly Phe
        275                 280                 285
Glu Glu Leu Thr Ser Thr Leu Ile Asp Arg Leu Glu Asp Leu Ser Glu
290                 295                 300
Asp Trp Arg Gln Lys Leu Pro Gly Ser Val Leu Ser Ser Leu Leu
305                 310                 315                 320
Ser Lys Thr Met Leu Pro Glu Ala Thr Leu Leu Ile Met Ile Arg Phe
                325                 330                 335
Thr Ser Trp Gln Thr Cys Lys Pro Leu Leu Lys Cys Pro Ser Leu Val
            340                 345                 350
Thr Leu Pro Gly Phe Asn Thr Met Glu Lys Ile Lys Tyr Phe Gln Met
        355                 360                 365
Tyr Phe Gly His Thr Glu Glu Gly Asp Gln Val Leu Ser Phe Ala Met
    370                 375                 380
Glu Asn Thr Ile Leu Phe Ser Met Cys Arg Val Pro Val Val Cys Trp
385                 390                 395                 400
Met Val Cys Ser Gly Leu Lys Gln Gln Met Glu Arg Gly Asn Asn Leu
                405                 410                 415
Thr Gln Ser Cys Pro Asn Ala Thr Ser Val Phe Val Arg Tyr Ile Ser
            420                 425                 430
Ser Leu Phe Pro Thr Arg Ala Glu Asn Phe Ser Arg Lys Ile His Gln
        435                 440                 445
Ala Gln Leu Glu Gly Leu Cys His Leu Ala Ala Asp Ser Met Trp His
    450                 455                 460
Arg Lys Trp Val Leu Gly Lys Glu Asp Leu Glu Glu Ala Lys Leu Asp
465                 470                 475                 480
Gln Thr Gly Val Thr Ala Phe Leu Gly Met Ser Ile Leu Arg Arg Ile
                485                 490                 495
Ala Gly Glu Glu Asp His Tyr Val Phe Thr Leu Val Thr Phe Gln Glu
            500                 505                 510
Phe Phe Ala Ala Leu Phe Tyr Val Leu Cys Phe Pro Gln Arg Leu Lys
        515                 520                 525
Asn Phe His Val Leu Ser His Val Asn Ile Gln Arg Leu Ile Ala Ser
    530                 535                 540
Pro Arg Gly Ser Lys Ser Tyr Leu Ser His Met Gly Leu Phe Leu Phe
545                 550                 555                 560
Gly Phe Leu Asn Glu Ala Cys Ala Ser Ala Val Glu Gln Ser Phe Gln
                565                 570                 575
Cys Lys Val Ser Phe Gly Asn Lys Arg Lys Leu Leu Lys Val Ile Pro
            580                 585                 590
Leu Leu His Lys Cys Asp Pro Pro Ser Pro Gly Ser Gly Val Pro Gln
        595                 600                 605
Leu Phe Tyr Cys Leu His Glu Ile Arg Glu Glu Ala Phe Val Ser Gln
```

```
                     610                 615                 620
Ala Leu Asn Asp Tyr His Lys Val Val Leu Arg Ile Gly Asn Asn Lys
625                 630                 635                 640

Glu Val Gln Val Ser Ala Phe Cys Leu Lys Arg Cys Gln Tyr Leu His
                645                 650                 655

Glu Val Glu Leu Thr Val Thr Leu Asn Phe Met Asn Val Trp Lys Leu
                660                 665                 670

Ser Ser Ser Ser His Pro Gly Ser Glu
            675                 680

<210> SEQ ID NO 21
<211> LENGTH: 1515
<212> TYPE: DNA
<213> ORGANISM: Homo sapien
<220> FEATURE:
<221> NAME/KEY: CDS
<222> LOCATION: (1)...(1512)

<400> SEQUENCE: 21 atg gcc atg gcc aag gcc aga aag ccc cgg gag gca ttg ctc tgg gcc        48
Met Ala Met Ala Lys Ala Arg Lys Pro Arg Glu Ala Leu Leu Trp Ala
 1               5                  10                  15 ttg agt gac ctt gag gag aac gat ttc aag aag tta aag ttc tac tta        96
Leu Ser Asp Leu Glu Glu Asn Asp Phe Lys Lys Leu Lys Phe Tyr Leu
                20                  25                  30 cgg gat atg acc ctg tct gag ggc cag ccc cca ctg gcc aga ggg gag       144
Arg Asp Met Thr Leu Ser Glu Gly Gln Pro Pro Leu Ala Arg Gly Glu
            35                  40                  45 ttg gag ggc ctg att ccg gtg gac ctg gca gaa tta ctg att tca aag       192
Leu Glu Gly Leu Ile Pro Val Asp Leu Ala Glu Leu Leu Ile Ser Lys
        50                  55                  60 tat gga gaa aag gag gct gtg aaa gtt gtc ctc aag ggc ttg aag gtc       240
Tyr Gly Glu Lys Glu Ala Val Lys Val Val Leu Lys Gly Leu Lys Val
65                  70                  75                  80 atg aac ctg ttg gaa ctt gtg gac cag ctc agc cat att tgt ctg cat       288
Met Asn Leu Leu Glu Leu Val Asp Gln Leu Ser His Ile Cys Leu His
                85                  90                  95 ggg gtc ggc tgg cac tgg aaa gac aac tct cgc cag aaa aag gtg ttg       336
Gly Val Gly Trp His Trp Lys Asp Asn Ser Arg Gln Lys Lys Val Leu
            100                 105                 110 gac tgg gcc acc ggt act ctg tac cca ggc cgg ttt gat tat gtc ttt       384
Asp Trp Ala Thr Gly Thr Leu Tyr Pro Gly Arg Phe Asp Tyr Val Phe
        115                 120                 125 tat gta agc tgc aaa gaa gtg gtc ctg ctg ctg gag agc aaa ctg gag       432
Tyr Val Ser Cys Lys Glu Val Val Leu Leu Leu Glu Ser Lys Leu Glu
130                 135                 140 cag ctc ctt ttc tgg tgc tgc ggg gac aat caa gcc cct gtc aca gag       480
Gln Leu Leu Phe Trp Cys Cys Gly Asp Asn Gln Ala Pro Val Thr Glu
145                 150                 155                 160 att ctg agg cag cca gag cgg ctc ctg ttc atc ctg gat ggc ttt gat       528
Ile Leu Arg Gln Pro Glu Arg Leu Leu Phe Ile Leu Asp Gly Phe Asp
                165                 170                 175 gag ctg cag agg ccc ttt gaa gaa aag ttg aag aag agg ggt ttg agt       576
Glu Leu Gln Arg Pro Phe Glu Glu Lys Leu Lys Lys Arg Gly Leu Ser
            180                 185                 190 ccc aag gag agc ctg ctg cac ctt cta att agg aga cat aca ctc ccc       624
Pro Lys Glu Ser Leu Leu His Leu Leu Ile Arg Arg His Thr Leu Pro
        195                 200                 205 acg tgc tcc ctt ctc atc acc acc cgg ccc ctg gct ttg agg aat ctg       672
Thr Cys Ser Leu Leu Ile Thr Thr Arg Pro Leu Ala Leu Arg Asn Leu
```

```
                210                 215                 220
gag ccc ttg ctg aaa caa gca cgt cat gtc cat atc cta ggc ttc tct    720
Glu Pro Leu Leu Lys Gln Ala Arg His Val His Ile Leu Gly Phe Ser
225                 230                 235                 240 gag gag gag agg gcg agg tac ttc agc tcc tat ttc acg gat gag aag    768
Glu Glu Glu Arg Ala Arg Tyr Phe Ser Ser Tyr Phe Thr Asp Glu Lys
                    245                 250                 255 caa gct gac cgt gcc ttc gac att gta cag aaa aat gac att ctc tac    816
Gln Ala Asp Arg Ala Phe Asp Ile Val Gln Lys Asn Asp Ile Leu Tyr
                260                 265                 270 aaa gcg tgt cag gtt cca ggc att tgc tgg gtg gtc tgc tcc tgg ctg    864
Lys Ala Cys Gln Val Pro Gly Ile Cys Trp Val Val Cys Ser Trp Leu
            275                 280                 285 cag ggg cag atg gag aga ggc aaa gtt gtc tta gag aca cct aga aac    912
Gln Gly Gln Met Glu Arg Gly Lys Val Val Leu Glu Thr Pro Arg Asn
        290                 295                 300 agc act gac atc ttc atg gct tac gtc tcc acc ttt ctg ccg ccc gat    960
Ser Thr Asp Ile Phe Met Ala Tyr Val Ser Thr Phe Leu Pro Pro Asp
305                 310                 315                 320 gat gat ggg ggc tgc tcc gag ctt tcc cgg cac agg gtc ctg agg agt   1008
Asp Asp Gly Gly Cys Ser Glu Leu Ser Arg His Arg Val Leu Arg Ser
                    325                 330                 335 ctg tgc tcc cta gca gct gaa ggg att cag cac cag agg ttc cta ttt   1056
Leu Cys Ser Leu Ala Ala Glu Gly Ile Gln His Gln Arg Phe Leu Phe
                340                 345                 350 gaa gaa gct gag ctc agg aaa cat aat tta gat ggc ccc agg ctt gcc   1104
Glu Glu Ala Glu Leu Arg Lys His Asn Leu Asp Gly Pro Arg Leu Ala
            355                 360                 365 gct ttc ctg agt agt aac gac tac caa ttg gga ctt gcc atc aag aag   1152
Ala Phe Leu Ser Ser Asn Asp Tyr Gln Leu Gly Leu Ala Ile Lys Lys
        370                 375                 380 ttc tac agc ttc cgc cac atc agc ttc cag gac ttt ttt cat gcc atg   1200
Phe Tyr Ser Phe Arg His Ile Ser Phe Gln Asp Phe Phe His Ala Met
385                 390                 395                 400 tct tac ctg gtg aaa gag gac caa agc cgg ctg ggg aag gag tcc cgc   1248
Ser Tyr Leu Val Lys Glu Asp Gln Ser Arg Leu Gly Lys Glu Ser Arg
                    405                 410                 415 aga gaa gtg caa agg ctg ctg gag gta aag gag cag gaa ggg aat gat   1296
Arg Glu Val Gln Arg Leu Leu Glu Val Lys Glu Gln Glu Gly Asn Asp
                420                 425                 430 gag atg acc ctc act atg cag ttt tta ctg gac atc tcg aaa aaa gac   1344
Glu Met Thr Leu Thr Met Gln Phe Leu Leu Asp Ile Ser Lys Lys Asp
            435                 440                 445 agc ttc tcg aac ttg gag ctc aag ttc tgc ttc aga att tct ccc tgt   1392
Ser Phe Ser Asn Leu Glu Leu Lys Phe Cys Phe Arg Ile Ser Pro Cys
        450                 455                 460 tta gcg cag gat ctg aag cat ttt aaa gaa cag atg gaa tct atg aag   1440
Leu Ala Gln Asp Leu Lys His Phe Lys Glu Gln Met Glu Ser Met Lys
465                 470                 475                 480 cac aac agg acc tgg gat ttg gaa ttc tcc ctg tat gaa gct aaa ata   1488
His Asn Arg Thr Trp Asp Leu Glu Phe Ser Leu Tyr Glu Ala Lys Ile
                    485                 490                 495 aag aat ctg gta aaa gta ttc aga tga                               1515
Lys Asn Leu Val Lys Val Phe Arg
                500

<210> SEQ ID NO 22
<211> LENGTH: 504
<212> TYPE: PRT
<213> ORGANISM: Homo sapien
```

<400> SEQUENCE: 22

```
Met Ala Met Ala Lys Ala Arg Lys Pro Arg Glu Ala Leu Leu Trp Ala
1               5                   10                  15
Leu Ser Asp Leu Glu Glu Asn Asp Phe Lys Leu Lys Phe Tyr Leu
            20                  25                  30
Arg Asp Met Thr Leu Ser Glu Gly Gln Pro Leu Ala Arg Gly Glu
            35                  40                  45
Leu Glu Gly Leu Ile Pro Val Asp Leu Ala Glu Leu Leu Ile Ser Lys
    50                  55                  60
Tyr Gly Glu Lys Glu Ala Val Lys Val Val Leu Lys Gly Leu Lys Val
65                  70                  75                  80
Met Asn Leu Leu Glu Leu Val Asp Gln Leu Ser His Ile Cys Leu His
                85                  90                  95
Gly Val Gly Trp His Trp Lys Asp Asn Ser Arg Gln Lys Lys Val Leu
            100                 105                 110
Asp Trp Ala Thr Gly Thr Leu Tyr Pro Gly Arg Phe Asp Tyr Val Phe
        115                 120                 125
Tyr Val Ser Cys Lys Glu Val Val Leu Leu Glu Ser Lys Leu Glu
    130                 135                 140
Gln Leu Leu Phe Trp Cys Cys Gly Asp Asn Gln Ala Pro Val Thr Glu
145                 150                 155                 160
Ile Leu Arg Gln Pro Glu Arg Leu Leu Phe Ile Leu Asp Gly Phe Asp
                165                 170                 175
Glu Leu Gln Arg Pro Phe Glu Glu Lys Leu Lys Lys Arg Gly Leu Ser
            180                 185                 190
Pro Lys Glu Ser Leu Leu His Leu Leu Ile Arg Arg His Thr Leu Pro
        195                 200                 205
Thr Cys Ser Leu Leu Ile Thr Thr Arg Pro Leu Ala Leu Arg Asn Leu
    210                 215                 220
Glu Pro Leu Leu Lys Gln Ala Arg His Val His Ile Leu Gly Phe Ser
225                 230                 235                 240
Glu Glu Glu Arg Ala Arg Tyr Phe Ser Ser Tyr Phe Thr Asp Glu Lys
                245                 250                 255
Gln Ala Asp Arg Ala Phe Asp Ile Val Gln Lys Asn Asp Ile Leu Tyr
            260                 265                 270
Lys Ala Cys Gln Val Pro Gly Ile Cys Trp Val Val Cys Ser Trp Leu
        275                 280                 285
Gln Gly Gln Met Glu Arg Gly Lys Val Val Leu Glu Thr Pro Arg Asn
    290                 295                 300
Ser Thr Asp Ile Phe Met Ala Tyr Val Ser Thr Phe Leu Pro Pro Asp
305                 310                 315                 320
Asp Asp Gly Gly Cys Ser Glu Leu Ser Arg His Arg Val Leu Arg Ser
                325                 330                 335
Leu Cys Ser Leu Ala Ala Glu Gly Ile Gln His Gln Arg Phe Leu Phe
            340                 345                 350
Glu Glu Ala Glu Leu Arg Lys His Asn Leu Asp Gly Pro Arg Leu Ala
        355                 360                 365
Ala Phe Leu Ser Ser Asn Asp Tyr Gln Leu Gly Leu Ala Ile Lys Lys
    370                 375                 380
Phe Tyr Ser Phe Arg His Ile Ser Phe Gln Asp Phe Phe His Ala Met
385                 390                 395                 400
Ser Tyr Leu Val Lys Glu Asp Gln Ser Arg Leu Gly Lys Glu Ser Arg
```

```
              405                 410                 415
Arg Glu Val Gln Arg Leu Leu Glu Val Lys Glu Gln Glu Gly Asn Asp
            420                 425                 430

Glu Met Thr Leu Thr Met Gln Phe Leu Leu Asp Ile Ser Lys Lys Asp
            435                 440                 445

Ser Phe Ser Asn Leu Glu Leu Lys Phe Cys Phe Arg Ile Ser Pro Cys
            450                 455                 460

Leu Ala Gln Asp Leu Lys His Phe Lys Glu Gln Met Glu Ser Met Lys
465                 470                 475                 480

His Asn Arg Thr Trp Asp Leu Glu Phe Ser Leu Tyr Glu Ala Lys Ile
                485                 490                 495

Lys Asn Leu Val Lys Val Phe Arg
            500

<210> SEQ ID NO 23
<211> LENGTH: 3108
<212> TYPE: DNA
<213> ORGANISM: Homo sapien
<220> FEATURE:
<221> NAME/KEY: CDS
<222> LOCATION: (1)...(3105)

<400> SEQUENCE: 23 atg cta cga acc gca ggc agg gac ggc ctc tgt cgc ctg tcc acc tac       48
Met Leu Arg Thr Ala Gly Arg Asp Gly Leu Cys Arg Leu Ser Thr Tyr
  1               5                  10                  15 ttg gaa gaa ctc gag gct gtg gaa ctg aag aag ttc aag tta tac ctg       96
Leu Glu Glu Leu Glu Ala Val Glu Leu Lys Lys Phe Lys Leu Tyr Leu
                 20                  25                  30 ggg acc gcg aca gag ctg gga gaa ggc aag atc ccc tgg gga agc atg      144
Gly Thr Ala Thr Glu Leu Gly Glu Gly Lys Ile Pro Trp Gly Ser Met
             35                  40                  45 gag aag gcc ggt ccc ctg gaa atg gcc cag ctg ctc atc acc cac ttc      192
Glu Lys Ala Gly Pro Leu Glu Met Ala Gln Leu Leu Ile Thr His Phe
         50                  55                  60 ggg cca gag gag gcc tgg agg ttg gct ctc agc acc ttt gag cgg ata      240
Gly Pro Glu Glu Ala Trp Arg Leu Ala Leu Ser Thr Phe Glu Arg Ile
 65                  70                  75                  80 aac agg aag gac ctg tgg gag aga gga cag aga gag gac ctg gtg agg      288
Asn Arg Lys Asp Leu Trp Glu Arg Gly Gln Arg Glu Asp Leu Val Arg
                 85                  90                  95 gat ccc cag gaa acc tac agg gac tat gtc cgc agg aaa ttc cgg ctc      336
Asp Pro Gln Glu Thr Tyr Arg Asp Tyr Val Arg Arg Lys Phe Arg Leu
                100                 105                 110 atg gaa gac cgc aat gcg cgc cta ggg gaa tgt gtc aac ctc agc cac      384
Met Glu Asp Arg Asn Ala Arg Leu Gly Glu Cys Val Asn Leu Ser His
            115                 120                 125 cgg tac acc cgg ctc ctg ctg gtg aag gag cac tca aac ccc atg cag      432
Arg Tyr Thr Arg Leu Leu Leu Val Lys Glu His Ser Asn Pro Met Gln
        130                 135                 140 gtc cag cag cag ctt ctg gac aca ggc cgg gga cac gcg agg acc gtg      480
Val Gln Gln Gln Leu Leu Asp Thr Gly Arg Gly His Ala Arg Thr Val
145                 150                 155                 160 gga cac cag gct agc ccc atc aag ata gag acc ctc ttt gag cca gac      528
Gly His Gln Ala Ser Pro Ile Lys Ile Glu Thr Leu Phe Glu Pro Asp
                165                 170                 175 gag gag cgc ccc gag cca ccg cgc acc gtg gtc atg caa ggc gcg gca      576
Glu Glu Arg Pro Glu Pro Pro Arg Thr Val Val Met Gln Gly Ala Ala
            180                 185                 190
```

|  |  |
|---|---|
| ggg ata ggc aag tcc atg ctg gca cac aag gtg atg ctg gac tgg gcg<br>Gly Ile Gly Lys Ser Met Leu Ala His Lys Val Met Leu Asp Trp Ala<br>        195                       200                       205 | 624 |
| gac ggg aag ctc ttc caa ggc aga ttt gat tat ctc ttc tac atc aac<br>Asp Gly Lys Leu Phe Gln Gly Arg Phe Asp Tyr Leu Phe Tyr Ile Asn<br>210                       215                     220 | 672 |
| tgc agg gag atg aac cag agt gcc acg gaa tgc agc atg caa gac ctc<br>Cys Arg Glu Met Asn Gln Ser Ala Thr Glu Cys Ser Met Gln Asp Leu<br>225                   230                     235                 240 | 720 |
| atc ttc agc tgc tgg cct gag ccc agc gcg cct ctc cag gag ctc atc<br>Ile Phe Ser Cys Trp Pro Glu Pro Ser Ala Pro Leu Gln Glu Leu Ile<br>                       245                     250                     255 | 768 |
| cga gtt ccc gag cgc ctc ctt ttc atc atc gac ggc ttc gat gag ctc<br>Arg Val Pro Glu Arg Leu Leu Phe Ile Ile Asp Gly Phe Asp Glu Leu<br>                 260                     265                     270 | 816 |
| aag cct tct ttc cac gat cct cag gga ccc tgg tgc ctc tgc tgg gag<br>Lys Pro Ser Phe His Asp Pro Gln Gly Pro Trp Cys Leu Cys Trp Glu<br>                       275                     280                     285 | 864 |
| gag aaa cgg ccc acg gag ctg ctt ctt aac agc tta att cgg aag aag<br>Glu Lys Arg Pro Thr Glu Leu Leu Leu Asn Ser Leu Ile Arg Lys Lys<br>               290                     295                     300 | 912 |
| ctg ctc cct gag cta tct ttg ctc atc acc aca cgg ccc acg gct ttg<br>Leu Leu Pro Glu Leu Ser Leu Leu Ile Thr Thr Arg Pro Thr Ala Leu<br>305                   310                     315                 320 | 960 |
| gag aag ctc cac cgt ctg ctg gag cac ccc agg cat gtg gag atc ctg<br>Glu Lys Leu His Arg Leu Leu Glu His Pro Arg His Val Glu Ile Leu<br>                       325                     330                     335 | 1008 |
| ggc ttc tct gag gca gaa agg aag gaa tac ttc tac aag tat ttc cac<br>Gly Phe Ser Glu Ala Glu Arg Lys Glu Tyr Phe Tyr Lys Tyr Phe His<br>                       340                     345                     350 | 1056 |
| aat gca gag cag gcg ggc caa gtc ttc aat tac gtg agg gac aac gag<br>Asn Ala Glu Gln Ala Gly Gln Val Phe Asn Tyr Val Arg Asp Asn Glu<br>                       355                     360                     365 | 1104 |
| cct ctc ttc acc atg tgc ttc gtc ccc ctg gtg tgc tgg gtg gtg tgt<br>Pro Leu Phe Thr Met Cys Phe Val Pro Leu Val Cys Trp Val Val Cys<br>                       370                     375                     380 | 1152 |
| acc tgc ctc cag cag cag ctg gag ggt ggg ggg ctg ttg aga cag acg<br>Thr Cys Leu Gln Gln Gln Leu Glu Gly Gly Gly Leu Leu Arg Gln Thr<br>385                   390                     395                     400 | 1200 |
| tcc agg acc acc act gca gtg tac atg ctc tac ctg ctg agt ctg atg<br>Ser Arg Thr Thr Thr Ala Val Tyr Met Leu Tyr Leu Leu Ser Leu Met<br>                       405                     410                     415 | 1248 |
| caa ccc aag ccg ggg gcc ccg cgc ctc cag ccc cca ccc aac cag aga<br>Gln Pro Lys Pro Gly Ala Pro Arg Leu Gln Pro Pro Pro Asn Gln Arg<br>                       420                     425                     430 | 1296 |
| ggg ttg tgc tcc ttg gcg gca gat ggg ctc tgg aat cag aaa atc cta<br>Gly Leu Cys Ser Leu Ala Ala Asp Gly Leu Trp Asn Gln Lys Ile Leu<br>                       435                     440                     445 | 1344 |
| ttt gag gag cag gac ctc cgg aag cac ggc cta gac ggg gaa gac gtc<br>Phe Glu Glu Gln Asp Leu Arg Lys His Gly Leu Asp Gly Glu Asp Val<br>450                   455                     460 | 1392 |
| tct gcc ttc ctc aac atg aac atc ttc cag aag gac atc aac tgt gag<br>Ser Ala Phe Leu Asn Met Asn Ile Phe Gln Lys Asp Ile Asn Cys Glu<br>465                   470                     475                 480 | 1440 |
| agg tac tac agc ttc atc cac ttg agt ttc cag gaa ttc ttt gca gct<br>Arg Tyr Tyr Ser Phe Ile His Leu Ser Phe Gln Glu Phe Phe Ala Ala<br>                       485                     490                     495 | 1488 |
| atg tac tat atc ctg gac gag ggg gag ggc ggg gca ggc cca gac cag<br>Met Tyr Tyr Ile Leu Asp Glu Gly Glu Gly Gly Ala Gly Pro Asp Gln<br>                       500                     505                     510 | 1536 |

-continued

| | |
|---|---|
| gac gtg acc agg ctg ttg acc gag tac gcg ttt tct gaa agg agc ttc<br>Asp Val Thr Arg Leu Leu Thr Glu Tyr Ala Phe Ser Glu Arg Ser Phe<br>515                   520                   525 | 1584 |
| ctg gca ctc acc agc cgc ttc ctg ttt gga ctc ctg aac gag gag acc<br>Leu Ala Leu Thr Ser Arg Phe Leu Phe Gly Leu Leu Asn Glu Glu Thr<br>530                   535                   540 | 1632 |
| agg agc cac ctg gag aag agt ctc tgc tgg aag gtc tcg ccg cac atc<br>Arg Ser His Leu Glu Lys Ser Leu Cys Trp Lys Val Ser Pro His Ile<br>545                   550                   555                   560 | 1680 |
| aag atg gac ctg ttg cag tgg atc caa agc aaa gct cag agc gac ggc<br>Lys Met Asp Leu Leu Gln Trp Ile Gln Ser Lys Ala Gln Ser Asp Gly<br>                 565                   570                   575 | 1728 |
| tcc acc ctg cag cag ggc tcc ttg gag ttc ttc agc tgc ttg tac gag<br>Ser Thr Leu Gln Gln Gly Ser Leu Glu Phe Phe Ser Cys Leu Tyr Glu<br>            580                   585                   590 | 1776 |
| atc cag gag gag gag ttt atc cag cag gcc ctg agc cac ttc cag gtg<br>Ile Gln Glu Glu Glu Phe Ile Gln Gln Ala Leu Ser His Phe Gln Val<br>                 595                   600                   605 | 1824 |
| atc gtg gtc agc aac att gcc tcc aag atg gag cac atg gtc tcc tcg<br>Ile Val Val Ser Asn Ile Ala Ser Lys Met Glu His Met Val Ser Ser<br>610                   615                   620 | 1872 |
| ttc tgt ctg aag cgc tgc agg agc gcc cag gtg ctg cac ttg tat ggc<br>Phe Cys Leu Lys Arg Cys Arg Ser Ala Gln Val Leu His Leu Tyr Gly<br>625                   630                   635                   640 | 1920 |
| gcc acc tac agc gcg gac ggg gaa gac cgc gcg agg tgc tcc gca gga<br>Ala Thr Tyr Ser Ala Asp Gly Glu Asp Arg Ala Arg Cys Ser Ala Gly<br>                 645                   650                   655 | 1968 |
| gcg cac acg ctg ttg gtg cag ctc aga cca gag agg acc gtt ctg ctg<br>Ala His Thr Leu Leu Val Gln Leu Arg Pro Glu Arg Thr Val Leu Leu<br>660                   665                   670 | 2016 |
| gac gcc tac agt gaa cat ctg gca gcg gcc ctg tgc acc aat cca aac<br>Asp Ala Tyr Ser Glu His Leu Ala Ala Ala Leu Cys Thr Asn Pro Asn<br>675                   680                   685 | 2064 |
| ctg ata gag ctg tct ctg tac cga aat gcc ctg ggc agc cgg ggg gtg<br>Leu Ile Glu Leu Ser Leu Tyr Arg Asn Ala Leu Gly Ser Arg Gly Val<br>690                   695                   700 | 2112 |
| aag ctg ctc tgt caa gga ctc aga cac ccc aac tgc aaa ctt cag aac<br>Lys Leu Leu Cys Gln Gly Leu Arg His Pro Asn Cys Lys Leu Gln Asn<br>705                   710                   715                   720 | 2160 |
| ctg agg ctg aag agg tgc cgc atc tcc agc tca gcc tgc gag gac ctc<br>Leu Arg Leu Lys Arg Cys Arg Ile Ser Ser Ser Ala Cys Glu Asp Leu<br>                 725                   730                   735 | 2208 |
| tct gca gct ctc ata gcc aat aag aat ttg aca agg atg gat ctc agt<br>Ser Ala Ala Leu Ile Ala Asn Lys Asn Leu Thr Arg Met Asp Leu Ser<br>            740                   745                   750 | 2256 |
| ggc aac ggc gtt gga ttc cca ggc atg atg ctg ctt tgc gag ggc ctg<br>Gly Asn Gly Val Gly Phe Pro Gly Met Met Leu Leu Cys Glu Gly Leu<br>                 755                   760                   765 | 2304 |
| cgg cat ccc cag tgc agg ctg cag atg att cag ttg agg aag tgt cag<br>Arg His Pro Gln Cys Arg Leu Gln Met Ile Gln Leu Arg Lys Cys Gln<br>770                   775                   780 | 2352 |
| ctg gag tcc ggg gct tgt cag gag atg gct tct gtg ctc ggc acc aac<br>Leu Glu Ser Gly Ala Cys Gln Glu Met Ala Ser Val Leu Gly Thr Asn<br>785                   790                   795                   800 | 2400 |
| cca cat ctg gtt gag ttg gac ctg aca gga aat gca ctg gag gat ttg<br>Pro His Leu Val Glu Leu Asp Leu Thr Gly Asn Ala Leu Glu Asp Leu<br>                 805                   810                   815 | 2448 |
| ggc ctg agg tta cta tgc cag gga ctg agg cac cca gtc tgc aga cta<br>Gly Leu Arg Leu Leu Cys Gln Gly Leu Arg His Pro Val Cys Arg Leu | 2496 |

-continued

```
                        820                 825                 830
cgg act ttg tgg ctg aag atc tgc cgc ctc act gct gct gcc tgt gac      2544
Arg Thr Leu Trp Leu Lys Ile Cys Arg Leu Thr Ala Ala Ala Cys Asp
            835                 840                 845 gag ctg gcc tca act ctc agt gtg aac cag agc ctg aga gag ctg gac      2592
Glu Leu Ala Ser Thr Leu Ser Val Asn Gln Ser Leu Arg Glu Leu Asp
        850                 855                 860 ctg agc ctg aat gag ctg ggg gac ctc ggg gtg ctg ctg tgt gag          2640
Leu Ser Leu Asn Glu Leu Gly Asp Leu Gly Val Leu Leu Cys Glu
865                 870                 875                 880 ggc ctc agg cat ccc acg tgc aag ctc cag acc ctg cgg ttg ggc atc      2688
Gly Leu Arg His Pro Thr Cys Lys Leu Gln Thr Leu Arg Leu Gly Ile
                885                 890                 895 tgc cgg ctg ggc tct gcc gcc tgt gag ggt ctt tct gtg gtg ctc cag      2736
Cys Arg Leu Gly Ser Ala Ala Cys Glu Gly Leu Ser Val Val Leu Gln
            900                 905                 910 gcc aac cac aac ctc cgg gag ctg gac ttg agt ttc aac gac ctg gga      2784
Ala Asn His Asn Leu Arg Glu Leu Asp Leu Ser Phe Asn Asp Leu Gly
        915                 920                 925 gac tgg ggc ctg tgg ttg ctg gct gag ggg ctg caa cat ccc gcc tgc      2832
Asp Trp Gly Leu Trp Leu Leu Ala Glu Gly Leu Gln His Pro Ala Cys
    930                 935                 940 aga ctc cag aaa ctg tgg ctg gat agc tgt ggc ctc aca gcc aag gct      2880
Arg Leu Gln Lys Leu Trp Leu Asp Ser Cys Gly Leu Thr Ala Lys Ala
945                 950                 955                 960 tgt gag aat ctt tac ttc acc ctg ggg atc aac cag acc ttg acc gac      2928
Cys Glu Asn Leu Tyr Phe Thr Leu Gly Ile Asn Gln Thr Leu Thr Asp
                965                 970                 975 ctt tac ctg acc aac aac gcc cta ggg gac aca ggt gtc cga ctg ctt      2976
Leu Tyr Leu Thr Asn Asn Ala Leu Gly Asp Thr Gly Val Arg Leu Leu
            980                 985                 990 tgc aag cgg ctg agc cat cct ggc tgc aaa ctc cga gtc ctc tgg tta      3024
Cys Lys Arg Leu Ser His Pro Gly Cys Lys Leu Arg Val Leu Trp Leu
        995                 1000                1005 ttt ggg atg gac ctg aat aaa atg acc cac agt agg ttg gca gcg ctt      3072
Phe Gly Met Asp Leu Asn Lys Met Thr His Ser Arg Leu Ala Ala Leu
    1010                1015                1020 cga gta aca aaa cct tat ttg gac att ggc tgc tga                      3108
Arg Val Thr Lys Pro Tyr Leu Asp Ile Gly Cys
1025                1030                1035

<210> SEQ ID NO 24
<211> LENGTH: 1035
<212> TYPE: PRT
<213> ORGANISM: Homo sapien

<400> SEQUENCE: 24

Met Leu Arg Thr Ala Gly Arg Asp Gly Leu Cys Arg Leu Ser Thr Tyr
1               5                   10                  15

Leu Glu Glu Leu Glu Ala Val Glu Leu Lys Lys Phe Lys Leu Tyr Leu
            20                  25                  30

Gly Thr Ala Thr Glu Leu Gly Glu Gly Lys Ile Pro Trp Gly Ser Met
        35                  40                  45

Glu Lys Ala Gly Pro Leu Glu Met Ala Gln Leu Leu Ile Thr His Phe
    50                  55                  60

Gly Pro Glu Glu Ala Trp Arg Leu Ala Leu Ser Thr Phe Glu Arg Ile
65                  70                  75                  80

Asn Arg Lys Asp Leu Trp Glu Arg Gly Gln Arg Glu Asp Leu Val Arg
                85                  90                  95
```

```
Asp Pro Gln Glu Thr Tyr Arg Asp Tyr Val Arg Arg Lys Phe Arg Leu
            100                 105                 110

Met Glu Asp Arg Asn Ala Arg Leu Gly Glu Cys Val Asn Leu Ser His
        115                 120                 125

Arg Tyr Thr Arg Leu Leu Val Lys Glu His Ser Asn Pro Met Gln
    130                 135                 140

Val Gln Gln Leu Leu Asp Thr Gly Arg Gly His Ala Arg Thr Val
145                 150                 155                 160

Gly His Gln Ala Ser Pro Ile Lys Ile Glu Thr Leu Phe Glu Pro Asp
                165                 170                 175

Glu Glu Arg Pro Glu Pro Pro Arg Thr Val Met Gln Gly Ala Ala
            180                 185                 190

Gly Ile Gly Lys Ser Met Leu Ala His Lys Val Met Leu Asp Trp Ala
                195                 200                 205

Asp Gly Lys Leu Phe Gln Gly Arg Phe Asp Tyr Leu Phe Tyr Ile Asn
        210                 215                 220

Cys Arg Glu Met Asn Gln Ser Ala Thr Glu Cys Ser Met Gln Asp Leu
225                 230                 235                 240

Ile Phe Ser Cys Trp Pro Glu Pro Ser Ala Pro Leu Gln Glu Leu Ile
                245                 250                 255

Arg Val Pro Glu Arg Leu Leu Phe Ile Ile Asp Gly Phe Asp Glu Leu
            260                 265                 270

Lys Pro Ser Phe His Asp Pro Gln Gly Pro Trp Cys Leu Cys Trp Glu
        275                 280                 285

Glu Lys Arg Pro Thr Glu Leu Leu Asn Ser Leu Ile Arg Lys Lys
            290                 295                 300

Leu Leu Pro Glu Leu Ser Leu Leu Ile Thr Thr Arg Pro Thr Ala Leu
305                 310                 315                 320

Glu Lys Leu His Arg Leu Leu Glu His Pro Arg His Val Glu Ile Leu
                325                 330                 335

Gly Phe Ser Glu Ala Glu Arg Lys Glu Tyr Phe Tyr Lys Tyr Phe His
        340                 345                 350

Asn Ala Glu Gln Ala Gly Gln Val Phe Asn Tyr Val Arg Asp Asn Glu
        355                 360                 365

Pro Leu Phe Thr Met Cys Phe Val Pro Leu Val Cys Trp Val Val Cys
    370                 375                 380

Thr Cys Leu Gln Gln Leu Glu Gly Gly Leu Leu Arg Gln Thr
385                 390                 395                 400

Ser Arg Thr Thr Thr Ala Val Tyr Met Leu Tyr Leu Leu Ser Leu Met
            405                 410                 415

Gln Pro Lys Pro Gly Ala Pro Arg Leu Gln Pro Pro Asn Gln Arg
        420                 425                 430

Gly Leu Cys Ser Leu Ala Ala Asp Gly Leu Trp Asn Gln Lys Ile Leu
        435                 440                 445

Phe Glu Glu Gln Asp Leu Arg Lys His Gly Leu Asp Gly Glu Asp Val
    450                 455                 460

Ser Ala Phe Leu Asn Met Asn Ile Phe Gln Lys Asp Ile Asn Cys Glu
465                 470                 475                 480

Arg Tyr Tyr Ser Phe Ile His Leu Ser Phe Gln Glu Phe Phe Ala Ala
            485                 490                 495

Met Tyr Tyr Ile Leu Asp Glu Gly Glu Gly Gly Ala Gly Pro Asp Gln
        500                 505                 510
```

-continued

```
Asp Val Thr Arg Leu Leu Thr Glu Tyr Ala Phe Ser Glu Arg Ser Phe
        515                 520                 525

Leu Ala Leu Thr Ser Arg Phe Leu Phe Gly Leu Leu Asn Glu Glu Thr
        530                 535                 540

Arg Ser His Leu Glu Lys Ser Leu Cys Trp Lys Val Ser Pro His Ile
545                 550                 555                 560

Lys Met Asp Leu Leu Gln Trp Ile Gln Ser Lys Ala Gln Ser Asp Gly
                565                 570                 575

Ser Thr Leu Gln Gln Gly Ser Leu Glu Phe Phe Ser Cys Leu Tyr Glu
        580                 585                 590

Ile Gln Glu Glu Glu Phe Ile Gln Gln Ala Leu Ser His Phe Gln Val
        595                 600                 605

Ile Val Val Ser Asn Ile Ala Ser Lys Met Glu His Met Val Ser Ser
        610                 615                 620

Phe Cys Leu Lys Arg Cys Arg Ser Ala Gln Val Leu His Leu Tyr Gly
625                 630                 635                 640

Ala Thr Tyr Ser Ala Asp Gly Glu Asp Arg Ala Arg Cys Ser Ala Gly
                645                 650                 655

Ala His Thr Leu Leu Val Gln Leu Arg Pro Glu Arg Thr Val Leu Leu
        660                 665                 670

Asp Ala Tyr Ser Glu His Leu Ala Ala Leu Cys Thr Asn Pro Asn
        675                 680                 685

Leu Ile Glu Leu Ser Leu Tyr Arg Asn Ala Leu Gly Ser Arg Gly Val
        690                 695                 700

Lys Leu Leu Cys Gln Gly Leu Arg His Pro Asn Cys Lys Leu Gln Asn
705                 710                 715                 720

Leu Arg Leu Lys Arg Cys Arg Ile Ser Ser Ala Cys Glu Asp Leu
                725                 730                 735

Ser Ala Ala Leu Ile Ala Asn Lys Asn Leu Thr Arg Met Asp Leu Ser
                740                 745                 750

Gly Asn Gly Val Gly Phe Pro Gly Met Met Leu Leu Cys Glu Gly Leu
        755                 760                 765

Arg His Pro Gln Cys Arg Leu Gln Met Ile Gln Leu Arg Lys Cys Gln
        770                 775                 780

Leu Glu Ser Gly Ala Cys Gln Glu Met Ala Ser Val Leu Gly Thr Asn
785                 790                 795                 800

Pro His Leu Val Glu Leu Asp Leu Thr Gly Asn Ala Leu Glu Asp Leu
                805                 810                 815

Gly Leu Arg Leu Leu Cys Gln Gly Leu Arg His Pro Val Cys Arg Leu
        820                 825                 830

Arg Thr Leu Trp Leu Lys Ile Cys Arg Leu Thr Ala Ala Ala Cys Asp
        835                 840                 845

Glu Leu Ala Ser Thr Leu Ser Val Asn Gln Ser Leu Arg Glu Leu Asp
850                 855                 860

Leu Ser Leu Asn Glu Leu Gly Asp Leu Gly Val Leu Leu Leu Cys Glu
865                 870                 875                 880

Gly Leu Arg His Pro Thr Cys Lys Leu Gln Thr Leu Arg Leu Gly Ile
                885                 890                 895

Cys Arg Leu Gly Ser Ala Ala Cys Glu Gly Leu Ser Val Val Leu Gln
                900                 905                 910

Ala Asn His Asn Leu Arg Glu Leu Asp Leu Ser Phe Asn Asp Leu Gly
        915                 920                 925

Asp Trp Gly Leu Trp Leu Leu Ala Glu Gly Leu Gln His Pro Ala Cys
```

```
                    930                 935                 940
Arg Leu Gln Lys Leu Trp Leu Asp Ser Cys Gly Leu Thr Ala Lys Ala
945                 950                 955                 960

Cys Glu Asn Leu Tyr Phe Thr Leu Gly Ile Asn Gln Thr Leu Thr Asp
                    965                 970                 975

Leu Tyr Leu Thr Asn Asn Ala Leu Gly Asp Thr Gly Val Arg Leu Leu
                980                 985                 990

Cys Lys Arg Leu Ser His Pro Gly Cys Lys Leu Arg Val Leu Trp Leu
            995                1000                1005

Phe Gly Met Asp Leu Asn Lys Met Thr His Ser Arg Leu Ala Ala Leu
       1010                1015                1020

Arg Val Thr Lys Pro Tyr Leu Asp Ile Gly Cys
1025                1030                1035

<210> SEQ ID NO 25
<211> LENGTH: 243
<212> TYPE: DNA
<213> ORGANISM: Homo sapien
<220> FEATURE:
<221> NAME/KEY: CDS
<222> LOCATION: (1)...(243)

<400> SEQUENCE: 25 atg gca agc acc cgc tgc aag ctg gcc agg tac ctg gag gac ctg gag      48
Met Ala Ser Thr Arg Cys Lys Leu Ala Arg Tyr Leu Glu Asp Leu Glu
 1               5                  10                  15 gat gtg gac ttg aag aaa ttt aag atg cac tta gag gac tat cct ccc      96
Asp Val Asp Leu Lys Lys Phe Lys Met His Leu Glu Asp Tyr Pro Pro
             20                  25                  30 cag aag ggc tgc atc ccc ctc ccg agg ggt cag aca gag aag gca gac     144
Gln Lys Gly Cys Ile Pro Leu Pro Arg Gly Gln Thr Glu Lys Ala Asp
         35                  40                  45 cat gtg gat cta gcc acg cta atg atc gac ttc aat ggg gag gag aag     192
His Val Asp Leu Ala Thr Leu Met Ile Asp Phe Asn Gly Glu Glu Lys
     50                  55                  60 gcg tgg gcc atg gtc gtg tgg atc ttc gct gcg atc aac agg aga gac     240
Ala Trp Ala Met Val Val Trp Ile Phe Ala Ala Ile Asn Arg Arg Asp
 65                  70                  75                  80 ctt                                                                 243
Leu

<210> SEQ ID NO 26
<211> LENGTH: 81
<212> TYPE: PRT
<213> ORGANISM: Homo sapien

<400> SEQUENCE: 26

Met Ala Ser Thr Arg Cys Lys Leu Ala Arg Tyr Leu Glu Asp Leu Glu
 1               5                  10                  15

Asp Val Asp Leu Lys Lys Phe Lys Met His Leu Glu Asp Tyr Pro Pro
             20                  25                  30

Gln Lys Gly Cys Ile Pro Leu Pro Arg Gly Gln Thr Glu Lys Ala Asp
         35                  40                  45

His Val Asp Leu Ala Thr Leu Met Ile Asp Phe Asn Gly Glu Glu Lys
     50                  55                  60

Ala Trp Ala Met Val Val Trp Ile Phe Ala Ala Ile Asn Arg Arg Asp
 65                  70                  75                  80

Leu
```

```
<210> SEQ ID NO 27
<211> LENGTH: 270
<212> TYPE: DNA
<213> ORGANISM: Homo sapien
<220> FEATURE:
<221> NAME/KEY: CDS
<222> LOCATION: (1)...(267)

<400> SEQUENCE: 27 atg gga acg aag cgc gag gcc atc ctg aag gtg ctg gag aac ctg aca      48
Met Gly Thr Lys Arg Glu Ala Ile Leu Lys Val Leu Glu Asn Leu Thr
  1               5                  10                  15 ccg gag gag ctc aag aag ttc aag atg aag ctg ggg acg gtg ccg ctg      96
Pro Glu Glu Leu Lys Lys Phe Lys Met Lys Leu Gly Thr Val Pro Leu
             20                  25                  30 cgc gag ggc ttt gag cgc atc ccg cgg ggc gcg ctc ggg cag cta gat     144
Arg Glu Gly Phe Glu Arg Ile Pro Arg Gly Ala Leu Gly Gln Leu Asp
         35                  40                  45 atc gtg gac ctc acc gac aag ctg gtc gcc tcc tac tac gag gac tac     192
Ile Val Asp Leu Thr Asp Lys Leu Val Ala Ser Tyr Tyr Glu Asp Tyr
     50                  55                  60 gca gcc gag ctc gtc gtg gcc gtg ctg cgc gac atg cgc atg ttg gag     240
Ala Ala Glu Leu Val Val Ala Val Leu Arg Asp Met Arg Met Leu Glu
 65                  70                  75                  80 gag gcc gca cgg ctg cag cgg gct gcg tga                             270
Glu Ala Ala Arg Leu Gln Arg Ala Ala
                 85

<210> SEQ ID NO 28
<211> LENGTH: 89
<212> TYPE: PRT
<213> ORGANISM: Homo sapien

<400> SEQUENCE: 28

Met Gly Thr Lys Arg Glu Ala Ile Leu Lys Val Leu Glu Asn Leu Thr
  1               5                  10                  15

Pro Glu Glu Leu Lys Lys Phe Lys Met Lys Leu Gly Thr Val Pro Leu
             20                  25                  30

Arg Glu Gly Phe Glu Arg Ile Pro Arg Gly Ala Leu Gly Gln Leu Asp
         35                  40                  45

Ile Val Asp Leu Thr Asp Lys Leu Val Ala Ser Tyr Tyr Glu Asp Tyr
     50                  55                  60

Ala Ala Glu Leu Val Val Ala Val Leu Arg Asp Met Arg Met Leu Glu
 65                  70                  75                  80

Glu Ala Ala Arg Leu Gln Arg Ala Ala
                 85

<210> SEQ ID NO 29
<211> LENGTH: 6
<212> TYPE: PRT
<213> ORGANISM: Homo sapien
<220> FEATURE:
<221> NAME/KEY: VARIANT
<222> LOCATION: (4)...(5)
<223> OTHER INFORMATION: Xaa=any amino acid

<400> SEQUENCE: 29

Lys Phe Lys Xaa Xaa Leu
  1               5

<210> SEQ ID NO 30
<211> LENGTH: 6
```

```
<212> TYPE: PRT
<213> ORGANISM: Homo sapien
<220> FEATURE:
<221> NAME/KEY: VARIANT
<222> LOCATION: (4)...(5)
<223> OTHER INFORMATION: Xaa=any amino acid

<400> SEQUENCE: 30

Lys Leu Lys Xaa Xaa Leu
1               5

<210> SEQ ID NO 31
<211> LENGTH: 6
<212> TYPE: PRT
<213> ORGANISM: Homo sapien
<220> FEATURE:
<221> NAME/KEY: VARIANT
<222> LOCATION: (4)...(5)
<223> OTHER INFORMATION: Xaa=any amino acid

<400> SEQUENCE: 31

Arg Phe Arg Xaa Xaa Leu
1               5

<210> SEQ ID NO 32
<211> LENGTH: 6
<212> TYPE: PRT
<213> ORGANISM: Homo sapien
<220> FEATURE:
<221> NAME/KEY: VARIANT
<222> LOCATION: (4)...(5)
<223> OTHER INFORMATION: Xaa=any amino acid

<400> SEQUENCE: 32

Arg Phe Lys Xaa Xaa Leu
1               5

<210> SEQ ID NO 33
<211> LENGTH: 6
<212> TYPE: PRT
<213> ORGANISM: Homo sapien
<220> FEATURE:
<221> NAME/KEY: VARIANT
<222> LOCATION: (4)...(5)
<223> OTHER INFORMATION: Xaa=any amino acid

<400> SEQUENCE: 33

Lys Phe Arg Xaa Xaa Leu
1               5

<210> SEQ ID NO 34
<211> LENGTH: 6
<212> TYPE: PRT
<213> ORGANISM: Homo sapien
<220> FEATURE:
<221> NAME/KEY: VARIANT
<222> LOCATION: (4)...(5)
<223> OTHER INFORMATION: Xaa=any amino acid

<400> SEQUENCE: 34

Lys Phe Lys Xaa Xaa Ile
1               5

<210> SEQ ID NO 35
<211> LENGTH: 39
<212> TYPE: DNA
<213> ORGANISM: Artificial Sequence
<220> FEATURE:
<223> OTHER INFORMATION: synthetic primer
```

<400> SEQUENCE: 35
ccggaattca ccatggcagc ctctttcttc tctgatttt        39

<210> SEQ ID NO 36
<211> LENGTH: 41
<212> TYPE: DNA
<213> ORGANISM: Artificial Sequence
<220> FEATURE:
<223> OTHER INFORMATION: synthetic primer

<400> SEQUENCE: 36
ccgctcgagt cacgtagagc tgtgttcatc ctctttctta a     41

<210> SEQ ID NO 37
<211> LENGTH: 319
<212> TYPE: PRT
<213> ORGANISM: Homo sapiens

<400> SEQUENCE: 37

```
Gln Pro Arg Thr Val Ile Ile Gln Gly Pro Gln Gly Ile Gly Lys Thr
 1               5                  10                  15

Thr Leu Leu Met Lys Leu Met Met Ala Trp Ser Asp Asn Lys Ile Phe
            20                  25                  30

Arg Asp Arg Phe Leu Tyr Thr Phe Tyr Phe Cys Cys Arg Glu Leu Arg
        35                  40                  45

Glu Leu Pro Pro Thr Ser Leu Ala Asp Leu Ile Ser Arg Glu Trp Pro
    50                  55                  60

Asp Pro Ala Ala Pro Ile Thr Glu Ile Val Ser Gln Pro Glu Arg Leu
65                  70                  75                  80

Leu Phe Val Ile Asp Ser Phe Glu Glu Leu Gln Gly Gly Leu Asn Glu
                85                  90                  95

Pro Asp Ser Asp Leu Cys Gly Asp Leu Met Glu Lys Arg Pro Val Gln
            100                 105                 110

Val Leu Leu Ser Ser Leu Leu Arg Lys Lys Met Leu Pro Glu Ala Ser
        115                 120                 125

Leu Leu Ile Ala Ile Lys Pro Val Cys Pro Lys Glu Leu Arg Asp Gln
    130                 135                 140

Val Thr Ile Ser Glu Ile Tyr Gln Pro Arg Gly Phe Asn Glu Ser Asp
145                 150                 155                 160

Arg Leu Val Tyr Phe Cys Cys Phe Phe Lys Asp Pro Lys Arg Ala Met
                165                 170                 175

Glu Ala Phe Asn Leu Val Arg Glu Ser Glu Gln Leu Phe Ser Ile Cys
            180                 185                 190

Gln Ile Pro Leu Leu Cys Trp Ile Leu Cys Thr Ser Leu Lys Gln Glu
        195                 200                 205

Met Gln Lys Gly Lys Asp Leu Ala Leu Thr Cys Gln Ser Thr Thr Ser
    210                 215                 220

Val Tyr Ser Ser Phe Val Phe Asn Leu Phe Thr Pro Glu Gly Ala Glu
225                 230                 235                 240

Gly Pro Thr Pro Gln Thr Gln His Gln Leu Lys Ala Leu Cys Ser Leu
                245                 250                 255

Ala Ala Glu Gly Met Trp Thr Asp Thr Phe Glu Phe Cys Glu Asp Asp
            260                 265                 270

Leu Arg Arg Asn Gly Val Val Asp Ala Asp Ile Pro Ala Leu Leu Gly
        275                 280                 285
```

```
Thr Lys Ile Leu Leu Lys Tyr Gly Glu Arg Glu Ser Ser Tyr Val Phe
    290                 295                 300

Leu His Val Cys Ile Gln Glu Phe Cys Ala Ala Leu Phe Tyr Leu
305                 310                 315
```

<210> SEQ ID NO 38
<211> LENGTH: 270
<212> TYPE: PRT
<213> ORGANISM: Homo sapiens

<400> SEQUENCE: 38

```
Ser Ile Cys Gln Ile Pro Leu Cys Trp Ile Leu Cys Thr Ser Leu
1               5                   10                  15

Lys Gln Glu Met Gln Lys Gly Lys Asp Leu Ala Leu Thr Cys Gln Ser
                20                  25                  30

Thr Thr Ser Val Tyr Ser Ser Phe Val Phe Asn Leu Phe Thr Pro Glu
            35                  40                  45

Gly Ala Glu Gly Pro Thr Pro Gln Thr Gln His Gln Leu Lys Ala Leu
50                  55                  60

Cys Ser Leu Ala Ala Glu Gly Met Trp Thr Asp Thr Phe Glu Phe Cys
65                  70                  75                  80

Glu Asp Asp Leu Arg Arg Asn Gly Val Val Asp Ala Asp Ile Pro Ala
                85                  90                  95

Leu Leu Gly Thr Lys Ile Leu Lys Tyr Gly Arg Glu Ser Ser
            100                 105                 110

Tyr Val Phe Leu His Val Cys Ile Gln Glu Phe Cys Ala Ala Leu Phe
            115                 120                 125

Tyr Leu Leu Lys Ser His Leu Asp His Pro His Pro Ala Val Arg Cys
130                 135                 140

Val Gln Glu Leu Leu Val Ala Asn Phe Glu Lys Ala Arg Arg Ala His
145                 150                 155                 160

Trp Ile Phe Leu Gly Cys Phe Leu Thr Gly Leu Leu Asn Lys Lys Glu
                165                 170                 175

Gln Glu Lys Leu Asp Ala Phe Phe Gly Phe Gln Leu Ser Gln Glu Ile
            180                 185                 190

Lys Gln Gln Ile His Gln Cys Leu Lys Ser Leu Gly Glu Arg Gly Asn
        195                 200                 205

Pro Gln Gly Gln Val Asp Ser Leu Ala Ile Phe Tyr Cys Leu Phe Glu
210                 215                 220

Met Gln Asp Pro Ala Phe Val Lys Gln Ala Val Asn Leu Leu Gln Glu
225                 230                 235                 240

Ala Asn Phe His Ile Ile Asp Asn Val Asp Leu Val Val Ser Ala Tyr
                245                 250                 255

Cys Leu Lys Tyr Cys Ser Ser Leu Arg Lys Leu Cys Phe Ser
            260                 265                 270
```

<210> SEQ ID NO 39
<211> LENGTH: 375
<212> TYPE: PRT
<213> ORGANISM: Homo sapiens

<400> SEQUENCE: 39

```
Ser Asp Tyr Ser Leu Ile Cys Trp His His Ile Cys Ser Val Leu Thr
1               5                   10                  15

Thr Ser Gly His Leu Arg Glu Leu Gln Val Gln Asp Ser Thr Leu Ser
            20                  25                  30
```

Glu Ser Thr Phe Val Thr Trp Cys Asn Gln Leu Arg His Pro Ser Cys
         35                  40                  45

Arg Leu Gln Lys Leu Gly Ile Asn Asn Val Ser Phe Ser Gly Gln Ser
     50                  55                  60

Val Leu Leu Phe Glu Val Leu Phe Tyr Gln Pro Asp Leu Lys Tyr Leu
65                  70                  75                  80

Ser Phe Thr Leu Thr Lys Leu Ser Arg Asp Asp Ile Arg Ser Leu Cys
             85                  90                  95

Asp Ala Leu Asn Tyr Pro Ala Gly Asn Val Lys Glu Leu Ala Leu Val
            100                 105                 110

Asn Cys His Leu Ser Pro Ile Asp Cys Glu Val Leu Ala Gly Leu Leu
            115                 120                 125

Thr Asn Asn Lys Lys Leu Thr Tyr Leu Asn Val Ser Cys Asn Gln Leu
            130                 135                 140

Asp Thr Gly Val Pro Leu Leu Cys Glu Ala Leu Cys Ser Pro Asp Thr
145                 150                 155                 160

Val Leu Val Tyr Leu Met Leu Ala Phe Cys His Leu Ser Glu Gln Cys
                165                 170                 175

Cys Glu Tyr Ile Ser Glu Met Leu Leu Arg Asn Lys Ser Val Arg Tyr
            180                 185                 190

Leu Asp Leu Ser Ala Asn Val Leu Lys Asp Glu Gly Leu Lys Thr Leu
        195                 200                 205

Cys Glu Ala Leu Lys His Pro Asp Cys Cys Leu Asp Ser Leu Cys Leu
    210                 215                 220

Val Lys Cys Phe Ile Thr Ala Ala Gly Cys Glu Asp Leu Ala Ser Ala
225                 230                 235                 240

Leu Ile Ser Asn Gln Asn Leu Lys Ile Leu Gln Ile Gly Cys Asn Glu
                245                 250                 255

Ile Gly Asp Val Gly Val Gln Leu Leu Cys Arg Ala Leu Thr His Thr
            260                 265                 270

Asp Cys Arg Leu Glu Ile Leu Gly Leu Glu Glu Cys Gly Leu Thr Ser
        275                 280                 285

Thr Cys Cys Lys Asp Leu Ala Ser Val Leu Thr Cys Ser Lys Thr Leu
    290                 295                 300

Gln Gln Leu Asn Leu Thr Leu Asn Thr Leu Asp His Thr Gly Val Val
305                 310                 315                 320

Val Leu Cys Glu Ala Leu Arg His Pro Glu Cys Ala Leu Gln Val Leu
                325                 330                 335

Gly Leu Arg Lys Thr Asp Phe Asp Glu Glu Thr Gln Ala Leu Leu Thr
            340                 345                 350

Ala Glu Glu Glu Arg Asn Pro Asn Leu Thr Ile Thr Asp Asp Cys Asp
            355                 360                 365

Thr Ile Thr Arg Val Glu Ile
            370                 375

<210> SEQ ID NO 40
<211> LENGTH: 38
<212> TYPE: DNA
<213> ORGANISM: Artificial Sequence
<220> FEATURE:
<223> OTHER INFORMATION: synthetic primer

<400> SEQUENCE: 40
cctctcgagt cagatctcta cccttgtgat tgtgtcac                            38

```
<210> SEQ ID NO 41
<211> LENGTH: 24
<212> TYPE: DNA
<213> ORGANISM: Artificial Sequence
<220> FEATURE:
<223> OTHER INFORMATION: synthetic primer

<400> SEQUENCE: 41
gaattcgatc ctggagccat gggg                                          24

<210> SEQ ID NO 42
<211> LENGTH: 24
<212> TYPE: DNA
<213> ORGANISM: Artificial Sequence
<220> FEATURE:
<223> OTHER INFORMATION: synthetic primer

<400> SEQUENCE: 42
ctcgagccgg agtgttgctg ggaa                                          24

<210> SEQ ID NO 43
<211> LENGTH: 24
<212> TYPE: DNA
<213> ORGANISM: Artificial Sequence
<220> FEATURE:
<223> OTHER INFORMATION: synthetic primer

<400> SEQUENCE: 43
gaattcgatc ctggagccat gggg                                          24

<210> SEQ ID NO 44
<211> LENGTH: 24
<212> TYPE: DNA
<213> ORGANISM: Artificial Sequence
<220> FEATURE:
<223> OTHER INFORMATION: synthetic primer

<400> SEQUENCE: 44
ctcgagtcag cttggctgcc gact                                          24

<210> SEQ ID NO 45
<211> LENGTH: 31
<212> TYPE: DNA
<213> ORGANISM: Artificial Sequence
<220> FEATURE:
<223> OTHER INFORMATION: synthetic primer

<400> SEQUENCE: 45 cccccctcgag ggcctggctt ggctgccgac t                                 31

<210> SEQ ID NO 46
<211> LENGTH: 24
<212> TYPE: DNA
<213> ORGANISM: Artificial Sequence
<220> FEATURE:
<223> OTHER INFORMATION: synthetic primer

<400> SEQUENCE: 46
gaattccctc agtcggcagc caag                                          24

<210> SEQ ID NO 47
<211> LENGTH: 24
<212> TYPE: DNA
<213> ORGANISM: Artificial Sequence
<220> FEATURE:
<223> OTHER INFORMATION: synthetic primer
```

```
<400> SEQUENCE: 47
ctcgagccgg agtgttgctg ggaa                                              24

<210> SEQ ID NO 48
<211> LENGTH: 22
<212> TYPE: DNA
<213> ORGANISM: Artificial Sequence
<220> FEATURE:
<223> OTHER INFORMATION: synthetic primer

<400> SEQUENCE: 48
gaattcgagg cgcagggctg tg                                                22

<210> SEQ ID NO 49
<211> LENGTH: 24
<212> TYPE: DNA
<213> ORGANISM: Artificial Sequence
<220> FEATURE:
<223> OTHER INFORMATION: synthetic primer

<400> SEQUENCE: 49
ctcgaggctt cacaggcgtt gcat                                              24

<210> SEQ ID NO 50
<211> LENGTH: 24
<212> TYPE: DNA
<213> ORGANISM: Artificial Sequence
<220> FEATURE:
<223> OTHER INFORMATION: synthetic primer

<400> SEQUENCE: 50
ctcgaggcta cacaggcgtt gcat                                              24

<210> SEQ ID NO 51
<211> LENGTH: 30
<212> TYPE: DNA
<213> ORGANISM: Artificial Sequence
<220> FEATURE:
<223> OTHER INFORMATION: synthetic primer

<400> SEQUENCE: 51
gaattcctct gggccttgag tgaccttgag                                        30

<210> SEQ ID NO 52
<211> LENGTH: 29
<212> TYPE: DNA
<213> ORGANISM: Artificial Sequence
<220> FEATURE:
<223> OTHER INFORMATION: synthetic primer

<400> SEQUENCE: 52
ccagccgacc tcgagcagtc aaatatggc                                         29

<210> SEQ ID NO 53
<211> LENGTH: 21
<212> TYPE: DNA
<213> ORGANISM: Artificial Sequence
<220> FEATURE:
<223> OTHER INFORMATION: synthetic primer

<400> SEQUENCE: 53
ttgctcgagt catctgaata c                                                 21

<210> SEQ ID NO 54
<211> LENGTH: 25
```

```
<212> TYPE: DNA
<213> ORGANISM: Artificial Sequence
<220> FEATURE:
<223> OTHER INFORMATION: synthetic primer

<400> SEQUENCE: 54
atggccatgg ccaaggccag aaagc                                         25

<210> SEQ ID NO 55
<211> LENGTH: 21
<212> TYPE: DNA
<213> ORGANISM: Artificial Sequence
<220> FEATURE:
<223> OTHER INFORMATION: synthetic primer

<400> SEQUENCE: 55
ttgctcgagt catctgaata c                                             21

<210> SEQ ID NO 56
<211> LENGTH: 31
<212> TYPE: DNA
<213> ORGANISM: Artificial Sequence
<220> FEATURE:
<223> OTHER INFORMATION: synthetic primer

<400> SEQUENCE: 56
gacggatcct gtggcatggc cacctacttg g                                  31

<210> SEQ ID NO 57
<211> LENGTH: 29
<212> TYPE: DNA
<213> ORGANISM: Artificial Sequence
<220> FEATURE:
<223> OTHER INFORMATION: synthetic primer

<400> SEQUENCE: 57
atccctcacg aattccctc actgtcctc                                      29

<210> SEQ ID NO 58
<211> LENGTH: 2524
<212> TYPE: DNA
<213> ORGANISM: Homo sapiens
<220> FEATURE:
<221> NAME/KEY: CDS
<222> LOCATION: (176)...(2332)
<220> FEATURE:
<221> NAME/KEY: misc_feature
<222> LOCATION: (306)...(458)
<223> OTHER INFORMATION: n = A,T,C or G

<400> SEQUENCE: 58
ttaaagattt tgacttgtta cagtcatgtg acatttttt  ctttctgttt gctgagtttt    60 tgataaattta tatctctcaa agtggagact ttaaaaaaga ctcatccgtg tgccgtgttc   120
actgcctggt atcttagtgt ggaccgaagc ctaaggaccc tgaaaacagc tgcag atg    178
                                                              Met
                                                               1 aag atg gca agc acc cgc tgc aag ctg gcc agg tac ctg gag gac ctg    226
Lys Met Ala Ser Thr Arg Cys Lys Leu Ala Arg Tyr Leu Glu Asp Leu
        5                  10                  15 gag gat gtg gac ttg aag aaa ttt aag atg cac tta gag gac tat cct    274
Glu Asp Val Asp Leu Lys Lys Phe Lys Met His Leu Glu Asp Tyr Pro
         20                  25                  30 ccc cag aag ggc tgc atc ccc ctc ccg agg gnn nnn nnn nnn nnn nnn    322
Pro Gln Lys Gly Cys Ile Pro Leu Pro Arg Xaa Xaa Xaa Xaa Xaa Xaa
         35                  40                  45
```

-continued

| | | | | | | | | | | | | | | | | |
|---|---|---|---|---|---|---|---|---|---|---|---|---|---|---|---|---|
| nnn | nnn | nnn | nnn | nnn | nnn | nnn | nnn | nnn | nnn | nnn | nnn | nnn | nnn | nnn | nnn | 370 |
| Xaa | Xaa | Xaa | Xaa | Xaa | Xaa | Xaa | Xaa | Xaa | Xaa | Xaa | Xaa | Xaa | Xaa | Xaa | Xaa | |
| 50 | | | | | 55 | | | | | 60 | | | | | 65 | |
| nnn | nnn | nnn | nnn | nnn | nnn | nnn | nnn | nnn | nnn | nnn | nnn | nnn | nnn | nnn | nnn | 418 |
| Xaa | Xaa | Xaa | Xaa | Xaa | Xaa | Xaa | Xaa | Xaa | Xaa | Xaa | Xaa | Xaa | Xaa | Xaa | Xaa | |
| | | 70 | | | | | 75 | | | | | 80 | | | | |
| nnn | nnn | nnn | nnn | nnn | nnn | nnn | nnn | nnn | nnn | nnn | nnn | nnn | nnn | ngt | tca | gat | 466 |
| Xaa | Xaa | Xaa | Xaa | Xaa | Xaa | Xaa | Xaa | Xaa | Xaa | Xaa | Xaa | Xaa | Xaa | Xaa | Ser | Asp | |
| | | | 85 | | | | | 90 | | | | | 95 | | | | |
| aat | gca | cgt | gtt | tcg | aat | ccc | act | gtg | ata | tgc | cag | gaa | gac | agc | att | 514 |
| Asn | Ala | Arg | Val | Ser | Asn | Pro | Thr | Val | Ile | Cys | Gln | Glu | Asp | Ser | Ile | |
| | | 100 | | | | | 105 | | | | | 110 | | | | |
| gaa | gag | gag | tgg | atg | ggt | tta | ctg | gag | tac | ctt | tcg | aga | atc | tct | att | 562 |
| Glu | Glu | Glu | Trp | Met | Gly | Leu | Leu | Glu | Tyr | Leu | Ser | Arg | Ile | Ser | Ile | |
| 115 | | | | | 120 | | | | | 125 | | | | | | |
| tgt | aaa | atg | aag | aaa | gat | tac | cgt | aag | aag | tac | aga | aag | tac | gtg | aga | 610 |
| Cys | Lys | Met | Lys | Lys | Asp | Tyr | Arg | Lys | Lys | Tyr | Arg | Lys | Tyr | Val | Arg | |
| 130 | | | | | 135 | | | | | 140 | | | | | 145 | |
| agc | aga | ttc | cag | tgc | att | gaa | gac | agg | aat | gcc | cgt | ctg | ggt | gag | agt | 658 |
| Ser | Arg | Phe | Gln | Cys | Ile | Glu | Asp | Arg | Asn | Ala | Arg | Leu | Gly | Glu | Ser | |
| | | | | 150 | | | | | 155 | | | | | 160 | | |
| gtg | agc | ctc | aac | aaa | cgc | tac | aca | cga | ctg | cgt | ctc | atc | aag | gag | cac | 706 |
| Val | Ser | Leu | Asn | Lys | Arg | Tyr | Thr | Arg | Leu | Arg | Leu | Ile | Lys | Glu | His | |
| | | | 165 | | | | | 170 | | | | | 175 | | | |
| cgg | agc | cag | cag | gag | agg | gag | cag | gag | ctt | ctg | gcc | atc | ggc | aag | acc | 754 |
| Arg | Ser | Gln | Gln | Glu | Arg | Glu | Gln | Glu | Leu | Leu | Ala | Ile | Gly | Lys | Thr | |
| | | 180 | | | | | 185 | | | | | 190 | | | | |
| aag | acg | tgt | gag | agc | ccc | gtg | agt | ccc | att | aag | atg | gag | ttg | ctg | ttt | 802 |
| Lys | Thr | Cys | Glu | Ser | Pro | Val | Ser | Pro | Ile | Lys | Met | Glu | Leu | Leu | Phe | |
| 195 | | | | | 200 | | | | | 205 | | | | | | |
| gac | ccc | gat | gat | gag | cat | tct | gag | cct | gtg | cac | acc | gtg | gtg | ttc | cag | 850 |
| Asp | Pro | Asp | Asp | Glu | His | Ser | Glu | Pro | Val | His | Thr | Val | Val | Phe | Gln | |
| 210 | | | | | 215 | | | | | 220 | | | | | 225 | |
| ggg | gcg | gca | ggg | att | ggg | aaa | aca | atc | ctg | gcc | agg | aag | atg | atg | ttg | 898 |
| Gly | Ala | Ala | Gly | Ile | Gly | Lys | Thr | Ile | Leu | Ala | Arg | Lys | Met | Met | Leu | |
| | | | 230 | | | | | 235 | | | | | 240 | | | |
| gac | tgg | gcg | tcg | ggg | aca | ctc | tac | caa | gac | agg | ttt | gac | tat | ctg | ttc | 946 |
| Asp | Trp | Ala | Ser | Gly | Thr | Leu | Tyr | Gln | Asp | Arg | Phe | Asp | Tyr | Leu | Phe | |
| | | | 245 | | | | | 250 | | | | | 255 | | | |
| tat | atc | cac | tgt | cga | gag | gtg | agc | ctt | gtg | aca | cag | agg | agc | ctg | ggg | 994 |
| Tyr | Ile | His | Cys | Arg | Glu | Val | Ser | Leu | Val | Thr | Gln | Arg | Ser | Leu | Gly | |
| | | 260 | | | | | 265 | | | | | 270 | | | | |
| gac | ctg | atc | atg | agc | tgc | tgc | ccc | gac | cca | aac | cca | ccc | atc | cac | aag | 1042 |
| Asp | Leu | Ile | Met | Ser | Cys | Cys | Pro | Asp | Pro | Asn | Pro | Pro | Ile | His | Lys | |
| 275 | | | | | 280 | | | | | 285 | | | | | | |
| atc | gtg | aga | aaa | ccc | tcc | aga | atc | ctc | ttc | ctc | atg | gac | ggc | ttc | gat | 1090 |
| Ile | Val | Arg | Lys | Pro | Ser | Arg | Ile | Leu | Phe | Leu | Met | Asp | Gly | Phe | Asp | |
| 290 | | | | | 295 | | | | | 300 | | | | | 305 | |
| gag | ctg | caa | ggt | gcc | ttt | gac | gag | cac | ata | gga | ccg | ctc | tgc | act | gac | 1138 |
| Glu | Leu | Gln | Gly | Ala | Phe | Asp | Glu | His | Ile | Gly | Pro | Leu | Cys | Thr | Asp | |
| | | | | 310 | | | | | 315 | | | | | 320 | | |
| tgg | cag | aag | gcc | gag | cgg | gga | gac | att | ctc | ctg | agc | agc | ctc | atc | aga | 1186 |
| Trp | Gln | Lys | Ala | Glu | Arg | Gly | Asp | Ile | Leu | Leu | Ser | Ser | Leu | Ile | Arg | |
| | | | 325 | | | | | 330 | | | | | 335 | | | |
| aag | aag | ctg | ctt | ccc | gag | gcc | tct | ctg | ctc | atc | acc | acg | aga | cct | gtg | 1234 |
| Lys | Lys | Leu | Leu | Pro | Glu | Ala | Ser | Leu | Leu | Ile | Thr | Thr | Arg | Pro | Val | |
| | | 340 | | | | | 345 | | | | | 350 | | | | |
| gcc | ctg | gag | aaa | ctg | cag | cac | ttg | ctg | gac | cat | cct | cgg | cat | gtg | gag | 1282 |
| Ala | Leu | Glu | Lys | Leu | Gln | His | Leu | Leu | Asp | His | Pro | Arg | His | Val | Glu | |

```
                        355                 360                 365
atc ctg ggt ttc tcc gag gcc aaa agg aaa gag tac ttc ttc aag tac      1330
Ile Leu Gly Phe Ser Glu Ala Lys Arg Lys Glu Tyr Phe Phe Lys Tyr
370                 375                 380                 385 ttc tct gat gag gcc caa gcc agg gca gcc ttc agt ctg att cag gag      1378
Phe Ser Asp Glu Ala Gln Ala Arg Ala Ala Phe Ser Leu Ile Gln Glu
                390                 395                 400 aac gag gtc ctc ttc acc atg tgc ttc atc ccc ctg gtc tgc tgg atc      1426
Asn Glu Val Leu Phe Thr Met Cys Phe Ile Pro Leu Val Cys Trp Ile
            405                 410                 415 gtg tgc act gga ctg aaa cag cag atg gag agt ggc aag agc ctt gcc      1474
Val Cys Thr Gly Leu Lys Gln Gln Met Glu Ser Gly Lys Ser Leu Ala
        420                 425                 430 cag aca tcc aag acc acc acc gcg gtg tac gtc ttc ttc ctt tcc agt      1522
Gln Thr Ser Lys Thr Thr Thr Ala Val Tyr Val Phe Phe Leu Ser Ser
    435                 440                 445 ttg ctg cag ccc cgg gga ggg agc cag gag cac ggc ctc tgc gcc cac      1570
Leu Leu Gln Pro Arg Gly Gly Ser Gln Glu His Gly Leu Cys Ala His
450                 455                 460                 465 ctc tgg ggg ctc tgc tct ttg gct gca gat gga atc tgg aac cag aaa      1618
Leu Trp Gly Leu Cys Ser Leu Ala Ala Asp Gly Ile Trp Asn Gln Lys
                470                 475                 480 atc ctg ttt gag gag tcc gac ctc agg aat cat gga ctg cag aag gcg      1666
Ile Leu Phe Glu Glu Ser Asp Leu Arg Asn His Gly Leu Gln Lys Ala
                485                 490                 495 gat gtg tct gct ttc ctg agg atg aac ctg ttc caa aag gaa gtg gac      1714
Asp Val Ser Ala Phe Leu Arg Met Asn Leu Phe Gln Lys Glu Val Asp
            500                 505                 510 tgc gag aag ttc tac agc ttc atc cac atg act ttc cag gag ttc ttt      1762
Cys Glu Lys Phe Tyr Ser Phe Ile His Met Thr Phe Gln Glu Phe Phe
        515                 520                 525 gcc gcc atg tac tac ctg ctg gaa gag gaa aag gaa gga agg acg aac      1810
Ala Ala Met Tyr Tyr Leu Leu Glu Glu Glu Lys Glu Gly Arg Thr Asn
530                 535                 540                 545 gtt cca ggg agt cgt ttg aag ctt ccc agc cga gac gtg aca gtc ctt      1858
Val Pro Gly Ser Arg Leu Lys Leu Pro Ser Arg Asp Val Thr Val Leu
                550                 555                 560 ctg gaa aac tat ggc aaa ttc gaa aag ggg tat ttg att ttt gtt gta      1906
Leu Glu Asn Tyr Gly Lys Phe Glu Lys Gly Tyr Leu Ile Phe Val Val
                565                 570                 575 cgt ttc ctc ttt ggc ctg gta aac cag gag agg acc tcc tac ttg gag      1954
Arg Phe Leu Phe Gly Leu Val Asn Gln Glu Arg Thr Ser Tyr Leu Glu
            580                 585                 590 aag aaa tta agt tgc aag atc tct cag caa atc agg ctg gag ctg ctg      2002
Lys Lys Leu Ser Cys Lys Ile Ser Gln Gln Ile Arg Leu Glu Leu Leu
        595                 600                 605 aaa tgg att gaa gtg aaa gcc aaa gct aaa aag ctg cag atc cag ccc      2050
Lys Trp Ile Glu Val Lys Ala Lys Ala Lys Lys Leu Gln Ile Gln Pro
610                 615                 620                 625 agc cag ctg gaa ttg ttc tac tgt ttg tac gag atg cag gag gag gac      2098
Ser Gln Leu Glu Leu Phe Tyr Cys Leu Tyr Glu Met Gln Glu Glu Asp
                630                 635                 640 ttc gtg caa agg gcc atg gac tat ttc ccc aag att gag atc aat ctc      2146
Phe Val Gln Arg Ala Met Asp Tyr Phe Pro Lys Ile Glu Ile Asn Leu
            645                 650                 655 tcc acc aga atg gac cac atg gtt tct tcc ttt tgc att gag aac tgt      2194
Ser Thr Arg Met Asp His Met Val Ser Ser Phe Cys Ile Glu Asn Cys
        660                 665                 670 cat cgg gtg gag tca ctg tcc ctg ggg ttt ctc cat aac atg ccc aag      2242
```

```
                    His Arg Val Glu Ser Leu Ser Leu Gly Phe Leu His Asn Met Pro Lys
                        675                 680                 685 gag gaa gag gag gag gaa aag gaa ggc cga cac ctt gat atg gtg cag          2290
Glu Glu Glu Glu Glu Glu Lys Glu Gly Arg His Leu Asp Met Val Gln
690                 695                 700                 705 tgt gtc ctc cca agc tcc tct cat gct gcc tgt tct cat ggg                  2332
Cys Val Leu Pro Ser Ser Ser His Ala Ala Cys Ser His Gly
                710                 715 taaggaaact cggcttccag gtgcttcctc ctgcttcctc gccagcttct tcttggcgct        2392
tgcctcctct catctctttt caactatctt ccaaatactg ttgccacagc tacatcataa        2452
tgccaccact gtctgtttga gactccttca tgagcaaaga ttgatgtatg gtaggtggat        2512
aaatgggatg ag                                                            2524

<210> SEQ ID NO 59
<211> LENGTH: 719
<212> TYPE: PRT
<213> ORGANISM: Homo sapiens
<220> FEATURE:
<221> NAME/KEY: VARIANT
<222> LOCATION: 44, 45, 46, 47, 48, 49, 50, 51, 52, 53, 54, 55, 56, 57,
      58, 59, 60, 61, 62, 63, 64, 65, 66, 67, 68, 69, 70, 71
<223> OTHER INFORMATION: Xaa = Any Amino Acid
<220> FEATURE:
<221> NAME/KEY: VARIANT
<222> LOCATION: 72, 73, 74, 75, 76, 77, 78, 79, 80, 81, 82, 83, 84, 85,
      86, 87, 88, 89, 90, 91, 92, 93, 94, 95
<223> OTHER INFORMATION: Xaa = Any Amino Acid

<400> SEQUENCE: 59

Met Lys Met Ala Ser Thr Arg Cys Lys Leu Ala Arg Tyr Leu Glu Asp
1               5                   10                  15

Leu Glu Asp Val Asp Leu Lys Lys Phe Lys Met His Leu Glu Asp Tyr
                20                  25                  30

Pro Pro Gln Lys Gly Cys Ile Pro Leu Pro Arg Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Ser
                85                  90                  95

Asp Asn Ala Arg Val Ser Asn Pro Thr Val Ile Cys Gln Glu Asp Ser
                100                 105                 110

Ile Glu Glu Glu Trp Met Gly Leu Leu Glu Tyr Leu Ser Arg Ile Ser
            115                 120                 125

Ile Cys Lys Met Lys Lys Asp Tyr Arg Lys Lys Tyr Arg Lys Tyr Val
130                 135                 140

Arg Ser Arg Phe Gln Cys Ile Glu Asp Arg Asn Ala Arg Leu Gly Glu
145                 150                 155                 160

Ser Val Ser Leu Asn Lys Arg Tyr Thr Arg Leu Arg Leu Ile Lys Glu
                165                 170                 175

His Arg Ser Gln Gln Glu Arg Glu Gln Glu Leu Leu Ala Ile Gly Lys
            180                 185                 190

Thr Lys Thr Cys Glu Ser Pro Val Ser Pro Ile Lys Met Glu Leu Leu
        195                 200                 205

Phe Asp Pro Asp Asp Glu His Ser Glu Pro Val His Thr Val Val Phe
    210                 215                 220
```

-continued

```
Gln Gly Ala Ala Gly Ile Gly Lys Thr Ile Leu Ala Arg Lys Met Met
225                 230                 235                 240

Leu Asp Trp Ala Ser Gly Thr Leu Tyr Gln Asp Arg Phe Asp Tyr Leu
            245                 250                 255

Phe Tyr Ile His Cys Arg Glu Val Ser Leu Val Thr Gln Arg Ser Leu
            260                 265                 270

Gly Asp Leu Ile Met Ser Cys Cys Pro Asp Pro Asn Pro Ile His
        275                 280                 285

Lys Ile Val Arg Lys Pro Ser Arg Ile Leu Phe Leu Met Asp Gly Phe
        290                 295                 300

Asp Glu Leu Gln Gly Ala Phe Asp Glu His Ile Gly Pro Leu Cys Thr
305                 310                 315                 320

Asp Trp Gln Lys Ala Glu Arg Gly Asp Ile Leu Leu Ser Ser Leu Ile
                325                 330                 335

Arg Lys Lys Leu Leu Pro Glu Ala Ser Leu Leu Ile Thr Thr Arg Pro
            340                 345                 350

Val Ala Leu Glu Lys Leu Gln His Leu Leu Asp His Pro Arg His Val
        355                 360                 365

Glu Ile Leu Gly Phe Ser Glu Ala Lys Arg Lys Glu Tyr Phe Phe Lys
370                 375                 380

Tyr Phe Ser Asp Glu Ala Gln Ala Arg Ala Ala Phe Ser Leu Ile Gln
385                 390                 395                 400

Glu Asn Glu Val Leu Phe Thr Met Cys Phe Ile Pro Leu Val Cys Trp
                405                 410                 415

Ile Val Cys Thr Gly Leu Lys Gln Gln Met Glu Ser Gly Lys Ser Leu
            420                 425                 430

Ala Gln Thr Ser Lys Thr Thr Thr Ala Val Tyr Val Phe Phe Leu Ser
        435                 440                 445

Ser Leu Leu Gln Pro Arg Gly Gly Ser Gln Glu His Gly Leu Cys Ala
450                 455                 460

His Leu Trp Gly Leu Cys Ser Leu Ala Ala Asp Gly Ile Trp Asn Gln
465                 470                 475                 480

Lys Ile Leu Phe Glu Glu Ser Asp Leu Arg Asn His Gly Leu Gln Lys
                485                 490                 495

Ala Asp Val Ser Ala Phe Leu Arg Met Asn Leu Phe Gln Lys Glu Val
            500                 505                 510

Asp Cys Glu Lys Phe Tyr Ser Phe Ile His Met Thr Phe Gln Glu Phe
        515                 520                 525

Phe Ala Ala Met Tyr Tyr Leu Leu Glu Glu Glu Lys Glu Gly Arg Thr
530                 535                 540

Asn Val Pro Gly Ser Arg Leu Lys Leu Pro Ser Arg Asp Val Thr Val
545                 550                 555                 560

Leu Leu Glu Asn Tyr Gly Lys Phe Glu Lys Gly Tyr Leu Ile Phe Val
                565                 570                 575

Val Arg Phe Leu Phe Gly Leu Val Asn Gln Glu Arg Thr Ser Tyr Leu
            580                 585                 590

Glu Lys Lys Leu Ser Cys Lys Ile Ser Gln Gln Ile Arg Leu Glu Leu
        595                 600                 605

Leu Lys Trp Ile Glu Val Lys Ala Lys Ala Lys Lys Leu Gln Ile Gln
        610                 615                 620

Pro Ser Gln Leu Glu Leu Phe Tyr Cys Leu Tyr Glu Met Gln Glu Glu
625                 630                 635                 640

Asp Phe Val Gln Arg Ala Met Asp Tyr Phe Pro Lys Ile Glu Ile Asn
```

```
                     645                 650                 655
Leu Ser Thr Arg Met Asp His Met Val Ser Ser Phe Cys Ile Glu Asn
            660                 665                 670
Cys His Arg Val Glu Ser Leu Ser Leu Gly Phe Leu His Asn Met Pro
            675                 680                 685
Lys Glu Glu Glu Glu Glu Lys Glu Gly Arg His Leu Asp Met Val
        690                 695                 700
Gln Cys Val Leu Pro Ser Ser His Ala Ala Cys Ser His Gly
705                 710                 715

<210> SEQ ID NO 60
<211> LENGTH: 317
<212> TYPE: PRT
<213> ORGANISM: Homo sapiens

<400> SEQUENCE: 60

Leu Thr Val Val Leu Gln Gly Pro Ala Gly Ile Gly Lys Thr Met Ala
1               5                   10                  15
Ala Lys Lys Ile Leu Tyr Asp Trp Ala Ala Gly Lys Leu Tyr Gln Gly
            20                  25                  30
Gln Val Asp Phe Ala Phe Phe Met Pro Cys Gly Glu Leu Leu Glu Arg
        35                  40                  45
Pro Gly Thr Arg Ser Leu Ala Asp Leu Ile Leu Asp Gln Cys Pro Asp
    50                  55                  60
Arg Gly Ala Pro Val Pro Gln Met Leu Ala Gln Pro Gln Arg Leu Leu
65                  70                  75                  80
Phe Ile Leu Asp Gly Ala Asp Glu Leu Pro Ala Leu Gly Gly Pro Glu
                85                  90                  95
Ala Ala Pro Cys Thr Asp Pro Phe Glu Ala Ala Ser Gly Ala Arg Val
            100                 105                 110
Leu Gly Gly Leu Leu Ser Lys Ala Leu Leu Pro Thr Ala Leu Leu Leu
        115                 120                 125
Val Thr Thr Arg Ala Ala Pro Gly Arg Leu Gln Gly Arg Leu Cys
    130                 135                 140
Ser Pro Gln Cys Ala Glu Val Arg Gly Phe Ser Asp Lys Asp Lys Lys
145                 150                 155                 160
Lys Tyr Phe Tyr Lys Phe Phe Arg Asp Glu Arg Arg Ala Glu Arg Ala
                165                 170                 175
Tyr Arg Phe Val Lys Glu Asn Glu Thr Leu Phe Ala Leu Cys Phe Val
            180                 185                 190
Pro Phe Val Cys Trp Ile Val Cys Thr Val Leu Arg Gln Gln Leu Glu
        195                 200                 205
Leu Gly Arg Asp Leu Ser Arg Thr Ser Lys Thr Thr Thr Ser Val Tyr
    210                 215                 220
Leu Leu Phe Ile Thr Ser Val Leu Ser Ser Ala Pro Val Ala Asp Gly
225                 230                 235                 240
Pro Arg Leu Gln Gly Asp Leu Arg Asn Leu Cys Arg Leu Ala Arg Glu
                245                 250                 255
Gly Val Leu Gly Arg Arg Ala Gln Phe Ala Glu Lys Glu Leu Glu Gln
            260                 265                 270
Leu Glu Leu Arg Gly Ser Lys Val Gln Thr Leu Phe Leu Ser Lys Lys
        275                 280                 285
Glu Leu Pro Gly Val Leu Glu Thr Glu Val Thr Tyr Gln Phe Ile Asp
    290                 295                 300
```

```
Gln Ser Phe Gln Glu Phe Leu Ala Ala Leu Ser Tyr Leu
305                 310                 315

<210> SEQ ID NO 61
<211> LENGTH: 290
<212> TYPE: PRT
<213> ORGANISM: Homo sapiens

<400> SEQUENCE: 61

Val Leu Ser Tyr Cys Val Arg Cys Cys Pro Ala Gly Gln Ala Leu Arg
1               5                   10                  15

Leu Ile Ser Cys Arg Leu Val Ala Gln Glu Lys Lys Lys Ser
            20                  25                  30

Leu Gly Lys Arg Leu Gln Ala Ser Leu Gly Gly Ser Trp Leu Gly
        35                  40                  45

Thr Gln Leu Ala Pro Glu Val Pro Phe Arg Pro Pro Cys Cys Asp Ile
    50                  55                  60

Cys Pro Thr Pro Pro Asp Pro Arg Leu Leu Gln Gly Lys Ala Phe
65              70                  75                  80

Ala Arg Val Pro Leu Asn Ile Ala Pro Ile Gln Pro Leu Pro Arg Gly
                85                  90                  95

Leu Ala Ser Val Glu Arg Met Asn Val Thr Val Leu Ala Gly Ala Gly
            100                 105                 110

Pro Gly Asp Pro Lys Thr His Ala Met Thr Asp Pro Leu Cys His Leu
        115                 120                 125

Ser Ser Leu Thr Leu Ser His Cys Lys Leu Pro Asp Ala Val Cys Arg
    130                 135                 140

Asp Leu Ser Glu Ala Leu Arg Ala Ala Pro Ala Leu Thr Glu Leu Gly
145                 150                 155                 160

Leu Leu His Asn Arg Leu Ser Glu Ala Gly Leu Arg Met Leu Ser Glu
                165                 170                 175

Gly Leu Ala Trp Pro Gln Cys Arg Val Gln Thr Val Arg Val Gln Leu
            180                 185                 190

Pro Asp Pro Gln Arg Gly Leu Gln Tyr Leu Val Gly Met Leu Arg Gln
        195                 200                 205

Ser Pro Ala Leu Thr Thr Leu Asp Leu Ser Gly Cys Gln Leu Pro Ala
    210                 215                 220

Pro Met Val Thr Tyr Leu Cys Ala Val Leu Gln His Gln Gly Cys Gly
225                 230                 235                 240

Leu Gln Thr Leu Ser Leu Ala Ser Val Glu Leu Ser Glu Gln Ser Leu
                245                 250                 255

Gln Glu Leu Gln Ala Val Lys Arg Ala Lys Pro Asp Leu Val Ile Thr
            260                 265                 270

His Pro Ala Leu Asp Gly His Pro Gln Pro Lys Glu Leu Ile Ser
        275                 280                 285

Thr Phe
    290

<210> SEQ ID NO 62
<211> LENGTH: 181
<212> TYPE: PRT
<213> ORGANISM: Homo sapiens

<400> SEQUENCE: 62

Ile Cys Leu His Gly Val Gly Trp His Trp Lys Asp Asn Ser Arg Gln
1               5                   10                  15
```

```
Lys Lys Val Leu Asp Trp Ala Thr Gly Thr Leu Tyr Pro Gly Arg Phe
             20                  25                  30

Asp Tyr Val Phe Tyr Val Ser Cys Lys Glu Val Val Leu Leu Leu Glu
             35                  40                  45

Ser Lys Leu Glu Gln Leu Leu Phe Trp Cys Cys Gly Asp Asn Gln Ala
 50                  55                  60

Pro Val Thr Glu Ile Leu Arg Gln Pro Glu Arg Leu Leu Phe Ile Leu
 65                  70                  75                  80

Asp Gly Phe Asp Glu Leu Gln Arg Pro Phe Glu Lys Leu Lys Lys
                 85                  90                  95

Arg Gly Leu Ser Pro Lys Glu Ser Leu His Leu Leu Ile Arg Arg
             100                 105                 110

His Thr Leu Pro Thr Cys Ser Leu Leu Ile Thr Thr Arg Pro Leu Ala
             115                 120                 125

Leu Arg Asn Leu Glu Pro Leu Leu Lys Gln Ala Arg His Val His Ile
 130                 135                 140

Leu Gly Phe Ser Glu Glu Glu Arg Ala Arg Tyr Phe Ser Ser Tyr Phe
 145                 150                 155                 160

Thr Asp Glu Lys Gln Ala Asp Arg Ala Phe Asp Ile Val Gln Lys Asn
             165                 170                 175

Asp Ile Leu Tyr Lys
             180

<210> SEQ ID NO 63
<211> LENGTH: 190
<212> TYPE: PRT
<213> ORGANISM: Homo sapiens

<400> SEQUENCE: 63

Pro Arg Thr Val Val Met Gln Gly Ala Gly Ile Gly Lys Ser Met
 1               5                  10                  15

Leu Ala His Lys Val Met Leu Asp Trp Ala Asp Gly Lys Leu Phe Gln
             20                  25                  30

Gly Arg Phe Asp Tyr Leu Phe Tyr Ile Asn Cys Arg Glu Met Asn Gln
             35                  40                  45

Ser Ala Thr Glu Cys Ser Met Gln Asp Leu Ile Phe Ser Cys Trp Pro
 50                  55                  60

Glu Pro Ser Ala Pro Leu Gln Glu Leu Ile Arg Val Pro Glu Arg Leu
 65                  70                  75                  80

Leu Phe Ile Ile Asp Gly Phe Asp Glu Leu Lys Pro Ser Phe His Asp
                 85                  90                  95

Pro Gln Gly Pro Trp Cys Leu Cys Trp Glu Glu Lys Arg Pro Thr Glu
             100                 105                 110

Leu Leu Leu Asn Ser Leu Ile Arg Lys Lys Leu Leu Pro Glu Leu Ser
             115                 120                 125

Leu Leu Ile Thr Thr Arg Pro Thr Ala Leu Glu Lys Leu His Arg Leu
 130                 135                 140

Leu Glu His Pro Arg His Val Glu Ile Leu Gly Phe Ser Glu Ala Glu
 145                 150                 155                 160

Arg Lys Glu Tyr Phe Tyr Lys Tyr Phe His Asn Ala Glu Gln Ala Gly
             165                 170                 175

Gln Val Phe Asn Tyr Val Arg Asp Asn Glu Pro Leu Phe Thr
             180                 185                 190

<210> SEQ ID NO 64
```

<211> LENGTH: 603
<212> TYPE: PRT
<213> ORGANISM: Homo sapiens

<400> SEQUENCE: 64

```
Pro Asn Gln Arg Gly Leu Cys Ser Leu Ala Ala Asp Gly Leu Trp Asn
1               5                   10                  15

Gln Lys Ile Leu Phe Glu Glu Gln Asp Leu Arg Lys His Gly Leu Asp
            20                  25                  30

Gly Glu Asp Val Ser Ala Phe Leu Asn Met Asn Ile Phe Gln Lys Asp
        35                  40                  45

Ile Asn Cys Glu Arg Tyr Tyr Ser Phe Ile His Leu Ser Phe Gln Glu
    50                  55                  60

Phe Phe Ala Ala Met Tyr Tyr Ile Leu Asp Glu Gly Glu Gly Gly Ala
65                  70                  75                  80

Gly Pro Asp Gln Asp Val Thr Arg Leu Leu Thr Glu Tyr Ala Phe Ser
                85                  90                  95

Glu Arg Ser Phe Leu Ala Leu Thr Ser Arg Phe Leu Phe Gly Leu Leu
            100                 105                 110

Asn Glu Glu Thr Arg Ser His Leu Glu Lys Ser Leu Cys Trp Lys Val
        115                 120                 125

Ser Pro His Ile Lys Met Asp Leu Leu Gln Trp Ile Gln Ser Lys Ala
130                 135                 140

Gln Ser Asp Gly Ser Thr Leu Gln Gln Gly Ser Leu Glu Phe Phe Ser
145                 150                 155                 160

Cys Leu Tyr Glu Ile Gln Glu Glu Glu Phe Ile Gln Ala Leu Ser
                165                 170                 175

His Phe Gln Val Ile Val Val Ser Asn Ile Ala Ser Lys Met Glu His
            180                 185                 190

Met Val Ser Ser Phe Cys Leu Lys Arg Cys Arg Ser Ala Gln Val Leu
        195                 200                 205

His Leu Tyr Gly Ala Thr Tyr Ser Ala Asp Gly Glu Asp Arg Ala Arg
    210                 215                 220

Cys Ser Ala Gly Ala His Thr Leu Leu Val Gln Leu Arg Pro Glu Arg
225                 230                 235                 240

Thr Val Leu Leu Asp Ala Tyr Ser Glu His Leu Ala Ala Ala Leu Cys
                245                 250                 255

Thr Asn Pro Asn Leu Ile Glu Leu Ser Leu Tyr Arg Asn Ala Leu Gly
            260                 265                 270

Ser Arg Gly Val Lys Leu Leu Cys Gln Gly Leu Arg His Pro Asn Cys
        275                 280                 285

Lys Leu Gln Asn Leu Arg Leu Lys Arg Cys Arg Ile Ser Ser Ser Ala
    290                 295                 300

Cys Glu Asp Leu Ser Ala Ala Leu Ile Ala Asn Lys Asn Leu Thr Arg
305                 310                 315                 320

Met Asp Leu Ser Gly Asn Gly Val Gly Phe Pro Gly Met Met Leu Leu
                325                 330                 335

Cys Glu Gly Leu Arg His Pro Gln Cys Arg Leu Gln Met Ile Gln Leu
            340                 345                 350

Arg Lys Cys Gln Leu Glu Ser Gly Ala Cys Gln Glu Met Ala Ser Val
        355                 360                 365

Leu Gly Thr Asn Pro His Leu Val Glu Leu Asp Leu Thr Gly Asn Ala
    370                 375                 380

Leu Glu Asp Leu Gly Leu Arg Leu Leu Cys Gln Gly Leu Arg His Pro
```

```
                385                 390                 395                 400
Val Cys Arg Leu Arg Thr Leu Trp Leu Lys Ile Cys Arg Leu Thr Ala
                    405                 410                 415

Ala Ala Cys Asp Glu Leu Ala Ser Thr Leu Ser Val Asn Gln Ser Leu
                420                 425                 430

Arg Glu Leu Asp Leu Ser Leu Asn Glu Leu Gly Asp Leu Gly Val Leu
            435                 440                 445

Leu Leu Cys Glu Gly Leu Arg His Pro Thr Cys Lys Leu Gln Thr Leu
    450                 455                 460

Arg Leu Gly Ile Cys Arg Leu Gly Ser Ala Cys Glu Gly Leu Ser
465                 470                 475                 480

Val Val Leu Gln Ala Asn His Asn Leu Arg Glu Leu Asp Leu Ser Phe
                485                 490                 495

Asn Asp Leu Gly Asp Trp Gly Leu Trp Leu Leu Ala Glu Gly Leu Gln
                500                 505                 510

His Pro Ala Cys Arg Leu Gln Lys Leu Trp Leu Asp Ser Cys Gly Leu
            515                 520                 525

Thr Ala Lys Ala Cys Glu Asn Leu Tyr Phe Thr Leu Gly Ile Asn Gln
    530                 535                 540

Thr Leu Thr Asp Leu Tyr Leu Thr Asn Asn Ala Leu Gly Asp Thr Gly
545                 550                 555                 560

Val Arg Leu Leu Cys Lys Arg Leu Ser His Pro Gly Cys Lys Leu Arg
                565                 570                 575

Val Leu Trp Leu Phe Gly Met Asp Leu Asn Lys Met Thr His Ser Arg
                580                 585                 590

Leu Ala Ala Leu Arg Val Thr Lys Pro Tyr Leu
            595                 600

<210> SEQ ID NO 65
<211> LENGTH: 2708
<212> TYPE: DNA
<213> ORGANISM: Homo sapiens
<220> FEATURE:
<221> NAME/KEY: CDS
<222> LOCATION: (1)...(2708)

<400> SEQUENCE: 65 atg gac cag cca gag gcc ccc tgc tcc agc acg ggg ccg cgc ctc gcg      48
Met Asp Gln Pro Glu Ala Pro Cys Ser Ser Thr Gly Pro Arg Leu Ala
 1               5                  10                  15 gtg gcc cgc gag ctg ctc ctg gct gcg ctg gag gaa ctg agc caa gag      96
Val Ala Arg Glu Leu Leu Leu Ala Ala Leu Glu Glu Leu Ser Gln Glu
            20                  25                  30 cag ctg aag cgc ttc cgc cac aag ctg cgc gac gtg ggc ccg gac gga     144
Gln Leu Lys Arg Phe Arg His Lys Leu Arg Asp Val Gly Pro Asp Gly
        35                  40                  45 cgc agc atc ccg tgg ggg cgg ctg gag cgc gcg gac gcc gtg gac ctc     192
Arg Ser Ile Pro Trp Gly Arg Leu Glu Arg Ala Asp Ala Val Asp Leu
    50                  55                  60 gcg gag cag ctg gcc cag ttc tac ggc ccg gag cct gcc ctg gag gtg     240
Ala Glu Gln Leu Ala Gln Phe Tyr Gly Pro Glu Pro Ala Leu Glu Val
65                  70                  75                  80 gcc cgc aag acc ctc aag agg gcg gac gcg cgc gac gtg gcg gcg cag     288
Ala Arg Lys Thr Leu Lys Arg Ala Asp Ala Arg Asp Val Ala Ala Gln
                85                  90                  95 ctc cag gag cgg cgg ctg cag cgg ctc ggg ctc ggc tcc ggg acg ctg     336
Leu Gln Glu Arg Arg Leu Gln Arg Leu Gly Leu Gly Ser Gly Thr Leu
           100                 105                 110
```

-continued

| | |
|---|---|
| ctc tcc gtg tcc gag tac aag aag aag tac cgg gag cac gtg ctg cag<br>Leu Ser Val Ser Glu Tyr Lys Lys Lys Tyr Arg Glu His Val Leu Gln<br>115                    120                    125 | 384 |
| ctg cac gct cgg gtg aag gag agg aac gcc cgc tcc gtg aag atc acc<br>Leu His Ala Arg Val Lys Glu Arg Asn Ala Arg Ser Val Lys Ile Thr<br>130                    135                    140 | 432 |
| aag cgc ttc acc aag ctg ctc atc gcg ccc gag agc gcc gcc ccg gag<br>Lys Arg Phe Thr Lys Leu Leu Ile Ala Pro Glu Ser Ala Ala Pro Glu<br>145                    150                    155                    160 | 480 |
| gag gcg ctg ggg ccc gcg gaa gag cct gag ccg ggg cgc gcg cgg cgc<br>Glu Ala Leu Gly Pro Ala Glu Glu Pro Glu Pro Gly Arg Ala Arg Arg<br>                    165                    170                    175 | 528 |
| tcg gac acg cac act ttc aac cgc ctc ttc cgc cgc gac gag gag ggc<br>Ser Asp Thr His Thr Phe Asn Arg Leu Phe Arg Arg Asp Glu Glu Gly<br>                180                    185                    190 | 576 |
| cgg cgg ccg ctg acc gtg gtg ctg cag ggc ccg gcg ggc atc ggc aag<br>Arg Arg Pro Leu Thr Val Val Leu Gln Gly Pro Ala Gly Ile Gly Lys<br>                    195                    200                    205 | 624 |
| acc atg gcg gcc aaa aag atc ctg tac gac tgg gcg gcg ggc aag ctg<br>Thr Met Ala Ala Lys Lys Ile Leu Tyr Asp Trp Ala Ala Gly Lys Leu<br>210                    215                    220 | 672 |
| tac cag ggc cag gtg gac ttc gcc ttc ttc atg ccc tgc ggc gag ctg<br>Tyr Gln Gly Gln Val Asp Phe Ala Phe Phe Met Pro Cys Gly Glu Leu<br>225                      230                    235                    240 | 720 |
| ctg gag agg ccg ggc acg cgc agc ctg gct gac ctg atc ctg gac cag<br>Leu Glu Arg Pro Gly Thr Arg Ser Leu Ala Asp Leu Ile Leu Asp Gln<br>                    245                    250                    255 | 768 |
| tgc ccc gac cgc ggc gcg ccg gtg ccg cag atg ctg gcc cag ccg cag<br>Cys Pro Asp Arg Gly Ala Pro Val Pro Gln Met Leu Ala Gln Pro Gln<br>                        260                    265                    270 | 816 |
| cgg ctg ctc ttc atc ctg gac ggc gcg gac gag ctg ccg gcg ctg ggg<br>Arg Leu Leu Phe Ile Leu Asp Gly Ala Asp Glu Leu Pro Ala Leu Gly<br>275                    280                    285 | 864 |
| ggc ccc gag gcc gcg ccc tgc aca gac ccc ttc gag gcg gcg agc ggc<br>Gly Pro Glu Ala Ala Pro Cys Thr Asp Pro Phe Glu Ala Ala Ser Gly<br>290                    295                    300 | 912 |
| gcg cgg gtg cta ggc ggg ctg ctg agc aag gcg ctg ctg ccc acg gcc<br>Ala Arg Val Leu Gly Gly Leu Leu Ser Lys Ala Leu Leu Pro Thr Ala<br>305                    310                    315                    320 | 960 |
| ctc ctg ctg gtg acc acg cgc gcc gcc gcc ccc ggg agg ctg cag ggc<br>Leu Leu Leu Val Thr Thr Arg Ala Ala Ala Pro Gly Arg Leu Gln Gly<br>                    325                    330                    335 | 1008 |
| cgc ctg tgt tcc ccg cag tgc gcc gag gtg cgc ggc ttc tcc gac aag<br>Arg Leu Cys Ser Pro Gln Cys Ala Glu Val Arg Gly Phe Ser Asp Lys<br>                    340                    345                    350 | 1056 |
| gac aag aag aag tat ttc tac aag ttc ttc cgg gat gag agg agg gcc<br>Asp Lys Lys Lys Tyr Phe Tyr Lys Phe Phe Arg Asp Glu Arg Arg Ala<br>                    355                    360                    365 | 1104 |
| gag cgc gcc tac cgc ttc gtg aag gag aac gag acg ctg ttc gcg ctg<br>Glu Arg Ala Tyr Arg Phe Val Lys Glu Asn Glu Thr Leu Phe Ala Leu<br>370                    375                    380 | 1152 |
| tgc ttc gtg ccc ttc gtg tgc tgg atc gtg tgc acc gtg ctg cgc cag<br>Cys Phe Val Pro Phe Val Cys Trp Ile Val Cys Thr Val Leu Arg Gln<br>385                    390                    395                    400 | 1200 |
| cag ctg gag ctc ggt cgg gac ctg tcg cgc acg tcc aag acc acc acg<br>Gln Leu Glu Leu Gly Arg Asp Leu Ser Arg Thr Ser Lys Thr Thr Thr<br>                    405                    410                    415 | 1248 |
| tca gtg tac ctg ctt ttc atc acc agc gtt ctg agc tcg gct ccg gta<br>Ser Val Tyr Leu Leu Phe Ile Thr Ser Val Leu Ser Ser Ala Pro Val | 1296 |

```
                420              425              430
gcc gac ggg ccc cgg ttg cag ggc gac ctg cgc aat ctg tgc cgc ctg   1344
Ala Asp Gly Pro Arg Leu Gln Gly Asp Leu Arg Asn Leu Cys Arg Leu
        435              440              445 gcc cgc gag ggc gtc ctc gga cgc agg gcg cag ttt gcc gag aag gaa   1392
Ala Arg Glu Gly Val Leu Gly Arg Arg Ala Gln Phe Ala Glu Lys Glu
450              455              460 ctg gag caa ctg gag ctt cgt ggc tcc aaa gtg cag acg ctg ttt ctc   1440
Leu Glu Gln Leu Glu Leu Arg Gly Ser Lys Val Gln Thr Leu Phe Leu
465              470              475              480 agc aaa aag gag ctg ccg ggc gtg ctg gag aca gag gtc acc tac cag   1488
Ser Lys Lys Glu Leu Pro Gly Val Leu Glu Thr Glu Val Thr Tyr Gln
                485              490              495 ttc atc gac cag agc ttc cag gag ttc ctc gcg gca ctg tcc tac ctg   1536
Phe Ile Asp Gln Ser Phe Gln Glu Phe Leu Ala Ala Leu Ser Tyr Leu
            500              505              510 ctg gag gac ggc ggg gtg ccc agg acc gcg gct ggc ggc gtt ggg aca   1584
Leu Glu Asp Gly Gly Val Pro Arg Thr Ala Ala Gly Gly Val Gly Thr
        515              520              525 ctc ctg cgt ggg gac gcc cag ccg cac agc cac ttg gtg ctc acc acg   1632
Leu Leu Arg Gly Asp Ala Gln Pro His Ser His Leu Val Leu Thr Thr
530              535              540 cgc ttc ctc ttc gga ctg ctg agc gcg gag cgg atg cgc gac atc gag   1680
Arg Phe Leu Phe Gly Leu Leu Ser Ala Glu Arg Met Arg Asp Ile Glu
545              550              555              560 cgc cac ttc ggc tgc atg gtt tca gag cgt gtg aag cag gag gcc ctg   1728
Arg His Phe Gly Cys Met Val Ser Glu Arg Val Lys Gln Glu Ala Leu
                565              570              575 cgg tgg gtg cag gga cag gga cag ggc tgc ccc gga gtg gca cca gag   1776
Arg Trp Val Gln Gly Gln Gly Gln Gly Cys Pro Gly Val Ala Pro Glu
            580              585              590 gtg acc gag ggg gcc aaa ggg ctc gag gac acc gaa gag cca gag gag   1824
Val Thr Glu Gly Ala Lys Gly Leu Glu Asp Thr Glu Glu Pro Glu Glu
        595              600              605 gag gag gag gga gag gag ccc aac tac cca ctg gag ttg ctg tac tgc   1872
Glu Glu Glu Gly Glu Glu Pro Asn Tyr Pro Leu Glu Leu Leu Tyr Cys
610              615              620 ctg tac gag acg cag gag gac gcg ttt gtg cgc caa gcc ctg tgc cgg   1920
Leu Tyr Glu Thr Gln Glu Asp Ala Phe Val Arg Gln Ala Leu Cys Arg
625              630              635              640 ttc ccg gag ctg gcg ctg cag cga gtg cgc ttc tgc cgc atg gac gtg   1968
Phe Pro Glu Leu Ala Leu Gln Arg Val Arg Phe Cys Arg Met Asp Val
                645              650              655 gct gtt ctg agc tac tgc gtg agg tgc tgc cct gct gga cag gca ctg   2016
Ala Val Leu Ser Tyr Cys Val Arg Cys Cys Pro Ala Gly Gln Ala Leu
            660              665              670 cgg ctg atc agc tgc aga ttg gtt gct gcg cag gag aag aag aag aag   2064
Arg Leu Ile Ser Cys Arg Leu Val Ala Ala Gln Glu Lys Lys Lys Lys
        675              680              685 agc ctg ggg aag cgg ctc cag gcc agc ctg ggt ggc ggc agc tgg ctg   2112
Ser Leu Gly Lys Arg Leu Gln Ala Ser Leu Gly Gly Gly Ser Trp Leu
690              695              700 ggg acc caa ctg gct cca gaa gta ccc ttt cga cca ccc tgc tgt gac   2160
Gly Thr Gln Leu Ala Pro Glu Val Pro Phe Arg Pro Pro Cys Cys Asp
705              710              715              720 atc tgc ccc aca cct cca cca gac cct cgg ctc ctc cag ggc aag gct   2208
Ile Cys Pro Thr Pro Pro Pro Asp Pro Arg Leu Leu Gln Gly Lys Ala
                725              730              735 ttt gcc aga gtt cct ttg aat ata gct cca att cag ccc ctg ccc agg   2256
```

```
              Phe Ala Arg Val Pro Leu Asn Ile Ala Pro Ile Gln Pro Leu Pro Arg
                              740                 745                 750 ggc ttg gca tct gtt gag agg atg aat gtc acg gtg ttg gca ggg gct        2304
Gly Leu Ala Ser Val Glu Arg Met Asn Val Thr Val Leu Ala Gly Ala
            755                 760                 765 ggg cct ggg gac cca aag acc cat gca atg act gac cca ctg tgc cat        2352
Gly Pro Gly Asp Pro Lys Thr His Ala Met Thr Asp Pro Leu Cys His
770                 775                 780 ctg agc agc ctc acg ctg tcc cac tgc aaa ctc cct gac gcg gtc tgc        2400
Leu Ser Ser Leu Thr Leu Ser His Cys Lys Leu Pro Asp Ala Val Cys
785                 790                 795                 800 cga gac ctt tct gag gcc ctg agg gca gcc ccc gca ctg acg gag ctg        2448
Arg Asp Leu Ser Glu Ala Leu Arg Ala Ala Pro Ala Leu Thr Glu Leu
                805                 810                 815 ggc ctc ctc cac aac agg ctc agt gag gca gga ctg cgt atg ctg agt        2496
Gly Leu Leu His Asn Arg Leu Ser Glu Ala Gly Leu Arg Met Leu Ser
            820                 825                 830 gag ggc cta gcc tgg ccg cag tgc agg gtg cag acg gtc agg gta cag        2544
Glu Gly Leu Ala Trp Pro Gln Cys Arg Val Gln Thr Val Arg Val Gln
        835                 840                 845 ctg cct gac ccc cag cga ggg ctc cag tac ctg gtg ggt atg ctt cgg        2592
Leu Pro Asp Pro Gln Arg Gly Leu Gln Tyr Leu Val Gly Met Leu Arg
850                 855                 860 cag agc cct gcc ctg acc acc ctg gat ctc agc ggc tgc caa ctg ccc        2640
Gln Ser Pro Ala Leu Thr Thr Leu Asp Leu Ser Gly Cys Gln Leu Pro
865                 870                 875                 880 gcc ccc atg gtg acc tac ctg tgt gca gtc ctg cag cac cag gga tgc        2688
Ala Pro Met Val Thr Tyr Leu Cys Ala Val Leu Gln His Gln Gly Cys
                885                 890                 895 ggc ctg cag acc ctc agc ct                                             2708
Gly Leu Gln Thr Leu Ser
            900

<210> SEQ ID NO 66
<211> LENGTH: 902
<212> TYPE: PRT
<213> ORGANISM: Homo sapiens

<400> SEQUENCE: 66

Met Asp Gln Pro Glu Ala Pro Cys Ser Ser Thr Gly Pro Arg Leu Ala
1               5                   10                  15

Val Ala Arg Glu Leu Leu Leu Ala Ala Leu Glu Glu Leu Ser Gln Glu
                20                  25                  30

Gln Leu Lys Arg Phe Arg His Lys Leu Arg Asp Val Gly Pro Asp Gly
            35                  40                  45

Arg Ser Ile Pro Trp Gly Arg Leu Glu Arg Ala Asp Ala Val Asp Leu
        50                  55                  60

Ala Glu Gln Leu Ala Gln Phe Tyr Gly Pro Glu Pro Ala Leu Glu Val
65                  70                  75                  80

Ala Arg Lys Thr Leu Lys Arg Ala Asp Ala Arg Asp Val Ala Ala Gln
                85                  90                  95

Leu Gln Glu Arg Arg Leu Gln Arg Leu Gly Leu Gly Ser Gly Thr Leu
            100                 105                 110

Leu Ser Val Ser Glu Tyr Lys Lys Tyr Arg Glu His Val Leu Gln
        115                 120                 125

Leu His Ala Arg Val Lys Glu Arg Asn Ala Arg Ser Val Lys Ile Thr
    130                 135                 140

Lys Arg Phe Thr Lys Leu Leu Ile Ala Pro Glu Ser Ala Ala Pro Glu
```

```
145                 150                 155                 160
Glu Ala Leu Gly Pro Ala Glu Pro Glu Pro Gly Arg Ala Arg Arg
                165                 170                 175
Ser Asp Thr His Thr Phe Asn Arg Leu Phe Arg Arg Asp Glu Gly
                180                 185                 190
Arg Arg Pro Leu Thr Val Val Leu Gln Gly Pro Ala Gly Ile Gly Lys
            195                 200                 205
Thr Met Ala Ala Lys Lys Ile Leu Tyr Asp Trp Ala Ala Gly Lys Leu
        210                 215                 220
Tyr Gln Gly Gln Val Asp Phe Ala Phe Met Pro Cys Gly Glu Leu
225                 230                 235                 240
Leu Glu Arg Pro Gly Thr Arg Ser Leu Ala Asp Leu Ile Leu Asp Gln
                245                 250                 255
Cys Pro Asp Arg Gly Ala Pro Val Pro Gln Met Leu Ala Gln Pro Gln
                260                 265                 270
Arg Leu Leu Phe Ile Leu Asp Gly Ala Asp Glu Leu Pro Ala Leu Gly
            275                 280                 285
Gly Pro Glu Ala Ala Pro Cys Thr Asp Pro Phe Glu Ala Ala Ser Gly
        290                 295                 300
Ala Arg Val Leu Gly Gly Leu Leu Ser Lys Ala Leu Leu Pro Thr Ala
305                 310                 315                 320
Leu Leu Leu Val Thr Thr Arg Ala Ala Pro Gly Arg Leu Gln Gly
                325                 330                 335
Arg Leu Cys Ser Pro Gln Cys Ala Glu Val Arg Gly Phe Ser Asp Lys
            340                 345                 350
Asp Lys Lys Lys Tyr Phe Tyr Lys Phe Phe Arg Asp Glu Arg Arg Ala
        355                 360                 365
Glu Arg Ala Tyr Arg Phe Val Lys Glu Asn Glu Thr Leu Phe Ala Leu
        370                 375                 380
Cys Phe Val Pro Phe Val Cys Trp Ile Val Cys Thr Val Leu Arg Gln
385                 390                 395                 400
Gln Leu Glu Leu Gly Arg Asp Leu Ser Arg Thr Ser Lys Thr Thr Thr
                405                 410                 415
Ser Val Tyr Leu Leu Phe Ile Thr Ser Val Leu Ser Ser Ala Pro Val
            420                 425                 430
Ala Asp Gly Pro Arg Leu Gln Gly Asp Leu Arg Asn Leu Cys Arg Leu
        435                 440                 445
Ala Arg Glu Gly Val Leu Gly Arg Arg Ala Gln Phe Ala Glu Lys Glu
        450                 455                 460
Leu Glu Gln Leu Glu Leu Arg Gly Ser Lys Val Gln Thr Leu Phe Leu
465                 470                 475                 480
Ser Lys Lys Glu Leu Pro Gly Val Leu Glu Thr Glu Val Thr Tyr Gln
                485                 490                 495
Phe Ile Asp Gln Ser Phe Gln Glu Phe Leu Ala Ala Leu Ser Tyr Leu
            500                 505                 510
Leu Glu Asp Gly Gly Val Pro Arg Thr Ala Ala Gly Val Gly Thr
        515                 520                 525
Leu Leu Arg Gly Asp Ala Gln Pro His Ser His Leu Val Leu Thr Thr
        530                 535                 540
Arg Phe Leu Phe Gly Leu Leu Ser Ala Glu Arg Met Arg Asp Ile Glu
545                 550                 555                 560
Arg His Phe Gly Cys Met Val Ser Glu Arg Val Lys Gln Glu Ala Leu
                565                 570                 575
```

Arg Trp Val Gln Gly Gln Gly Gln Gly Cys Pro Gly Val Ala Pro Glu
              580                 585                 590

Val Thr Glu Gly Ala Lys Gly Leu Glu Asp Thr Glu Glu Pro Glu Glu
          595                 600                 605

Glu Glu Glu Gly Glu Glu Pro Asn Tyr Pro Leu Glu Leu Leu Tyr Cys
      610                 615                 620

Leu Tyr Glu Thr Gln Glu Asp Ala Phe Val Arg Gln Ala Leu Cys Arg
625                 630                 635                 640

Phe Pro Glu Leu Ala Leu Gln Arg Val Arg Phe Cys Arg Met Asp Val
              645                 650                 655

Ala Val Leu Ser Tyr Cys Val Arg Cys Cys Pro Ala Gly Gln Ala Leu
          660                 665                 670

Arg Leu Ile Ser Cys Arg Leu Val Ala Gln Glu Lys Lys Lys Lys
      675                 680                 685

Ser Leu Gly Lys Arg Leu Gln Ala Ser Leu Gly Gly Ser Trp Leu
      690                 695                 700

Gly Thr Gln Leu Ala Pro Glu Val Pro Phe Arg Pro Pro Cys Cys Asp
705                 710                 715                 720

Ile Cys Pro Thr Pro Pro Asp Pro Arg Leu Leu Gln Gly Lys Ala
              725                 730                 735

Phe Ala Arg Val Pro Leu Asn Ile Ala Pro Ile Gln Pro Leu Pro Arg
          740                 745                 750

Gly Leu Ala Ser Val Glu Arg Met Asn Val Thr Val Leu Ala Gly Ala
      755                 760                 765

Gly Pro Gly Asp Pro Lys Thr His Ala Met Thr Asp Pro Leu Cys His
      770                 775                 780

Leu Ser Ser Leu Thr Leu Ser His Cys Lys Leu Pro Asp Ala Val Cys
785                 790                 795                 800

Arg Asp Leu Ser Glu Ala Leu Arg Ala Ala Pro Ala Leu Thr Glu Leu
              805                 810                 815

Gly Leu Leu His Asn Arg Leu Ser Glu Ala Gly Leu Arg Met Leu Ser
          820                 825                 830

Glu Gly Leu Ala Trp Pro Gln Cys Arg Val Gln Thr Val Arg Val Gln
      835                 840                 845

Leu Pro Asp Pro Gln Arg Gly Leu Gln Tyr Leu Val Gly Met Leu Arg
      850                 855                 860

Gln Ser Pro Ala Leu Thr Thr Leu Asp Leu Ser Gly Cys Gln Leu Pro
865                 870                 875                 880

Ala Pro Met Val Thr Tyr Leu Cys Ala Val Leu Gln His Gln Gly Cys
              885                 890                 895

Gly Leu Gln Thr Leu Ser
          900

<210> SEQ ID NO 67
<211> LENGTH: 3218
<212> TYPE: DNA
<213> ORGANISM: Homo sapiens
<220> FEATURE:
<221> NAME/KEY: CDS
<222> LOCATION: (118)...(3200)

<400> SEQUENCE: 67
ctctccgccc gctgcctgtg aatgatgcaa tggaaggtgt gctggggtcg ccctgtgtcc      60
cgtgcatagg agcatctcag cctccaggtc ctctcctttg gggctcacgg cacccccatg     120
                                                                     Met

```
                                                                                1
cta cga acc gca ggc agg gac ggc ctc tgt cgc ctg tcc acc tac ttg          168
Leu Arg Thr Ala Gly Arg Asp Gly Leu Cys Arg Leu Ser Thr Tyr Leu
         5                  10                  15 gaa gaa ctc gag gct gtg gaa ctg aag aag ttc aag tta tac ctg ggg          216
Glu Glu Leu Glu Ala Val Glu Leu Lys Lys Phe Lys Leu Tyr Leu Gly
         20                  25                  30 acc gcg aca gag ctg gga gaa ggc aag atc ccc tgg gga agc atg gag          264
Thr Ala Thr Glu Leu Gly Glu Gly Lys Ile Pro Trp Gly Ser Met Glu
 35                  40                  45 aag gcc ggt ccc ctg gaa atg gcc cag ctg ctc atc acc cac ttc ggg          312
Lys Ala Gly Pro Leu Glu Met Ala Gln Leu Leu Ile Thr His Phe Gly
 50                  55                  60                  65 cca gag gag gcc tgg agg ttg gct ctc agc acc ttt gag cgg ata aac          360
Pro Glu Glu Ala Trp Arg Leu Ala Leu Ser Thr Phe Glu Arg Ile Asn
                 70                  75                  80 agg aag gac ctg tgg gag aga gga cag aga gag gac ctg gtg agg gat          408
Arg Lys Asp Leu Trp Glu Arg Gly Gln Arg Glu Asp Leu Val Arg Asp
             85                  90                  95 acc cca cct ggt ggc ccg tcc tca ctt ggg aac cag tca aca tgc ctt          456
Thr Pro Pro Gly Gly Pro Ser Ser Leu Gly Asn Gln Ser Thr Cys Leu
         100                 105                 110 ctg gaa gtc tct ctt gtc act cca aga aaa gat ccc cag gaa acc tac          504
Leu Glu Val Ser Leu Val Thr Pro Arg Lys Asp Pro Gln Glu Thr Tyr
 115                 120                 125 agg gac tat gtc cgc agg aaa ttc cgg ctc atg gaa gac cgc aat gcg          552
Arg Asp Tyr Val Arg Arg Lys Phe Arg Leu Met Glu Asp Arg Asn Ala
130                 135                 140                 145 cgc cta ggg gaa tgt gtc aac ctc agc cac cgg tac acc cgg ctc ctg          600
Arg Leu Gly Glu Cys Val Asn Leu Ser His Arg Tyr Thr Arg Leu Leu
                 150                 155                 160 ctg gtg aag gag cac tca aac ccc atg cag gtc cag cag cag ctt ctg          648
Leu Val Lys Glu His Ser Asn Pro Met Gln Val Gln Gln Gln Leu Leu
             165                 170                 175 gac aca ggc cgg gga cac gcg agg acc gtg gga cac cag gct agc ccc          696
Asp Thr Gly Arg Gly His Ala Arg Thr Val Gly His Gln Ala Ser Pro
         180                 185                 190 atc aag ata gag acc ctc ttt gag cca gac gag gag cgc ccc gag cca          744
Ile Lys Ile Glu Thr Leu Phe Glu Pro Asp Glu Glu Arg Pro Glu Pro
 195                 200                 205 ccg cgc acc gtg gtc atg caa ggc gcg gca ggg ata ggc aag tcc atg          792
Pro Arg Thr Val Val Met Gln Gly Ala Ala Gly Ile Gly Lys Ser Met
210                 215                 220                 225 ctg gca cac aag gtg atg ctg gac tgg gcg gac ggg aag ctc ttc caa          840
Leu Ala His Lys Val Met Leu Asp Trp Ala Asp Gly Lys Leu Phe Gln
                 230                 235                 240 ggc aga ttt gat tat ctc ttc tac atc aac tgc agg gag atg aac cag          888
Gly Arg Phe Asp Tyr Leu Phe Tyr Ile Asn Cys Arg Glu Met Asn Gln
             245                 250                 255 agt gcc acg gaa tgc agc atg caa gac ctc atc ttc agc tgc tgg cct          936
Ser Ala Thr Glu Cys Ser Met Gln Asp Leu Ile Phe Ser Cys Trp Pro
         260                 265                 270 gag ccc agc gcg cct ctc cag gag ctc atc cga gtt ccc gag cgc ctc          984
Glu Pro Ser Ala Pro Leu Gln Glu Leu Ile Arg Val Pro Glu Arg Leu
 275                 280                 285 ctt ttc atc atc gac ggc ttc gat gag ctc aag cct tct ttc cac gat         1032
Leu Phe Ile Ile Asp Gly Phe Asp Glu Leu Lys Pro Ser Phe His Asp
290                 295                 300                 305 cct cag gga ccc tgg tgc ctc tgc tgg gag gag aaa cgg ccc acg gag         1080
```

```
                Pro Gln Gly Pro Trp Cys Leu Cys Trp Glu Glu Lys Arg Pro Thr Glu
                            310                 315                 320 ctg ctt ctt aac agc tta att cgg aag aag ctg ctc cct gag cta tct         1128
Leu Leu Leu Asn Ser Leu Ile Arg Lys Lys Leu Leu Pro Glu Leu Ser
            325                 330                 335 ttg ctc atc acc aca cgg ccc acg gct ttg gag aag ctc cac cgt ctg         1176
Leu Leu Ile Thr Thr Arg Pro Thr Ala Leu Glu Lys Leu His Arg Leu
            340                 345                 350 ctg gag cac ccc agg cat gtg gag atc ctg ggc ttc tct gag gca gaa         1224
Leu Glu His Pro Arg His Val Glu Ile Leu Gly Phe Ser Glu Ala Glu
        355                 360                 365 agg aag gaa tac ttc tac aag tat ttc cac aat gca gag cag gcg ggc         1272
Arg Lys Glu Tyr Phe Tyr Lys Tyr Phe His Asn Ala Glu Gln Ala Gly
370                 375                 380                 385 caa gtc ttc aat tac gtg agg gac aac gag cct ctc ttc acc atg tgc         1320
Gln Val Phe Asn Tyr Val Arg Asp Asn Glu Pro Leu Phe Thr Met Cys
                390                 395                 400 ttc gtc ccc ctg gtg tgc tgg gtg gtg tgt acc tgc ctc cag cag cag         1368
Phe Val Pro Leu Val Cys Trp Val Val Cys Thr Cys Leu Gln Gln Gln
            405                 410                 415 ctg gag ggt ggg ggg ctg ttg aga cag acg tcc agg acc acc act gca         1416
Leu Glu Gly Gly Gly Leu Leu Arg Gln Thr Ser Arg Thr Thr Thr Ala
        420                 425                 430 gtg tac atg ctc tac ctg ctg agt ctg atg caa ccc aag ccg ggg gcc         1464
Val Tyr Met Leu Tyr Leu Leu Ser Leu Met Gln Pro Lys Pro Gly Ala
435                 440                 445 ccg cgc ctc cag ccc cca ccc aac cag aga ggg ttg tgc tcc ttg gcg         1512
Pro Arg Leu Gln Pro Pro Pro Asn Gln Arg Gly Leu Cys Ser Leu Ala
450                 455                 460                 465 gca gat ggg ctc tgg aat cag aaa atc cta ttt gag gag cag gac ctc         1560
Ala Asp Gly Leu Trp Asn Gln Lys Ile Leu Phe Glu Glu Gln Asp Leu
                470                 475                 480 cgg aag cac ggc cta gac ggg gaa gac gtc tct gcc ttc ctc aac atg         1608
Arg Lys His Gly Leu Asp Gly Glu Asp Val Ser Ala Phe Leu Asn Met
            485                 490                 495 aac atc ttc cag aag gac atc aac tgt gag agg tac tac agc ttc atc         1656
Asn Ile Phe Gln Lys Asp Ile Asn Cys Glu Arg Tyr Tyr Ser Phe Ile
        500                 505                 510 cac ttg agt ttc cag gaa ttc ttt gca gct atg tac tat atc ctg gac         1704
His Leu Ser Phe Gln Glu Phe Phe Ala Ala Met Tyr Tyr Ile Leu Asp
    515                 520                 525 gag ggg gag ggc ggg gca ggc cca gac cag gac gtg acc agg ctg ttg         1752
Glu Gly Glu Gly Gly Ala Gly Pro Asp Gln Asp Val Thr Arg Leu Leu
530                 535                 540                 545 acc gag tac gcg ttt tct gaa agg agc ttc ctg gca ctc acc agc cgc         1800
Thr Glu Tyr Ala Phe Ser Glu Arg Ser Phe Leu Ala Leu Thr Ser Arg
                550                 555                 560 ttc ctg ttt gga ctc ctg aac gag gag acc agg agc cac ctg gag aag         1848
Phe Leu Phe Gly Leu Leu Asn Glu Glu Thr Arg Ser His Leu Glu Lys
            565                 570                 575 agt ctc tgc tgg aag gtc tcg ccg cac atc aag atg gac ctg ttg cag         1896
Ser Leu Cys Trp Lys Val Ser Pro His Ile Lys Met Asp Leu Leu Gln
        580                 585                 590 tgg atc caa agc aaa gct cag agc gac ggc tcc acc ctg cag cag ggc         1944
Trp Ile Gln Ser Lys Ala Gln Ser Asp Gly Ser Thr Leu Gln Gln Gly
    595                 600                 605 tcc ttg gag ttc ttc agc tgc ttg tac gag atc cag gag gag gag ttt         1992
Ser Leu Glu Phe Phe Ser Cys Leu Tyr Glu Ile Gln Glu Glu Glu Phe
610                 615                 620                 625
```

```
atc cag cag gcc ctg agc cac ttc cag gtg atc gtg gtc agc aac att       2040
Ile Gln Gln Ala Leu Ser His Phe Gln Val Ile Val Val Ser Asn Ile
                630                 635                 640 gcc tcc aag atg gag cac atg gtc tcc tcg ttc tgt ctg aag cgc tgc       2088
Ala Ser Lys Met Glu His Met Val Ser Ser Phe Cys Leu Lys Arg Cys
    645                 650                 655 agg agc gcc cag gtg ctg cac ttg tat ggc gcc acc tac agc gcg gac       2136
Arg Ser Ala Gln Val Leu His Leu Tyr Gly Ala Thr Tyr Ser Ala Asp
660                 665                 670 ggg gaa gac cgc gcg agg tgc tcc gca gga gcg cac acg ctg ttg gtg       2184
Gly Glu Asp Arg Ala Arg Cys Ser Ala Gly Ala His Thr Leu Leu Val
    675                 680                 685 cag ctc aga cca gag agg acc gtt ctg ctg gac gcc tac agt gaa cat       2232
Gln Leu Arg Pro Glu Arg Thr Val Leu Leu Asp Ala Tyr Ser Glu His
690                 695                 700                 705 ctg gca gcg gcc ctg tgc acc aat cca aac ctg ata gag ctg tct ctg       2280
Leu Ala Ala Ala Leu Cys Thr Asn Pro Asn Leu Ile Glu Leu Ser Leu
                710                 715                 720 tac cga aat gcc ctg ggc agc cgg ggg gtg aag ctc ctc tgt caa gga       2328
Tyr Arg Asn Ala Leu Gly Ser Arg Gly Val Lys Leu Leu Cys Gln Gly
            725                 730                 735 ctc aga cac ccc aac tgc aaa ctt cag aac ctg agg ctg aag agg tgc       2376
Leu Arg His Pro Asn Cys Lys Leu Gln Asn Leu Arg Leu Lys Arg Cys
        740                 745                 750 cgc atc tcc agc tca gcc tgc gag gac ctc tct gca gct ctc ata gcc       2424
Arg Ile Ser Ser Ser Ala Cys Glu Asp Leu Ser Ala Ala Leu Ile Ala
    755                 760                 765 aat aag aat ttg aca agg atg gat ctc agt ggc aac ggc gtt gga ttc       2472
Asn Lys Asn Leu Thr Arg Met Asp Leu Ser Gly Asn Gly Val Gly Phe
770                 775                 780                 785 cca ggc atg atg ctg ctt tgc gag ggc ctg cgg cat ccc cag tgc agg       2520
Pro Gly Met Met Leu Leu Cys Glu Gly Leu Arg His Pro Gln Cys Arg
                790                 795                 800 ctg cag atg att cag ttg agg aag tgt cag ctg gag tcc ggg gct tgt       2568
Leu Gln Met Ile Gln Leu Arg Lys Cys Gln Leu Glu Ser Gly Ala Cys
            805                 810                 815 cag gag atg gct tct gtg ctc ggc acc aac cca cat ctg gtt gag ttg       2616
Gln Glu Met Ala Ser Val Leu Gly Thr Asn Pro His Leu Val Glu Leu
        820                 825                 830 gac ctg aca gga aat gca ctg gag gat ttg ggc ctg agg tta cta tgc       2664
Asp Leu Thr Gly Asn Ala Leu Glu Asp Leu Gly Leu Arg Leu Leu Cys
    835                 840                 845 cag gga ctg agg cac cca gtc tgc aga cta cgg act ttg tgg ctg aag       2712
Gln Gly Leu Arg His Pro Val Cys Arg Leu Arg Thr Leu Trp Leu Lys
850                 855                 860                 865 atc tgc cgc ctc act gct gct gcc tgt gac gag ctg gcc tca act ctc       2760
Ile Cys Arg Leu Thr Ala Ala Ala Cys Asp Glu Leu Ala Ser Thr Leu
                870                 875                 880 agt gtg aac cag agc ctg aga gag ctg gac ctg agc ctg aat gag ctg       2808
Ser Val Asn Gln Ser Leu Arg Glu Leu Asp Leu Ser Leu Asn Glu Leu
            885                 890                 895 ggg gac ctc ggg gtg ctg ctg tgt gag ggc ctc agg cat ccc acg       2856
Gly Asp Leu Gly Val Leu Leu Cys Glu Gly Leu Arg His Pro Thr
        900                 905                 910 tgc aag ctc cag acc ctg cgg ttg ggc atc tgc cgg ctg ggc tct gcc       2904
Cys Lys Leu Gln Thr Leu Arg Leu Gly Ile Cys Arg Leu Gly Ser Ala
    915                 920                 925 gcc tgt gag ggt ctt tct gtg gtg ctc cag gcc aac cac aac ctc cgg       2952
Ala Cys Glu Gly Leu Ser Val Val Leu Gln Ala Asn His Asn Leu Arg
930                 935                 940                 945
```

-continued

```
gag ctg gac ttg agt ttc aac gac ctg gga gac tgg ggc ctg tgg ttg    3000
Glu Leu Asp Leu Ser Phe Asn Asp Leu Gly Asp Trp Gly Leu Trp Leu
            950                 955                 960 ctg gct gag ggg ctg caa cat ccc gcc tgc aga ctc cag aaa ctg tgg    3048
Leu Ala Glu Gly Leu Gln His Pro Ala Cys Arg Leu Gln Lys Leu Trp
        965                 970                 975 ctg gat agc tgt ggc ctc aca gcc aag gct tgt gag aat ctt tac ttc    3096
Leu Asp Ser Cys Gly Leu Thr Ala Lys Ala Cys Glu Asn Leu Tyr Phe
    980                 985                 990 acc ctg ggg atc aac cag acc ttg acc gac ctt tac ctg acc aac aac    3144
Thr Leu Gly Ile Asn Gln Thr Leu Thr Asp Leu Tyr Leu Thr Asn Asn
995                 1000                1005 gcc cta ggg gac aca ggt gtc cga ctg ctt tgc aag cgg ctg agc cat    3192
Ala Leu Gly Asp Thr Gly Val Arg Leu Leu Cys Lys Arg Leu Ser His
1010                1015                1020                1025 cct ggc tg caaactccga gtcctctg                                     3218
Pro Gly

<210> SEQ ID NO 68
<211> LENGTH: 1027
<212> TYPE: PRT
<213> ORGANISM: Homo sapiens

<400> SEQUENCE: 68

Met Leu Arg Thr Ala Gly Arg Asp Gly Leu Cys Arg Leu Ser Thr Tyr
1               5                   10                  15

Leu Glu Glu Leu Glu Ala Val Glu Leu Lys Lys Phe Lys Leu Tyr Leu
            20                  25                  30

Gly Thr Ala Thr Glu Leu Gly Glu Gly Lys Ile Pro Trp Gly Ser Met
        35                  40                  45

Glu Lys Ala Gly Pro Leu Glu Met Ala Gln Leu Leu Ile Thr His Phe
    50                  55                  60

Gly Pro Glu Glu Ala Trp Arg Leu Ala Leu Ser Thr Phe Glu Arg Ile
65                  70                  75                  80

Asn Arg Lys Asp Leu Trp Glu Arg Gly Gln Arg Glu Asp Leu Val Arg
                85                  90                  95

Asp Thr Pro Pro Gly Pro Ser Ser Leu Gly Asn Gln Ser Thr Cys
            100                 105                 110

Leu Leu Glu Val Ser Leu Val Thr Pro Arg Lys Asp Pro Gln Glu Thr
        115                 120                 125

Tyr Arg Asp Tyr Val Arg Arg Lys Phe Arg Leu Met Glu Asp Arg Asn
    130                 135                 140

Ala Arg Leu Gly Glu Cys Val Asn Leu Ser His Arg Tyr Thr Arg Leu
145                 150                 155                 160

Leu Leu Val Lys Glu His Ser Asn Pro Met Gln Val Gln Gln Leu
                165                 170                 175

Leu Asp Thr Gly Arg Gly His Ala Arg Thr Val Gly His Gln Ala Ser
            180                 185                 190

Pro Ile Lys Ile Glu Thr Leu Phe Glu Pro Asp Glu Arg Pro Glu
        195                 200                 205

Pro Pro Arg Thr Val Val Met Gln Gly Ala Ala Gly Ile Gly Lys Ser
    210                 215                 220

Met Leu Ala His Lys Val Met Leu Asp Trp Ala Asp Gly Lys Leu Phe
225                 230                 235                 240

Gln Gly Arg Phe Asp Tyr Leu Phe Tyr Ile Asn Cys Arg Glu Met Asn
                245                 250                 255
```

```
Gln Ser Ala Thr Glu Cys Ser Met Gln Asp Leu Ile Phe Ser Cys Trp
            260                 265                 270

Pro Glu Pro Ser Ala Pro Leu Gln Glu Leu Ile Arg Val Pro Glu Arg
            275                 280                 285

Leu Leu Phe Ile Ile Asp Gly Phe Asp Glu Leu Lys Pro Ser Phe His
            290                 295                 300

Asp Pro Gln Gly Pro Trp Cys Leu Cys Trp Glu Glu Lys Arg Pro Thr
305                 310                 315                 320

Glu Leu Leu Leu Asn Ser Leu Ile Arg Lys Lys Leu Pro Glu Leu
            325                 330                 335

Ser Leu Leu Ile Thr Thr Arg Pro Thr Ala Leu Glu Lys Leu His Arg
            340                 345                 350

Leu Leu Glu His Pro Arg His Val Glu Ile Leu Gly Phe Ser Glu Ala
            355                 360                 365

Glu Arg Lys Glu Tyr Phe Tyr Lys Tyr Phe His Asn Ala Glu Gln Ala
            370                 375                 380

Gly Gln Val Phe Asn Tyr Val Arg Asp Asn Glu Pro Leu Phe Thr Met
385                 390                 395                 400

Cys Phe Val Pro Leu Val Cys Trp Val Val Cys Thr Cys Leu Gln Gln
            405                 410                 415

Gln Leu Glu Gly Gly Leu Leu Arg Gln Thr Ser Arg Thr Thr Thr
            420                 425                 430

Ala Val Tyr Met Leu Tyr Leu Leu Ser Leu Met Gln Pro Lys Pro Gly
            435                 440                 445

Ala Pro Arg Leu Gln Pro Pro Asn Gln Arg Gly Leu Cys Ser Leu
            450                 455                 460

Ala Ala Asp Gly Leu Trp Asn Gln Lys Ile Leu Phe Glu Glu Gln Asp
465                 470                 475                 480

Leu Arg Lys His Gly Leu Asp Gly Glu Asp Val Ser Ala Phe Leu Asn
            485                 490                 495

Met Asn Ile Phe Gln Lys Asp Ile Asn Cys Glu Arg Tyr Tyr Ser Phe
            500                 505                 510

Ile His Leu Ser Phe Gln Glu Phe Ala Ala Met Tyr Tyr Ile Leu
            515                 520                 525

Asp Glu Gly Glu Gly Gly Ala Gly Pro Asp Gln Asp Val Thr Arg Leu
            530                 535                 540

Leu Thr Glu Tyr Ala Phe Ser Glu Arg Ser Phe Leu Ala Leu Thr Ser
545                 550                 555                 560

Arg Phe Leu Phe Gly Leu Leu Asn Glu Glu Thr Arg Ser His Leu Glu
            565                 570                 575

Lys Ser Leu Cys Trp Lys Val Ser Pro His Ile Lys Met Asp Leu Leu
            580                 585                 590

Gln Trp Ile Gln Ser Lys Ala Gln Ser Asp Gly Ser Thr Leu Gln Gln
            595                 600                 605

Gly Ser Leu Glu Phe Phe Ser Cys Leu Tyr Glu Ile Gln Glu Glu Glu
            610                 615                 620

Phe Ile Gln Gln Ala Leu Ser His Phe Gln Val Ile Val Ser Asn
625                 630                 635                 640

Ile Ala Ser Lys Met Glu His Met Val Ser Ser Phe Cys Leu Lys Arg
            645                 650                 655

Cys Arg Ser Ala Gln Val Leu His Leu Tyr Gly Ala Thr Tyr Ser Ala
            660                 665                 670
```

```
Asp Gly Glu Asp Arg Ala Arg Cys Ser Ala Gly Ala His Thr Leu Leu
            675                 680                 685

Val Gln Leu Arg Pro Glu Arg Thr Val Leu Leu Asp Ala Tyr Ser Glu
        690                 695                 700

His Leu Ala Ala Ala Leu Cys Thr Asn Pro Asn Leu Ile Glu Leu Ser
705                 710                 715                 720

Leu Tyr Arg Asn Ala Leu Gly Ser Arg Gly Val Lys Leu Leu Cys Gln
                725                 730                 735

Gly Leu Arg His Pro Asn Cys Lys Leu Gln Asn Leu Arg Leu Lys Arg
            740                 745                 750

Cys Arg Ile Ser Ser Ser Ala Cys Glu Asp Leu Ser Ala Ala Leu Ile
        755                 760                 765

Ala Asn Lys Asn Leu Thr Arg Met Asp Leu Ser Gly Asn Gly Val Gly
770                 775                 780

Phe Pro Gly Met Met Leu Leu Cys Glu Gly Leu Arg His Pro Gln Cys
785                 790                 795                 800

Arg Leu Gln Met Ile Gln Leu Arg Lys Cys Gln Leu Glu Ser Gly Ala
                805                 810                 815

Cys Gln Glu Met Ala Ser Val Leu Gly Thr Asn Pro His Leu Val Glu
            820                 825                 830

Leu Asp Leu Thr Gly Asn Ala Leu Glu Asp Leu Gly Leu Arg Leu Leu
        835                 840                 845

Cys Gln Gly Leu Arg His Pro Val Cys Arg Leu Arg Thr Leu Trp Leu
    850                 855                 860

Lys Ile Cys Arg Leu Thr Ala Ala Ala Cys Asp Glu Leu Ala Ser Thr
865                 870                 875                 880

Leu Ser Val Asn Gln Ser Leu Arg Glu Leu Asp Leu Ser Leu Asn Glu
                885                 890                 895

Leu Gly Asp Leu Gly Val Leu Leu Leu Cys Glu Gly Leu Arg His Pro
            900                 905                 910

Thr Cys Lys Leu Gln Thr Leu Arg Leu Gly Ile Cys Arg Leu Gly Ser
        915                 920                 925

Ala Ala Cys Glu Gly Leu Ser Val Val Leu Gln Ala Asn His Asn Leu
    930                 935                 940

Arg Glu Leu Asp Leu Ser Phe Asn Asp Leu Gly Asp Trp Gly Leu Trp
945                 950                 955                 960

Leu Leu Ala Glu Gly Leu Gln His Pro Ala Cys Arg Leu Gln Lys Leu
                965                 970                 975

Trp Leu Asp Ser Cys Gly Leu Thr Ala Lys Ala Cys Glu Asn Leu Tyr
            980                 985                 990

Phe Thr Leu Gly Ile Asn Gln Thr Leu Thr Asp Leu Tyr Leu Thr Asn
        995                 1000                1005

Asn Ala Leu Gly Asp Thr Gly Val Arg Leu Leu Cys Lys Arg Leu Ser
    1010                1015                1020

His Pro Gly
1025

<210> SEQ ID NO 69
<211> LENGTH: 2859
<212> TYPE: DNA
<213> ORGANISM: Homo sapiens
<220> FEATURE:
<221> NAME/KEY: CDS
<222> LOCATION: (1)...(2859)

<400> SEQUENCE: 69
```

-continued

```
atg aca tcg ccc cag cta gag tgg act ctg cag acc ctt ctg gag cag     48
Met Thr Ser Pro Gln Leu Glu Trp Thr Leu Gln Thr Leu Leu Glu Gln
 1               5                  10                  15 ctg aac gag gat gaa tta aag agt ttc aaa tcc ctt tta tgg gct ttt     96
Leu Asn Glu Asp Glu Leu Lys Ser Phe Lys Ser Leu Leu Trp Ala Phe
            20                  25                  30 ccc ctc gaa gac gtg cta cag aag acc cca tgg tct gag gtg gaa gag    144
Pro Leu Glu Asp Val Leu Gln Lys Thr Pro Trp Ser Glu Val Glu Glu
         35                  40                  45 gct gat ggc aag aaa ctg gca gaa att ctg gtc aac acc tcc tca gaa    192
Ala Asp Gly Lys Lys Leu Ala Glu Ile Leu Val Asn Thr Ser Ser Glu
     50                  55                  60 aat tgg ata agg aat gcg act gtg aac atc ttg gaa gag atg aat ctc    240
Asn Trp Ile Arg Asn Ala Thr Val Asn Ile Leu Glu Glu Met Asn Leu
 65                  70                  75                  80 acg gaa ttg tgt aag atg gca aag gct gag atg atg gag gac gga cag    288
Thr Glu Leu Cys Lys Met Ala Lys Ala Glu Met Met Glu Asp Gly Gln
                 85                  90                  95 gtg caa gaa ata gat aat cct gag ctg gga gat gca gaa gaa gac tcg    336
Val Gln Glu Ile Asp Asn Pro Glu Leu Gly Asp Ala Glu Glu Asp Ser
            100                 105                 110 gag tta gca aag cca ggt gaa aag gaa gga tgg aga aat tca atg gag    384
Glu Leu Ala Lys Pro Gly Glu Lys Glu Gly Trp Arg Asn Ser Met Glu
        115                 120                 125 aaa cag tct ttg gtc tgg aag aac acc ttt tgg caa gga gac att gac    432
Lys Gln Ser Leu Val Trp Lys Asn Thr Phe Trp Gln Gly Asp Ile Asp
    130                 135                 140 aat ttc cat gac gac gtc act ctg aga aac caa cgg ttc att cca ttc    480
Asn Phe His Asp Asp Val Thr Leu Arg Asn Gln Arg Phe Ile Pro Phe
145                 150                 155                 160 ttg aat ccc aga aca ccc agg aag cta aca cct tac acg gtg gtg ctg    528
Leu Asn Pro Arg Thr Pro Arg Lys Leu Thr Pro Tyr Thr Val Val Leu
                165                 170                 175 cac ggc ccc gca ggc gtg ggg aaa acc acg ctg gcc aaa aag tgt atg    576
His Gly Pro Ala Gly Val Gly Lys Thr Thr Leu Ala Lys Lys Cys Met
            180                 185                 190 ctg gac tgg aca gac tgc aac ctc agc ccg acg ctc aga tac gcg ttc    624
Leu Asp Trp Thr Asp Cys Asn Leu Ser Pro Thr Leu Arg Tyr Ala Phe
        195                 200                 205 tac ctc agc tgc aag gag ctc agc cgc atg ggc ccc tgc agt ttt gca    672
Tyr Leu Ser Cys Lys Glu Leu Ser Arg Met Gly Pro Cys Ser Phe Ala
    210                 215                 220 gag ctg atc tcc aaa gac tgg cct gaa ttg cag gat gac att cca agc    720
Glu Leu Ile Ser Lys Asp Trp Pro Glu Leu Gln Asp Asp Ile Pro Ser
225                 230                 235                 240 atc cta gcc caa gca cag aga atc ctg ttc gtg gtc gat ggc ctt gat    768
Ile Leu Ala Gln Ala Gln Arg Ile Leu Phe Val Val Asp Gly Leu Asp
                245                 250                 255 gag ctg aaa gtc cca cct ggg gcg ctg atc cag gac atc tgc ggg gac    816
Glu Leu Lys Val Pro Pro Gly Ala Leu Ile Gln Asp Ile Cys Gly Asp
            260                 265                 270 tgg gag aag aag aag ccg gtc ccc gtc ctc ctg ggg agt ttg ctg aag    864
Trp Glu Lys Lys Lys Pro Val Pro Val Leu Leu Gly Ser Leu Leu Lys
        275                 280                 285 agg aag atg tta ccc agg gca gcc ttg ctg gtc acc acg cgg ccc agg    912
Arg Lys Met Leu Pro Arg Ala Ala Leu Leu Val Thr Thr Arg Pro Arg
    290                 295                 300 gca ctg agg gac ctc cag ctc ctg gcg cag cag ccg atc tac gta agg    960
Ala Leu Arg Asp Leu Gln Leu Leu Ala Gln Gln Pro Ile Tyr Val Arg
```

-continued

```
             305                 310                 315                 320
gtg gag ggc ttc ctg gag gag gac agg agg gcc tat ttc ctg aga cac        1008
Val Glu Gly Phe Leu Glu Glu Asp Arg Arg Ala Tyr Phe Leu Arg His
                    325                 330                 335 ttt gga gac gag gac caa gcc atg cgt gcc ttt gag cta atg agg agc        1056
Phe Gly Asp Glu Asp Gln Ala Met Arg Ala Phe Glu Leu Met Arg Ser
                340                 345                 350 aac gcg gcc ctg ttc cag ctg ggc tcg gcc ccc gcg gtg tgc tgg att        1104
Asn Ala Ala Leu Phe Gln Leu Gly Ser Ala Pro Ala Val Cys Trp Ile
            355                 360                 365 gtg tgc acg act ctg aag ctg cag atg gag aag ggg gag gac ccg gtc        1152
Val Cys Thr Thr Leu Lys Leu Gln Met Glu Lys Gly Glu Asp Pro Val
        370                 375                 380 ccc acc tgc ctc acc cgc acg ggg ctg ttc ctg cgt ttc ctc tgc agc        1200
Pro Thr Cys Leu Thr Arg Thr Gly Leu Phe Leu Arg Phe Leu Cys Ser
385                 390                 395                 400 cgg ttc ccg cag ggc gca cag ctg cgg gcg ctg cgg acg ctg agc            1248
Arg Phe Pro Gln Gly Ala Gln Leu Arg Gly Ala Leu Arg Thr Leu Ser
                405                 410                 415 ctc ctg gcc gcg cag ggc ctg tgg gcg cag atg tcc gtg ttc cac cga        1296
Leu Leu Ala Ala Gln Gly Leu Trp Ala Gln Met Ser Val Phe His Arg
                420                 425                 430 gag gac ctg gaa agg ctc ggg gtg cag gag tcc gac ctc cgt ctg ttc        1344
Glu Asp Leu Glu Arg Leu Gly Val Gln Glu Ser Asp Leu Arg Leu Phe
            435                 440                 445 ctg gac gga gac atc ctc cgc cag gac aga gtc tcc aaa ggc tgc tac        1392
Leu Asp Gly Asp Ile Leu Arg Gln Asp Arg Val Ser Lys Gly Cys Tyr
        450                 455                 460 tcc ttc atc cac ctc agc ttc cag cag ttt ctc act gcc ctg ttc tac        1440
Ser Phe Ile His Leu Ser Phe Gln Gln Phe Leu Thr Ala Leu Phe Tyr
465                 470                 475                 480 gcc ctg gag aag gag gag ggg gag gac agg gac ggc cac gcc tgg gac        1488
Ala Leu Glu Lys Glu Glu Gly Glu Asp Arg Asp Gly His Ala Trp Asp
                485                 490                 495 atc ggg gac gta cag aag ctg ctt tcc gga gaa gaa aga ctc aag aac        1536
Ile Gly Asp Val Gln Lys Leu Leu Ser Gly Glu Glu Arg Leu Lys Asn
                500                 505                 510 ccc gac ctg att caa gta gga cac ttc tta ttc ggc ctc gct aac gag        1584
Pro Asp Leu Ile Gln Val Gly His Phe Leu Phe Gly Leu Ala Asn Glu
            515                 520                 525 aag aga gcc aag gag ttg gag gcc act ttt ggc tgc cgg atg tca ccg        1632
Lys Arg Ala Lys Glu Leu Glu Ala Thr Phe Gly Cys Arg Met Ser Pro
        530                 535                 540 gac atc aaa cag gaa ttg ctg caa tgc aaa gca cat ctt cat gca aat        1680
Asp Ile Lys Gln Glu Leu Leu Gln Cys Lys Ala His Leu His Ala Asn
545                 550                 555                 560 aag ccc tta tcc gtg acc gac ctg aag gag gtc ttg ggc tgc ctg tat        1728
Lys Pro Leu Ser Val Thr Asp Leu Lys Glu Val Leu Gly Cys Leu Tyr
                565                 570                 575 gag tct cag gag gag gag ctg gcg aag gtg gtg gtg gcc ccg ttc aag        1776
Glu Ser Gln Glu Glu Glu Leu Ala Lys Val Val Val Ala Pro Phe Lys
                580                 585                 590 gaa att tct att cac ctg aca aat act tct gaa gtg atg cat tgt tcc        1824
Glu Ile Ser Ile His Leu Thr Asn Thr Ser Glu Val Met His Cys Ser
            595                 600                 605 ttc agc ctg aag cat tgt caa gac ttg cag aaa ctc tca ctg cag gta        1872
Phe Ser Leu Lys His Cys Gln Asp Leu Gln Lys Leu Ser Leu Gln Val
        610                 615                 620 gca aag ggg gtg ttc ctg gag aat tac atg gat ttt gaa ctg gac att        1920
Ala Lys Gly Val Phe Leu Glu Asn Tyr Met Asp Phe Glu Leu Asp Ile
```

```
Ala Lys Gly Val Phe Leu Glu Asn Tyr Met Asp Phe Glu Leu Asp Ile
625                 630                 635                 640 gaa ttt gaa agc tca aac agc aac ctc aag ttt ctg gaa gtg aaa caa      1968
Glu Phe Glu Ser Ser Asn Ser Asn Leu Lys Phe Leu Glu Val Lys Gln
                    645                 650                 655 agc ttc ctg agt gac tct tct gtg cgg att ctt tgt gac cac gta acc      2016
Ser Phe Leu Ser Asp Ser Ser Val Arg Ile Leu Cys Asp His Val Thr
                660                 665                 670 cgt agc acc tgt cat ctg cag aaa gtg gag att aaa aac gtc acc cct      2064
Arg Ser Thr Cys His Leu Gln Lys Val Glu Ile Lys Asn Val Thr Pro
            675                 680                 685 gac acc gcg tac cgg gac ttc tgt ctt gct ttc att ggg aag aag acc      2112
Asp Thr Ala Tyr Arg Asp Phe Cys Leu Ala Phe Ile Gly Lys Lys Thr
        690                 695                 700 ctc acg cac ctg acc ctg gca ggg cac atc gag tgg gaa cgc acg atg      2160
Leu Thr His Leu Thr Leu Ala Gly His Ile Glu Trp Glu Arg Thr Met
705                 710                 715                 720 atg ctg atg ctg tgt gac ctg ctc aga aat cat aaa tgc aac ctg cag      2208
Met Leu Met Leu Cys Asp Leu Leu Arg Asn His Lys Cys Asn Leu Gln
                    725                 730                 735 tac ctg agg ttg gga ggt cac tgt gcc acc ccg gag cag tgg gct gaa      2256
Tyr Leu Arg Leu Gly Gly His Cys Ala Thr Pro Glu Gln Trp Ala Glu
                740                 745                 750 ttc ttc tat gtc ctc aaa gcc aac cag tcc ctg aag cac ctg cgt ctc      2304
Phe Phe Tyr Val Leu Lys Ala Asn Gln Ser Leu Lys His Leu Arg Leu
            755                 760                 765 tca gcc aat gtg ctc ctg gat gag ggt gcc atg ttg ctg tac aag acc      2352
Ser Ala Asn Val Leu Leu Asp Glu Gly Ala Met Leu Leu Tyr Lys Thr
        770                 775                 780 atg aca cgc cca aaa cac ttc ctg cag atg ttg tcg ttg gaa aac tgt      2400
Met Thr Arg Pro Lys His Phe Leu Gln Met Leu Ser Leu Glu Asn Cys
785                 790                 795                 800 cgt ctt aca gaa gcc agt tgc aag gac ctt gct gct gtc ttg gtt gtc      2448
Arg Leu Thr Glu Ala Ser Cys Lys Asp Leu Ala Ala Val Leu Val Val
                    805                 810                 815 agc aag aag ctg aca cac ctg tgc ttg gcc aag aac ccc att ggg gat      2496
Ser Lys Lys Leu Thr His Leu Cys Leu Ala Lys Asn Pro Ile Gly Asp
                820                 825                 830 aca ggg gtg aag ttt ctg tgt gag ggc ttg agt tac cct gat tgt aaa      2544
Thr Gly Val Lys Phe Leu Cys Glu Gly Leu Ser Tyr Pro Asp Cys Lys
            835                 840                 845 ctg cag acc ttg gtg tta cag caa tgc agc ata acc aag ctt ggc tgt      2592
Leu Gln Thr Leu Val Leu Gln Gln Cys Ser Ile Thr Lys Leu Gly Cys
        850                 855                 860 aga tac ctc tca gag gcg ctc caa gaa gcc tgc agc ctc aca aac ctg      2640
Arg Tyr Leu Ser Glu Ala Leu Gln Glu Ala Cys Ser Leu Thr Asn Leu
865                 870                 875                 880 gac ttg agt atc aac cag ata gct cgt gga ttg tgg att ctc tgt cag      2688
Asp Leu Ser Ile Asn Gln Ile Ala Arg Gly Leu Trp Ile Leu Cys Gln
                    885                 890                 895 gcg tta gag aat cca aac tgt aac cta aaa cac cta cgg ttg aag acc      2736
Ala Leu Glu Asn Pro Asn Cys Asn Leu Lys His Leu Arg Leu Lys Thr
                900                 905                 910 tat gaa act aat ttg gaa atc aag aag ctg ttg gag gaa gtg aaa gaa      2784
Tyr Glu Thr Asn Leu Glu Ile Lys Lys Leu Leu Glu Glu Val Lys Glu
            915                 920                 925 aag aat ccc aag ctg act att gat tgc aat gct tcc ggg gca acg gca      2832
Lys Asn Pro Lys Leu Thr Ile Asp Cys Asn Ala Ser Gly Ala Thr Ala
        930                 935                 940
```

```
cct ccg tgc tgt gac ttt ttt tgc tga                                    2859
Pro Pro Cys Cys Asp Phe Phe Cys *
945             950
```

<210> SEQ ID NO 70
<211> LENGTH: 952
<212> TYPE: PRT
<213> ORGANISM: Homo sapiens

<400> SEQUENCE: 70

```
Met Thr Ser Pro Gln Leu Glu Trp Thr Leu Gln Thr Leu Leu Glu Gln
 1               5                  10                  15

Leu Asn Glu Asp Glu Leu Lys Ser Phe Lys Ser Leu Leu Trp Ala Phe
            20                  25                  30

Pro Leu Glu Asp Val Leu Gln Lys Thr Pro Trp Ser Glu Val Glu Glu
        35                  40                  45

Ala Asp Gly Lys Lys Leu Ala Glu Ile Leu Val Asn Thr Ser Ser Glu
    50                  55                  60

Asn Trp Ile Arg Asn Ala Thr Val Asn Ile Leu Glu Glu Met Asn Leu
65                  70                  75                  80

Thr Glu Leu Cys Lys Met Ala Lys Ala Glu Met Met Glu Asp Gly Gln
                85                  90                  95

Val Gln Glu Ile Asp Asn Pro Glu Leu Gly Asp Ala Glu Glu Asp Ser
            100                 105                 110

Glu Leu Ala Lys Pro Gly Glu Lys Glu Gly Trp Arg Asn Ser Met Glu
        115                 120                 125

Lys Gln Ser Leu Val Trp Lys Asn Thr Phe Trp Gln Gly Asp Ile Asp
    130                 135                 140

Asn Phe His Asp Asp Val Thr Leu Arg Asn Gln Arg Phe Ile Pro Phe
145                 150                 155                 160

Leu Asn Pro Arg Thr Pro Arg Lys Leu Thr Pro Tyr Thr Val Val Leu
                165                 170                 175

His Gly Pro Ala Gly Val Gly Lys Thr Thr Leu Ala Lys Lys Cys Met
            180                 185                 190

Leu Asp Trp Thr Asp Cys Asn Leu Ser Pro Thr Leu Arg Tyr Ala Phe
        195                 200                 205

Tyr Leu Ser Cys Lys Glu Leu Ser Arg Met Gly Pro Cys Ser Phe Ala
    210                 215                 220

Glu Leu Ile Ser Lys Asp Trp Pro Glu Leu Gln Asp Ile Pro Ser
225                 230                 235                 240

Ile Leu Ala Gln Ala Gln Arg Ile Leu Phe Val Asp Gly Leu Asp
                245                 250                 255

Glu Leu Lys Val Pro Pro Gly Ala Leu Ile Gln Asp Ile Cys Gly Asp
            260                 265                 270

Trp Glu Lys Lys Lys Pro Val Pro Val Leu Leu Gly Ser Leu Leu Lys
        275                 280                 285

Arg Lys Met Leu Pro Arg Ala Ala Leu Leu Val Thr Thr Arg Pro Arg
    290                 295                 300

Ala Leu Arg Asp Leu Gln Leu Leu Ala Gln Gln Pro Ile Tyr Val Arg
305                 310                 315                 320

Val Glu Gly Phe Leu Glu Glu Asp Arg Arg Ala Tyr Phe Leu Arg His
                325                 330                 335

Phe Gly Asp Glu Asp Gln Ala Met Arg Ala Phe Glu Leu Met Arg Ser
            340                 345                 350

Asn Ala Ala Leu Phe Gln Leu Gly Ser Ala Pro Ala Val Cys Trp Ile
```

```
                355                 360                 365
Val Cys Thr Thr Leu Lys Leu Gln Met Glu Lys Gly Glu Asp Pro Val
370                 375                 380

Pro Thr Cys Leu Thr Arg Thr Gly Leu Phe Leu Arg Phe Leu Cys Ser
385                 390                 395                 400

Arg Phe Pro Gln Gly Ala Gln Leu Arg Gly Ala Leu Arg Thr Leu Ser
            405                 410                 415

Leu Leu Ala Ala Gln Gly Leu Trp Ala Gln Met Ser Val Phe His Arg
                420                 425                 430

Glu Asp Leu Glu Arg Leu Gly Val Gln Glu Ser Asp Leu Arg Leu Phe
            435                 440                 445

Leu Asp Gly Asp Ile Leu Arg Gln Asp Arg Val Ser Lys Gly Cys Tyr
450                 455                 460

Ser Phe Ile His Leu Ser Phe Gln Gln Phe Leu Thr Ala Leu Phe Tyr
465                 470                 475                 480

Ala Leu Glu Lys Glu Gly Glu Asp Arg Asp Gly His Ala Trp Asp
                485                 490                 495

Ile Gly Asp Val Gln Lys Leu Leu Ser Gly Glu Glu Arg Leu Lys Asn
            500                 505                 510

Pro Asp Leu Ile Gln Val Gly His Phe Leu Phe Gly Leu Ala Asn Glu
515                 520                 525

Lys Arg Ala Lys Glu Leu Glu Ala Thr Phe Gly Cys Arg Met Ser Pro
530                 535                 540

Asp Ile Lys Gln Glu Leu Leu Gln Cys Lys Ala His Leu His Ala Asn
545                 550                 555                 560

Lys Pro Leu Ser Val Thr Asp Leu Lys Glu Val Leu Gly Cys Leu Tyr
            565                 570                 575

Glu Ser Gln Glu Glu Leu Ala Lys Val Val Ala Pro Phe Lys
            580                 585                 590

Glu Ile Ser Ile His Leu Thr Asn Thr Ser Glu Val Met His Cys Ser
            595                 600                 605

Phe Ser Leu Lys His Cys Gln Asp Leu Gln Lys Leu Ser Leu Gln Val
610                 615                 620

Ala Lys Gly Val Phe Leu Glu Asn Tyr Met Asp Phe Glu Leu Asp Ile
625                 630                 635                 640

Glu Phe Glu Ser Ser Asn Ser Asn Leu Lys Phe Leu Glu Val Lys Gln
                645                 650                 655

Ser Phe Leu Ser Asp Ser Ser Val Arg Ile Leu Cys Asp His Val Thr
            660                 665                 670

Arg Ser Thr Cys His Leu Gln Lys Val Glu Ile Lys Asn Val Thr Pro
            675                 680                 685

Asp Thr Ala Tyr Arg Asp Phe Cys Leu Ala Phe Ile Gly Lys Lys Thr
690                 695                 700

Leu Thr His Leu Thr Leu Ala Gly His Ile Glu Trp Glu Arg Thr Met
705                 710                 715                 720

Met Leu Met Leu Cys Asp Leu Leu Arg Asn His Lys Cys Asn Leu Gln
                725                 730                 735

Tyr Leu Arg Leu Gly Gly His Cys Ala Thr Pro Glu Gln Trp Ala Glu
            740                 745                 750

Phe Phe Tyr Val Leu Lys Ala Asn Gln Ser Leu Lys His Leu Arg Leu
            755                 760                 765

Ser Ala Asn Val Leu Leu Asp Glu Gly Ala Met Leu Leu Tyr Lys Thr
770                 775                 780
```

```
Met Thr Arg Pro Lys His Phe Leu Gln Met Leu Ser Leu Glu Asn Cys
785                 790                 795                 800

Arg Leu Thr Glu Ala Ser Cys Lys Asp Leu Ala Ala Val Leu Val Val
            805                 810                 815

Ser Lys Lys Leu Thr His Leu Cys Leu Ala Lys Asn Pro Ile Gly Asp
                820                 825                 830

Thr Gly Val Lys Phe Leu Cys Glu Gly Leu Ser Tyr Pro Asp Cys Lys
            835                 840                 845

Leu Gln Thr Leu Val Leu Gln Gln Cys Ser Ile Thr Lys Leu Gly Cys
        850                 855                 860

Arg Tyr Leu Ser Glu Ala Leu Gln Glu Ala Cys Ser Leu Thr Asn Leu
865                 870                 875                 880

Asp Leu Ser Ile Asn Gln Ile Ala Arg Gly Leu Trp Ile Leu Cys Gln
                885                 890                 895

Ala Leu Glu Asn Pro Asn Cys Asn Leu Lys His Leu Arg Leu Lys Thr
            900                 905                 910

Tyr Glu Thr Asn Leu Glu Ile Lys Lys Leu Leu Glu Glu Val Lys Glu
        915                 920                 925

Lys Asn Pro Lys Leu Thr Ile Asp Cys Asn Ala Ser Gly Ala Thr Ala
    930                 935                 940

Pro Pro Cys Cys Asp Phe Phe Cys
945                 950

<210> SEQ ID NO 71
<211> LENGTH: 2199
<212> TYPE: DNA
<213> ORGANISM: Homo sapiens
<220> FEATURE:
<221> NAME/KEY: CDS
<222> LOCATION: (1)...(2199)

<400> SEQUENCE: 71 atg gca gat tca tca tca tct tct ttc ttt cct gat ttt ggg ctg cta        48
Met Ala Asp Ser Ser Ser Ser Ser Phe Phe Pro Asp Phe Gly Leu Leu
1               5                   10                  15 ttg tat ttg gag gag cta aac aaa gag gaa tta aat aca ttc aag tta        96
Leu Tyr Leu Glu Glu Leu Asn Lys Glu Glu Leu Asn Thr Phe Lys Leu
            20                  25                  30 ttc cta aag gag acc atg gaa cct gag cat ggc ctg aca ccc tgg aat       144
Phe Leu Lys Glu Thr Met Glu Pro Glu His Gly Leu Thr Pro Trp Asn
        35                  40                  45 gaa gtg aag aag gcc agg cgg gag gac ctg gcc aat ttg atg aag aaa       192
Glu Val Lys Lys Ala Arg Arg Glu Asp Leu Ala Asn Leu Met Lys Lys
    50                  55                  60 tat tat cca gga gag aaa gcc tgg agt gtg tct ctc aaa atc ttt ggc       240
Tyr Tyr Pro Gly Glu Lys Ala Trp Ser Val Ser Leu Lys Ile Phe Gly
65                  70                  75                  80 aag atg aac ctg aag gat ctg tgt gag aga gcg aaa gaa gag atc aac       288
Lys Met Asn Leu Lys Asp Leu Cys Glu Arg Ala Lys Glu Glu Ile Asn
            85                  90                  95 tgg tcg gcc cag act ata gga cca gat gat gcc aag gct gga gag aca       336
Trp Ser Ala Gln Thr Ile Gly Pro Asp Asp Ala Lys Ala Gly Glu Thr
        100                 105                 110 caa gaa gat cag gag gca gtg ctg gtc ata gtt aac aca ggg gtc ccc       384
Gln Glu Asp Gln Glu Ala Val Leu Val Ile Val Asn Thr Gly Val Pro
    115                 120                 125 aac tcc tgg gcc aca gac ccc tac tgg tcg gcg gcc cct cgg gaa tca       432
Asn Ser Trp Ala Thr Asp Pro Tyr Trp Ser Ala Ala Pro Arg Glu Ser
```

```
              130                 135                 140
ggt cgc ata gca gga ggt gat gga aca gaa tac aga aat aga ata aag     480
Gly Arg Ile Ala Gly Gly Asp Gly Thr Glu Tyr Arg Asn Arg Ile Lys
145                 150                 155                 160 gaa aaa ttt tgc atc act tgg gac aag aag tct ttg gct gga aag cct     528
Glu Lys Phe Cys Ile Thr Trp Asp Lys Lys Ser Leu Ala Gly Lys Pro
                165                 170                 175 gaa gat ttc cat cat gga att gca gag aaa gat aga aaa ctg ttg gaa     576
Glu Asp Phe His His Gly Ile Ala Glu Lys Asp Arg Lys Leu Leu Glu
            180                 185                 190 cac ttg ttc gat gtg gat gtc aaa acc ggt gca cag cca cag atc gtg     624
His Leu Phe Asp Val Asp Val Lys Thr Gly Ala Gln Pro Gln Ile Val
        195                 200                 205 gtg ctt cag gga gct gct gga gtt ggg aaa aca acc ttg gtg aga aag     672
Val Leu Gln Gly Ala Ala Gly Val Gly Lys Thr Thr Leu Val Arg Lys
    210                 215                 220 gca atg tta gat tgg gca gag ggc agt ctc tac cag cag agg ttt aag     720
Ala Met Leu Asp Trp Ala Glu Gly Ser Leu Tyr Gln Gln Arg Phe Lys
225                 230                 235                 240 tat gtt ttt tat ctc aat ggg aga gaa att aac cag ctg aaa gag aga     768
Tyr Val Phe Tyr Leu Asn Gly Arg Glu Ile Asn Gln Leu Lys Glu Arg
                245                 250                 255 agc ttt gct caa ttg ata tca aag gac tgg ccc agc aca gaa ggc ccc     816
Ser Phe Ala Gln Leu Ile Ser Lys Asp Trp Pro Ser Thr Glu Gly Pro
            260                 265                 270 att gaa gaa atc atg tac cag cca agc agc ctc ttg ttt att att gac     864
Ile Glu Glu Ile Met Tyr Gln Pro Ser Ser Leu Leu Phe Ile Ile Asp
        275                 280                 285 agt ttc gat gaa ctg aac ttt gcc ttt gaa gaa cct gag ttt gca ctg     912
Ser Phe Asp Glu Leu Asn Phe Ala Phe Glu Glu Pro Glu Phe Ala Leu
    290                 295                 300 tgc gaa gac tgg acc caa gaa cac cca gtg tcc ttc ctc atg agt agt     960
Cys Glu Asp Trp Thr Gln Glu His Pro Val Ser Phe Leu Met Ser Ser
305                 310                 315                 320 ttg ctg agg aaa gtg atg ctc cct gag gca tcc tta ttg gtg aca aca    1008
Leu Leu Arg Lys Val Met Leu Pro Glu Ala Ser Leu Leu Val Thr Thr
                325                 330                 335 aga ctc aca act tct aag aga cta aag cag ttg ttg aag aat cac cat    1056
Arg Leu Thr Thr Ser Lys Arg Leu Lys Gln Leu Leu Lys Asn His His
            340                 345                 350 tat gta gag cta cta gga atg tct gag gat gca aga gag gag tat att    1104
Tyr Val Glu Leu Leu Gly Met Ser Glu Asp Ala Arg Glu Glu Tyr Ile
        355                 360                 365 tac cag ttt ttt gaa gat aag agg tgg gcc atg aaa gta ttc agt tca    1152
Tyr Gln Phe Phe Glu Asp Lys Arg Trp Ala Met Lys Val Phe Ser Ser
    370                 375                 380 cta aaa agc aat gag atg ctg ttt agc atg tgc caa gtc ccc cta gtg    1200
Leu Lys Ser Asn Glu Met Leu Phe Ser Met Cys Gln Val Pro Leu Val
385                 390                 395                 400 tgc tgg gcc gct tgt act tgt ctg aag cag caa atg gag aag ggt ggt    1248
Cys Trp Ala Ala Cys Thr Cys Leu Lys Gln Gln Met Glu Lys Gly Gly
                405                 410                 415 gat gtc aca ttg acc tgc caa aca acc aca gct ctg ttt acc tgc tat    1296
Asp Val Thr Leu Thr Cys Gln Thr Thr Thr Ala Leu Phe Thr Cys Tyr
            420                 425                 430 att tct agc ttg ttc aca cca gta gat gga ggc tct cct agt cta ccc    1344
Ile Ser Ser Leu Phe Thr Pro Val Asp Gly Gly Ser Pro Ser Leu Pro
        435                 440                 445 aac caa gcc cag ctg aga aga ctg tgc caa gtc gct gcc aaa gga ata    1392
```

```
            Asn Gln Ala Gln Leu Arg Arg Leu Cys Gln Val Ala Ala Lys Gly Ile
                450                 455                 460 tgg act atg act tac gtg ttt tac aga gaa aat ctc aga agg ctt ggg         1440
Trp Thr Met Thr Tyr Val Phe Tyr Arg Glu Asn Leu Arg Arg Leu Gly
465                 470                 475                 480 tta act caa tct gat gtc tct agt ttt atg gac agc aat att att cag         1488
Leu Thr Gln Ser Asp Val Ser Ser Phe Met Asp Ser Asn Ile Ile Gln
                485                 490                 495 aag gac gca gag tat gaa aac tgc tat gtg ttc acc cac ctt cat gtt         1536
Lys Asp Ala Glu Tyr Glu Asn Cys Tyr Val Phe Thr His Leu His Val
            500                 505                 510 cag gag ttt ttt gca gct atg ttc tat atg ttg aaa ggc agt tgg gaa         1584
Gln Glu Phe Phe Ala Ala Met Phe Tyr Met Leu Lys Gly Ser Trp Glu
        515                 520                 525 gct ggg aac cct tcc tgc cag cct ttt gaa gat ttg aag tca tta ctt         1632
Ala Gly Asn Pro Ser Cys Gln Pro Phe Glu Asp Leu Lys Ser Leu Leu
    530                 535                 540 caa agc aca agt tat aaa gac ccc cat ttg aca cag atg aag tgc ttt         1680
Gln Ser Thr Ser Tyr Lys Asp Pro His Leu Thr Gln Met Lys Cys Phe
545                 550                 555                 560 ttg ttt ggc ctt ttg aat gaa gat cga gta aaa caa ctg gag agg act         1728
Leu Phe Gly Leu Leu Asn Glu Asp Arg Val Lys Gln Leu Glu Arg Thr
                565                 570                 575 ttt aac tgt aaa atg tca ctg aag ata aaa tca aag tta ctt cag tgt         1776
Phe Asn Cys Lys Met Ser Leu Lys Ile Lys Ser Lys Leu Leu Gln Cys
            580                 585                 590 atg gaa gta tta gga aac agt gac tat tct cca tca cag ctg gga ttt         1824
Met Glu Val Leu Gly Asn Ser Asp Tyr Ser Pro Ser Gln Leu Gly Phe
        595                 600                 605 ctg gag ttg ttt cac tgt ctg tat gag act caa gat aaa gcg ttt ata         1872
Leu Glu Leu Phe His Cys Leu Tyr Glu Thr Gln Asp Lys Ala Phe Ile
    610                 615                 620 agc cag gca atg aga tgt ttc cca aag gtt gcc att aat att tgt gag         1920
Ser Gln Ala Met Arg Cys Phe Pro Lys Val Ala Ile Asn Ile Cys Glu
625                 630                 635                 640 aaa ata cat ttg ctt gta tct tct ttc tgc ctt aag cac tgc cgg tgt         1968
Lys Ile His Leu Leu Val Ser Ser Phe Cys Leu Lys His Cys Arg Cys
                645                 650                 655 ttg cgg acc atc agg ctg tct gta act gtg gta ttt gag aag aag ata         2016
Leu Arg Thr Ile Arg Leu Ser Val Thr Val Val Phe Glu Lys Lys Ile
            660                 665                 670 tta aaa aca agc ctc cca act aac act tgg gag tgg atg gga aac ggg         2064
Leu Lys Thr Ser Leu Pro Thr Asn Thr Trp Glu Trp Met Gly Asn Gly
        675                 680                 685 aga gct att gga caa ata aga cct ctg gag tgc cca gag gaa gac ttc         2112
Arg Ala Ile Gly Gln Ile Arg Pro Leu Glu Cys Pro Glu Glu Asp Phe
    690                 695                 700 ctg gtg gac tgt gcc cac ggt gga gct gca ctg gat gct ctt gcc ttt         2160
Leu Val Asp Cys Ala His Gly Gly Ala Ala Leu Asp Ala Leu Ala Phe
705                 710                 715                 720 cca aag tac act tac ttt tac tcc aat act atc ctc tga                     2199
Pro Lys Tyr Thr Tyr Phe Tyr Ser Asn Thr Ile Leu *
                725                 730

<210> SEQ ID NO 72
<211> LENGTH: 732
<212> TYPE: PRT
<213> ORGANISM: Homo sapiens

<400> SEQUENCE: 72
```

-continued

```
Met Ala Asp Ser Ser Ser Ser Phe Phe Pro Asp Phe Gly Leu Leu
 1               5                  10                  15

Leu Tyr Leu Glu Glu Leu Asn Lys Glu Glu Leu Asn Thr Phe Lys Leu
             20                  25                  30

Phe Leu Lys Glu Thr Met Glu Pro Glu His Gly Leu Thr Pro Trp Asn
         35                  40                  45

Glu Val Lys Lys Ala Arg Arg Glu Asp Leu Ala Asn Leu Met Lys Lys
 50                  55                  60

Tyr Tyr Pro Gly Glu Lys Ala Trp Ser Val Ser Leu Lys Ile Phe Gly
 65                  70                  75                  80

Lys Met Asn Leu Lys Asp Leu Cys Glu Arg Ala Lys Glu Glu Ile Asn
             85                  90                  95

Trp Ser Ala Gln Thr Ile Gly Pro Asp Asp Ala Lys Ala Gly Glu Thr
         100                 105                 110

Gln Glu Asp Gln Glu Ala Val Leu Val Ile Val Asn Thr Gly Val Pro
     115                 120                 125

Asn Ser Trp Ala Thr Asp Pro Tyr Trp Ser Ala Ala Pro Arg Glu Ser
 130                 135                 140

Gly Arg Ile Ala Gly Gly Asp Gly Thr Glu Tyr Arg Asn Arg Ile Lys
145                 150                 155                 160

Glu Lys Phe Cys Ile Thr Trp Asp Lys Lys Ser Leu Ala Gly Lys Pro
             165                 170                 175

Glu Asp Phe His His Gly Ile Ala Glu Lys Asp Arg Lys Leu Leu Glu
         180                 185                 190

His Leu Phe Asp Val Asp Val Lys Thr Gly Ala Gln Pro Gln Ile Val
     195                 200                 205

Val Leu Gln Gly Ala Ala Gly Val Gly Lys Thr Thr Leu Val Arg Lys
210                 215                 220

Ala Met Leu Asp Trp Ala Glu Gly Ser Leu Tyr Gln Gln Arg Phe Lys
225                 230                 235                 240

Tyr Val Phe Tyr Leu Asn Gly Arg Glu Ile Asn Gln Leu Lys Glu Arg
             245                 250                 255

Ser Phe Ala Gln Leu Ile Ser Lys Asp Trp Pro Ser Thr Glu Gly Pro
         260                 265                 270

Ile Glu Glu Ile Met Tyr Gln Pro Ser Ser Leu Leu Phe Ile Ile Asp
     275                 280                 285

Ser Phe Asp Glu Leu Asn Phe Ala Phe Glu Glu Pro Glu Phe Ala Leu
 290                 295                 300

Cys Glu Asp Trp Thr Gln Glu His Pro Val Ser Phe Leu Met Ser Ser
305                 310                 315                 320

Leu Leu Arg Lys Val Met Leu Pro Glu Ala Ser Leu Leu Val Thr Thr
             325                 330                 335

Arg Leu Thr Thr Ser Lys Arg Leu Lys Gln Leu Leu Lys Asn His His
         340                 345                 350

Tyr Val Glu Leu Leu Gly Met Ser Glu Asp Ala Arg Glu Glu Tyr Ile
     355                 360                 365

Tyr Gln Phe Phe Glu Asp Lys Arg Trp Ala Met Lys Val Phe Ser Ser
 370                 375                 380

Leu Lys Ser Asn Glu Met Leu Phe Ser Met Cys Gln Val Pro Leu Val
385                 390                 395                 400

Cys Trp Ala Ala Cys Thr Cys Leu Lys Gln Gln Met Glu Lys Gly Gly
             405                 410                 415

Asp Val Thr Leu Thr Cys Gln Thr Thr Thr Ala Leu Phe Thr Cys Tyr
```

-continued

```
                420                 425                 430
Ile Ser Ser Leu Phe Thr Pro Val Asp Gly Gly Ser Pro Ser Leu Pro
        435                 440                 445
Asn Gln Ala Gln Leu Arg Arg Leu Cys Gln Val Ala Ala Lys Gly Ile
    450                 455                 460
Trp Thr Met Thr Tyr Val Phe Tyr Arg Glu Asn Leu Arg Arg Leu Gly
465                 470                 475                 480
Leu Thr Gln Ser Asp Val Ser Ser Phe Met Asp Ser Asn Ile Ile Gln
            485                 490                 495
Lys Asp Ala Glu Tyr Glu Asn Cys Tyr Val Phe Thr His Leu His Val
                500                 505                 510
Gln Glu Phe Phe Ala Ala Met Phe Tyr Met Leu Lys Gly Ser Trp Glu
            515                 520                 525
Ala Gly Asn Pro Ser Cys Gln Pro Phe Glu Asp Leu Lys Ser Leu Leu
        530                 535                 540
Gln Ser Thr Ser Tyr Lys Asp Pro His Leu Thr Gln Met Lys Cys Phe
545                 550                 555                 560
Leu Phe Gly Leu Leu Asn Glu Asp Arg Val Lys Gln Leu Glu Arg Thr
                565                 570                 575
Phe Asn Cys Lys Met Ser Leu Lys Ile Lys Ser Lys Leu Leu Gln Cys
            580                 585                 590
Met Glu Val Leu Gly Asn Ser Asp Tyr Ser Pro Ser Gln Leu Gly Phe
        595                 600                 605
Leu Glu Leu Phe His Cys Leu Tyr Glu Thr Gln Asp Lys Ala Phe Ile
    610                 615                 620
Ser Gln Ala Met Arg Cys Phe Pro Lys Val Ala Ile Asn Ile Cys Glu
625                 630                 635                 640
Lys Ile His Leu Leu Val Ser Ser Phe Cys Leu Lys His Cys Arg Cys
                645                 650                 655
Leu Arg Thr Ile Arg Leu Ser Val Thr Val Val Phe Glu Lys Lys Ile
            660                 665                 670
Leu Lys Thr Ser Leu Pro Thr Asn Thr Trp Glu Trp Met Gly Asn Gly
        675                 680                 685
Arg Ala Ile Gly Gln Ile Arg Pro Leu Glu Cys Pro Glu Glu Asp Phe
    690                 695                 700
Leu Val Asp Cys Ala His Gly Gly Ala Ala Leu Asp Ala Leu Ala Phe
705                 710                 715                 720
Pro Lys Tyr Thr Tyr Phe Tyr Ser Asn Thr Ile Leu
                725                 730

<210> SEQ ID NO 73
<211> LENGTH: 1816
<212> TYPE: DNA
<213> ORGANISM: Homo sapiens
<220> FEATURE:
<221> NAME/KEY: CDS
<222> LOCATION: (1)...(1816)

<400> SEQUENCE: 73 atg tat gag ttt tat att cac aaa ggt tat gat gat gtg tct tca gac      48
Met Tyr Glu Phe Tyr Ile His Lys Gly Tyr Asp Asp Val Ser Ser Asp
 1               5                  10                  15 aac agc aga gag aaa atc aaa ggt gaa ccc tct gaa tgt gag ttg ggg      96
Asn Ser Arg Glu Lys Ile Lys Gly Glu Pro Ser Glu Cys Glu Leu Gly
                20                  25                  30 cac ttc ccg cgt atc ccc tgg gca aac ttg aga gct gcc gac cct ttg     144
```

```
                His Phe Pro Arg Ile Pro Trp Ala Asn Leu Arg Ala Ala Asp Pro Leu
                            35                  40                  45 aat ctg tcc ttt ctt ttg gat gaa cac ttc cca aaa ggt cag gca tgg         192
Asn Leu Ser Phe Leu Leu Asp Glu His Phe Pro Lys Gly Gln Ala Trp
 50                  55                  60 aaa gtg gtc ctc ggc atc ttc cag aca atg aat ctg acc tca ctg tgt         240
Lys Val Val Leu Gly Ile Phe Gln Thr Met Asn Leu Thr Ser Leu Cys
 65                  70                  75                  80 gag aaa gtt aga gcc gag atg aaa gag aat gtg cag acc caa gag ctg         288
Glu Lys Val Arg Ala Glu Met Lys Glu Asn Val Gln Thr Gln Glu Leu
                 85                  90                  95 caa gat cca acc cag gaa gat cta gag atg cta gaa gca gca gca ggg         336
Gln Asp Pro Thr Gln Glu Asp Leu Glu Met Leu Glu Ala Ala Ala Gly
                100                 105                 110 aat atg cag acc cag gga tgc caa gat cca aac caa gaa gaa cta gac         384
Asn Met Gln Thr Gln Gly Cys Gln Asp Pro Asn Gln Glu Glu Leu Asp
            115                 120                 125 gag cta gaa gaa gaa aca ggg aat gta cag gcc cag gga tgc caa gat         432
Glu Leu Glu Glu Glu Thr Gly Asn Val Gln Ala Gln Gly Cys Gln Asp
            130                 135                 140 cca aac caa gaa gaa cca gag atg cta gag gaa gca gac cac aga aga         480
Pro Asn Gln Glu Glu Pro Glu Met Leu Glu Glu Ala Asp His Arg Arg
145                 150                 155                 160 aaa tac aga gag aac atg aag gct gaa cta ctg gag aca tgg gac aac         528
Lys Tyr Arg Glu Asn Met Lys Ala Glu Leu Leu Glu Thr Trp Asp Asn
                165                 170                 175 atc agt tgg cct aaa gac cac gta tat atc cgt aat aca tca aag gac         576
Ile Ser Trp Pro Lys Asp His Val Tyr Ile Arg Asn Thr Ser Lys Asp
            180                 185                 190 gaa cat gag gaa ctg cag cgc cta ctg gat cct aat agg act aga gcc         624
Glu His Glu Glu Leu Gln Arg Leu Leu Asp Pro Asn Arg Thr Arg Ala
            195                 200                 205 cag gcc cag acg ata gtc ttg gtg ggg agg gca ggg gtt ggg aag acc         672
Gln Ala Gln Thr Ile Val Leu Val Gly Arg Ala Gly Val Gly Lys Thr
            210                 215                 220 acc ttg gca atg cgg gct atg ctg cac tgg gca aat gga gtt ctc ttt         720
Thr Leu Ala Met Arg Ala Met Leu His Trp Ala Asn Gly Val Leu Phe
225                 230                 235                 240 cag caa agg ttc tcc tat gtt ttc tat ctc agc tgc cat aaa ata agg         768
Gln Gln Arg Phe Ser Tyr Val Phe Tyr Leu Ser Cys His Lys Ile Arg
                245                 250                 255 tac atg aag gaa act acc ttt gct gaa ttg att tct ttg gat tgg ccc         816
Tyr Met Lys Glu Thr Thr Phe Ala Glu Leu Ile Ser Leu Asp Trp Pro
            260                 265                 270 gat ttt gat gcc ccc att gaa gag ttc atg tct caa cca gag aag ctc         864
Asp Phe Asp Ala Pro Ile Glu Glu Phe Met Ser Gln Pro Glu Lys Leu
            275                 280                 285 ctg ttt att att gat ggc ttt gag gaa ata atc ata tct gag tca cgc         912
Leu Phe Ile Ile Asp Gly Phe Glu Glu Ile Ile Ile Ser Glu Ser Arg
            290                 295                 300 tct gag agc ttg gat gat ggc tcg cca tgt aca gac tgg tac cag gag         960
Ser Glu Ser Leu Asp Asp Gly Ser Pro Cys Thr Asp Trp Tyr Gln Glu
305                 310                 315                 320 ctc cca gtg acc aaa atc cta cac agc ttg ttg aag aaa gaa ttg gtt        1008
Leu Pro Val Thr Lys Ile Leu His Ser Leu Leu Lys Lys Glu Leu Val
                325                 330                 335 ccc ctg gct acc tta ctg atc acg atc aag acc tgg ttt gtg aga gat        1056
Pro Leu Ala Thr Leu Leu Ile Thr Ile Lys Thr Trp Phe Val Arg Asp
            340                 345                 350
```

```
ctt aag gcc tca tta gtg aat cca tgc ttt gta caa att aca ggg ttc    1104
Leu Lys Ala Ser Leu Val Asn Pro Cys Phe Val Gln Ile Thr Gly Phe
        355                 360                 365 aca ggg gac gac cta cgg gta tat ttc atg aga cac ttt gat gac tca    1152
Thr Gly Asp Asp Leu Arg Val Tyr Phe Met Arg His Phe Asp Asp Ser
    370                 375                 380 agt gaa gtt gag aaa atc ctg cag cag cta aga aaa aac gaa act ctc    1200
Ser Glu Val Glu Lys Ile Leu Gln Gln Leu Arg Lys Asn Glu Thr Leu
385                 390                 395                 400 ttt cat tcc tgc agt gcc ccc atg gtg tgt tgg act gta tgt tcc tgt    1248
Phe His Ser Cys Ser Ala Pro Met Val Cys Trp Thr Val Cys Ser Cys
                405                 410                 415 ctg aag cag ccg aag gtg agg tat tac gat ctc cag tca atc act cag    1296
Leu Lys Gln Pro Lys Val Arg Tyr Tyr Asp Leu Gln Ser Ile Thr Gln
            420                 425                 430 act acc acc agt ctg tat gcc tat ttt ttc tcc aac ttg ttc tcc aca    1344
Thr Thr Thr Ser Leu Tyr Ala Tyr Phe Phe Ser Asn Leu Phe Ser Thr
        435                 440                 445 gca gag gta gat ttg gca gat gac agc tgg cca gga caa tgg agg gcc    1392
Ala Glu Val Asp Leu Ala Asp Asp Ser Trp Pro Gly Gln Trp Arg Ala
    450                 455                 460 ctc tgc agc ctg gcc ata gaa ggg ctg tgg tct atg aac ttc aca ttt    1440
Leu Cys Ser Leu Ala Ile Glu Gly Leu Trp Ser Met Asn Phe Thr Phe
465                 470                 475                 480 aac aaa gaa gac act gag att gag ggc ctg gaa gtg cct ttc att gat    1488
Asn Lys Glu Asp Thr Glu Ile Glu Gly Leu Glu Val Pro Phe Ile Asp
                485                 490                 495 tct ctc tac gag ttc aat att ctt caa aag atc aat gac tgt ggg ggt    1536
Ser Leu Tyr Glu Phe Asn Ile Leu Gln Lys Ile Asn Asp Cys Gly Gly
            500                 505                 510 tgc act act ttc acc cac cta agt ttc cag gag ttt ttt gca gcc atg    1584
Cys Thr Thr Phe Thr His Leu Ser Phe Gln Glu Phe Phe Ala Ala Met
        515                 520                 525 tcc ttt gtg cta gag gaa cct aga gaa ttc cct ccc cat tcc aca aag    1632
Ser Phe Val Leu Glu Glu Pro Arg Glu Phe Pro Pro His Ser Thr Lys
    530                 535                 540 cca caa gag atg aag atg tta ctg caa cac gtc ttg ctt gac aaa gaa    1680
Pro Gln Glu Met Lys Met Leu Leu Gln His Val Leu Leu Asp Lys Glu
545                 550                 555                 560 gcc tac tgg act cca gtg gtt ctg ttc ttc ttt ggt ctt tta aat aaa    1728
Ala Tyr Trp Thr Pro Val Val Leu Phe Phe Phe Gly Leu Leu Asn Lys
                565                 570                 575 aac ata gca aga gaa ctg gaa gat act ttg cat tgt aaa ata tct ccc    1776
Asn Ile Ala Arg Glu Leu Glu Asp Thr Leu His Cys Lys Ile Ser Pro
            580                 585                 590 agg gta atg gag gaa tta tta aag tgg gga gaa gag tta g              1816
Arg Val Met Glu Glu Leu Leu Lys Trp Gly Glu Glu Leu
        595                 600                 605

<210> SEQ ID NO 74
<211> LENGTH: 605
<212> TYPE: PRT
<213> ORGANISM: Homo sapiens

<400> SEQUENCE: 74

Met Tyr Glu Phe Tyr Ile His Lys Gly Tyr Asp Asp Val Ser Ser Asp
 1               5                  10                  15

Asn Ser Arg Glu Lys Ile Lys Gly Glu Pro Ser Glu Cys Glu Leu Gly
            20                  25                  30

His Phe Pro Arg Ile Pro Trp Ala Asn Leu Arg Ala Ala Asp Pro Leu
```

-continued

```
            35                  40                  45
Asn Leu Ser Phe Leu Leu Asp Glu His Phe Pro Lys Gly Gln Ala Trp
 50                  55                  60
Lys Val Leu Gly Ile Phe Gln Thr Met Asn Leu Thr Ser Leu Cys
 65                  70                  75                  80
Glu Lys Val Arg Ala Glu Met Lys Glu Asn Val Gln Thr Gln Glu Leu
                 85                  90                  95
Gln Asp Pro Thr Gln Glu Asp Leu Glu Met Leu Glu Ala Ala Ala Gly
                100                 105                 110
Asn Met Gln Thr Gln Gly Cys Gln Asp Pro Asn Gln Glu Glu Leu Asp
                115                 120                 125
Glu Leu Glu Glu Glu Thr Gly Asn Val Gln Ala Gln Gly Cys Gln Asp
130                 135                 140
Pro Asn Gln Glu Glu Pro Glu Met Leu Glu Glu Ala Asp His Arg Arg
145                 150                 155                 160
Lys Tyr Arg Glu Asn Met Lys Ala Glu Leu Leu Glu Thr Trp Asp Asn
                165                 170                 175
Ile Ser Trp Pro Lys Asp His Val Tyr Ile Arg Asn Thr Ser Lys Asp
                180                 185                 190
Glu His Glu Glu Leu Gln Arg Leu Leu Asp Pro Asn Arg Thr Arg Ala
                195                 200                 205
Gln Ala Gln Thr Ile Val Leu Val Gly Arg Ala Gly Val Gly Lys Thr
                210                 215                 220
Thr Leu Ala Met Arg Ala Met Leu His Trp Ala Asn Gly Val Leu Phe
225                 230                 235                 240
Gln Gln Arg Phe Ser Tyr Val Phe Tyr Leu Ser Cys His Lys Ile Arg
                245                 250                 255
Tyr Met Lys Glu Thr Thr Phe Ala Glu Leu Ile Ser Leu Asp Trp Pro
                260                 265                 270
Asp Phe Asp Ala Pro Ile Glu Glu Phe Met Ser Gln Pro Glu Lys Leu
                275                 280                 285
Leu Phe Ile Ile Asp Gly Phe Glu Glu Ile Ile Ser Glu Ser Arg
                290                 295                 300
Ser Glu Ser Leu Asp Asp Gly Ser Pro Cys Thr Asp Trp Tyr Gln Glu
305                 310                 315                 320
Leu Pro Val Thr Lys Ile Leu His Ser Leu Leu Lys Lys Glu Leu Val
                325                 330                 335
Pro Leu Ala Thr Leu Leu Ile Thr Ile Lys Thr Trp Phe Val Arg Asp
                340                 345                 350
Leu Lys Ala Ser Leu Val Asn Pro Cys Phe Val Gln Ile Thr Gly Phe
                355                 360                 365
Thr Gly Asp Asp Leu Arg Val Tyr Phe Met Arg His Phe Asp Asp Ser
                370                 375                 380
Ser Glu Val Glu Lys Ile Leu Gln Gln Leu Arg Lys Asn Glu Thr Leu
385                 390                 395                 400
Phe His Ser Cys Ser Ala Pro Met Val Cys Trp Thr Val Cys Ser Cys
                405                 410                 415
Leu Lys Gln Pro Lys Val Arg Tyr Tyr Asp Leu Gln Ser Ile Thr Gln
                420                 425                 430
Thr Thr Thr Ser Leu Tyr Ala Tyr Phe Phe Ser Asn Leu Phe Ser Thr
                435                 440                 445
Ala Glu Val Asp Leu Ala Asp Asp Ser Trp Pro Gly Gln Trp Arg Ala
450                 455                 460
```

```
Leu Cys Ser Leu Ala Ile Glu Gly Leu Trp Ser Met Asn Phe Thr Phe
465                 470                 475                 480

Asn Lys Glu Asp Thr Glu Ile Glu Gly Leu Glu Val Pro Phe Ile Asp
                485                 490                 495

Ser Leu Tyr Glu Phe Asn Ile Leu Gln Lys Ile Asn Asp Cys Gly Gly
            500                 505                 510

Cys Thr Thr Phe Thr His Leu Ser Phe Gln Glu Phe Ala Ala Met
            515                 520                 525

Ser Phe Val Leu Glu Glu Pro Arg Glu Phe Pro Pro His Ser Thr Lys
530                 535                 540

Pro Gln Glu Met Lys Met Leu Leu Gln His Val Leu Leu Asp Lys Glu
545                 550                 555                 560

Ala Tyr Trp Thr Pro Val Val Leu Phe Phe Gly Leu Leu Asn Lys
                565                 570                 575

Asn Ile Ala Arg Glu Leu Glu Asp Thr Leu His Cys Lys Ile Ser Pro
            580                 585                 590

Arg Val Met Glu Glu Leu Leu Lys Trp Gly Glu Leu
            595                 600                 605

<210> SEQ ID NO 75
<211> LENGTH: 2356
<212> TYPE: DNA
<213> ORGANISM: Homo sapiens
<220> FEATURE:
<221> NAME/KEY: CDS
<222> LOCATION: (64)...(2356)

<400> SEQUENCE: 75
gatctcatat ttcttgtgcc tcaaaatccc ttctctgaag tctgccttcc ctggagaagc       60 aag atg gca gaa tcg gat tct act gac ttt gac ctg ctg tgg tat cta      108
    Met Ala Glu Ser Asp Ser Thr Asp Phe Asp Leu Leu Trp Tyr Leu
    1               5                   10                  15 gag aat ctc agt gac aag gaa ttt cag agt ttt aag aag tat ctg gca      156
Glu Asn Leu Ser Asp Lys Glu Phe Gln Ser Phe Lys Lys Tyr Leu Ala
                20                  25                  30 cgc aag att ctt gat ttc aaa ctg cca cag ttt cca ctg ata cag atg      204
Arg Lys Ile Leu Asp Phe Lys Leu Pro Gln Phe Pro Leu Ile Gln Met
            35                  40                  45 aca aaa gaa gaa ctg gct aac gtg ttg cca atc tct tat gag gga cag      252
Thr Lys Glu Glu Leu Ala Asn Val Leu Pro Ile Ser Tyr Glu Gly Gln
        50                  55                  60 tat ata tgg aat atg ctc ttc agc ata ttt tca atg atg cgt aag gaa      300
Tyr Ile Trp Asn Met Leu Phe Ser Ile Phe Ser Met Met Arg Lys Glu
65                  70                  75 gat ctt tgt agg aag atc att ggc aga cga aac cgc aat cag gag gca      348
Asp Leu Cys Arg Lys Ile Ile Gly Arg Arg Asn Arg Asn Gln Glu Ala
80                  85                  90                  95 tgc aaa gct gtc atg agg aga aaa ttc atg ctg caa tgg gaa agt cac      396
Cys Lys Ala Val Met Arg Arg Lys Phe Met Leu Gln Trp Glu Ser His
                100                 105                 110 act ttt gga aaa ttt cat tat aaa ttt ttt cgt gac gtt tcg tca gat      444
Thr Phe Gly Lys Phe His Tyr Lys Phe Phe Arg Asp Val Ser Ser Asp
            115                 120                 125 gtg ttc tac ata ctt caa tta gcc tat gat tct acc agc tat tat tca      492
Val Phe Tyr Ile Leu Gln Leu Ala Tyr Asp Ser Thr Ser Tyr Tyr Ser
        130                 135                 140 gca aac aat ctc aat gtg ttc ctg atg gga gag aga gca tct gga aaa      540
Ala Asn Asn Leu Asn Val Phe Leu Met Gly Glu Arg Ala Ser Gly Lys
```

```
          145                 150                 155
act att gtt ata aat ctg gct gtg ttg agg tgg atc aag ggt gag atg    588
Thr Ile Val Ile Asn Leu Ala Val Leu Arg Trp Ile Lys Gly Glu Met
160                 165                 170                 175 tgg cag aac atg atc tcg tac gtc gtt cac ctc act gct cac gaa ata    636
Trp Gln Asn Met Ile Ser Tyr Val Val His Leu Thr Ala His Glu Ile
                180                 185                 190 aac cag atg acc aac agc agc ttg gct gag cta atc gcc aag gac tgg    684
Asn Gln Met Thr Asn Ser Ser Leu Ala Glu Leu Ile Ala Lys Asp Trp
        195                 200                 205 cct gac ggc cag gct ccc att gca gac atc ctg tct gat ccc aag aaa    732
Pro Asp Gly Gln Ala Pro Ile Ala Asp Ile Leu Ser Asp Pro Lys Lys
            210                 215                 220 ctc ctt ttc atc ctc gag gac ttg gac aac ata aga ttc gag tta aat    780
Leu Leu Phe Ile Leu Glu Asp Leu Asp Asn Ile Arg Phe Glu Leu Asn
        225                 230                 235 gtc aat gaa agt gct ttg tgt agt aac agc acc cag aaa gtt ccc att    828
Val Asn Glu Ser Ala Leu Cys Ser Asn Ser Thr Gln Lys Val Pro Ile
240                 245                 250                 255 cca gtt ctc ctg gtc agt ttg ctg aag aga aaa atg gct cca ggc tgc    876
Pro Val Leu Leu Val Ser Leu Leu Lys Arg Lys Met Ala Pro Gly Cys
                260                 265                 270 tgg ttc ctc atc tcc tca agg ccc aca cgt ggg aat aat gta aaa acg    924
Trp Phe Leu Ile Ser Ser Arg Pro Thr Arg Gly Asn Asn Val Lys Thr
        275                 280                 285 ttc ttg aaa gag gta gat tgc tgc acg acc ttg cag ctg tcg aat ggg    972
Phe Leu Lys Glu Val Asp Cys Cys Thr Thr Leu Gln Leu Ser Asn Gly
            290                 295                 300 aag agg gag ata tat ttt aac tct ttc ttt aaa gac cgc cag agg gcg   1020
Lys Arg Glu Ile Tyr Phe Asn Ser Phe Phe Lys Asp Arg Gln Arg Ala
        305                 310                 315 tcg gca gcc ctc cag ctt gta cat gag gat gaa ata ctc gtg ggt ctg   1068
Ser Ala Ala Leu Gln Leu Val His Glu Asp Glu Ile Leu Val Gly Leu
320                 325                 330                 335 tgc cga gtc gcc atc tta tgc tgg atc acg tgt act gtc ctg aag cgg   1116
Cys Arg Val Ala Ile Leu Cys Trp Ile Thr Cys Thr Val Leu Lys Arg
                340                 345                 350 cag atg gac aag ggg cgt gac ttc cag ctc tgc tgc caa aca ccc act   1164
Gln Met Asp Lys Gly Arg Asp Phe Gln Leu Cys Cys Gln Thr Pro Thr
        355                 360                 365 gat cta cat gcc cac ttt ctt gct gat gcg ttg aca tca gag gct gga   1212
Asp Leu His Ala His Phe Leu Ala Asp Ala Leu Thr Ser Glu Ala Gly
            370                 375                 380 ctt act gcc aat cag tat cac cta ggt ctc cta aaa cgt ctg tgt ttg   1260
Leu Thr Ala Asn Gln Tyr His Leu Gly Leu Leu Lys Arg Leu Cys Leu
385                 390                 395 ctg gct gca gga gga ctg ttt ctg agc acc ctg aat ttc agt ggt gaa   1308
Leu Ala Ala Gly Gly Leu Phe Leu Ser Thr Leu Asn Phe Ser Gly Glu
400                 405                 410                 415 gac ctc aga tgt gtt ggg ttt act gag gct gat gtc tct gtg ttg cag   1356
Asp Leu Arg Cys Val Gly Phe Thr Glu Ala Asp Val Ser Val Leu Gln
                420                 425                 430 gcc gcg aat att ctt ttg ccg agc aac act cat aaa gac cgt tac aag   1404
Ala Ala Asn Ile Leu Leu Pro Ser Asn Thr His Lys Asp Arg Tyr Lys
        435                 440                 445 ttc ata cac ttg aac gtc cag gag ttt tgt aca gcc att gca ttt ctg   1452
Phe Ile His Leu Asn Val Gln Glu Phe Cys Thr Ala Ile Ala Phe Leu
            450                 455                 460 atg gca gta ccc aac tat ctg atc ccc tca ggc agc aga gag tat aaa   1500
```

```
Met Ala Val Pro Asn Tyr Leu Ile Pro Ser Gly Ser Arg Glu Tyr Lys
    465                 470                 475 gag aag aga gaa caa tac tct gac ttt aat caa gtg ttt act ttc att    1548
Glu Lys Arg Glu Gln Tyr Ser Asp Phe Asn Gln Val Phe Thr Phe Ile
480                 485                 490                 495 ttt ggt ctt cta aat gca aac agg aga aag att ctt gag aca tcc ttt    1596
Phe Gly Leu Leu Asn Ala Asn Arg Arg Lys Ile Leu Glu Thr Ser Phe
                500                 505                 510 gga tac cag cta ccg atg gta gac agc ttc aag tgg tac tcg gtg gga    1644
Gly Tyr Gln Leu Pro Met Val Asp Ser Phe Lys Trp Tyr Ser Val Gly
            515                 520                 525 tac atg aaa cat ttg gac cgt gac ccg gaa aag ttg acg cac cat atg    1692
Tyr Met Lys His Leu Asp Arg Asp Pro Glu Lys Leu Thr His His Met
        530                 535                 540 cct ttg ttt tac tgt ctc tat gag aat cgg gaa gaa gaa ttt gtg aag    1740
Pro Leu Phe Tyr Cys Leu Tyr Glu Asn Arg Glu Glu Glu Phe Val Lys
    545                 550                 555 acg att gtg gat gct ctc atg gag gtt aca gtt tac ctt caa tca gac    1788
Thr Ile Val Asp Ala Leu Met Glu Val Thr Val Tyr Leu Gln Ser Asp
560                 565                 570                 575 aag gat atg atg gtc tca tta tac tgc ctg gat tac tgc tgt cac ctg    1836
Lys Asp Met Met Val Ser Leu Tyr Cys Leu Asp Tyr Cys Cys His Leu
                580                 585                 590 agg aca ctt aag ttg agt gtt cag cgc atc ttt caa aac aaa gag cca    1884
Arg Thr Leu Lys Leu Ser Val Gln Arg Ile Phe Gln Asn Lys Glu Pro
            595                 600                 605 ctt ata agg cca act gct agg ttg tcc tat gtc tcg act gct tct ggt    1932
Leu Ile Arg Pro Thr Ala Arg Leu Ser Tyr Val Ser Thr Ala Ser Gly
        610                 615                 620 ttt gaa gac tta ctc aag gct ttg gct cgt aat cgg agc ctg aca tac    1980
Phe Glu Asp Leu Leu Lys Ala Leu Ala Arg Asn Arg Ser Leu Thr Tyr
    625                 630                 635 ctg agt atc aac tgt acg tcc att tcc cta aat atg ttt tca ctt ctg    2028
Leu Ser Ile Asn Cys Thr Ser Ile Ser Leu Asn Met Phe Ser Leu Leu
640                 645                 650                 655 cat gac atc ctg cac gag ccc aca tgc caa ata agt cat ctg agc ttg    2076
His Asp Ile Leu His Glu Pro Thr Cys Gln Ile Ser His Leu Ser Leu
                660                 665                 670 atg aaa tgt gat ttg cga gcc agc gaa tgc gaa gaa atc gcc tct ctc    2124
Met Lys Cys Asp Leu Arg Ala Ser Glu Cys Glu Glu Ile Ala Ser Leu
            675                 680                 685 ctc atc agt ggc ggg agt ctg aga aaa ctg acc tta tcc agc aat ccg    2172
Leu Ile Ser Gly Gly Ser Leu Arg Lys Leu Thr Leu Ser Ser Asn Pro
        690                 695                 700 ctg agg agc gac ggg atg aac ata ctg tgt gat gcc ttg ctt cat ccc    2220
Leu Arg Ser Asp Gly Met Asn Ile Leu Cys Asp Ala Leu Leu His Pro
    705                 710                 715 aac tgc act ctt ata tca ctg gtg tta gtc ttc tgc tgt ctc act gaa    2268
Asn Cys Thr Leu Ile Ser Leu Val Leu Val Phe Cys Cys Leu Thr Glu
720                 725                 730                 735 aat tgc tgc agc gcc ctt gga aga gtg ctt ctg ttc agc cca act cta    2316
Asn Cys Cys Ser Ala Leu Gly Arg Val Leu Leu Phe Ser Pro Thr Leu
                740                 745                 750 aga caa cta gac ctg tgt gtg aat cgc tta aaa aat tac g              2356
Arg Gln Leu Asp Leu Cys Val Asn Arg Leu Lys Asn Tyr
            755                 760

<210> SEQ ID NO 76
<211> LENGTH: 764
<212> TYPE: PRT
```

<213> ORGANISM: Homo sapiens

<400> SEQUENCE: 76

```
Met Ala Glu Ser Asp Ser Thr Asp Phe Asp Leu Leu Trp Tyr Leu Glu
 1               5                  10                  15
Asn Leu Ser Asp Lys Glu Phe Gln Ser Phe Lys Lys Tyr Leu Ala Arg
            20                  25                  30
Lys Ile Leu Asp Phe Lys Leu Pro Gln Phe Pro Leu Ile Gln Met Thr
        35                  40                  45
Lys Glu Glu Leu Ala Asn Val Leu Pro Ile Ser Tyr Glu Gly Gln Tyr
 50                  55                  60
Ile Trp Asn Met Leu Phe Ser Ile Phe Ser Met Met Arg Lys Glu Asp
 65                  70                  75                  80
Leu Cys Arg Lys Ile Ile Gly Arg Arg Asn Arg Asn Gln Glu Ala Cys
                85                  90                  95
Lys Ala Val Met Arg Arg Lys Phe Met Leu Gln Trp Glu Ser His Thr
            100                 105                 110
Phe Gly Lys Phe His Tyr Lys Phe Phe Arg Asp Val Ser Ser Asp Val
        115                 120                 125
Phe Tyr Ile Leu Gln Leu Ala Tyr Asp Ser Thr Ser Tyr Tyr Ser Ala
130                 135                 140
Asn Asn Leu Asn Val Phe Leu Met Gly Glu Arg Ala Ser Gly Lys Thr
145                 150                 155                 160
Ile Val Ile Asn Leu Ala Val Leu Arg Trp Ile Lys Gly Glu Met Trp
                165                 170                 175
Gln Asn Met Ile Ser Tyr Val Val His Leu Thr Ala His Glu Ile Asn
            180                 185                 190
Gln Met Thr Asn Ser Ser Leu Ala Glu Leu Ile Ala Lys Asp Trp Pro
        195                 200                 205
Asp Gly Gln Ala Pro Ile Ala Asp Ile Leu Ser Asp Pro Lys Lys Leu
210                 215                 220
Leu Phe Ile Leu Glu Asp Leu Asp Asn Ile Arg Phe Glu Leu Asn Val
225                 230                 235                 240
Asn Glu Ser Ala Leu Cys Ser Asn Ser Thr Gln Lys Val Pro Ile Pro
                245                 250                 255
Val Leu Leu Val Ser Leu Leu Lys Arg Lys Met Ala Pro Gly Cys Trp
            260                 265                 270
Phe Leu Ile Ser Ser Arg Pro Thr Arg Gly Asn Asn Val Lys Thr Phe
        275                 280                 285
Leu Lys Glu Val Asp Cys Cys Thr Thr Leu Gln Leu Ser Asn Gly Lys
290                 295                 300
Arg Glu Ile Tyr Phe Asn Ser Phe Phe Lys Asp Arg Gln Arg Ala Ser
305                 310                 315                 320
Ala Ala Leu Gln Leu Val His Glu Asp Glu Ile Leu Val Gly Leu Cys
                325                 330                 335
Arg Val Ala Ile Leu Cys Trp Ile Thr Cys Thr Val Leu Lys Arg Gln
            340                 345                 350
Met Asp Lys Gly Arg Asp Phe Gln Leu Cys Cys Gln Thr Pro Thr Asp
        355                 360                 365
Leu His Ala His Phe Leu Ala Asp Ala Leu Thr Ser Glu Ala Gly Leu
370                 375                 380
Thr Ala Asn Gln Tyr His Leu Gly Leu Leu Lys Arg Leu Cys Leu Leu
385                 390                 395                 400
```

```
Ala Ala Gly Gly Leu Phe Leu Ser Thr Leu Asn Phe Ser Gly Glu Asp
            405                 410                 415

Leu Arg Cys Val Gly Phe Thr Glu Ala Asp Val Ser Val Leu Gln Ala
            420                 425                 430

Ala Asn Ile Leu Leu Pro Ser Asn Thr His Lys Asp Arg Tyr Lys Phe
            435                 440                 445

Ile His Leu Asn Val Gln Glu Phe Cys Thr Ala Ile Ala Phe Leu Met
            450                 455                 460

Ala Val Pro Asn Tyr Leu Ile Pro Ser Gly Ser Arg Glu Tyr Lys Glu
465                 470                 475                 480

Lys Arg Glu Gln Tyr Ser Asp Phe Asn Gln Val Phe Thr Phe Ile Phe
                    485                 490                 495

Gly Leu Leu Asn Ala Asn Arg Arg Lys Ile Leu Glu Thr Ser Phe Gly
                500                 505                 510

Tyr Gln Leu Pro Met Val Asp Ser Phe Lys Trp Tyr Ser Val Gly Tyr
            515                 520                 525

Met Lys His Leu Asp Arg Asp Pro Glu Lys Leu Thr His His Met Pro
            530                 535                 540

Leu Phe Tyr Cys Leu Tyr Glu Asn Arg Glu Glu Phe Val Lys Thr
545                 550                 555                 560

Ile Val Asp Ala Leu Met Glu Val Thr Val Tyr Leu Gln Ser Asp Lys
                565                 570                 575

Asp Met Met Val Ser Leu Tyr Cys Leu Asp Tyr Cys His Leu Arg
                580                 585                 590

Thr Leu Lys Leu Ser Val Gln Arg Ile Phe Gln Asn Lys Glu Pro Leu
            595                 600                 605

Ile Arg Pro Thr Ala Arg Leu Ser Tyr Val Ser Thr Ala Ser Gly Phe
610                 615                 620

Glu Asp Leu Leu Lys Ala Leu Ala Arg Asn Arg Ser Leu Thr Tyr Leu
625                 630                 635                 640

Ser Ile Asn Cys Thr Ser Ile Ser Leu Asn Met Phe Ser Leu Leu His
                645                 650                 655

Asp Ile Leu His Glu Pro Thr Cys Gln Ile Ser His Leu Ser Leu Met
                660                 665                 670

Lys Cys Asp Leu Arg Ala Ser Glu Cys Glu Glu Ile Ala Ser Leu Leu
            675                 680                 685

Ile Ser Gly Gly Ser Leu Arg Lys Leu Thr Leu Ser Ser Asn Pro Leu
            690                 695                 700

Arg Ser Asp Gly Met Asn Ile Leu Cys Asp Ala Leu Leu His Pro Asn
705                 710                 715                 720

Cys Thr Leu Ile Ser Leu Val Leu Val Phe Cys Cys Leu Thr Glu Asn
                725                 730                 735

Cys Cys Ser Ala Leu Gly Arg Val Leu Leu Phe Ser Pro Thr Leu Arg
            740                 745                 750

Gln Leu Asp Leu Cys Val Asn Arg Leu Lys Asn Tyr
            755                 760

<210> SEQ ID NO 77

<400> SEQUENCE: 77

000

<210> SEQ ID NO 78
```

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83
<211> LENGTH: 1968
<212> TYPE: DNA
<213> ORGANISM: Homo sapiens
<220> FEATURE:
<221> NAME/KEY: CDS
<222> LOCATION: (1)...(1968)

<400> SEQUENCE: 83

| | | | | | | | | | | | | | | | | |
|---|---|---|---|---|---|---|---|---|---|---|---|---|---|---|---|---|
| atg | gcc | atg | gcc | aag | gcc | aga | aag | ccc | cgg | gag | gca | ttg | ctc | tgg | gcc | 48 |
| Met | Ala | Met | Ala | Lys | Ala | Arg | Lys | Pro | Arg | Glu | Ala | Leu | Leu | Trp | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttg | agt | gac | ctt | gag | gag | aac | gat | ttc | aag | aag | tta | aag | ttc | tac | tta | 96 |
| Leu | Ser | Asp | Leu | Glu | Glu | Asn | Asp | Phe | Lys | Lys | Leu | Lys | Phe | Tyr | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| cgg | gat | atg | acc | ctg | tct | gag | ggc | cag | ccc | cca | ctg | gcc | aga | ggg | gag | 144 |
| Arg | Asp | Met | Thr | Leu | Ser | Glu | Gly | Gln | Pro | Pro | Leu | Ala | Arg | Gly | Glu | |
| | | | 35 | | | | | 40 | | | | | 45 | | | |

| | | | | | | | | | | | | | | | | |
|---|---|---|---|---|---|---|---|---|---|---|---|---|---|---|---|---|
| ttg | gag | ggc | ctg | att | ccg | gtg | gac | ctg | gca | gaa | tta | ctg | att | tca | aag | 192 |
| Leu | Glu | Gly | Leu | Ile | Pro | Val | Asp | Leu | Ala | Glu | Leu | Leu | Ile | Ser | Lys | |
| | | 50 | | | | | 55 | | | | | 60 | | | | |

| | | | | | | | | | | | | | | | | |
|---|---|---|---|---|---|---|---|---|---|---|---|---|---|---|---|---|
| tat | gga | gaa | aag | gag | gct | gtg | aaa | gtt | gtc | ctc | aag | ggc | ttg | aag | gtc | 240 |
| Tyr | Gly | Glu | Lys | Glu | Ala | Val | Lys | Val | Val | Leu | Lys | Gly | Leu | Lys | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| atg | aac | ctg | ttg | gaa | ctt | gtg | gac | cag | ctc | agc | cat | att | tgt | ctg | cat | 288 |
| Met | Asn | Leu | Leu | Glu | Leu | Val | Asp | Gln | Leu | Ser | His | Ile | Cys | Leu | His | |
| | | | | 85 | | | | | 90 | | | | | 95 | | |

| | | | | | | | | | | | | | | | | |
|---|---|---|---|---|---|---|---|---|---|---|---|---|---|---|---|---|
| gat | tac | aga | gaa | gta | tac | cga | gag | cat | gtg | cgc | tgc | cta | gag | gaa | tgg | 336 |
| Asp | Tyr | Arg | Glu | Val | Tyr | Arg | Glu | His | Val | Arg | Cys | Leu | Glu | Glu | Trp | |
| | | | 100 | | | | | 105 | | | | | 110 | | | |

| | | | | | | | | | | | | | | | | |
|---|---|---|---|---|---|---|---|---|---|---|---|---|---|---|---|---|
| cag | gaa | gca | gga | gtc | aat | ggc | aga | tac | aac | cag | gtg | ctc | ctg | gtg | gcc | 384 |
| Gln | Glu | Ala | Gly | Val | Asn | Gly | Arg | Tyr | Asn | Gln | Val | Leu | Leu | Val | Ala | |
| | | | 115 | | | | | 120 | | | | | 125 | | | |

| | | | | | | | | | | | | | | | | |
|---|---|---|---|---|---|---|---|---|---|---|---|---|---|---|---|---|
| aag | ccc | agc | tca | gag | agc | cca | gaa | tca | ctt | gcc | tgc | ccc | ttc | ccg | gag | 432 |
| Lys | Pro | Ser | Ser | Glu | Ser | Pro | Glu | Ser | Leu | Ala | Cys | Pro | Phe | Pro | Glu | |
| | 130 | | | | | 135 | | | | | 140 | | | | | |

-continued

| | |
|---|---|
| cag gag ctg gag tct gtc acg gtg gag gct cta ttt gat tca ggg gaa<br>Gln Glu Leu Glu Ser Val Thr Val Glu Ala Leu Phe Asp Ser Gly Glu<br>145                     150                     155                     160 | 480 |
| aag ccc tca ctg gcc cca tcc tta gtt gtg cta cag ggg tcg gct ggc<br>Lys Pro Ser Leu Ala Pro Ser Leu Val Val Leu Gln Gly Ser Ala Gly<br>                 165                     170                     175 | 528 |
| act gga aag aca act ctc gcc aga aaa atg gtg ttg gac tgg gcc acc<br>Thr Gly Lys Thr Thr Leu Ala Arg Lys Met Val Leu Asp Trp Ala Thr<br>        180                     185                     190 | 576 |
| ggt act ctg tac cca ggc cgg ttt gat tat gtc ttt tat gta agc tgc<br>Gly Thr Leu Tyr Pro Gly Arg Phe Asp Tyr Val Phe Tyr Val Ser Cys<br>                 195                     200                     205 | 624 |
| aaa gaa gtg gtc ctg ctg ctg gag agc aaa ctg gag cag ctc ctt ttc<br>Lys Glu Val Val Leu Leu Leu Glu Ser Lys Leu Glu Gln Leu Leu Phe<br>210                     215                     220 | 672 |
| tgg tgc tgc ggg gac aat caa gcc cct gtc aca gag att ctg agg cag<br>Trp Cys Cys Gly Asp Asn Gln Ala Pro Val Thr Glu Ile Leu Arg Gln<br>225                     230                     235                     240 | 720 |
| cca gag cgg ctc ctg ttc atc ctg gat ggc ttt gat gag ctg cag agg<br>Pro Glu Arg Leu Leu Phe Ile Leu Asp Gly Phe Asp Glu Leu Gln Arg<br>                 245                     250                     255 | 768 |
| ccc ttt gaa gaa aag ttg aag aag agg ggt ttg agt ccc aag gag agc<br>Pro Phe Glu Glu Lys Leu Lys Lys Arg Gly Leu Ser Pro Lys Glu Ser<br>        260                     265                     270 | 816 |
| ctg ctg cac ctt cta att agg aga cat aca ctc ccc acg tgc tcc ctt<br>Leu Leu His Leu Leu Ile Arg Arg His Thr Leu Pro Thr Cys Ser Leu<br>                 275                     280                     285 | 864 |
| ctc atc acc acc cgg ccc ctg gct ttg agg aat ctg gag ccc ttg ctg<br>Leu Ile Thr Thr Arg Pro Leu Ala Leu Arg Asn Leu Glu Pro Leu Leu<br>290                     295                     300 | 912 |
| aaa caa gca cgt cat gtc cat atc cta ggc ttc tct gag gag gag agg<br>Lys Gln Ala Arg His Val His Ile Leu Gly Phe Ser Glu Glu Glu Arg<br>305                     310                     315                     320 | 960 |
| gcg agg tac ttc agc tcc tat ttc acg gat gag aag caa gct gac cgt<br>Ala Arg Tyr Phe Ser Ser Tyr Phe Thr Asp Glu Lys Gln Ala Asp Arg<br>                 325                     330                     335 | 1008 |
| gcc ttc gac att gta cag aaa aat gac att ctc tac aaa gcg tgt cag<br>Ala Phe Asp Ile Val Gln Lys Asn Asp Ile Leu Tyr Lys Ala Cys Gln<br>        340                     345                     350 | 1056 |
| gtt cca ggc att tgc tgg gtg gtc tgc tcc tgg ctg cag ggg cag atg<br>Val Pro Gly Ile Cys Trp Val Val Cys Ser Trp Leu Gln Gly Gln Met<br>                 355                     360                     365 | 1104 |
| gag aga ggc aaa gtt gtc tta gag aca cct aga aac agc act gac atc<br>Glu Arg Gly Lys Val Val Leu Glu Thr Pro Arg Asn Ser Thr Asp Ile<br>370                     375                     380 | 1152 |
| ttc atg gct tac gtc tcc acc ttt ctg ccg ccc gat gat gat ggg ggc<br>Phe Met Ala Tyr Val Ser Thr Phe Leu Pro Pro Asp Asp Asp Gly Gly<br>385                     390                     395                     400 | 1200 |
| tgc tcc gag ctt tcc cgg cac agg gtc ctg agg agt ctg tgc tcc cta<br>Cys Ser Glu Leu Ser Arg His Arg Val Leu Arg Ser Leu Cys Ser Leu<br>                 405                     410                     415 | 1248 |
| gca gct gaa ggg att cag cac cag agg ttc cta ttt gaa gaa gct gag<br>Ala Ala Glu Gly Ile Gln His Gln Arg Phe Leu Phe Glu Glu Ala Glu<br>        420                     425                     430 | 1296 |
| ctc agg aaa cat aat tta gat ggc ccc agg ctt gcc gct ttc ctg agt<br>Leu Arg Lys His Asn Leu Asp Gly Pro Arg Leu Ala Ala Phe Leu Ser<br>                 435                     440                     445 | 1344 |
| agt aac gac tac caa ttg gga ctt gcc atc aag aag ttc tac agc ttc<br>Ser Asn Asp Tyr Gln Leu Gly Leu Ala Ile Lys Lys Phe Tyr Ser Phe<br>450                     455                     460 | 1392 |

```
cgc cac atc agc ttc cag gac ttt ttt cat gcc atg tct tac ctg gtg      1440
Arg His Ile Ser Phe Gln Asp Phe Phe His Ala Met Ser Tyr Leu Val
465                 470                 475                 480 aaa gag gac caa agc cgg ctg ggg aag gag tcc cgc aga gaa gtg caa      1488
Lys Glu Asp Gln Ser Arg Leu Gly Lys Glu Ser Arg Arg Glu Val Gln
                485                 490                 495 agg ctg ctg gag gta aag gag cag gaa ggg aat gat gag atg acc ctc      1536
Arg Leu Leu Glu Val Lys Glu Gln Glu Gly Asn Asp Glu Met Thr Leu
            500                 505                 510 act atg cag ttt tta ctg gac atc tcg aaa aaa gac agc ttc tcg aac      1584
Thr Met Gln Phe Leu Leu Asp Ile Ser Lys Lys Asp Ser Phe Ser Asn
        515                 520                 525 ttg gag ctc aag ttc tgc ttc aga att tct ccc tgt tta gcg cag gat      1632
Leu Glu Leu Lys Phe Cys Phe Arg Ile Ser Pro Cys Leu Ala Gln Asp
    530                 535                 540 ctg aag cat ttt aaa gaa cag atg gaa tct atg aag cac aac agg acc      1680
Leu Lys His Phe Lys Glu Gln Met Glu Ser Met Lys His Asn Arg Thr
545                 550                 555                 560 tgg gat ttg gaa ttc tcc ctg tat gaa gct aaa ata aag aat ctg gta      1728
Trp Asp Leu Glu Phe Ser Leu Tyr Glu Ala Lys Ile Lys Asn Leu Val
                565                 570                 575 aaa ggt att cag atg aac aat gta tca ttc aag ata aaa cat tca aat      1776
Lys Gly Ile Gln Met Asn Asn Val Ser Phe Lys Ile Lys His Ser Asn
            580                 585                 590 gaa aag aaa tca cag agc cag aat tta ttt tct gtc aaa agc agc ttg      1824
Glu Lys Lys Ser Gln Ser Gln Asn Leu Phe Ser Val Lys Ser Ser Leu
        595                 600                 605 agt cat gga cct aag gag gag caa aaa tgt cct tct gtc cat gga cag      1872
Ser His Gly Pro Lys Glu Glu Gln Lys Cys Pro Ser Val His Gly Gln
    610                 615                 620 aag gag ggc aaa gat aat ata gca gga aca caa aag gaa gct tct act      1920
Lys Glu Gly Lys Asp Asn Ile Ala Gly Thr Gln Lys Glu Ala Ser Thr
625                 630                 635                 640 gga aaa ggc aga ggg aca gag gaa aca cca aaa aat act tac ata taa     1968
Gly Lys Gly Arg Gly Thr Glu Glu Thr Pro Lys Asn Thr Tyr Ile *
                645                 650                 655

<210> SEQ ID NO 84
<211> LENGTH: 655
<212> TYPE: PRT
<213> ORGANISM: Homo sapiens

<400> SEQUENCE: 84

Met Ala Met Ala Lys Ala Arg Lys Pro Arg Glu Ala Leu Leu Trp Ala
1               5                   10                  15

Leu Ser Asp Leu Glu Glu Asn Asp Phe Lys Lys Leu Lys Phe Tyr Leu
                20                  25                  30

Arg Asp Met Thr Leu Ser Glu Gly Gln Pro Pro Leu Ala Arg Gly Glu
            35                  40                  45

Leu Glu Gly Leu Ile Pro Val Asp Leu Ala Glu Leu Leu Ile Ser Lys
        50                  55                  60

Tyr Gly Glu Lys Glu Ala Val Lys Val Val Leu Lys Gly Leu Lys Val
65                  70                  75                  80

Met Asn Leu Leu Glu Leu Val Asp Gln Leu Ser His Ile Cys Leu His
                85                  90                  95

Asp Tyr Arg Glu Val Tyr Arg Glu His Val Arg Cys Leu Glu Glu Trp
            100                 105                 110

Gln Glu Ala Gly Val Asn Gly Arg Tyr Asn Gln Val Leu Leu Val Ala
```

-continued

```
            115                 120                 125
Lys Pro Ser Ser Glu Ser Pro Glu Ser Leu Ala Cys Pro Phe Pro Glu
        130                 135                 140
Gln Glu Leu Glu Ser Val Thr Val Glu Ala Leu Phe Asp Ser Gly Glu
145                 150                 155                 160
Lys Pro Ser Leu Ala Pro Ser Leu Val Val Leu Gln Gly Ser Ala Gly
                165                 170                 175
Thr Gly Lys Thr Thr Leu Ala Arg Lys Met Val Leu Asp Trp Ala Thr
            180                 185                 190
Gly Thr Leu Tyr Pro Gly Arg Phe Asp Tyr Val Phe Tyr Val Ser Cys
            195                 200                 205
Lys Glu Val Val Leu Leu Leu Glu Ser Lys Leu Glu Gln Leu Leu Phe
210                 215                 220
Trp Cys Cys Gly Asp Asn Gln Ala Pro Val Thr Glu Ile Leu Arg Gln
225                 230                 235                 240
Pro Glu Arg Leu Leu Phe Ile Leu Asp Gly Phe Asp Glu Leu Gln Arg
                245                 250                 255
Pro Phe Glu Glu Lys Leu Lys Lys Arg Gly Leu Ser Pro Lys Glu Ser
                260                 265                 270
Leu Leu His Leu Leu Ile Arg Arg His Thr Leu Pro Thr Cys Ser Leu
            275                 280                 285
Leu Ile Thr Thr Arg Pro Leu Ala Leu Arg Asn Leu Glu Pro Leu Leu
        290                 295                 300
Lys Gln Ala Arg His Val His Ile Leu Gly Phe Ser Glu Glu Glu Arg
305                 310                 315                 320
Ala Arg Tyr Phe Ser Ser Tyr Phe Thr Asp Glu Lys Gln Ala Asp Arg
                325                 330                 335
Ala Phe Asp Ile Val Gln Lys Asn Asp Ile Leu Tyr Lys Ala Cys Gln
                340                 345                 350
Val Pro Gly Ile Cys Trp Val Val Cys Ser Trp Leu Gln Gly Gln Met
            355                 360                 365
Glu Arg Gly Lys Val Val Leu Glu Thr Pro Arg Asn Ser Thr Asp Ile
        370                 375                 380
Phe Met Ala Tyr Val Ser Thr Phe Leu Pro Pro Asp Asp Gly Gly
385                 390                 395                 400
Cys Ser Glu Leu Ser Arg His Arg Val Leu Arg Ser Leu Cys Ser Leu
                405                 410                 415
Ala Ala Glu Gly Ile Gln His Gln Arg Phe Leu Phe Glu Glu Ala Glu
            420                 425                 430
Leu Arg Lys His Asn Leu Asp Gly Pro Arg Leu Ala Ala Phe Leu Ser
            435                 440                 445
Ser Asn Asp Tyr Gln Leu Gly Leu Ala Ile Lys Lys Phe Tyr Ser Phe
450                 455                 460
Arg His Ile Ser Phe Gln Asp Phe Phe His Ala Met Ser Tyr Leu Val
465                 470                 475                 480
Lys Glu Asp Gln Ser Arg Leu Gly Lys Glu Ser Arg Arg Glu Val Gln
                485                 490                 495
Arg Leu Leu Glu Val Lys Glu Gln Gly Asn Asp Glu Met Thr Leu
            500                 505                 510
Thr Met Gln Phe Leu Leu Asp Ile Ser Lys Lys Asp Ser Phe Ser Asn
            515                 520                 525
Leu Glu Leu Lys Phe Cys Phe Arg Ile Ser Pro Cys Leu Ala Gln Asp
        530                 535                 540
```

```
Leu Lys His Phe Lys Glu Gln Met Glu Ser Met Lys His Asn Arg Thr
545                 550                 555                 560

Trp Asp Leu Glu Phe Ser Leu Tyr Glu Ala Lys Ile Lys Asn Leu Val
                565                 570                 575

Lys Gly Ile Gln Met Asn Asn Val Ser Phe Lys Ile Lys His Ser Asn
            580                 585                 590

Glu Lys Lys Ser Gln Ser Gln Asn Leu Phe Ser Val Lys Ser Ser Leu
        595                 600                 605

Ser His Gly Pro Lys Glu Glu Gln Lys Cys Pro Ser Val His Gly Gln
    610                 615                 620

Lys Glu Gly Lys Asp Asn Ile Ala Gly Thr Gln Lys Glu Ala Ser Thr
625                 630                 635                 640

Gly Lys Gly Arg Gly Thr Glu Glu Thr Pro Lys Asn Thr Tyr Ile
                645                 650                 655
```

<210> SEQ ID NO 85
<211> LENGTH: 650
<212> TYPE: PRT
<213> ORGANISM: Homo sapiens

<400> SEQUENCE: 85

```
Met Val Ser Ser Ala Gln Met Gly Phe Asn Leu Gln Ala Leu Leu Glu
1               5                   10                  15

Gln Leu Ser Gln Asp Glu Leu Ser Lys Phe Lys Tyr Leu Ile Thr Thr
            20                  25                  30

Phe Ser Leu Ala His Glu Leu Gln Lys Ile Pro His Lys Glu Val Asp
        35                  40                  45

Lys Ala Asp Gly Lys Gln Leu Val Glu Ile Leu Thr Thr His Cys Asp
    50                  55                  60

Ser Tyr Trp Val Glu Met Ala Ser Leu Gln Val Phe Glu Lys Met His
65                  70                  75                  80

Arg Met Asp Leu Ser Glu Arg Ala Lys Asp Glu Val Arg Glu Ala Ala
                85                  90                  95

Leu Lys Ser Phe Asn Lys Arg Lys Pro Leu Ser Leu Gly Ile Thr Arg
            100                 105                 110

Lys Glu Arg Pro Pro Leu Asp Val Asp Glu Met Leu Glu Arg Phe Lys
        115                 120                 125

Thr Glu Ala Gln Ala Phe Thr Glu Thr Lys Gly Asn Val Ile Cys Leu
    130                 135                 140

Gly Lys Glu Val Phe Lys Gly Lys Pro Asp Lys Asp Asn Arg Cys
145                 150                 155                 160

Arg Tyr Ile Leu Lys Thr Lys Phe Arg Glu Met Trp Lys Ser Trp Pro
                165                 170                 175

Gly Asp Ser Lys Glu Val Gln Val Met Ala Glu Arg Tyr Lys Met Leu
            180                 185                 190

Ile Pro Phe Ser Asn Pro Arg Val Leu Pro Gly Pro Phe Ser Tyr Thr
        195                 200                 205

Val Val Leu Tyr Gly Pro Ala Gly Leu Gly Lys Thr Thr Leu Ala Gln
    210                 215                 220

Lys Leu Met Leu Asp Trp Ala Glu Asp Asn Leu Ile His Lys Phe Lys
225                 230                 235                 240

Tyr Ala Phe Tyr Leu Ser Cys Arg Glu Leu Ser Arg Leu Gly Pro Cys
                245                 250                 255

Ser Phe Ala Glu Leu Val Phe Arg Asp Trp Pro Glu Leu Gln Asp Asp
```

```
                260                 265                 270
Ile Pro His Ile Leu Ala Gln Ala Arg Lys Ile Leu Phe Val Ile Asp
            275                 280                 285
Gly Phe Asp Glu Leu Gly Ala Ala Pro Gly Ala Leu Ile Glu Asp Ile
        290                 295                 300
Cys Gly Asp Trp Glu Lys Lys Pro Val Pro Val Leu Leu Gly Ser
305                 310                 315                 320
Leu Leu Asn Arg Val Met Leu Pro Lys Ala Leu Leu Val Thr Thr
                325                 330                 335
Arg Pro Arg Ala Leu Arg Asp Leu Arg Ile Leu Ala Glu Glu Pro Ile
            340                 345                 350
Tyr Ile Arg Val Glu Gly Phe Leu Glu Glu Asp Arg Arg Ala Tyr Phe
            355                 360                 365
Leu Arg His Phe Gly Asp Glu Asp Gln Ala Met Arg Ala Phe Glu Leu
        370                 375                 380
Met Arg Ser Asn Ala Ala Leu Phe Gln Leu Gly Ser Ala Pro Ala Val
385                 390                 395                 400
Cys Trp Ile Val Cys Thr Thr Leu Lys Leu Gln Met Glu Lys Gly Glu
                405                 410                 415
Asp Pro Val Pro Thr Cys Leu Thr Arg Thr Gly Leu Phe Leu Arg Phe
            420                 425                 430
Leu Cys Ser Arg Phe Pro Gln Gly Ala Gln Leu Arg Gly Ala Leu Arg
        435                 440                 445
Thr Leu Ser Leu Leu Ala Ala Gln Gly Leu Trp Ala Gln Thr Ser Val
    450                 455                 460
Leu His Arg Glu Asp Leu Glu Arg Leu Gly Val Gln Glu Ser Asp Leu
465                 470                 475                 480
Arg Leu Phe Leu Asp Gly Asp Ile Leu Arg Gln Asp Arg Val Ser Lys
                485                 490                 495
Gly Cys Tyr Ser Phe Ile His Leu Ser Phe Gln Gln Phe Leu Thr Ala
            500                 505                 510
Leu Phe Tyr Thr Leu Glu Lys Glu Glu Glu Asp Arg Asp Gly His
            515                 520                 525
Thr Trp Asp Ile Gly Asp Val Gln Lys Leu Leu Ser Gly Val Glu Arg
        530                 535                 540
Leu Arg Asn Pro Asp Leu Ile Gln Ala Gly Tyr Tyr Ser Phe Gly Leu
545                 550                 555                 560
Ala Asn Glu Lys Arg Ala Lys Glu Leu Glu Ala Thr Phe Gly Cys Arg
                565                 570                 575
Met Ser Pro Asp Ile Lys Gln Glu Leu Leu Arg Cys Asp Ile Ser Cys
            580                 585                 590
Lys Gly Gly His Ser Thr Val Thr Asp Leu Gln Glu Leu Leu Gly Cys
        595                 600                 605
Leu Tyr Glu Ser Gln Glu Glu Glu Leu Val Lys Glu Val Met Ala Gln
    610                 615                 620
Phe Lys Glu Ile Ser Leu His Leu Asn Ala Val Asp Val Val Pro Ser
625                 630                 635                 640
Ser Phe Cys Val Lys His Cys Arg Asn Leu
                645                 650

<210> SEQ ID NO 86
<211> LENGTH: 650
<212> TYPE: PRT
<213> ORGANISM: Homo sapiens
```

<400> SEQUENCE: 86

```
Met Val Ser Ser Ala Gln Met Gly Phe Asn Leu Gln Ala Leu Leu Glu
 1               5                  10                  15
Gln Leu Ser Gln Asp Glu Leu Ser Lys Phe Lys Tyr Leu Ile Thr Thr
             20                  25                  30
Phe Ser Leu Ala His Glu Leu Gln Lys Ile Pro His Lys Glu Val Asp
         35                  40                  45
Lys Ala Asp Gly Lys Gln Leu Val Glu Ile Leu Thr Thr His Cys Asp
 50                  55                  60
Ser Tyr Trp Val Glu Met Ala Ser Leu Gln Val Phe Glu Lys Met His
 65                  70                  75                  80
Arg Met Asp Leu Ser Glu Arg Ala Lys Asp Glu Val Arg Glu Ala Ala
                 85                  90                  95
Leu Lys Ser Phe Asn Lys Arg Lys Pro Leu Ser Leu Gly Ile Thr Arg
            100                 105                 110
Lys Glu Arg Pro Pro Leu Asp Val Asp Glu Met Leu Glu Arg Phe Lys
        115                 120                 125
Thr Glu Ala Gln Ala Phe Thr Glu Thr Lys Gly Asn Val Ile Cys Leu
    130                 135                 140
Gly Lys Glu Val Phe Lys Gly Lys Pro Asp Lys Asp Asn Arg Cys
145                 150                 155                 160
Arg Tyr Ile Leu Lys Thr Lys Phe Arg Glu Met Trp Lys Ser Trp Pro
                165                 170                 175
Gly Asp Ser Lys Glu Val Gln Val Met Ala Glu Arg Tyr Lys Met Leu
            180                 185                 190
Ile Pro Phe Ser Asn Pro Arg Val Leu Pro Gly Pro Phe Ser Tyr Thr
        195                 200                 205
Val Val Leu Tyr Gly Pro Ala Gly Leu Gly Lys Thr Thr Leu Ala Gln
    210                 215                 220
Lys Leu Met Leu Asp Trp Ala Glu Asp Asn Leu Ile His Lys Phe Lys
225                 230                 235                 240
Tyr Ala Phe Tyr Leu Ser Cys Arg Glu Leu Ser Arg Leu Gly Pro Cys
                245                 250                 255
Ser Phe Ala Glu Leu Val Phe Arg Asp Trp Pro Glu Leu Gln Asp Asp
            260                 265                 270
Ile Pro His Ile Leu Ala Gln Ala Arg Lys Ile Leu Phe Val Ile Asp
        275                 280                 285
Gly Phe Asp Glu Leu Gly Ala Ala Pro Gly Ala Leu Ile Glu Asp Ile
    290                 295                 300
Cys Gly Asp Trp Glu Lys Lys Pro Val Pro Val Leu Leu Gly Ser
305                 310                 315                 320
Leu Leu Asn Arg Val Met Leu Pro Lys Ala Ala Leu Leu Val Thr Thr
                325                 330                 335
Arg Pro Arg Ala Leu Arg Asp Leu Arg Ile Leu Ala Glu Glu Pro Ile
            340                 345                 350
Tyr Ile Arg Val Glu Gly Phe Leu Glu Glu Asp Arg Ala Tyr Phe Leu
        355                 360                 365
Leu Arg His Phe Gly Asp Glu Asp Gln Ala Met Arg Ala Phe Glu Leu
    370                 375                 380
Met Arg Ser Asn Ala Ala Leu Phe Gln Leu Gly Ser Ala Pro Ala Val
385                 390                 395                 400
Cys Trp Ile Val Cys Thr Thr Leu Lys Leu Gln Met Glu Lys Gly Glu
```

-continued

```
                405                 410                 415
Asp Pro Val Pro Thr Cys Leu Thr Arg Thr Gly Leu Phe Leu Arg Phe
            420                 425                 430

Leu Cys Ser Arg Phe Pro Gln Gly Ala Gln Leu Arg Gly Ala Leu Arg
        435                 440                 445

Thr Leu Ser Leu Leu Ala Ala Gln Gly Leu Trp Ala Gln Thr Ser Val
    450                 455                 460

Leu His Arg Glu Asp Leu Glu Arg Leu Gly Val Gln Glu Ser Asp Leu
465                 470                 475                 480

Arg Leu Phe Leu Asp Gly Asp Ile Leu Arg Gln Asp Arg Val Ser Lys
                485                 490                 495

Gly Cys Tyr Ser Phe Ile His Leu Ser Phe Gln Gln Phe Leu Thr Ala
            500                 505                 510

Leu Phe Tyr Thr Leu Glu Lys Glu Glu Glu Asp Arg Asp Gly His
        515                 520                 525

Thr Trp Asp Ile Gly Asp Val Gln Lys Leu Leu Ser Gly Val Glu Arg
    530                 535                 540

Leu Arg Asn Pro Asp Leu Ile Gln Ala Gly Tyr Tyr Ser Phe Gly Leu
545                 550                 555                 560

Ala Asn Glu Lys Arg Ala Lys Glu Leu Glu Ala Thr Phe Gly Cys Arg
                565                 570                 575

Met Ser Pro Asp Ile Lys Gln Glu Leu Leu Arg Cys Asp Ile Ser Cys
            580                 585                 590

Lys Gly Gly His Ser Thr Val Thr Asp Leu Gln Glu Leu Leu Gly Cys
        595                 600                 605

Leu Tyr Glu Ser Gln Glu Glu Leu Val Lys Glu Val Met Ala Gln
    610                 615                 620

Phe Lys Glu Ile Ser Leu His Leu Asn Ala Val Asp Val Val Pro Ser
625                 630                 635                 640

Ser Phe Cys Val Lys His Cys Arg Asn Leu
                645                 650

<210> SEQ ID NO 87
<211> LENGTH: 622
<212> TYPE: PRT
<213> ORGANISM: Homo sapiens

<400> SEQUENCE: 87

His Thr Arg Ser Thr Met Thr Ser Pro Gln Leu Glu Trp Thr Leu Gln
1               5                   10                  15

Thr Leu Leu Glu Gln Leu Asn Glu Asp Glu Leu Lys Ser Phe Lys Ser
            20                  25                  30

Leu Leu Trp Ala Phe Pro Leu Glu Asp Val Leu Gln Lys Thr Pro Trp
        35                  40                  45

Ser Glu Val Glu Ala Asp Gly Lys Lys Leu Ala Glu Ile Leu Val
    50                  55                  60

Asn Thr Ser Ser Glu Asn Trp Ile Arg Asn Ala Thr Val Asn Ile Leu
65              70                  75                  80

Glu Glu Met Asn Leu Thr Glu Leu Cys Lys Met Ala Lys Ala Glu Met
                85                  90                  95

Met Glu Asp Gly Gln Val Gln Glu Ile Asp Asn Pro Glu Leu Gly Asp
            100                 105                 110

Ala Glu Glu Asp Ser Glu Leu Ala Lys Pro Gly Glu Lys Glu Gly Trp
        115                 120                 125
```

-continued

```
Arg Asn Ser Met Glu Lys Gln Ser Leu Val Trp Lys Asn Thr Phe Trp
        130                 135                 140
Gln Gly Asp Ile Asp Asn Phe His Asp Asp Val Thr Leu Arg Asn Gln
145                 150                 155                 160
Arg Phe Ile Pro Phe Leu Asn Pro Arg Thr Pro Arg Lys Leu Thr Pro
                165                 170                 175
Tyr Thr Val Val Leu His Gly Pro Ala Gly Val Gly Lys Thr Thr Leu
            180                 185                 190
Ala Lys Lys Cys Met Leu Asp Trp Thr Asp Cys Asn Leu Ser Pro Thr
        195                 200                 205
Leu Arg Tyr Ala Phe Tyr Leu Ser Cys Lys Glu Leu Ser Arg Met Gly
    210                 215                 220
Pro Cys Ser Phe Ala Glu Leu Ile Ser Lys Asp Trp Pro Glu Leu Gln
225                 230                 235                 240
Asp Asp Ile Pro Ser Ile Leu Ala Gln Ala Gln Arg Ile Leu Phe Val
                245                 250                 255
Val Asp Gly Leu Asp Glu Leu Lys Val Pro Pro Gly Ala Leu Ile Gln
            260                 265                 270
Asp Ile Cys Gly Asp Trp Glu Lys Lys Pro Val Pro Val Leu Leu
        275                 280                 285
Gly Ser Leu Leu Lys Arg Lys Met Leu Pro Arg Ala Ala Leu Leu Val
    290                 295                 300
Thr Thr Arg Pro Arg Ala Leu Arg Asp Leu Gln Leu Leu Ala Gln Gln
305                 310                 315                 320
Pro Ile Tyr Val Arg Val Glu Gly Phe Leu Glu Asp Arg Arg Ala
                325                 330                 335
Tyr Phe Leu Arg His Phe Gly Asp Glu Asp Gln Ala Met Arg Ala Phe
            340                 345                 350
Glu Leu Met Arg Ser Asn Ala Ala Leu Phe Gln Leu Gly Ser Ala Pro
        355                 360                 365
Ala Val Cys Trp Ile Val Cys Thr Thr Leu Lys Leu Gln Met Glu Lys
    370                 375                 380
Gly Glu Asp Pro Val Pro Thr Cys Leu Thr Arg Thr Gly Leu Phe Leu
385                 390                 395                 400
Arg Phe Leu Cys Ser Arg Phe Pro Gln Gly Ala Gln Leu Arg Gly Ala
                405                 410                 415
Leu Arg Thr Leu Ser Leu Leu Ala Ala Gln Gly Leu Trp Ala Gln Met
            420                 425                 430
Ser Val Phe His Arg Glu Asp Leu Glu Arg Leu Gly Val Gln Glu Ser
        435                 440                 445
Asp Leu Arg Leu Phe Leu Asp Gly Asp Ile Leu Arg Gln Asp Arg Val
    450                 455                 460
Ser Lys Gly Cys Tyr Ser Phe Ile His Leu Ser Phe Gln Gln Phe Leu
465                 470                 475                 480
Thr Ala Leu Phe Tyr Ala Leu Glu Lys Glu Glu Gly Glu Asp Arg Asp
                485                 490                 495
Gly His Ala Trp Asp Ile Gly Asp Val Gln Lys Leu Leu Ser Gly Glu
            500                 505                 510
Glu Arg Leu Lys Asn Pro Asp Leu Ile Gln Val Gly His Phe Leu Phe
        515                 520                 525
Gly Leu Ala Asn Glu Lys Arg Ala Lys Glu Leu Glu Ala Thr Phe Gly
    530                 535                 540
Cys Arg Met Ser Pro Asp Ile Lys Gln Glu Leu Leu Gln Cys Lys Ala
```

```
                   545                 550                 555                 560

His Leu His Ala Asn Lys Pro Leu Ser Val Thr Asp Leu Lys Glu Val
                565                 570                 575

Leu Gly Cys Leu Tyr Glu Ser Gln Glu Glu Leu Ala Lys Val Val
                580                 585                 590

Val Ala Pro Phe Lys Glu Ile Ser Ile His Leu Thr Asn Thr Ser Glu
                595                 600                 605

Val Met His Cys Ser Phe Ser Leu Lys His Cys Gln Asp Leu
                610                 615                 620

<210> SEQ ID NO 88
<211> LENGTH: 612
<212> TYPE: PRT
<213> ORGANISM: Mus musculus

<400> SEQUENCE: 88

Leu Leu Lys Met Thr Ser Val Arg Cys Lys Leu Ala Gln Tyr Leu Glu
  1               5                  10                  15

Asp Leu Glu Asp Val Asp Leu Lys Lys Phe Lys Met His Leu Glu Asp
                 20                  25                  30

Tyr Pro Pro Glu Lys Gly Cys Ile Pro Val Pro Arg Gly Gln Met Glu
             35                  40                  45

Lys Ala Asp His Leu Asp Leu Ala Thr Leu Met Ile Asp Phe Asn Gly
         50                  55                  60

Glu Glu Lys Ala Asp Tyr Cys Lys Met Tyr Arg Arg His Val Arg Ser
 65                  70                  75                  80

Arg Phe Tyr Ser Ile Lys Asp Arg Asn Ala Arg Leu Gly Glu Ser Val
                 85                  90                  95

Asp Leu Asn Ser Arg Tyr Thr Gln Leu Gln Leu Val Lys Glu His Pro
            100                 105                 110

Ser Lys Gln Glu Arg Glu His Glu Leu Leu Thr Ile Gly Arg Thr Lys
        115                 120                 125

Met Arg Asp Ser Pro Met Ser Ser Leu Lys Leu Glu Leu Leu Phe Glu
    130                 135                 140

Pro Glu Asp Gly His Ser Glu Pro Val His Thr Val Phe Gln Gly
145                 150                 155                 160

Ala Ala Gly Ile Gly Lys Thr Ile Leu Ala Arg Lys Ile Met Leu Asp
                165                 170                 175

Trp Ala Leu Gly Lys Leu Phe Lys Asp Lys Phe Asp Tyr Leu Phe Phe
            180                 185                 190

Ile His Cys Arg Glu Val Ser Leu Arg Thr Pro Arg Ser Leu Ala Asp
        195                 200                 205

Leu Ile Val Ser Cys Trp Pro Asp Pro Asn Pro Val Cys Lys Ile
    210                 215                 220

Leu Arg Lys Pro Ser Arg Ile Leu Phe Leu Met Asp Gly Phe Asp Glu
225                 230                 235                 240

Leu Gln Gly Ala Phe Asp Glu His Ile Gly Glu Val Cys Thr Asp Trp
                245                 250                 255

Gln Lys Ala Val Arg Gly Asp Ile Leu Leu Ser Ser Leu Ile Arg Lys
            260                 265                 270

Lys Leu Leu Pro Lys Ala Ser Leu Leu Ile Thr Thr Arg Pro Val Ala
        275                 280                 285

Leu Glu Lys Leu Gln His Leu Leu Asp His Pro Arg His Val Glu Ile
    290                 295                 300
```

```
Leu Gly Phe Ser Glu Ala Lys Arg Lys Glu Tyr Phe Phe Lys Tyr Phe
305                 310                 315                 320

Ser Asn Glu Leu Gln Ala Arg Glu Ala Phe Arg Leu Ile Gln Glu Asn
                325                 330                 335

Glu Val Leu Phe Thr Met Cys Phe Ile Pro Leu Val Cys Trp Ile Val
            340                 345                 350

Cys Thr Gly Leu Lys Gln Gln Met Glu Thr Gly Lys Ser Leu Ala Gln
        355                 360                 365

Thr Ser Lys Thr Thr Thr Ala Val Tyr Val Phe Phe Leu Ser Ser Leu
    370                 375                 380

Leu Gln Ser Arg Gly Gly Ile Glu Glu His Leu Phe Ser Asp Tyr Leu
385                 390                 395                 400

Gln Gly Leu Cys Ser Leu Ala Ala Asp Gly Ile Trp Asn Gln Lys Ile
                405                 410                 415

Leu Phe Glu Glu Cys Asp Leu Arg Lys His Gly Leu Gln Lys Thr Asp
            420                 425                 430

Val Ser Ala Phe Leu Arg Met Asn Val Phe Gln Lys Glu Val Asp Cys
        435                 440                 445

Glu Arg Phe Tyr Ser Phe Ser His Met Thr Phe Gln Glu Phe Phe Ala
    450                 455                 460

Ala Met Tyr Tyr Leu Leu Glu Glu Ala Glu Gly Glu Thr Val Arg
465                 470                 475                 480

Lys Gly Pro Gly Gly Cys Ser Asp Leu Leu Asn Arg Asp Val Lys Val
                485                 490                 495

Leu Leu Glu Asn Tyr Gly Lys Phe Glu Lys Gly Tyr Leu Ile Phe Val
            500                 505                 510

Val Arg Phe Leu Phe Gly Leu Val Asn Gln Glu Arg Thr Ser Tyr Leu
        515                 520                 525

Glu Lys Lys Leu Ser Cys Lys Ile Ser Gln Gln Val Arg Leu Glu Leu
    530                 535                 540

Leu Lys Trp Ile Glu Val Lys Ala Lys Ala Lys Leu Gln Trp Gln
545                 550                 555                 560

Pro Ser Gln Leu Glu Leu Phe Tyr Cys Leu Tyr Glu Met Gln Glu Glu
                565                 570                 575

Asp Phe Val Gln Ser Ala Met Asp His Phe Pro Lys Ile Glu Ile Asn
            580                 585                 590

Leu Ser Thr Arg Met Asp His Val Ser Ser Phe Cys Ile Lys Asn
        595                 600                 605

Cys His Arg Val
    610

<210> SEQ ID NO 89
<211> LENGTH: 674
<212> TYPE: PRT
<213> ORGANISM: Homo sapiens

<400> SEQUENCE: 89

Met Ala Ser Thr Arg Cys Lys Leu Ala Arg Tyr Leu Glu Asp Leu Glu
1               5                   10                  15

Asp Val Asp Leu Lys Lys Phe Lys Met His Leu Glu Asp Tyr Pro Pro
                20                  25                  30

Gln Lys Gly Cys Ile Pro Leu Pro Arg Gly Gln Thr Glu Lys Ala Asp
            35                  40                  45

His Val Asp Leu Ala Thr Leu Met Ile Asp Phe Asn Gly Glu Glu Lys
        50                  55                  60
```

-continued

```
Ala Trp Ala Met Ala Val Trp Ile Phe Ala Ala Ile Asn Arg Arg Asp
 65                  70                  75                  80

Leu Tyr Glu Lys Ala Lys Arg Asp Glu Pro Lys Trp Gly Ser Asp Asn
                 85                  90                  95

Ala Arg Val Ser Asn Pro Thr Val Ile Cys Gln Glu Asp Ser Ile Glu
            100                 105                 110

Glu Glu Trp Met Gly Leu Leu Glu Tyr Leu Ser Arg Ile Ser Ile Cys
        115                 120                 125

Lys Met Lys Lys Asp Tyr Arg Lys Lys Tyr Arg Lys Tyr Val Arg Ser
    130                 135                 140

Arg Phe Gln Cys Ile Glu Asp Arg Asn Ala Arg Leu Gly Glu Ser Val
145                 150                 155                 160

Ser Leu Asn Lys Arg Tyr Thr Arg Leu Arg Leu Ile Lys Glu His Arg
                165                 170                 175

Ser Gln Gln Glu Arg Glu Gln Glu Leu Leu Ala Ile Gly Lys Thr Lys
            180                 185                 190

Thr Cys Glu Ser Pro Val Ser Pro Ile Lys Met Glu Leu Leu Phe Asp
        195                 200                 205

Pro Asp Asp Glu His Ser Glu Pro Val His Thr Val Val Phe Gln Gly
    210                 215                 220

Ala Ala Gly Ile Gly Lys Thr Ile Leu Ala Arg Lys Met Met Leu Asp
225                 230                 235                 240

Trp Ala Ser Gly Thr Leu Tyr Gln Asp Arg Phe Asp Tyr Leu Phe Tyr
                245                 250                 255

Ile His Cys Arg Glu Val Ser Leu Val Thr Gln Arg Ser Leu Gly Asp
            260                 265                 270

Leu Ile Met Ser Cys Cys Pro Asp Pro Asn Pro Ile His Lys Ile
        275                 280                 285

Val Arg Lys Pro Ser Arg Ile Leu Phe Leu Met Asp Gly Phe Asp Glu
290                 295                 300

Leu Gln Gly Ala Phe Asp Glu His Ile Gly Pro Leu Cys Thr Asp Trp
305                 310                 315                 320

Gln Lys Ala Glu Arg Gly Asp Ile Leu Leu Ser Ser Leu Ile Arg Lys
                325                 330                 335

Lys Leu Leu Pro Glu Ala Ser Leu Leu Ile Thr Thr Arg Pro Val Ala
            340                 345                 350

Leu Glu Lys Leu Gln His Leu Leu Asp His Pro Arg His Val Glu Ile
        355                 360                 365

Leu Gly Phe Ser Glu Ala Lys Arg Lys Glu Tyr Phe Phe Lys Tyr Phe
    370                 375                 380

Ser Asp Glu Ala Gln Ala Arg Ala Ala Phe Ser Leu Ile Gln Glu Asn
385                 390                 395                 400

Glu Val Leu Phe Thr Met Cys Phe Ile Pro Leu Val Cys Trp Ile Val
                405                 410                 415

Cys Thr Gly Leu Lys Gln Gln Met Glu Ser Gly Lys Ser Leu Ala Gln
            420                 425                 430

Thr Ser Lys Thr Thr Thr Ala Val Tyr Val Phe Phe Leu Ser Ser Leu
        435                 440                 445

Leu Gln Pro Arg Gly Gly Ser Gln Glu His Gly Leu Cys Ala His Leu
    450                 455                 460

Trp Gly Leu Cys Ser Leu Ala Ala Asp Gly Ile Trp Asn Gln Lys Ile
465                 470                 475                 480
```

```
Leu Phe Glu Glu Ser Asp Leu Arg Asn His Gly Leu Gln Lys Ala Asp
                485                 490                 495

Val Ser Ala Phe Leu Arg Met Asn Leu Phe Gln Lys Glu Val Asp Cys
            500                 505                 510

Glu Lys Phe Tyr Ser Phe Ile His Met Thr Phe Gln Glu Phe Phe Ala
        515                 520                 525

Ala Met Tyr Tyr Leu Leu Glu Glu Lys Glu Gly Arg Thr Asn Val
    530                 535                 540

Pro Gly Ser Arg Leu Lys Leu Pro Ser Arg Asp Val Thr Val Leu Leu
545                 550                 555                 560

Glu Asn Tyr Gly Lys Phe Glu Lys Gly Tyr Leu Ile Phe Val Val Arg
                565                 570                 575

Phe Leu Phe Gly Leu Val Asn Gln Glu Arg Thr Ser Tyr Leu Glu Lys
            580                 585                 590

Lys Leu Ser Cys Lys Ile Ser Gln Gln Ile Arg Leu Glu Leu Leu Lys
        595                 600                 605

Trp Ile Glu Val Lys Ala Lys Ala Lys Lys Leu Gln Ile Gln Pro Ser
    610                 615                 620

Gln Leu Glu Leu Phe Tyr Cys Leu Tyr Glu Met Gln Glu Glu Asp Phe
625                 630                 635                 640

Val Gln Arg Ala Met Asp Tyr Phe Pro Lys Ile Glu Ile Asn Leu Ser
                645                 650                 655

Thr Arg Met Asp His Met Val Ser Ser Phe Cys Ile Glu Asn Cys His
            660                 665                 670

Arg Val

<210> SEQ ID NO 90
<211> LENGTH: 635
<212> TYPE: PRT
<213> ORGANISM: Homo sapiens

<400> SEQUENCE: 90

Met Leu Arg Thr Ala Gly Arg Asp Gly Leu Cys Arg Leu Ser Thr Tyr
1               5                   10                  15

Leu Glu Glu Leu Glu Ala Val Glu Leu Lys Lys Phe Lys Leu Tyr Leu
                20                  25                  30

Gly Thr Ala Thr Glu Leu Gly Gly Lys Ile Pro Trp Gly Ser Met
            35                  40                  45

Glu Lys Ala Gly Pro Leu Glu Met Ala Gln Leu Leu Ile Thr His Phe
        50                  55                  60

Gly Pro Glu Glu Ala Trp Arg Leu Ala Leu Ser Thr Phe Glu Arg Ile
65                  70                  75                  80

Asn Arg Lys Asp Leu Trp Glu Arg Gly Gln Arg Glu Asp Leu Val Arg
                85                  90                  95

Asp Pro Gln Glu Thr Tyr Arg Asp Tyr Val Arg Arg Lys Phe Arg Leu
            100                 105                 110

Met Glu Asp Arg Asn Ala Arg Leu Gly Glu Cys Val Asn Leu Ser His
        115                 120                 125

Arg Tyr Thr Arg Leu Leu Leu Val Lys Glu His Ser Asn Pro Met Gln
    130                 135                 140

Val Gln Gln Gln Leu Leu Asp Thr Gly Arg Gly His Ala Arg Thr Val
145                 150                 155                 160

Gly His Gln Ala Ser Pro Ile Lys Ile Glu Thr Leu Phe Glu Pro Asp
                165                 170                 175
```

-continued

```
Glu Glu Arg Pro Glu Pro Pro Arg Thr Val Val Met Gln Gly Ala Ala
            180                 185                 190

Gly Ile Gly Lys Ser Met Leu Ala His Lys Val Met Leu Asp Trp Ala
        195                 200                 205

Asp Gly Lys Leu Phe Gln Gly Arg Phe Asp Tyr Leu Phe Tyr Ile Asn
    210                 215                 220

Cys Arg Glu Met Asn Gln Ser Ala Thr Glu Cys Ser Met Gln Asp Leu
225                 230                 235                 240

Ile Phe Ser Cys Trp Pro Glu Pro Ser Ala Pro Leu Gln Glu Leu Ile
                245                 250                 255

Arg Val Pro Glu Arg Leu Leu Phe Ile Ile Asp Gly Phe Asp Glu Leu
            260                 265                 270

Lys Pro Ser Phe His Asp Pro Gln Gly Pro Trp Cys Leu Cys Trp Glu
        275                 280                 285

Glu Lys Arg Pro Thr Glu Leu Leu Asn Ser Leu Ile Arg Lys Lys
    290                 295                 300

Leu Leu Pro Glu Leu Ser Leu Leu Ile Thr Thr Arg Pro Thr Ala Leu
305                 310                 315                 320

Glu Lys Leu His Arg Leu Leu Glu His Pro Arg His Val Glu Ile Leu
                325                 330                 335

Gly Phe Ser Glu Ala Glu Arg Lys Glu Tyr Phe Tyr Lys Tyr Phe His
            340                 345                 350

Asn Ala Glu Gln Ala Gly Gln Val Phe Asn Tyr Val Arg Asp Asn Glu
        355                 360                 365

Pro Leu Phe Thr Met Cys Phe Val Pro Leu Val Cys Trp Val Val Cys
    370                 375                 380

Thr Cys Leu Gln Gln Leu Glu Gly Gly Leu Leu Arg Gln Thr
385                 390                 395                 400

Ser Arg Thr Thr Thr Ala Val Tyr Met Leu Tyr Leu Leu Ser Leu Met
                405                 410                 415

Gln Pro Lys Pro Gly Ala Pro Arg Leu Gln Pro Pro Asn Gln Arg
            420                 425                 430

Gly Leu Cys Ser Leu Ala Ala Asp Gly Leu Trp Asn Gln Lys Ile Leu
        435                 440                 445

Phe Glu Glu Gln Asp Leu Arg Lys His Gly Leu Asp Gly Glu Asp Val
    450                 455                 460

Ser Ala Phe Leu Asn Met Asn Ile Phe Gln Lys Asp Ile Asn Cys Glu
465                 470                 475                 480

Arg Tyr Tyr Ser Phe Ile His Leu Ser Phe Gln Glu Phe Ala Ala
                485                 490                 495

Met Tyr Tyr Ile Leu Asp Glu Gly Glu Gly Ala Gly Pro Asp Gln
            500                 505                 510

Asp Val Thr Arg Leu Leu Thr Glu Tyr Ala Phe Ser Glu Arg Ser Phe
        515                 520                 525

Leu Ala Leu Thr Ser Arg Phe Leu Phe Gly Leu Leu Asn Glu Glu Thr
    530                 535                 540

Arg Ser His Leu Glu Lys Ser Leu Cys Trp Lys Val Ser Pro His Ile
545                 550                 555                 560

Lys Met Asp Leu Leu Gln Trp Ile Gln Ser Lys Ala Gln Ser Asp Gly
                565                 570                 575

Ser Thr Leu Gln Gln Gly Ser Leu Glu Phe Phe Ser Cys Leu Tyr Glu
            580                 585                 590

Ile Gln Glu Glu Glu Phe Ile Gln Gln Ala Leu Ser His Phe Gln Val
```

-continued

```
                 595                 600                 605

Ile Val Val Ser Asn Ile Ala Ser Lys Met Glu His Met Val Ser Ser
    610                 615                 620

Phe Cys Leu Lys Arg Cys Arg Ser Ala Gln Val
625                 630                 635

<210> SEQ ID NO 91
<211> LENGTH: 659
<212> TYPE: PRT
<213> ORGANISM: Homo sapiens

<400> SEQUENCE: 91

Cys Ser Ser Thr Gly Pro Arg Leu Ala Val Ala Arg Glu Leu Leu Leu
1               5                   10                  15

Ala Ala Leu Glu Glu Leu Ser Gln Glu Gln Leu Lys Arg Phe Arg His
                20                  25                  30

Lys Leu Arg Asp Val Gly Pro Asp Gly Arg Ser Ile Pro Trp Gly Arg
            35                  40                  45

Leu Glu Arg Ala Asp Ala Val Asp Leu Ala Glu Gln Leu Ala Gln Phe
        50                  55                  60

Tyr Gly Pro Glu Pro Ala Leu Glu Val Ala Arg Lys Thr Leu Lys Arg
65                  70                  75                  80

Ala Asp Ala Arg Asp Val Ala Ala Gln Leu Gln Glu Arg Arg Leu Gln
                85                  90                  95

Arg Leu Gly Leu Gly Ser Gly Thr Leu Leu Ser Val Ser Glu Tyr Lys
            100                 105                 110

Lys Lys Tyr Arg Glu His Val Leu Gln Leu His Ala Arg Val Lys Glu
        115                 120                 125

Arg Asn Ala Arg Ser Val Lys Ile Thr Lys Arg Phe Thr Lys Leu Leu
    130                 135                 140

Ile Ala Pro Glu Ser Ala Ala Pro Glu Glu Ala Leu Gly Pro Ala Glu
145                 150                 155                 160

Glu Pro Glu Pro Gly Arg Ala Arg Arg Ser Asp Thr His Thr Phe Asn
                165                 170                 175

Arg Leu Phe Arg Arg Asp Glu Glu Gly Arg Arg Pro Leu Thr Val Val
            180                 185                 190

Leu Gln Gly Pro Ala Gly Ile Gly Lys Thr Met Ala Ala Lys Lys Ile
        195                 200                 205

Leu Tyr Asp Trp Ala Ala Gly Lys Leu Tyr Gln Gly Gln Val Asp Phe
    210                 215                 220

Ala Phe Phe Met Pro Cys Gly Glu Leu Leu Glu Arg Pro Gly Thr Arg
225                 230                 235                 240

Ser Leu Ala Asp Leu Ile Leu Asp Gln Cys Pro Asp Arg Gly Ala Pro
                245                 250                 255

Val Pro Gln Met Leu Ala Gln Pro Gln Arg Leu Leu Phe Ile Leu Asp
            260                 265                 270

Gly Ala Asp Glu Leu Pro Ala Leu Gly Gly Pro Glu Ala Ala Pro Cys
        275                 280                 285

Thr Asp Pro Phe Glu Ala Ala Ser Gly Ala Arg Val Leu Gly Gly Leu
    290                 295                 300

Leu Ser Lys Ala Leu Leu Pro Thr Ala Leu Leu Val Thr Thr Arg Arg
305                 310                 315                 320

Ala Ala Ala Pro Gly Arg Leu Gln Gly Arg Leu Cys Ser Pro Gln Cys
                325                 330                 335
```

```
Ala Glu Val Arg Gly Phe Ser Asp Lys Asp Lys Lys Tyr Phe Tyr
            340                 345                 350

Lys Phe Phe Arg Asp Glu Arg Ala Glu Arg Ala Tyr Arg Phe Val
            355                 360                 365

Lys Glu Asn Glu Thr Leu Phe Ala Leu Cys Phe Val Pro Phe Val Cys
            370                 375                 380

Trp Ile Val Cys Thr Val Leu Arg Gln Gln Leu Glu Leu Gly Arg Asp
385                 390                 395                 400

Leu Ser Arg Thr Ser Lys Thr Thr Ser Val Tyr Leu Leu Phe Ile
            405                 410                 415

Thr Ser Val Leu Ser Ser Ala Pro Val Ala Asp Gly Pro Arg Leu Gln
            420                 425                 430

Gly Asp Leu Arg Asn Leu Cys Arg Leu Ala Arg Glu Gly Val Leu Gly
            435                 440                 445

Arg Arg Ala Gln Phe Ala Glu Lys Glu Leu Glu Gln Leu Glu Leu Arg
450                 455                 460

Gly Ser Lys Val Gln Thr Leu Phe Leu Ser Lys Lys Glu Leu Pro Gly
465                 470                 475                 480

Val Leu Glu Thr Glu Val Thr Tyr Gln Phe Ile Asp Gln Ser Phe Gln
            485                 490                 495

Glu Phe Leu Ala Ala Leu Ser Tyr Leu Leu Glu Asp Gly Gly Val Pro
            500                 505                 510

Arg Thr Ala Ala Gly Gly Val Gly Thr Leu Leu Arg Gly Asp Ala Gln
            515                 520                 525

Pro His Ser His Leu Val Leu Thr Thr Arg Phe Leu Phe Gly Leu Leu
            530                 535                 540

Ser Ala Glu Arg Met Arg Asp Ile Glu Arg His Phe Gly Cys Met Val
545                 550                 555                 560

Ser Glu Arg Val Lys Gln Glu Ala Leu Arg Trp Val Gln Gly Gln Gly
            565                 570                 575

Gln Gly Cys Pro Gly Val Ala Pro Glu Val Thr Gly Ala Lys Gly
            580                 585                 590

Leu Glu Asp Thr Glu Glu Pro Glu Glu Glu Glu Gly Glu Glu Pro
            595                 600                 605

Asn Tyr Pro Leu Glu Leu Leu Tyr Cys Leu Tyr Glu Thr Gln Glu Asp
            610                 615                 620

Ala Phe Val Arg Gln Ala Leu Cys Arg Phe Pro Glu Leu Ala Leu Gln
625                 630                 635                 640

Arg Val Arg Phe Cys Arg Met Asp Val Ala Val Leu Ser Tyr Cys Val
            645                 650                 655

Arg Cys Cys

<210> SEQ ID NO 92
<211> LENGTH: 764
<212> TYPE: PRT
<213> ORGANISM: Homo sapiens

<400> SEQUENCE: 92

Met Ala Gly Gly Ala Trp Gly Arg Leu Ala Cys Tyr Leu Glu Phe Leu
1               5                   10                  15

Lys Lys Glu Glu Leu Lys Glu Phe Gln Leu Leu Leu Ala Asn Lys Ala
            20                  25                  30

His Ser Arg Ser Ser Ser Gly Glu Thr Pro Ala Gln Pro Glu Lys Thr
            35                  40                  45
```

```
Ser Gly Met Glu Val Ala Ser Tyr Leu Val Ala Gln Tyr Gly Glu Gln
 50                  55                  60

Arg Ala Trp Asp Leu Ala Leu His Thr Trp Glu Gln Met Gly Leu Arg
 65                  70                  75                  80

Ser Leu Cys Ala Gln Ala Gln Glu Gly Ala Gly His Ser Pro Ser Phe
                 85                  90                  95

Pro Tyr Ser Pro Ser Glu Pro His Leu Gly Ser Pro Ser Gln Pro Thr
                100                 105                 110

Ser Thr Ala Val Leu Met Pro Trp Ile His Glu Leu Pro Ala Gly Cys
                115                 120                 125

Thr Gln Gly Ser Glu Arg Arg Val Leu Arg Gln Leu Pro Asp Thr Ser
130                 135                 140

Gly Arg Arg Trp Arg Glu Ile Ser Ala Ser Leu Leu Tyr Gln Ala Leu
145                 150                 155                 160

Pro Ser Ser Pro Asp His Glu Ser Pro Ser Gln Glu Ser Pro Asn Ala
                165                 170                 175

Pro Thr Ser Thr Ala Val Leu Gly Ser Trp Gly Ser Pro Pro Gln Pro
                180                 185                 190

Ser Leu Ala Pro Arg Glu Gln Glu Ala Pro Gly Thr Gln Trp Pro Leu
                195                 200                 205

Asp Glu Thr Ser Gly Ile Tyr Tyr Thr Glu Ile Arg Glu Arg Glu Arg
210                 215                 220

Glu Lys Ser Glu Lys Gly Arg Pro Pro Trp Ala Ala Val Val Gly Thr
225                 230                 235                 240

Pro Pro Gln Ala His Thr Ser Leu Gln Pro His His Pro Trp Glu
                245                 250                 255

Pro Ser Val Arg Glu Ser Leu Cys Ser Thr Trp Pro Trp Lys Asn Glu
                260                 265                 270

Asp Phe Asn Gln Lys Phe Thr Gln Leu Leu Leu Gln Arg Pro His
                275                 280                 285

Pro Arg Ser Gln Asp Pro Leu Val Lys Arg Ser Trp Pro Asp Tyr Val
290                 295                 300

Glu Glu Asn Arg Gly His Leu Ile Glu Ile Arg Asp Leu Phe Gly Pro
305                 310                 315                 320

Gly Leu Asp Thr Gln Glu Pro Arg Ile Val Ile Leu Gln Gly Ala Ala
                325                 330                 335

Gly Ile Gly Lys Ser Thr Leu Ala Arg Gln Val Lys Glu Ala Trp Gly
                340                 345                 350

Arg Gly Gln Leu Tyr Gly Asp Arg Phe Gln His Val Phe Tyr Phe Ser
                355                 360                 365

Cys Arg Glu Leu Ala Gln Ser Lys Val Val Ser Leu Ala Glu Leu Ile
370                 375                 380

Gly Lys Asp Gly Thr Ala Thr Pro Ala Pro Ile Arg Gln Ile Leu Ser
385                 390                 395                 400

Arg Pro Glu Arg Leu Leu Phe Ile Leu Asp Gly Val Asp Glu Pro Gly
                405                 410                 415

Trp Val Leu Gln Glu Pro Ser Ser Glu Leu Cys Leu His Trp Ser Gln
                420                 425                 430

Pro Gln Pro Ala Asp Ala Leu Leu Gly Ser Leu Leu Gly Lys Thr Ile
                435                 440                 445

Leu Pro Glu Ala Ser Phe Leu Ile Thr Ala Arg Thr Thr Ala Leu Gln
450                 455                 460

Asn Leu Ile Pro Ser Leu Glu Gln Ala Arg Trp Val Glu Val Leu Gly
```

-continued

```
                465                 470                 475                 480
        Phe Ser Glu Ser Ser Arg Lys Glu Tyr Phe Tyr Arg Tyr Phe Thr Asp
                        485                 490                 495
        Glu Arg Gln Ala Ile Arg Ala Phe Arg Leu Val Lys Ser Asn Lys Glu
                        500                 505                 510
        Leu Trp Ala Leu Cys Leu Val Pro Trp Val Ser Trp Leu Ala Cys Thr
                        515                 520                 525
        Cys Leu Met Gln Gln Met Lys Arg Glu Lys Leu Thr Leu Thr Ser
                        530                 535                 540
        Lys Thr Thr Thr Thr Leu Cys Leu His Tyr Leu Ala Gln Ala Leu Gln
        545                 550                 555                 560
        Ala Gln Pro Leu Gly Pro Gln Leu Arg Asp Leu Cys Ser Leu Ala Ala
                        565                 570                 575
        Glu Gly Ile Trp Gln Lys Lys Thr Leu Phe Ser Pro Asp Asp Leu Arg
                        580                 585                 590
        Lys His Gly Leu Asp Gly Ala Ile Ile Ser Thr Phe Leu Lys Met Gly
                        595                 600                 605
        Ile Leu Gln Glu His Pro Ile Pro Leu Ser Tyr Ser Phe Ile His Leu
                        610                 615                 620
        Cys Phe Gln Glu Phe Phe Ala Ala Met Ser Tyr Val Leu Glu Asp Glu
        625                 630                 635                 640
        Lys Gly Arg Gly Lys His Ser Asn Cys Ile Ile Asp Leu Glu Lys Thr
                        645                 650                 655
        Leu Glu Ala Tyr Gly Ile His Gly Leu Phe Gly Ala Ser Thr Thr Arg
                        660                 665                 670
        Phe Leu Leu Gly Leu Leu Ser Asp Glu Gly Glu Arg Glu Met Glu Asn
                        675                 680                 685
        Ile Phe His Cys Arg Leu Ser Gln Gly Arg Asn Leu Met Gln Trp Val
                        690                 695                 700
        Pro Ser Leu Gln Leu Leu Leu Gln Pro His Ser Leu Glu Ser Leu His
        705                 710                 715                 720
        Cys Leu Tyr Glu Thr Arg Asn Lys Thr Phe Leu Thr Gln Val Met Ala
                        725                 730                 735
        His Phe Glu Glu Met Gly Met Cys Val Glu Thr Asp Met Glu Leu Leu
                        740                 745                 750
        Val Cys Thr Phe Cys Ile Lys Phe Ser Arg His Val
                        755                 760

<210> SEQ ID NO 93
<211> LENGTH: 571
<212> TYPE: PRT
<213> ORGANISM: Mus musculus

<400> SEQUENCE: 93

Met Ala Leu Ala Arg Ala Asn Ser Pro Gln Glu Ala Leu Leu Trp Ala
1               5                   10                  15
Leu Asn Asp Leu Glu Glu Asn Ser Phe Lys Thr Leu Lys Phe His Leu
                20                  25                  30
Arg Asp Val Thr Gln Phe His Leu Ala Arg Gly Glu Leu Glu Ser Leu
                35                  40                  45
Ser Gln Val Asp Leu Ala Ser Lys Leu Ile Ser Met Tyr Gly Ala Gln
                50                  55                  60
Glu Ala Val Arg Val Val Ser Arg Ser Leu Leu Ala Met Asn Leu Met
65                  70                  75                  80
```

-continued

```
Glu Leu Val Asp Tyr Leu Asn Gln Val Cys Leu Asn His Leu Cys Tyr
                85                  90                  95

Ser Asp Tyr Arg Glu Ile Tyr Arg Glu His Val Arg Cys Leu Glu Glu
            100                 105                 110

Arg Gln Asp Trp Gly Val Asn Ser Ser His Asn Lys Leu Leu Leu Met
            115                 120                 125

Ala Thr Ser Ser Gly Gly Arg Arg Ser Pro Ser Cys Ser Asp Leu
130                 135                 140

Glu Gln Glu Leu Asp Pro Val Asp Val Glu Thr Leu Phe Ala Pro Glu
145                 150                 155                 160

Ala Glu Ser Tyr Ser Thr Pro Pro Ile Val Val Met Gln Gly Ser Ala
                165                 170                 175

Gly Thr Gly Lys Thr Thr Leu Val Lys Lys Leu Val Gln Asp Trp Ser
            180                 185                 190

Lys Gly Lys Leu Tyr Pro Gly Gln Phe Asp Tyr Val Phe Tyr Val Ser
            195                 200                 205

Cys Arg Glu Val Val Leu Leu Pro Lys Cys Asp Leu Pro Asn Leu Ile
        210                 215                 220

Cys Trp Cys Cys Gly Asp Asp Gln Ala Pro Val Thr Glu Ile Leu Arg
225                 230                 235                 240

Gln Pro Gly Arg Leu Leu Phe Ile Leu Asp Gly Tyr Asp Glu Leu Gln
                245                 250                 255

Lys Ser Ser Arg Ala Glu Cys Val Leu His Ile Leu Met Arg Arg Arg
            260                 265                 270

Glu Val Pro Cys Ser Leu Leu Ile Thr Thr Arg Pro Pro Ala Leu Gln
            275                 280                 285

Ser Leu Glu Pro Met Leu Gly Glu Arg Arg His Val Leu Val Leu Gly
290                 295                 300

Phe Ser Glu Glu Glu Arg Glu Thr Tyr Phe Ser Ser Cys Phe Thr Asp
305                 310                 315                 320

Lys Glu Gln Leu Lys Asn Ala Leu Glu Phe Val Gln Asn Asn Ala Val
                325                 330                 335

Leu Tyr Lys Ala Cys Gln Val Pro Gly Ile Cys Trp Val Val Cys Ser
            340                 345                 350

Trp Leu Lys Lys Lys Met Ala Arg Gly Gln Glu Val Ser Glu Thr Pro
            355                 360                 365

Ser Asn Ser Thr Asp Ile Phe Thr Ala Tyr Val Ser Thr Phe Leu Pro
370                 375                 380

Thr Asp Gly Asn Gly Asp Ser Ser Glu Leu Thr Arg His Lys Val Leu
385                 390                 395                 400

Lys Ser Leu Cys Ser Leu Ala Ala Glu Gly Met Arg His Gln Arg Leu
                405                 410                 415

Leu Phe Glu Glu Val Leu Arg Lys His Gly Leu Asp Gly Pro Ser
            420                 425                 430

Leu Thr Ala Phe Leu Asn Cys Ile Asp Tyr Arg Ala Gly Leu Gly Ile
        435                 440                 445

Lys Lys Phe Tyr Ser Phe Arg His Ile Ser Phe Gln Glu Phe Tyr
            450                 455                 460

Ala Met Ser Phe Leu Val Lys Glu Asp Gln Ser Gln Gly Glu Ala
465                 470                 475                 480

Thr His Lys Glu Val Ala Lys Leu Val Asp Pro Glu Asn His Glu Glu
                485                 490                 495

Val Thr Leu Ser Leu Gln Phe Leu Phe Asp Met Leu Lys Thr Glu Gly
```

```
                500             505             510
Thr Leu Ser Leu Gly Leu Lys Phe Cys Phe Arg Ile Ala Pro Ser Val
            515                 520                 525
Arg Gln Asp Leu Lys His Phe Lys Glu Gln Ile Glu Ala Ile Lys Tyr
        530                 535                 540
Lys Arg Ser Trp Asp Leu Glu Phe Ser Leu Tyr Asp Ser Lys Ile Lys
545                 550                 555                 560
Lys Leu Thr Gln Gly Ile Gln Met Lys Asp Val
                565                 570

<210> SEQ ID NO 94
<211> LENGTH: 590
<212> TYPE: PRT
<213> ORGANISM: Homo sapiens

<400> SEQUENCE: 94

Met Ala Met Ala Lys Ala Arg Lys Pro Arg Glu Ala Leu Leu Trp Ala
 1               5                  10                  15
Leu Ser Asp Leu Glu Glu Asn Asp Phe Lys Lys Leu Lys Phe Tyr Leu
             20                  25                  30
Arg Asp Met Thr Leu Ser Glu Gly Gln Pro Leu Ala Arg Gly Glu
         35                  40                  45
Leu Glu Gly Leu Ile Pro Val Asp Leu Ala Glu Leu Leu Ile Ser Lys
     50                  55                  60
Tyr Gly Glu Lys Glu Ala Val Lys Val Val Leu Lys Gly Leu Lys Val
 65                  70                  75                  80
Met Asn Leu Leu Glu Leu Val Asp Gln Leu Ser His Ile Cys Leu His
                 85                  90                  95
Asp Tyr Arg Glu Val Tyr Arg Glu His Val Arg Cys Leu Glu Glu Trp
            100                 105                 110
Gln Glu Ala Gly Val Asn Gly Arg Tyr Asn Gln Val Leu Leu Val Ala
        115                 120                 125
Lys Pro Ser Ser Glu Ser Pro Glu Ser Leu Ala Cys Pro Phe Pro Glu
    130                 135                 140
Gln Glu Leu Glu Ser Val Thr Val Glu Ala Leu Phe Asp Ser Gly Glu
145                 150                 155                 160
Lys Pro Ser Leu Ala Pro Ser Leu Val Val Leu Gln Gly Ser Ala Gly
                165                 170                 175
Thr Gly Lys Thr Thr Leu Ala Arg Lys Met Val Leu Asp Trp Ala Thr
            180                 185                 190
Gly Thr Leu Tyr Pro Gly Arg Phe Asp Tyr Val Phe Tyr Val Ser Cys
        195                 200                 205
Lys Glu Val Val Leu Leu Glu Ser Lys Leu Glu Gln Leu Leu Phe
    210                 215                 220
Trp Cys Cys Gly Asp Asn Gln Ala Pro Val Thr Glu Ile Leu Arg Gln
225                 230                 235                 240
Pro Glu Arg Leu Leu Phe Ile Leu Asp Gly Phe Asp Glu Leu Gln Arg
                245                 250                 255
Pro Phe Glu Glu Lys Leu Lys Lys Arg Gly Leu Ser Pro Lys Glu Ser
            260                 265                 270
Leu Leu His Leu Ile Arg Arg His Thr Leu Pro Thr Cys Ser Leu
        275                 280                 285
Leu Ile Thr Thr Arg Pro Leu Ala Leu Arg Asn Leu Glu Pro Leu Leu
    290                 295                 300
```

-continued

```
Lys Gln Ala Arg His Val His Ile Leu Gly Phe Ser Glu Glu Arg
305                 310                 315                 320

Ala Arg Tyr Phe Ser Ser Tyr Phe Thr Asp Glu Lys Gln Ala Asp Arg
            325                 330                 335

Ala Phe Asp Ile Val Gln Lys Asn Asp Ile Leu Tyr Lys Ala Cys Gln
            340                 345                 350

Val Pro Gly Ile Cys Trp Val Val Cys Ser Trp Leu Gln Gly Gln Met
            355                 360                 365

Glu Arg Gly Lys Val Val Leu Glu Thr Pro Arg Asn Ser Thr Asp Ile
370                 375                 380

Phe Met Ala Tyr Val Ser Thr Phe Leu Pro Pro Asp Asp Gly Gly
385                 390                 395                 400

Cys Ser Glu Leu Ser Arg His Arg Val Leu Arg Ser Leu Cys Ser Leu
            405                 410                 415

Ala Ala Glu Gly Ile Gln His Gln Arg Phe Leu Phe Glu Glu Ala Glu
            420                 425                 430

Leu Arg Lys His Asn Leu Asp Gly Pro Arg Leu Ala Ala Phe Leu Ser
435                 440                 445

Ser Asn Asp Tyr Gln Leu Gly Leu Ala Ile Lys Lys Phe Tyr Ser Phe
450                 455                 460

Arg His Ile Ser Phe Gln Asp Phe Phe His Ala Met Ser Tyr Leu Val
465                 470                 475                 480

Lys Glu Asp Gln Ser Arg Leu Gly Lys Glu Ser Arg Arg Glu Val Gln
            485                 490                 495

Arg Leu Leu Glu Val Lys Glu Gln Glu Gly Asn Asp Glu Met Thr Leu
            500                 505                 510

Thr Met Gln Phe Leu Leu Asp Ile Ser Lys Lys Asp Ser Phe Ser Asn
            515                 520                 525

Leu Glu Leu Lys Phe Cys Phe Arg Ile Ser Pro Cys Leu Ala Gln Asp
530                 535                 540

Leu Lys His Phe Lys Glu Gln Met Glu Ser Met Lys His Asn Arg Thr
545                 550                 555                 560

Trp Asp Leu Glu Phe Ser Leu Tyr Glu Ala Lys Ile Lys Asn Leu Val
            565                 570                 575

Lys Gly Ile Gln Met Asn Asn Val Ser Phe Lys Ile Lys His
            580                 585                 590

<210> SEQ ID NO 95
<211> LENGTH: 555
<212> TYPE: PRT
<213> ORGANISM: Homo sapiens

<400> SEQUENCE: 95

Met Ala Glu Ser Asp Ser Thr Asp Phe Asp Leu Leu Trp Tyr Leu Glu
1               5                   10                  15

Asn Leu Ser Asp Lys Glu Phe Gln Ser Phe Lys Lys Tyr Leu Ala Arg
            20                  25                  30

Lys Ile Leu Asp Phe Lys Leu Pro Gln Phe Pro Leu Ile Gln Met Thr
        35                  40                  45

Lys Glu Glu Leu Ala Asn Val Leu Pro Ile Ser Tyr Glu Gly Gln Tyr
    50                  55                  60

Ile Trp Asn Met Leu Phe Ser Ile Phe Ser Met Met Arg Lys Glu Asp
65              70                  75                  80

Leu Cys Arg Lys Ile Ile Gly Arg Asn His Val Phe Tyr Ile Leu
            85                  90                  95
```

```
Gln Leu Ala Tyr Asp Ser Thr Ser Tyr Ser Ala Asn Asn Leu Asn
                100                 105                 110

Val Phe Leu Met Gly Glu Arg Ala Ser Gly Lys Thr Ile Val Ile Asn
            115                 120                 125

Leu Ala Val Leu Arg Trp Ile Lys Gly Glu Met Trp Gln Asn Met Ile
        130                 135                 140

Ser Tyr Val Val His Leu Thr Ala His Glu Ile Asn Gln Met Thr Asn
145                 150                 155                 160

Ser Ser Leu Ala Glu Leu Ile Ala Lys Asp Trp Pro Asp Gly Gln Ala
                165                 170                 175

Pro Ile Ala Asp Ile Leu Ser Asp Pro Lys Lys Leu Leu Phe Ile Leu
            180                 185                 190

Glu Asp Leu Asp Asn Ile Arg Phe Glu Leu Asn Val Asn Glu Ser Ala
        195                 200                 205

Leu Cys Ser Asn Ser Thr Gln Lys Val Pro Ile Pro Val Leu Leu Val
    210                 215                 220

Ser Leu Leu Lys Arg Lys Met Ala Pro Gly Cys Trp Phe Leu Ile Ser
225                 230                 235                 240

Ser Arg Pro Thr Arg Gly Asn Asn Val Lys Thr Phe Leu Lys Glu Val
                245                 250                 255

Asp Cys Cys Thr Thr Leu Gln Leu Ser Asn Gly Lys Arg Glu Ile Tyr
            260                 265                 270

Phe Asn Ser Phe Phe Lys Asp Arg Gln Arg Ala Ser Ala Ala Leu Gln
        275                 280                 285

Leu Val His Glu Asp Glu Ile Leu Val Gly Leu Cys Arg Val Ala Ile
    290                 295                 300

Leu Cys Trp Ile Thr Cys Thr Val Leu Lys Arg Gln Met Asp Lys Gly
305                 310                 315                 320

Arg Asp Phe Gln Leu Cys Cys Gln Thr Pro Thr Asp Leu His Ala His
                325                 330                 335

Phe Leu Ala Asp Ala Leu Thr Ser Glu Ala Gly Leu Thr Ala Asn Gln
            340                 345                 350

Tyr His Leu Gly Leu Leu Lys Arg Leu Cys Leu Leu Ala Ala Gly Gly
        355                 360                 365

Leu Phe Leu Ser Thr Leu Asn Phe Ser Gly Glu Asp Leu Arg Cys Val
    370                 375                 380

Gly Phe Thr Glu Ala Asp Val Ser Val Leu Gln Ala Ala Asn Ile Leu
385                 390                 395                 400

Leu Pro Ser Asn Thr His Lys Asp Arg Tyr Lys Phe Ile His Leu Asn
                405                 410                 415

Val Gln Glu Phe Cys Thr Ala Ile Ala Phe Leu Met Ala Val Pro Asn
            420                 425                 430

Tyr Leu Ile Pro Ser Gly Ser Arg Glu Tyr Lys Glu Lys Arg Glu Gln
        435                 440                 445

Tyr Ser Asp Phe Asn Gln Val Phe Thr Phe Ile Phe Gly Leu Leu Asn
    450                 455                 460

Ala Asn Arg Arg Lys Ile Leu Glu Thr Ser Phe Gly Tyr Gln Leu Pro
465                 470                 475                 480

Met Val Asp Ser Phe Lys Trp Tyr Ser Val Gly Tyr Met Lys His Leu
                485                 490                 495

Asp Arg Asp Pro Glu Lys Leu Thr His His Met Pro Leu Phe Tyr Cys
            500                 505                 510
```

```
Leu Tyr Glu Asn Arg Glu Glu Phe Val Lys Thr Ile Val Asp Ala
            515                 520                 525

Leu Met Glu Val Thr Val Tyr Leu Gln Ser Asp Lys Asp Met Met Val
        530                 535                 540

Ser Leu Tyr Cys Leu Asp Tyr Cys Cys His Leu
545                 550                 555

<210> SEQ ID NO 96
<211> LENGTH: 682
<212> TYPE: PRT
<213> ORGANISM: Homo sapiens

<400> SEQUENCE: 96

Met Glu Gly Asp Lys Ser Leu Thr Phe Ser Ser Tyr Gly Leu Gln Trp
1               5                   10                  15

Cys Leu Tyr Glu Leu Asp Lys Glu Glu Phe Gln Thr Phe Lys Glu Leu
            20                  25                  30

Leu Lys Lys Lys Ser Ser Glu Ser Thr Thr Cys Ser Ile Pro Gln Phe
        35                  40                  45

Glu Ile Glu Asn Ala Asn Val Glu Cys Leu Ala Leu Leu Leu His Glu
50                  55                  60

Tyr Tyr Gly Ala Ser Leu Ala Trp Ala Thr Ser Ile Ser Ile Phe Glu
65                  70                  75                  80

Asn Met Asn Leu Arg Thr Leu Ser Glu Lys Ala Arg Asp Asp Met Lys
                85                  90                  95

Arg His Ser Pro Glu Asp Pro Glu Ala Thr Met Thr Asp Gln Gly Pro
            100                 105                 110

Ser Lys Glu Lys Val Pro Gly Ile Ser Gln Ala Val Gln Gln Asp Ser
        115                 120                 125

Ala Thr Ala Ala Glu Thr Lys Glu Gln Glu Ile Ser Gln Ala Met Glu
130                 135                 140

Gln Glu Gly Ala Thr Ala Ala Glu Thr Glu Glu Gln Glu Ile Ser Gln
145                 150                 155                 160

Ala Met Glu Gln Glu Gly Ala Thr Ala Ala Glu Thr Glu Glu Gln Gly
                165                 170                 175

His Gly Gly Asp Thr Trp Asp Tyr Lys Ser His Val Met Thr Lys Phe
            180                 185                 190

Ala Glu Glu Glu Asp Val Arg Arg Ser Phe Glu Asn Thr Ala Ala Asp
        195                 200                 205

Trp Pro Glu Met Gln Thr Leu Ala Gly Ala Phe Asp Ser Asp Arg Trp
210                 215                 220

Gly Phe Arg Pro Arg Thr Val Val Leu His Gly Lys Ser Gly Ile Gly
225                 230                 235                 240

Lys Ser Ala Leu Ala Arg Arg Ile Val Leu Cys Trp Ala Gln Gly Gly
                245                 250                 255

Leu Tyr Gln Gly Met Phe Ser Tyr Val Phe Leu Pro Val Arg Glu
            260                 265                 270

Met Gln Arg Lys Lys Glu Ser Ser Val Thr Glu Phe Ile Ser Arg Glu
        275                 280                 285

Trp Pro Asp Ser Gln Ala Pro Val Thr Glu Ile Met Ser Arg Pro Glu
290                 295                 300

Arg Leu Leu Phe Ile Ile Asp Gly Phe Asp Glu Leu Gly Ser Val Leu
305                 310                 315                 320

Asn Asn Asp Thr Lys Leu Cys Lys Asp Trp Ala Glu Lys Gln Pro Pro
                325                 330                 335
```

```
Phe Thr Leu Ile Arg Ser Leu Leu Arg Lys Val Leu Pro Glu Ser
            340                 345                 350

Phe Leu Ile Val Thr Val Arg Asp Val Gly Thr Glu Lys Leu Lys Ser
            355                 360                 365

Glu Val Val Ser Pro Arg Tyr Leu Leu Val Arg Gly Ile Ser Gly Glu
        370                 375                 380

Gln Arg Ile His Leu Leu Glu Arg Gly Ile Gly Glu His Gln Lys
385                 390                 395                 400

Thr Gln Gly Leu Arg Ala Ile Met Asn Asn Arg Glu Leu Leu Asp Gln
                405                 410                 415

Cys Gln Val Pro Ala Val Gly Ser Leu Ile Cys Val Ala Leu Gln Leu
            420                 425                 430

Gln Asp Val Val Gly Glu Ser Val Ala Pro Phe Asn Gln Thr Leu Thr
        435                 440                 445

Gly Leu His Ala Ala Phe Val Phe His Gln Leu Thr Pro Arg Gly Val
    450                 455                 460

Val Arg Arg Cys Leu Asn Leu Glu Glu Arg Val Val Leu Lys Arg Phe
465                 470                 475                 480

Cys Arg Met Ala Val Glu Gly Val Trp Asn Arg Lys Ser Val Phe Asp
                485                 490                 495

Gly Asp Asp Leu Met Val Gln Gly Leu Gly Glu Ser Glu Leu Arg Ala
            500                 505                 510

Leu Phe His Met Asn Ile Leu Leu Pro Asp Ser His Cys Glu Glu Tyr
        515                 520                 525

Tyr Thr Phe Phe His Leu Ser Leu Gln Asp Phe Cys Ala Ala Leu Tyr
    530                 535                 540

Tyr Val Leu Glu Gly Leu Gly Ile Glu Pro Ala Leu Cys Pro Leu Tyr
545                 550                 555                 560

Val Glu Lys Thr Lys Arg Ser Met Glu Leu Lys Gln Ala Gly Phe His
                565                 570                 575

Ile His Ser Leu Trp Met Lys Arg Phe Leu Phe Gly Leu Val Ser Glu
            580                 585                 590

Asp Val Arg Arg Pro Leu Glu Val Leu Leu Gly Cys Pro Val Pro Leu
        595                 600                 605

Gly Val Lys Gln Lys Leu Leu His Trp Val Ser Leu Leu Gly Gln Gln
    610                 615                 620

Pro Asn Ala Thr Thr Pro Gly Asp Thr Leu Asp Ala Phe His Cys Leu
625                 630                 635                 640

Phe Glu Thr Gln Asp Lys Glu Phe Val Arg Leu Ala Leu Asn Ser Phe
                645                 650                 655

Gln Glu Val Trp Leu Pro Ile Asn Gln Asn Leu Asp Leu Ile Ala Ser
            660                 665                 670

Ser Phe Cys Leu Gln His Cys Pro Tyr Leu
        675                 680

<210> SEQ ID NO 97
<211> LENGTH: 598
<212> TYPE: PRT
<213> ORGANISM: Mus musculus

<400> SEQUENCE: 97

Phe Cys Leu Thr Leu Thr Pro Ala His Leu Ala Asp Phe Gly Phe Ile
1               5                   10                  15

Trp Tyr Trp Lys Glu Leu Asn Lys Ile Glu Phe Met Tyr Phe Lys Glu
```

-continued

```
                20                  25                  30
Leu Leu Ile His Glu Ile Leu Gln Met Gly Leu Lys Gln Ile Ser Trp
            35                  40                  45

Thr Glu Val Lys Glu Ala Ser Arg Glu Asp Leu Ala Ile Leu Leu Val
 50                  55                  60

Lys His Cys Asp Gly Asn Gln Ala Trp Asp Thr Thr Phe Arg Val Phe
 65                  70                  75                  80

Gln Met Ile Gly Arg Asn Val Ile Thr Asn Arg Ala Thr Gly Glu Ile
                 85                  90                  95

Ala Ala His Ser Thr Ile Tyr Arg Ala His Leu Lys Glu Lys Leu Thr
            100                 105                 110

His Asp Cys Ser Arg Lys Phe Asn Ile Ser Ile Gln Asn Phe Phe Gln
            115                 120                 125

Asp Glu Tyr Asp His Leu Glu Asn Leu Leu Val Pro Asn Gly Thr Glu
            130                 135                 140

Asn Asn Pro Lys Met Val Val Leu Gln Gly Val Ala Gly Ile Gly Lys
145                 150                 155                 160

Thr Ile Leu Leu Lys Asn Leu Met Ile Val Trp Ser Glu Gly Leu Val
                165                 170                 175

Phe Gln Asn Lys Phe Ser Tyr Ile Phe Tyr Phe Cys Cys His Asp Val
            180                 185                 190

Lys Gln Leu Gln Thr Ala Ser Leu Ala Asp Leu Ile Ser Arg Glu Trp
            195                 200                 205

Pro Ser Pro Ser Ala Pro Met Glu Glu Ile Leu Ser Gln Pro Glu Lys
            210                 215                 220

Leu Leu Phe Ile Ile Asp Ser Leu Glu Gly Met Glu Trp Asn Val Thr
225                 230                 235                 240

Gln Gln Asp Ser Gln Leu Cys Tyr Asn Cys Met Glu Lys Gln Pro Val
                245                 250                 255

Asn Val Leu Leu Ser Ser Leu Leu Arg Lys Lys Ile Leu Pro Glu Ser
            260                 265                 270

Ser Leu Leu Ile Ser Thr Ser Cys Glu Thr Phe Lys Asp Leu Lys Asp
            275                 280                 285

Trp Ile Glu Tyr Thr Asn Val Arg Thr Ile Thr Gly Phe Lys Glu Asn
            290                 295                 300

Asn Ile Asn Met Cys Phe His Ser Leu Phe Gln Asp Arg Asn Ile Ala
305                 310                 315                 320

Gln Glu Ala Phe Ser Leu Ile Arg Glu Asn Gln Leu Phe Thr Val
            325                 330                 335

Cys Gln Ala Pro Val Val Cys Tyr Met Val Ala Thr Cys Leu Lys Asn
            340                 345                 350

Glu Ile Glu Ser Gly Lys Asp Pro Val Ser Ile Cys Arg Arg Thr Thr
            355                 360                 365

Ser Leu Tyr Thr Thr His Ile Leu Asn Leu Phe Ile Pro His Asn Ala
            370                 375                 380

Gln Asn Pro Ser Asn Ser Glu Asp Leu Leu Asp Asn Leu Cys Phe
385                 390                 395                 400

Leu Ala Val Glu Gly Met Trp Thr Asp Ile Ser Val Phe Asn Glu Glu
                405                 410                 415

Ala Leu Arg Arg Asn Gly Ile Met Asp Ser Asp Ile Pro Thr Leu Leu
            420                 425                 430

Asp Ile Gly Ile Leu Glu Gln Ser Arg Glu Ser Glu Asn Ser Tyr Ile
            435                 440                 445
```

```
Phe Leu His Pro Ser Val Gln Glu Phe Cys Ala Ala Met Phe Tyr Leu
    450                 455                 460

Leu His Ser Glu Met Asp His Ser Cys Gln Gly Val Tyr Phe Ile Glu
465                 470                 475                 480

Thr Phe Leu Phe Thr Phe Leu Asn Lys Ile Lys Lys Gln Trp Val Phe
                485                 490                 495

Leu Gly Cys Phe Phe Gly Leu Leu His Glu Thr Glu Gln Glu Lys
            500                 505                 510

Leu Glu Ala Phe Phe Gly Tyr His Leu Ser Lys Glu Leu Arg Arg Gln
            515                 520                 525

Leu Phe Leu Trp Leu Glu Leu Leu Asp Thr Leu His Pro Asp Val
    530                 535                 540

Lys Lys Ile Asn Thr Met Lys Phe Phe Tyr Cys Leu Phe Glu Met Glu
545                 550                 555                 560

Glu Glu Val Phe Val Gln Ser Ala Met Asn Cys Arg Glu Gln Ile Asp
                565                 570                 575

Val Val Val Lys Gly Tyr Ser Asp Phe Ile Val Ala Ala Tyr Cys Leu
                580                 585                 590

Ser His Gly Ser Ala Leu
        595

<210> SEQ ID NO 98
<211> LENGTH: 628
<212> TYPE: PRT
<213> ORGANISM: Homo sapiens

<400> SEQUENCE: 98

Met Ala Asp Ser Ser Ser Ser Phe Phe Pro Asp Phe Gly Leu Leu
1               5                   10                  15

Leu Tyr Leu Glu Glu Leu Asn Lys Glu Glu Leu Asn Thr Phe Lys Leu
                20                  25                  30

Phe Leu Lys Glu Thr Met Glu Pro Glu His Gly Leu Thr Pro Trp Asn
            35                  40                  45

Glu Val Lys Lys Ala Arg Arg Glu Asp Leu Ala Asn Leu Met Lys Lys
    50                  55                  60

Tyr Tyr Pro Gly Glu Lys Ala Trp Ser Val Ser Leu Lys Ile Phe Gly
65                  70                  75                  80

Lys Met Asn Leu Lys Asp Leu Cys Glu Arg Ala Lys Glu Glu Ile Asn
                85                  90                  95

Trp Ser Ala Gln Thr Ile Gly Pro Asp Asp Ala Lys Ala Gly Glu Thr
            100                 105                 110

Gln Glu Asp Gln Glu Ala Val Leu Gly Asp Gly Thr Gly Tyr Arg Asn
        115                 120                 125

Arg Ile Lys Glu Lys Phe Cys Ile Thr Trp Asp Lys Lys Ser Leu Ala
    130                 135                 140

Gly Lys Pro Glu Asp Phe His His Gly Ile Ala Glu Lys Asp Arg Lys
145                 150                 155                 160

Leu Leu Glu His Leu Phe Asp Val Asp Val Lys Thr Gly Ala Gln Pro
                165                 170                 175

Gln Ile Val Val Leu Gln Gly Ala Ala Gly Val Gly Lys Thr Thr Leu
            180                 185                 190

Val Arg Lys Ala Met Leu Asp Trp Ala Glu Gly Ser Leu Tyr Gln Gln
        195                 200                 205

Arg Phe Lys Tyr Val Phe Tyr Leu Asn Gly Arg Glu Ile Asn Gln Leu
```

-continued

```
                210                 215                 220
Lys Glu Arg Ser Phe Ala Gln Leu Ile Ser Lys Asp Trp Pro Ser Thr
225                 230                 235                 240

Glu Gly Pro Ile Glu Ile Met Tyr Gln Pro Ser Ser Leu Leu Phe
                245                 250                 255

Ile Ile Asp Ser Phe Asp Glu Leu Asn Phe Ala Phe Glu Glu Pro Glu
                260                 265                 270

Phe Ala Leu Cys Glu Asp Trp Thr Gln Glu His Pro Val Ser Phe Leu
                275                 280                 285

Met Ser Ser Leu Leu Arg Lys Val Met Leu Pro Glu Ala Ser Leu Leu
                290                 295                 300

Val Thr Thr Arg Leu Thr Thr Ser Lys Arg Leu Lys Gln Leu Leu Lys
305                 310                 315                 320

Asn His His Tyr Val Glu Leu Leu Gly Met Ser Glu Asp Ala Arg Glu
                325                 330                 335

Glu Tyr Ile Tyr Gln Phe Phe Glu Asp Lys Arg Trp Ala Met Lys Val
                340                 345                 350

Phe Ser Ser Leu Lys Ser Asn Glu Met Leu Phe Ser Met Cys Gln Val
                355                 360                 365

Pro Leu Val Cys Trp Ala Ala Cys Thr Cys Leu Lys Gln Gln Met Glu
                370                 375                 380

Lys Gly Gly Asp Val Thr Leu Thr Cys Gln Thr Thr Thr Ala Leu Phe
385                 390                 395                 400

Thr Cys Tyr Ile Ser Ser Leu Phe Thr Pro Val Asp Gly Gly Ser Pro
                405                 410                 415

Ser Leu Pro Asn Gln Ala Gln Leu Arg Arg Leu Cys Gln Val Ala Ala
                420                 425                 430

Lys Gly Ile Trp Thr Met Thr Tyr Val Phe Tyr Arg Glu Asn Leu Arg
                435                 440                 445

Arg Leu Gly Leu Thr Gln Ser Asp Val Ser Ser Phe Met Asp Ser Asn
                450                 455                 460

Ile Ile Gln Lys Asp Ala Glu Tyr Glu Asn Cys Tyr Val Phe Thr His
465                 470                 475                 480

Leu His Val Gln Glu Phe Phe Ala Ala Met Phe Tyr Met Leu Lys Gly
                485                 490                 495

Ser Trp Glu Ala Gly Asn Pro Ser Cys Gln Pro Phe Glu Asp Leu Lys
                500                 505                 510

Ser Leu Leu Gln Ser Thr Ser Tyr Lys Asp Pro His Leu Thr Gln Met
                515                 520                 525

Lys Cys Phe Leu Phe Gly Leu Leu Asn Glu Asp Arg Val Lys Gln Leu
                530                 535                 540

Glu Arg Thr Phe Asn Cys Lys Met Ser Leu Lys Ile Lys Ser Lys Leu
545                 550                 555                 560

Leu Gln Cys Met Glu Val Leu Gly Asn Ser Asp Tyr Ser Pro Ser Gln
                565                 570                 575

Leu Gly Phe Leu Glu Leu Phe His Cys Leu Tyr Glu Thr Gln Asp Lys
                580                 585                 590

Ala Phe Ile Ser Gln Ala Met Arg Cys Phe Pro Lys Val Ala Ile Asn
                595                 600                 605

Ile Cys Glu Lys Ile His Leu Leu Val Ser Ser Phe Cys Leu Lys His
                610                 615                 620

Cys Arg Cys Leu
625
```

<210> SEQ ID NO 99
<211> LENGTH: 599
<212> TYPE: PRT
<213> ORGANISM: Homo sapiens

<400> SEQUENCE: 99

Met Ala Ala Ser Phe Phe Ser Asp Phe Gly Leu Met Trp Tyr Leu Glu
1               5                   10                  15

Glu Leu Lys Lys Glu Glu Phe Arg Lys Phe Lys Glu His Leu Lys Gln
            20                  25                  30

Met Thr Leu Gln Leu Glu Leu Lys Gln Ile Pro Trp Thr Glu Val Lys
        35                  40                  45

Lys Ala Ser Arg Glu Glu Leu Ala Asn Leu Leu Ile Lys His Tyr Glu
    50                  55                  60

Glu Gln Gln Ala Trp Asn Ile Thr Leu Arg Ile Phe Gln Lys Met Asp
65                  70                  75                  80

Arg Lys Asp Leu Cys Met Lys Val Met Arg Glu Arg Thr Gly Tyr Thr
                85                  90                  95

Lys Thr Tyr Gln Ala His Ala Lys Gln Lys Phe Ser Arg Leu Trp Ser
            100                 105                 110

Ser Lys Ser Val Thr Glu Ile His Leu Tyr Phe Glu Glu Glu Val Lys
        115                 120                 125

Gln Glu Glu Cys Asp His Leu Asp Arg Leu Phe Ala Pro Lys Glu Thr
    130                 135                 140

Gly Lys Gln Pro Arg Thr Val Ile Ile Gln Gly Pro Gln Gly Ile Gly
145                 150                 155                 160

Lys Thr Thr Leu Leu Met Lys Leu Met Met Ala Trp Ser Asp Asn Lys
                165                 170                 175

Ile Phe Arg Asp Arg Phe Leu Tyr Thr Phe Tyr Phe Cys Cys Arg Glu
            180                 185                 190

Leu Arg Glu Leu Pro Pro Thr Ser Leu Ala Asp Leu Ile Ser Arg Glu
        195                 200                 205

Trp Pro Asp Pro Ala Ala Pro Ile Thr Glu Ile Val Ser Gln Pro Glu
    210                 215                 220

Arg Leu Leu Phe Val Ile Asp Ser Phe Glu Glu Leu Gln Gly Gly Leu
225                 230                 235                 240

Asn Glu Pro Asp Ser Asp Leu Cys Gly Asp Leu Met Glu Lys Arg Pro
                245                 250                 255

Val Gln Val Leu Leu Ser Ser Leu Leu Arg Lys Lys Met Leu Pro Glu
            260                 265                 270

Ala Ser Leu Leu Ile Ala Ile Lys Pro Val Cys Pro Lys Glu Leu Arg
        275                 280                 285

Asp Gln Val Thr Ile Ser Glu Ile Tyr Gln Pro Arg Gly Phe Asn Glu
    290                 295                 300

Ser Asp Arg Leu Val Tyr Phe Cys Cys Phe Phe Lys Asp Pro Lys Arg
305                 310                 315                 320

Ala Met Glu Ala Phe Asn Leu Val Arg Glu Ser Glu Gln Leu Phe Ser
                325                 330                 335

Ile Cys Gln Ile Pro Leu Leu Cys Trp Ile Leu Cys Thr Ser Leu Lys
            340                 345                 350

Gln Glu Met Gln Lys Gly Lys Asp Leu Ala Leu Thr Cys Gln Ser Thr
        355                 360                 365

Thr Ser Val Tyr Ser Ser Phe Val Phe Asn Leu Phe Thr Pro Glu Gly

```
                370                 375                 380
Ala Glu Gly Pro Thr Pro Gln Thr Gln His Gln Leu Lys Ala Leu Cys
385                 390                 395                 400

Ser Leu Ala Ala Glu Gly Met Trp Thr Asp Thr Phe Glu Phe Cys Glu
                405                 410                 415

Asp Asp Leu Arg Arg Asn Gly Val Val Asp Ala Asp Ile Pro Ala Leu
            420                 425                 430

Leu Gly Thr Lys Ile Leu Leu Lys Tyr Gly Glu Arg Glu Ser Ser Tyr
        435                 440                 445

Val Phe Leu His Val Cys Ile Gln Glu Phe Cys Ala Ala Leu Phe Tyr
450                 455                 460

Leu Leu Lys Ser His Leu Asp His Pro His Pro Ala Val Arg Cys Val
465                 470                 475                 480

Gln Glu Leu Leu Val Ala Asn Phe Glu Lys Ala Arg Arg Ala His Trp
                485                 490                 495

Ile Phe Leu Gly Cys Phe Leu Thr Gly Leu Leu Asn Lys Lys Glu Gln
            500                 505                 510

Glu Lys Leu Asp Ala Phe Phe Gly Phe Gln Leu Ser Gln Glu Ile Lys
        515                 520                 525

Gln Gln Ile His Gln Cys Leu Lys Ser Leu Gly Glu Arg Gly Asn Pro
    530                 535                 540

Gln Gly Gln Val Asp Ser Leu Ala Ile Phe Tyr Cys Leu Phe Glu Met
545                 550                 555                 560

Gln Asp Pro Ala Phe Val Lys Gln Ala Val Asn Leu Leu Gln Glu Ala
                565                 570                 575

Asn Phe His Ile Ile Asp Asn Val Asp Leu Val Val Ser Ala Tyr Cys
            580                 585                 590

Leu Lys Tyr Cys Ser Ser Leu
        595

<210> SEQ ID NO 100
<211> LENGTH: 629
<212> TYPE: PRT
<213> ORGANISM: Homo sapiens

<400> SEQUENCE: 100

Trp Thr Phe Ser Cys Tyr Pro Gly Ser Pro Cys Glu Asn Gly Val Met
  1               5                  10                  15

Leu Tyr Met Arg Asn Val Ser His Glu Glu Leu Gln Arg Phe Lys Gln
                20                  25                  30

Leu Leu Leu Thr Glu Leu Ser Thr Gly Thr Met Pro Ile Thr Trp Asp
            35                  40                  45

Gln Val Glu Thr Ala Ser Trp Ala Glu Val Val His Leu Leu Ile Glu
    50                  55                  60

Arg Phe Pro Gly Arg Arg Ala Trp Asp Val Thr Ser Asn Ile Phe Ala
65                  70                  75                  80

Ile Met Asn Cys Asp Lys Met Cys Val Val Arg Arg Glu Ile Asn
                85                  90                  95

Ala Ile Leu Pro Thr Leu Glu Pro Glu Asp Leu Asn Val Gly Glu Thr
            100                 105                 110

Gln Val Asn Leu Glu Glu Gly Glu Ser Gly Lys Ile Arg Arg Tyr Lys
        115                 120                 125

Ser Asn Val Met Glu Lys Phe Phe Pro Ile Trp Asp Ile Thr Thr Trp
    130                 135                 140
```

-continued

```
Pro Gly Asn Gln Arg Asp Phe Phe Tyr Gln Gly Val His Arg His Glu
145                 150                 155                 160

Glu Tyr Leu Pro Cys Leu Leu Leu Pro Lys Arg Pro Gln Gly Arg Gln
                165                 170                 175

Pro Lys Thr Val Ala Ile Gln Gly Ala Pro Gly Ile Gly Lys Thr Ile
            180                 185                 190

Leu Ala Lys Lys Val Met Phe Glu Trp Ala Arg Asn Lys Phe Tyr Ala
        195                 200                 205

His Lys Arg Trp Cys Ala Phe Tyr Phe His Cys Gln Glu Val Asn Gln
    210                 215                 220

Thr Thr Asp Gln Ser Phe Ser Glu Leu Ile Glu Gln Lys Trp Pro Gly
225                 230                 235                 240

Ser Gln Asp Leu Val Ser Lys Ile Met Ser Lys Pro Asp Gln Leu Leu
                245                 250                 255

Leu Leu Leu Asp Gly Phe Glu Glu Leu Thr Ser Thr Leu Ile Asp Arg
            260                 265                 270

Leu Glu Asp Leu Ser Glu Asp Trp Arg Gln Lys Leu Pro Gly Ser Val
        275                 280                 285

Leu Leu Ser Ser Leu Leu Ser Lys Thr Met Leu Pro Glu Ala Thr Leu
    290                 295                 300

Leu Ile Met Ile Arg Phe Thr Ser Trp Gln Thr Cys Lys Pro Leu Leu
305                 310                 315                 320

Lys Cys Pro Ser Leu Val Thr Leu Pro Gly Phe Asn Thr Met Glu Lys
                325                 330                 335

Ile Lys Tyr Phe Gln Met Tyr Phe Gly His Thr Glu Glu Gly Asp Gln
            340                 345                 350

Val Leu Ser Phe Ala Met Glu Asn Thr Ile Leu Phe Ser Met Cys Arg
        355                 360                 365

Val Pro Val Val Cys Trp Met Val Cys Ser Gly Leu Lys Gln Gln Met
    370                 375                 380

Glu Arg Gly Asn Asn Leu Thr Gln Ser Cys Pro Asn Ala Thr Ser Val
385                 390                 395                 400

Phe Val Arg Tyr Ile Ser Ser Leu Phe Pro Thr Arg Ala Glu Asn Phe
                405                 410                 415

Ser Arg Lys Ile His Gln Ala Gln Leu Glu Gly Leu Cys His Leu Ala
            420                 425                 430

Ala Asp Ser Met Trp His Arg Lys Trp Val Leu Gly Lys Glu Asp Leu
        435                 440                 445

Glu Glu Ala Lys Leu Asp Gln Thr Gly Val Thr Ala Phe Leu Gly Met
    450                 455                 460

Ser Ile Leu Arg Arg Ile Ala Gly Glu Glu Asp His Tyr Val Phe Thr
465                 470                 475                 480

Leu Val Thr Phe Gln Glu Phe Ala Ala Leu Phe Tyr Val Leu Cys
                485                 490                 495

Phe Pro Gln Arg Leu Lys Asn Phe His Val Leu Ser His Val Asn Ile
            500                 505                 510

Gln Arg Leu Ile Ala Ser Pro Arg Gly Ser Lys Ser Tyr Leu Ser His
        515                 520                 525

Met Gly Leu Phe Leu Phe Gly Phe Leu Asn Glu Ala Cys Ala Ser Ala
    530                 535                 540

Val Glu Gln Ser Phe Gln Cys Lys Val Ser Phe Gly Asn Lys Arg Lys
545                 550                 555                 560

Leu Leu Lys Val Ile Pro Leu Leu His Lys Cys Asp Pro Pro Ser Pro
```

```
                    565                 570                 575
Gly Ser Gly Val Pro Gln Leu Phe Tyr Cys Leu His Glu Ile Arg Glu
            580                 585                 590

Glu Ala Phe Val Ser Gln Ala Leu Asn Asp Tyr His Lys Val Val Leu
            595                 600                 605

Arg Ile Gly Asn Asn Lys Glu Val Gln Val Ser Ala Phe Cys Leu Lys
            610                 615                 620

Arg Cys Gln Tyr Leu
625

<210> SEQ ID NO 101
<211> LENGTH: 662
<212> TYPE: PRT
<213> ORGANISM: Homo sapiens

<400> SEQUENCE: 101

Met Tyr Glu Phe Tyr Ile His Lys Gly Tyr Asp Asp Val Ser Ser Asp
 1               5                  10                  15

Asn Ser Arg Glu Lys Ile Lys Gly Glu Pro Ser Glu Cys Glu Leu Gly
            20                  25                  30

His Phe Pro Arg Ile Pro Trp Ala Asn Leu Arg Ala Ala Asp Pro Leu
        35                  40                  45

Asn Leu Ser Phe Leu Leu Asp Glu His Phe Pro Lys Gly Gln Ala Trp
50                  55                  60

Lys Val Val Leu Gly Ile Phe Gln Thr Met Asn Leu Thr Ser Leu Cys
65                  70                  75                  80

Glu Lys Val Arg Ala Glu Met Lys Glu Asn Val Gln Thr Gln Glu Leu
                85                  90                  95

Gln Asp Pro Thr Gln Glu Asp Leu Glu Met Leu Glu Ala Ala Ala Gly
            100                 105                 110

Asn Met Gln Thr Gln Gly Cys Gln Asp Pro Asn Gln Glu Glu Leu Asp
        115                 120                 125

Glu Leu Glu Glu Glu Thr Gly Asn Val Gln Ala Gln Gly Cys Gln Asp
130                 135                 140

Pro Asn Gln Glu Glu Pro Glu Met Leu Glu Glu Ala Asp His Arg Arg
145                 150                 155                 160

Lys Tyr Arg Glu Asn Met Lys Ala Glu Leu Leu Glu Thr Trp Asp Asn
                165                 170                 175

Ile Ser Trp Pro Lys Asp His Val Tyr Ile Arg Asn Thr Ser Lys Asp
            180                 185                 190

Glu His Glu Glu Leu Gln Arg Leu Leu Asp Pro Asn Arg Thr Arg Ala
        195                 200                 205

Gln Ala Gln Thr Ile Val Leu Val Gly Arg Ala Gly Val Gly Lys Thr
    210                 215                 220

Thr Leu Ala Met Arg Ala Met Leu His Trp Ala Asn Gly Val Leu Phe
225                 230                 235                 240

Gln Gln Arg Phe Ser Tyr Val Phe Tyr Leu Ser Cys His Lys Ile Arg
                245                 250                 255

Tyr Met Lys Glu Thr Thr Phe Ala Glu Leu Ile Ser Leu Asp Trp Pro
            260                 265                 270

Asp Phe Asp Ala Pro Ile Glu Glu Phe Met Ser Gln Pro Glu Lys Leu
        275                 280                 285

Leu Phe Ile Ile Asp Gly Phe Glu Glu Ile Ile Ser Glu Ser Arg
    290                 295                 300
```

```
Ser Glu Ser Leu Asp Asp Gly Ser Pro Cys Thr Asp Trp Tyr Gln Glu
305                 310                 315                 320

Leu Pro Val Thr Lys Ile Leu His Ser Leu Leu Lys Lys Glu Leu Val
            325                 330                 335

Pro Leu Ala Thr Leu Leu Ile Thr Ile Lys Thr Trp Phe Val Arg Asp
        340                 345                 350

Leu Lys Ala Ser Leu Val Asn Pro Cys Phe Val Gln Ile Thr Gly Phe
    355                 360                 365

Thr Gly Asp Asp Leu Arg Val Tyr Phe Met Arg His Phe Asp Asp Ser
370                 375                 380

Ser Glu Val Glu Lys Ile Leu Gln Gln Leu Arg Lys Asn Glu Thr Leu
385                 390                 395                 400

Phe His Ser Cys Ser Ala Pro Met Val Cys Trp Thr Val Cys Ser Cys
                405                 410                 415

Leu Lys Gln Pro Lys Val Arg Tyr Tyr Asp Leu Gln Ser Ile Thr Gln
            420                 425                 430

Thr Thr Thr Ser Leu Tyr Ala Tyr Phe Phe Ser Asn Leu Phe Ser Thr
        435                 440                 445

Ala Glu Val Asp Leu Ala Asp Asp Ser Trp Pro Gly Gln Trp Arg Ala
    450                 455                 460

Leu Cys Ser Leu Ala Ile Glu Gly Leu Trp Ser Met Asn Phe Thr Phe
465                 470                 475                 480

Asn Lys Glu Asp Thr Glu Ile Glu Gly Leu Glu Val Pro Phe Ile Asp
                485                 490                 495

Ser Leu Tyr Glu Phe Asn Ile Leu Gln Lys Ile Asn Asp Cys Gly Gly
            500                 505                 510

Cys Thr Thr Phe Thr His Leu Ser Phe Gln Glu Phe Ala Ala Met
        515                 520                 525

Ser Phe Val Leu Glu Glu Pro Arg Glu Phe Pro Pro His Ser Thr Lys
530                 535                 540

Pro Gln Glu Met Lys Met Leu Leu Gln His Val Leu Leu Asp Lys Glu
545                 550                 555                 560

Ala Tyr Trp Thr Pro Val Val Leu Phe Phe Gly Leu Leu Asn Lys
            565                 570                 575

Asn Ile Ala Arg Glu Leu Glu Asp Thr Leu His Cys Lys Ile Ser Pro
            580                 585                 590

Arg Val Met Glu Glu Leu Leu Lys Trp Gly Glu Glu Leu Gly Lys Ala
            595                 600                 605

Glu Ser Ala Ser Leu Gln Phe His Ile Leu Arg Leu Phe His Cys Leu
    610                 615                 620

His Glu Ser Gln Glu Glu Asp Phe Thr Lys Lys Met Leu Gly Arg Ile
625                 630                 635                 640

Phe Glu Val Asp Leu Asn Ile Leu Glu Asp Glu Glu Leu Gln Ala Leu
                645                 650                 655

Lys His Cys Lys Arg Leu
            660

<210> SEQ ID NO 102
<211> LENGTH: 322
<212> TYPE: PRT
<213> ORGANISM: ascidian

<400> SEQUENCE: 102

Thr Val Trp Val Val Gly Pro Pro Gly Val Gly Lys Thr Leu Leu
1               5                   10                  15
```

Lys Met Met Val Lys Gln Ile Leu Lys His Glu Phe Leu Pro Asp Thr
            20                  25                  30

Glu Tyr Ile Phe Phe Ile Asn Val Lys Asp Ile Asp Phe Asn Lys Glu
            35                  40                  45

Met Thr Leu Leu Glu Phe Leu Thr Thr Asn Ser Arg Val Lys Val Asn
        50                  55                  60

Tyr Thr Glu Glu Glu Ser Lys Ala Leu Ile Thr Phe Leu His Asn Asn
65                  70                  75                  80

Pro Asn Val Ala Ile Phe Phe Asp Gly Leu Asp Glu Ala Ser Thr Asn
                85                  90                  95

Glu Phe Ala Arg Ile Pro His Ile Cys Lys Leu Asp Gly Lys Ser Lys
            100                 105                 110

Pro Val Asp Ile Met Lys Asn Leu Phe Asn Leu Thr Leu Leu Pro Lys
            115                 120                 125

Ala Lys Ile Val Val Thr Ser Thr Leu His Gln Met Tyr Lys Leu His
        130                 135                 140

Pro Asp Tyr Arg Pro Thr Ser Ile Phe Glu Val Leu Gly Leu Leu Glu
145                 150                 155                 160

Glu Ala Lys Asn Asn Leu Gly Thr Gln Leu Cys Gly Glu Lys Tyr Pro
                165                 170                 175

Ala Ile Lys Lys Ile Leu Asp Gln Gln Pro Asn Leu Ala His Leu Cys
            180                 185                 190

Tyr Leu Pro Ile Asn Phe Ile Leu Ile Val Phe Cys Leu Leu Ser Asn
            195                 200                 205

Glu Gly Ser Asp Ile Lys Thr Met Thr Gln Val Leu Ile Phe Ser Met
    210                 215                 220

Thr Arg Phe Val Glu Leu Ser His Leu Lys Gly Glu Val Pro Leu Asp
225                 230                 235                 240

Lys Val Gly Ala Glu Met Val Lys Leu Ala Arg Leu Ala Tyr Lys Gly
                245                 250                 255

Leu Gln Gln Arg Lys Leu Val Phe Glu Lys Thr Asp Phe Asp Asp Val
            260                 265                 270

Lys Leu Ala Asp Glu Met Val Thr Asn Phe Phe His Thr Tyr Val Asp
        275                 280                 285

Lys Ser Ser Gly Ile Arg Met Lys Ile Leu Glu Gly Asn Lys Arg Ser
            290                 295                 300

Tyr Phe Thr His Leu Ile Trp Gln Glu Phe Tyr Ala Ala Val Tyr Leu
305                 310                 315                 320

Met Leu

<210> SEQ ID NO 103
<211> LENGTH: 82
<212> TYPE: PRT
<213> ORGANISM: Artificial Sequence
<220> FEATURE:
<223> OTHER INFORMATION: Synthetic construct

<400> SEQUENCE: 103

Phe Gly Leu Met Trp Tyr Leu Glu Glu Leu Lys Lys Glu Glu Phe Arg
1               5                   10                  15

Lys Phe Lys Glu His Leu Lys Gln Met Thr Leu Gln Leu Glu Leu Lys
            20                  25                  30

Gln Ile Pro Trp Thr Glu Val Lys Lys Ala Ser Arg Glu Glu Leu Ala
        35                  40                  45

```
Asn Leu Leu Ile Lys His Tyr Glu Glu Gln Gln Ala Trp Asn Ile Thr
 50                  55                  60

Leu Arg Ile Phe Gln Lys Met Asp Arg Lys Asp Leu Cys Met Lys Val
 65                  70                  75                  80

Met Arg

<210> SEQ ID NO 104
<211> LENGTH: 321
<212> TYPE: PRT
<213> ORGANISM: Artificial Sequence
<220> FEATURE:
<223> OTHER INFORMATION: Synthetic construct

<400> SEQUENCE: 104

Pro Arg Thr Val Ile Ile Gln Gly Pro Gln Gly Ile Gly Lys Thr Thr
  1               5                  10                  15

Leu Leu Met Lys Leu Met Met Ala Trp Ser Asp Asn Lys Ile Phe Arg
                 20                  25                  30

Asp Arg Phe Leu Tyr Thr Phe Tyr Phe Cys Cys Arg Glu Leu Arg Glu
             35                  40                  45

Leu Pro Pro Thr Ser Leu Ala Asp Leu Ile Ser Arg Glu Trp Pro Asp
 50                  55                  60

Pro Ala Ala Pro Ile Thr Glu Ile Val Ser Gln Pro Glu Arg Leu Leu
 65                  70                  75                  80

Phe Val Ile Asp Ser Phe Glu Glu Leu Gln Gly Gly Leu Asn Glu Pro
                 85                  90                  95

Asp Ser Asp Leu Cys Gly Asp Leu Met Glu Lys Arg Pro Val Gln Val
            100                 105                 110

Leu Leu Ser Ser Leu Leu Arg Lys Lys Met Leu Pro Glu Ala Ser Leu
            115                 120                 125

Leu Ile Ala Ile Lys Pro Val Cys Pro Lys Glu Leu Arg Asp Gln Val
130                 135                 140

Thr Ile Ser Glu Ile Tyr Gln Pro Arg Gly Phe Asn Glu Ser Asp Arg
145                 150                 155                 160

Leu Val Tyr Phe Cys Cys Phe Phe Lys Asp Pro Lys Arg Ala Met Glu
                165                 170                 175

Ala Phe Asn Leu Val Arg Glu Ser Glu Gln Leu Phe Ser Ile Cys Gln
            180                 185                 190

Ile Pro Leu Leu Cys Trp Ile Leu Cys Thr Ser Leu Lys Gln Glu Met
            195                 200                 205

Gln Lys Gly Lys Asp Leu Ala Leu Thr Cys Gln Ser Thr Thr Ser Val
210                 215                 220

Tyr Ser Ser Phe Val Phe Asn Leu Phe Thr Pro Glu Gly Ala Glu Gly
225                 230                 235                 240

Pro Thr Pro Gln Thr Gln His Gln Leu Lys Ala Leu Cys Ser Leu Ala
                245                 250                 255

Ala Glu Gly Met Trp Thr Asp Thr Phe Glu Phe Cys Glu Asp Asp Leu
            260                 265                 270

Arg Arg Asn Gly Val Val Asp Ala Asp Ile Pro Ala Leu Leu Gly Thr
            275                 280                 285

Lys Ile Leu Leu Lys Tyr Gly Glu Arg Glu Ser Ser Tyr Val Phe Leu
290                 295                 300

His Val Cys Ile Gln Glu Phe Cys Ala Ala Leu Phe Tyr Leu Leu Lys
305                 310                 315                 320

Ser
```

<210> SEQ ID NO 105
<211> LENGTH: 116
<212> TYPE: PRT
<213> ORGANISM: Artificial Sequence
<220> FEATURE:
<223> OTHER INFORMATION: Synthetic construct

<400> SEQUENCE: 105

```
Leu Val Ala Asn Phe Glu Lys Ala Arg Arg Ala His Trp Ile Phe Leu
 1               5                  10                  15
Gly Cys Phe Leu Thr Gly Leu Leu Asn Lys Lys Glu Gln Glu Lys Leu
                20                  25                  30
Asp Ala Phe Phe Gly Phe Gln Leu Ser Gln Glu Ile Lys Gln Gln Ile
            35                  40                  45
His Gln Cys Leu Lys Ser Leu Gly Glu Arg Gly Asn Pro Gln Gly Gln
        50                  55                  60
Val Asp Ser Leu Ala Ile Phe Tyr Cys Leu Phe Glu Met Gln Asp Pro
 65                  70                  75                  80
Ala Phe Val Lys Gln Ala Val Asn Leu Leu Gln Glu Ala Asn Phe His
                85                  90                  95
Ile Ile Asp Asn Val Asp Leu Val Ser Ala Tyr Cys Leu Lys Tyr
                100                 105                 110
Cys Ser Ser Leu
            115
```

<210> SEQ ID NO 106
<211> LENGTH: 81
<212> TYPE: PRT
<213> ORGANISM: Artificial Sequence
<220> FEATURE:
<223> OTHER INFORMATION: Synthetic construct

<400> SEQUENCE: 106

```
Arg Glu Leu Leu Leu Ala Ala Leu Glu Glu Leu Ser Gln Glu Gln Leu
 1               5                  10                  15
Lys Arg Phe Arg His Lys Leu Arg Asp Val Gly Pro Asp Gly Arg Ser
                20                  25                  30
Ile Pro Trp Gly Arg Leu Glu Arg Ala Asp Ala Val Asp Leu Ala Glu
            35                  40                  45
Gln Leu Ala Gln Phe Tyr Gly Pro Glu Pro Ala Leu Glu Val Ala Arg
        50                  55                  60
Lys Thr Leu Lys Arg Ala Asp Ala Arg Asp Val Ala Ala Gln Leu Gln
 65                  70                  75                  80
Glu
```

<210> SEQ ID NO 107
<211> LENGTH: 321
<212> TYPE: PRT
<213> ORGANISM: Artificial Sequence
<220> FEATURE:
<223> OTHER INFORMATION: Synthetic construct

<400> SEQUENCE: 107

```
Pro Leu Thr Val Val Leu Gln Gly Pro Ala Gly Ile Gly Lys Thr Met
 1               5                  10                  15
Ala Ala Lys Lys Ile Leu Tyr Asp Trp Ala Ala Gly Lys Leu Tyr Gln
                20                  25                  30
Gly Gln Val Asp Phe Ala Phe Phe Met Pro Cys Gly Glu Leu Leu Glu
```

```
                35                  40                  45
Arg Pro Gly Thr Arg Ser Leu Ala Asp Leu Ile Leu Asp Gln Cys Pro
    50                  55                  60

Asp Arg Gly Ala Pro Val Pro Gln Met Leu Ala Gln Pro Gln Arg Leu
65                  70                  75                  80

Leu Phe Ile Leu Asp Gly Ala Asp Glu Leu Pro Ala Leu Gly Gly Pro
                85                  90                  95

Glu Ala Ala Pro Cys Thr Asp Pro Phe Glu Ala Ala Ser Gly Ala Arg
            100                 105                 110

Val Leu Gly Gly Leu Leu Ser Lys Ala Leu Leu Pro Thr Ala Leu Leu
        115                 120                 125

Leu Val Thr Thr Arg Ala Ala Ala Pro Gly Arg Leu Gln Gly Arg Leu
    130                 135                 140

Cys Ser Pro Gln Cys Ala Glu Val Arg Gly Phe Ser Asp Lys Asp Lys
145                 150                 155                 160

Lys Lys Tyr Phe Tyr Lys Phe Phe Arg Asp Glu Arg Arg Ala Glu Arg
                165                 170                 175

Ala Tyr Arg Phe Val Lys Glu Asn Glu Thr Leu Phe Ala Leu Cys Phe
            180                 185                 190

Val Pro Phe Val Cys Trp Ile Val Cys Thr Val Leu Arg Gln Gln Leu
        195                 200                 205

Glu Leu Gly Arg Asp Leu Ser Arg Thr Ser Lys Thr Thr Thr Ser Val
    210                 215                 220

Tyr Leu Leu Phe Ile Thr Ser Val Leu Ser Ser Ala Pro Val Ala Asp
225                 230                 235                 240

Gly Pro Arg Leu Gln Gly Asp Leu Arg Asn Leu Cys Arg Leu Ala Arg
                245                 250                 255

Glu Gly Val Leu Gly Arg Arg Ala Gln Phe Ala Glu Lys Glu Leu Glu
            260                 265                 270

Gln Leu Glu Leu Arg Gly Ser Lys Val Gln Thr Leu Phe Leu Ser Lys
        275                 280                 285

Lys Glu Leu Pro Gly Val Leu Glu Thr Glu Val Thr Tyr Gln Phe Ile
    290                 295                 300

Asp Gln Ser Phe Gln Glu Phe Leu Ala Ala Leu Ser Tyr Leu Leu Glu
305                 310                 315                 320

Asp

<210> SEQ ID NO 108
<211> LENGTH: 138
<212> TYPE: PRT
<213> ORGANISM: Artificial Sequence
<220> FEATURE:
<223> OTHER INFORMATION: Synthetic construct

<400> SEQUENCE: 108

Leu Leu Arg Gly Asp Ala Gln Pro His Ser His Leu Val Leu Thr Thr
1               5                   10                  15

Arg Phe Leu Phe Gly Leu Leu Ser Ala Glu Arg Met Arg Asp Ile Glu
            20                  25                  30

Arg His Phe Gly Cys Met Val Ser Glu Arg Val Lys Gln Glu Ala Leu
        35                  40                  45

Arg Trp Val Gln Gly Gln Gly Gln Gly Cys Pro Gly Val Ala Pro Glu
    50                  55                  60

Val Thr Glu Gly Ala Lys Gly Leu Glu Asp Thr Glu Glu Pro Glu Glu
65                  70                  75                  80
```

```
Glu Glu Glu Gly Glu Glu Pro Asn Tyr Pro Leu Glu Leu Leu Tyr Cys
                85                  90                  95

Leu Tyr Glu Thr Gln Glu Asp Ala Phe Val Arg Gln Ala Leu Cys Arg
            100                 105                 110

Phe Pro Glu Leu Ala Leu Gln Arg Val Arg Phe Cys Arg Met Asp Val
        115                 120                 125

Ala Val Leu Ser Tyr Cys Val Arg Cys Cys
    130                 135

<210> SEQ ID NO 109
<211> LENGTH: 82
<212> TYPE: PRT
<213> ORGANISM: Artificial Sequence
<220> FEATURE:
<223> OTHER INFORMATION: Synthetic construct

<400> SEQUENCE: 109

Glu Asn Gly Val Met Leu Tyr Met Arg Asn Val Ser His Glu Glu Leu
 1               5                  10                  15

Gln Arg Phe Lys Gln Leu Leu Leu Thr Glu Leu Ser Thr Gly Thr Met
            20                  25                  30

Pro Ile Thr Trp Asp Gln Val Glu Thr Ala Ser Trp Ala Glu Val Val
        35                  40                  45

His Leu Leu Ile Glu Arg Phe Pro Gly Arg Arg Ala Trp Asp Val Thr
    50                  55                  60

Ser Asn Ile Phe Ala Ile Met Asn Cys Asp Lys Met Cys Val Val Val
65                  70                  75                  80

Arg Arg

<210> SEQ ID NO 110
<211> LENGTH: 321
<212> TYPE: PRT
<213> ORGANISM: Artificial Sequence
<220> FEATURE:
<223> OTHER INFORMATION: Synthetic construct

<400> SEQUENCE: 110

Pro Lys Thr Val Ala Ile Gln Gly Ala Pro Gly Ile Gly Lys Thr Ile
 1               5                  10                  15

Leu Ala Lys Lys Val Met Phe Glu Trp Ala Arg Asn Lys Phe Tyr Ala
            20                  25                  30

His Lys Arg Trp Cys Ala Phe Tyr Phe His Cys Gln Glu Val Asn Gln
        35                  40                  45

Thr Thr Asp Gln Ser Phe Ser Glu Leu Ile Gln Lys Trp Pro Gly
    50                  55                  60

Ser Gln Asp Leu Val Ser Lys Ile Met Ser Lys Pro Asp Gln Leu Leu
65                  70                  75                  80

Leu Leu Leu Asp Gly Phe Glu Glu Leu Thr Ser Thr Leu Ile Asp Arg
            85                  90                  95

Leu Glu Asp Leu Ser Glu Asp Trp Arg Gln Lys Leu Pro Gly Ser Val
            100                 105                 110

Leu Leu Ser Ser Leu Leu Ser Lys Thr Met Leu Pro Glu Ala Thr Leu
            115                 120                 125

Leu Ile Met Ile Arg Phe Thr Ser Trp Gln Thr Cys Lys Pro Leu Leu
        130                 135                 140

Lys Cys Pro Ser Leu Val Thr Leu Pro Gly Phe Asn Thr Met Glu Lys
145                 150                 155                 160
```

```
Ile Lys Tyr Phe Gln Met Tyr Phe Gly His Thr Glu Glu Gly Asp Gln
            165                 170                 175

Val Leu Ser Phe Ala Met Glu Asn Thr Ile Leu Phe Ser Met Cys Arg
            180                 185                 190

Val Pro Val Val Cys Trp Met Val Cys Ser Gly Leu Lys Gln Gln Met
            195                 200                 205

Glu Arg Gly Asn Asn Leu Thr Gln Ser Cys Pro Asn Ala Thr Ser Val
            210                 215                 220

Phe Val Arg Tyr Ile Ser Ser Leu Phe Pro Thr Arg Ala Glu Asn Phe
225                 230                 235                 240

Ser Arg Lys Ile His Gln Ala Gln Leu Glu Gly Leu Cys His Leu Ala
            245                 250                 255

Ala Asp Ser Met Trp His Arg Lys Trp Val Leu Gly Lys Glu Asp Leu
            260                 265                 270

Glu Glu Ala Lys Leu Asp Gln Thr Gly Val Thr Ala Phe Leu Gly Met
            275                 280                 285

Ser Ile Leu Arg Arg Ile Ala Gly Glu Glu Asp His Tyr Val Phe Thr
290                 295                 300

Leu Val Thr Phe Gln Glu Phe Phe Ala Ala Leu Phe Tyr Val Leu Cys
305                 310                 315                 320

Phe

<210> SEQ ID NO 111
<211> LENGTH: 115
<212> TYPE: PRT
<213> ORGANISM: Artificial Sequence
<220> FEATURE:
<223> OTHER INFORMATION: Synthetic construct

<400> SEQUENCE: 111

Leu Ile Ala Ser Pro Arg Gly Ser Lys Ser Tyr Leu Ser His Met Gly
1               5                   10                  15

Leu Phe Leu Phe Gly Phe Leu Asn Glu Ala Cys Ala Ser Ala Val Glu
            20                  25                  30

Gln Ser Phe Gln Cys Lys Val Ser Phe Gly Asn Lys Arg Lys Leu Leu
        35                  40                  45

Lys Val Ile Pro Leu Leu His Lys Cys Asp Pro Ser Pro Gly Ser
    50                  55                  60

Gly Val Pro Gln Leu Phe Tyr Cys Leu His Glu Ile Arg Glu Glu Ala
65                  70                  75                  80

Phe Val Ser Gln Ala Leu Asn Asp Tyr His Lys Val Val Leu Arg Ile
                85                  90                  95

Gly Asn Asn Lys Glu Val Gln Val Ser Ala Phe Cys Leu Lys Arg Cys
            100                 105                 110

Gln Tyr Leu
        115

<210> SEQ ID NO 112
<211> LENGTH: 82
<212> TYPE: PRT
<213> ORGANISM: Artificial Sequence
<220> FEATURE:
<223> OTHER INFORMATION: Synthetic construct

<400> SEQUENCE: 112

Arg Glu Ala Leu Leu Trp Ala Leu Ser Asp Leu Glu Glu Asn Asp Phe
1               5                   10                  15
```

```
Lys Lys Leu Lys Phe Tyr Leu Arg Asp Met Thr Leu Ser Glu Gly Gln
             20                  25                  30

Pro Pro Leu Ala Arg Gly Glu Leu Glu Gly Leu Ile Pro Val Asp Leu
             35                  40                  45

Ala Glu Leu Leu Ile Ser Lys Tyr Gly Glu Lys Glu Ala Val Lys Val
     50                  55                  60

Val Leu Lys Gly Leu Lys Val Met Asn Leu Leu Glu Leu Val Asp Gln
 65                  70                  75                  80

Leu Ser

<210> SEQ ID NO 113
<211> LENGTH: 317
<212> TYPE: PRT
<213> ORGANISM: Artificial Sequence
<220> FEATURE:
<223> OTHER INFORMATION: Synthetic construct

<400> SEQUENCE: 113

Pro Ser Leu Val Val Leu Gln Gly Ser Ala Gly Thr Gly Lys Thr Thr
  1               5                  10                  15

Leu Ala Arg Lys Met Val Leu Asp Trp Ala Thr Gly Thr Leu Tyr Pro
             20                  25                  30

Gly Arg Phe Asp Tyr Val Phe Tyr Val Ser Cys Lys Glu Val Val Leu
         35                  40                  45

Leu Leu Glu Ser Lys Leu Glu Gln Leu Leu Phe Trp Cys Cys Gly Asp
     50                  55                  60

Asn Gln Ala Pro Val Thr Glu Ile Leu Arg Gln Pro Glu Arg Leu Leu
 65                  70                  75                  80

Phe Ile Leu Asp Gly Phe Asp Glu Leu Gln Arg Pro Phe Glu Glu Lys
                 85                  90                  95

Leu Lys Lys Arg Gly Leu Ser Pro Lys Glu Ser Leu Leu His Leu Leu
            100                 105                 110

Ile Arg Arg His Thr Leu Pro Thr Cys Ser Leu Leu Ile Thr Thr Arg
        115                 120                 125

Pro Leu Ala Leu Arg Asn Leu Glu Pro Leu Leu Lys Gln Ala Arg His
    130                 135                 140

Val His Ile Leu Gly Phe Ser Glu Glu Glu Arg Ala Arg Tyr Phe Ser
145                 150                 155                 160

Ser Tyr Phe Thr Asp Glu Lys Gln Ala Asp Arg Ala Phe Asp Ile Val
                165                 170                 175

Gln Lys Asn Asp Ile Leu Tyr Lys Ala Cys Gln Val Pro Gly Ile Cys
            180                 185                 190

Trp Val Val Cys Ser Trp Leu Gln Gly Gln Met Glu Arg Gly Lys Val
        195                 200                 205

Val Leu Glu Thr Pro Arg Asn Ser Thr Asp Ile Phe Met Ala Tyr Val
    210                 215                 220

Ser Thr Phe Leu Pro Pro Asp Asp Gly Gly Cys Ser Glu Leu Ser
225                 230                 235                 240

Arg His Arg Val Leu Arg Ser Leu Cys Ser Leu Ala Ala Glu Gly Ile
                245                 250                 255

Gln His Gln Arg Phe Leu Phe Glu Glu Ala Glu Leu Arg Lys His Asn
            260                 265                 270

Leu Asp Gly Pro Arg Leu Ala Ala Phe Leu Ser Ser Asn Asp Tyr Gln
        275                 280                 285
```

```
Leu Gly Leu Ala Ile Lys Lys Phe Tyr Ser Phe Arg His Ile Ser Phe
    290                 295                 300

Gln Asp Phe Phe His Ala Met Ser Tyr Leu Val Lys Glu
305                 310                 315

<210> SEQ ID NO 114
<211> LENGTH: 93
<212> TYPE: PRT
<213> ORGANISM: Artificial Sequence
<220> FEATURE:
<223> OTHER INFORMATION: Synthetic construct

<400> SEQUENCE: 114

Leu Leu Glu Val Lys Glu Gln Glu Gly Asn Asp Glu Met Thr Leu Thr
1               5                   10                  15

Met Gln Phe Leu Leu Asp Ile Ser Lys Lys Asp Ser Phe Ser Asn Leu
                20                  25                  30

Glu Leu Lys Phe Cys Phe Arg Ile Ser Pro Cys Leu Ala Gln Asp Leu
            35                  40                  45

Lys His Phe Lys Glu Gln Met Glu Ser Met Lys His Asn Arg Thr Trp
        50                  55                  60

Asp Leu Glu Phe Ser Leu Tyr Glu Ala Lys Ile Lys Asn Leu Val Lys
65                  70                  75                  80

Gly Ile Gln Met Asn Asn Val Ser Phe Lys Ile Lys His
                85                  90

<210> SEQ ID NO 115
<211> LENGTH: 82
<212> TYPE: PRT
<213> ORGANISM: Artificial Sequence
<220> FEATURE:
<223> OTHER INFORMATION: Synthetic construct

<400> SEQUENCE: 115

Leu Cys Arg Leu Ser Thr Tyr Leu Glu Glu Leu Glu Ala Val Glu Leu
1               5                   10                  15

Lys Lys Phe Lys Leu Tyr Leu Gly Thr Ala Thr Glu Leu Gly Glu Gly
                20                  25                  30

Lys Ile Pro Trp Gly Ser Met Glu Lys Ala Gly Pro Leu Glu Met Ala
            35                  40                  45

Gln Leu Leu Ile Thr His Phe Gly Pro Glu Glu Ala Trp Arg Leu Ala
        50                  55                  60

Leu Ser Thr Phe Glu Arg Ile Asn Arg Lys Asp Leu Trp Glu Arg Gly
65                  70                  75                  80

Gln Arg

<210> SEQ ID NO 116
<211> LENGTH: 321
<212> TYPE: PRT
<213> ORGANISM: Artificial Sequence
<220> FEATURE:
<223> OTHER INFORMATION: Synthetic construct

<400> SEQUENCE: 116

Pro Arg Thr Val Val Met Gln Gly Ala Ala Gly Ile Gly Lys Ser Met
1               5                   10                  15

Leu Ala His Lys Val Met Leu Asp Trp Ala Asp Gly Lys Leu Phe Gln
                20                  25                  30

Gly Arg Phe Asp Tyr Leu Phe Tyr Ile Asn Cys Arg Glu Met Asn Gln
            35                  40                  45
```

Ser Ala Thr Glu Cys Ser Met Gln Asp Leu Ile Phe Ser Cys Trp Pro
 50                  55                  60

Glu Pro Ser Ala Pro Leu Gln Glu Leu Ile Arg Val Pro Glu Arg Leu
 65                  70                  75                  80

Leu Phe Ile Ile Asp Gly Phe Asp Glu Leu Lys Pro Ser Phe His Asp
                 85                  90                  95

Pro Gln Gly Pro Trp Cys Leu Cys Trp Glu Lys Arg Pro Thr Glu
             100                 105                 110

Leu Leu Leu Asn Ser Leu Ile Arg Lys Lys Leu Leu Pro Glu Leu Ser
             115                 120                 125

Leu Leu Ile Thr Thr Arg Pro Thr Ala Leu Glu Lys Leu His Arg Leu
         130                 135                 140

Leu Glu His Pro Arg His Val Glu Ile Leu Gly Phe Ser Glu Ala Glu
145                 150                 155                 160

Arg Lys Glu Tyr Phe Tyr Lys Tyr Phe His Asn Ala Glu Gln Ala Gly
                 165                 170                 175

Gln Val Phe Asn Tyr Val Arg Asp Asn Glu Pro Leu Phe Thr Met Cys
             180                 185                 190

Phe Val Pro Leu Val Cys Trp Val Val Cys Thr Cys Leu Gln Gln Gln
         195                 200                 205

Leu Glu Gly Gly Gly Leu Leu Arg Gln Thr Ser Arg Thr Thr Thr Ala
210                 215                 220

Val Tyr Met Leu Tyr Leu Leu Ser Leu Met Gln Pro Lys Pro Gly Ala
225                 230                 235                 240

Pro Arg Leu Gln Pro Pro Asn Gln Arg Gly Leu Cys Ser Leu Ala
             245                 250                 255

Ala Asp Gly Leu Trp Asn Gln Lys Ile Leu Phe Glu Glu Gln Asp Leu
             260                 265                 270

Arg Lys His Gly Leu Asp Gly Glu Asp Val Ser Ala Phe Leu Asn Met
         275                 280                 285

Asn Ile Phe Gln Lys Asp Ile Asn Cys Glu Arg Tyr Tyr Ser Phe Ile
290                 295                 300

His Leu Ser Phe Gln Glu Phe Phe Ala Ala Met Tyr Tyr Ile Leu Asp
305                 310                 315                 320

Glu

<210> SEQ ID NO 117
<211> LENGTH: 119
<212> TYPE: PRT
<213> ORGANISM: Artificial Sequence
<220> FEATURE:
<223> OTHER INFORMATION: Synthetic construct

<400> SEQUENCE: 117

Leu Leu Thr Glu Tyr Ala Phe Ser Glu Arg Ser Phe Leu Ala Leu Thr
 1               5                  10                  15

Ser Arg Phe Leu Phe Gly Leu Leu Asn Glu Glu Thr Arg Ser His Leu
                 20                  25                  30

Glu Lys Ser Leu Cys Trp Lys Val Ser Pro His Ile Lys Met Asp Leu
             35                  40                  45

Leu Gln Trp Ile Gln Ser Lys Ala Gln Ser Asp Gly Ser Thr Leu Gln
         50                  55                  60

Gln Gly Ser Leu Glu Phe Phe Ser Cys Leu Tyr Glu Ile Gln Glu Glu
65                  70                  75                  80

```
Glu Phe Ile Gln Gln Ala Leu Ser His Phe Gln Val Ile Val Val Ser
                85                  90                  95

Asn Ile Ala Ser Lys Met Glu His Met Val Ser Ser Phe Cys Leu Lys
            100                 105                 110

Arg Cys Arg Ser Ala Gln Val
        115
```

<210> SEQ ID NO 118
<211> LENGTH: 83
<212> TYPE: PRT
<213> ORGANISM: Artificial Sequence
<220> FEATURE:
<223> OTHER INFORMATION: Synthetic construct

<400> SEQUENCE: 118

```
Glu Trp Thr Leu Gln Thr Leu Leu Glu Gln Leu Asn Glu Asp Glu Leu
 1               5                  10                  15

Lys Ser Phe Lys Ser Leu Leu Trp Ala Phe Pro Leu Glu Asp Val Leu
            20                  25                  30

Gln Lys Thr Pro Trp Ser Glu Val Glu Glu Ala Asp Gly Lys Lys Leu
        35                  40                  45

Ala Glu Ile Leu Val Asn Thr Ser Ser Glu Asn Trp Ile Arg Asn Ala
    50                  55                  60

Thr Val Asn Ile Leu Glu Glu Met Asn Leu Thr Glu Leu Cys Lys Met
65                  70                  75                  80

Ala Lys Ala
```

<210> SEQ ID NO 119
<211> LENGTH: 314
<212> TYPE: PRT
<213> ORGANISM: Artificial Sequence
<220> FEATURE:
<223> OTHER INFORMATION: Synthetic construct

<400> SEQUENCE: 119

```
Pro Tyr Thr Val Val Leu His Gly Pro Ala Gly Val Gly Lys Thr Thr
 1               5                  10                  15

Leu Ala Lys Lys Cys Met Leu Asp Trp Thr Asp Cys Asn Leu Ser Pro
            20                  25                  30

Thr Leu Arg Tyr Ala Phe Tyr Leu Ser Cys Lys Glu Leu Ser Arg Met
        35                  40                  45

Gly Pro Cys Ser Phe Ala Glu Leu Ile Ser Lys Asp Trp Pro Glu Leu
    50                  55                  60

Gln Asp Asp Ile Pro Ser Ile Leu Ala Gln Ala Gln Arg Ile Leu Phe
65                  70                  75                  80

Val Val Asp Gly Leu Asp Glu Leu Lys Val Pro Pro Gly Ala Leu Ile
            85                  90                  95

Gln Asp Ile Cys Gly Asp Trp Glu Lys Lys Pro Val Pro Val Leu
            100                 105                 110

Leu Gly Ser Leu Leu Lys Arg Lys Met Leu Pro Arg Ala Ala Leu Leu
        115                 120                 125

Val Thr Thr Arg Pro Arg Ala Leu Arg Asp Leu Gln Leu Leu Ala Gln
    130                 135                 140

Gln Pro Ile Tyr Val Arg Val Glu Gly Phe Leu Glu Glu Asp Arg Arg
145                 150                 155                 160

Ala Tyr Phe Leu Arg His Phe Gly Asp Glu Asp Gln Ala Met Arg Ala
                165                 170                 175
```

```
Phe Glu Leu Met Arg Ser Asn Ala Ala Leu Phe Gln Leu Gly Ser Ala
            180                 185                 190

Pro Ala Val Cys Trp Ile Val Cys Thr Thr Leu Lys Leu Gln Met Glu
            195                 200                 205

Lys Gly Glu Asp Pro Val Pro Thr Cys Leu Thr Arg Thr Gly Leu Phe
210                 215                 220

Leu Arg Phe Leu Cys Ser Arg Phe Pro Gln Gly Ala Gln Leu Arg Gly
225                 230                 235                 240

Ala Leu Arg Thr Leu Ser Leu Leu Ala Ala Gln Gly Leu Trp Ala Gln
            245                 250                 255

Met Ser Val Phe His Arg Glu Asp Leu Glu Arg Leu Gly Val Gln Glu
            260                 265                 270

Ser Asp Leu Arg Leu Phe Leu Asp Gly Asp Ile Leu Arg Gln Asp Arg
            275                 280                 285

Val Ser Lys Gly Cys Tyr Ser Phe Ile His Leu Ser Phe Gln Gln Phe
            290                 295                 300

Leu Thr Ala Leu Phe Tyr Ala Leu Glu Lys
305                 310

<210> SEQ ID NO 120
<211> LENGTH: 115
<212> TYPE: PRT
<213> ORGANISM: Artificial Sequence
<220> FEATURE:
<223> OTHER INFORMATION: Synthetic construct

<400> SEQUENCE: 120

Leu Leu Ser Gly Glu Glu Arg Leu Lys Asn Pro Asp Leu Ile Gln Val
1               5                   10                  15

Gly His Phe Leu Phe Gly Leu Ala Asn Glu Lys Arg Ala Lys Glu Leu
            20                  25                  30

Glu Ala Thr Phe Gly Cys Arg Met Ser Pro Asp Ile Lys Gln Glu Leu
        35                  40                  45

Leu Gln Cys Lys Ala His Leu His Ala Asn Lys Pro Leu Ser Val Thr
    50                  55                  60

Asp Leu Lys Glu Val Leu Gly Cys Leu Tyr Glu Ser Gln Glu Glu Glu
65                  70                  75                  80

Leu Ala Lys Val Val Ala Pro Phe Lys Gly Ile Ser Ile His Leu
                85                  90                  95

Thr Asn Thr Ser Glu Val Met His Cys Ser Phe Ser Leu Lys His Cys
                100                 105                 110

Gln Asp Leu
        115

<210> SEQ ID NO 121
<211> LENGTH: 82
<212> TYPE: PRT
<213> ORGANISM: Artificial Sequence
<220> FEATURE:
<223> OTHER INFORMATION: Synthetic construct

<400> SEQUENCE: 121

Asp Phe Gly Leu Leu Leu Tyr Leu Glu Glu Leu Asn Lys Glu Glu Leu
1               5                   10                  15

Asn Thr Phe Lys Leu Phe Leu Lys Glu Thr Met Glu Pro Glu His Gly
            20                  25                  30

Leu Thr Pro Trp Asn Glu Val Lys Lys Ala Arg Arg Glu Asp Leu Ala
        35                  40                  45
```

```
Asn Leu Met Lys Lys Tyr Tyr Pro Gly Glu Lys Ala Trp Ser Val Ser
 50                  55                  60

Leu Lys Ile Phe Gly Lys Met Asn Leu Lys Asp Leu Cys Glu Arg Ala
 65                  70                  75                  80

Lys Glu

<210> SEQ ID NO 122
<211> LENGTH: 321
<212> TYPE: PRT
<213> ORGANISM: Artificial Sequence
<220> FEATURE:
<223> OTHER INFORMATION: Synthetic construct

<400> SEQUENCE: 122

Pro Gln Ile Val Val Leu Gln Gly Ala Ala Gly Val Gly Lys Thr Thr
 1               5                  10                  15

Leu Val Arg Lys Ala Met Leu Asp Trp Ala Glu Gly Ser Leu Tyr Gln
                 20                  25                  30

Gln Arg Phe Lys Tyr Val Phe Tyr Leu Asn Gly Arg Glu Ile Asn Gln
             35                  40                  45

Leu Lys Glu Arg Ser Phe Ala Gln Leu Ile Ser Lys Asp Trp Pro Ser
 50                  55                  60

Thr Glu Gly Pro Ile Glu Ile Met Tyr Gln Pro Ser Ser Leu Leu
 65                  70                  75                  80

Phe Ile Ile Asp Ser Phe Asp Glu Leu Asn Phe Ala Phe Glu Pro
                 85                  90                  95

Glu Phe Ala Leu Cys Glu Asp Trp Thr Gln Glu His Pro Val Ser Phe
                100                 105                 110

Leu Met Ser Ser Leu Leu Arg Lys Val Met Leu Pro Glu Ala Ser Leu
                115                 120                 125

Leu Val Thr Thr Arg Leu Thr Thr Ser Lys Arg Leu Lys Gln Leu Leu
                130                 135                 140

Lys Asn His His Tyr Val Glu Leu Leu Gly Met Ser Glu Asp Ala Arg
145                 150                 155                 160

Glu Glu Tyr Ile Tyr Gln Phe Phe Glu Asp Lys Arg Trp Ala Met Lys
                165                 170                 175

Val Phe Ser Ser Leu Lys Ser Asn Glu Met Leu Phe Ser Met Cys Gln
                180                 185                 190

Val Pro Leu Val Cys Trp Ala Ala Cys Thr Cys Leu Lys Gln Gln Met
                195                 200                 205

Glu Lys Gly Gly Asp Val Thr Leu Thr Cys Gln Thr Thr Ala Leu
                210                 215                 220

Phe Thr Cys Tyr Ile Ser Ser Leu Phe Thr Pro Val Asp Gly Gly Ser
225                 230                 235                 240

Pro Ser Leu Pro Asn Gln Ala Gln Leu Arg Arg Leu Cys Gln Val Ala
                245                 250                 255

Ala Lys Gly Ile Trp Thr Met Thr Tyr Val Phe Tyr Arg Glu Asn Leu
                260                 265                 270

Arg Arg Leu Gly Leu Thr Gln Ser Asp Val Ser Ser Phe Met Asp Ser
                275                 280                 285

Asn Ile Ile Gln Lys Asp Ala Glu Tyr Glu Asn Cys Tyr Val Phe Thr
                290                 295                 300

His Leu His Val Gln Glu Phe Phe Ala Ala Met Phe Tyr Met Leu Lys
305                 310                 315                 320
```

Gly

<210> SEQ ID NO 123
<211> LENGTH: 115
<212> TYPE: PRT
<213> ORGANISM: Artificial Sequence
<220> FEATURE:
<223> OTHER INFORMATION: Synthetic construct

<400> SEQUENCE: 123

```
Leu Leu Gln Ser Thr Ser Tyr Lys Asp Pro His Leu Thr Gln Met Lys
 1               5                  10                  15

Cys Phe Leu Phe Gly Leu Leu Asn Glu Asp Arg Val Lys Gln Leu Glu
             20                  25                  30

Arg Thr Phe Asn Cys Lys Met Ser Leu Lys Ile Lys Ser Lys Leu Leu
         35                  40                  45

Gln Cys Met Glu Val Leu Gly Asn Ser Asp Tyr Ser Pro Ser Gln Leu
     50                  55                  60

Gly Phe Leu Glu Leu Phe His Cys Leu Tyr Glu Thr Gln Asp Lys Ala
 65                  70                  75                  80

Phe Ile Ser Gln Ala Met Arg Cys Phe Pro Lys Val Ala Ile Asn Ile
                 85                  90                  95

Cys Glu Lys Ile His Leu Leu Val Ser Ser Phe Cys Leu Lys His Cys
            100                 105                 110

Arg Cys Leu
        115
```

<210> SEQ ID NO 124
<211> LENGTH: 83
<212> TYPE: PRT
<213> ORGANISM: Artificial Sequence
<220> FEATURE:
<223> OTHER INFORMATION: Synthetic construct

<400> SEQUENCE: 124

```
Glu Phe Tyr Ile His Lys Gly Tyr Asp Asp Val Ser Ser Asp Asn Ser
 1               5                  10                  15

Arg Glu Lys Ile Lys Gly Glu Pro Ser Glu Cys Glu Leu Gly His Phe
             20                  25                  30

Pro Arg Ile Pro Trp Ala Asn Leu Arg Ala Ala Asp Pro Leu Asn Leu
         35                  40                  45

Ser Phe Leu Leu Asp Glu His Phe Pro Lys Gly Gln Ala Trp Lys Val
     50                  55                  60

Val Leu Gly Ile Phe Gln Thr Met Asn Leu Thr Ser Leu Cys Glu Lys
 65                  70                  75                  80

Val Arg Ala
```

<210> SEQ ID NO 125
<211> LENGTH: 325
<212> TYPE: PRT
<213> ORGANISM: Artificial Sequence
<220> FEATURE:
<223> OTHER INFORMATION: Synthetic construct

<400> SEQUENCE: 125

```
Ala Gln Thr Ile Val Leu Val Gly Arg Ala Gly Val Gly Lys Thr Thr
 1               5                  10                  15

Leu Ala Met Arg Ala Met Leu His Trp Ala Asn Gly Val Leu Phe Gln
             20                  25                  30
```

```
Gln Arg Phe Ser Tyr Val Phe Tyr Leu Ser Cys His Lys Ile Arg Tyr
            35                  40                  45

Met Lys Glu Thr Thr Phe Ala Glu Leu Ile Ser Leu Asp Trp Pro Asp
 50                  55                  60

Phe Asp Ala Pro Ile Glu Glu Phe Met Ser Gln Pro Glu Lys Leu Leu
 65                  70                  75                  80

Phe Ile Ile Asp Gly Phe Glu Glu Ile Ile Ser Glu Ser Arg Ser
                    85                  90                  95

Glu Ser Leu Asp Asp Gly Ser Pro Cys Thr Asp Trp Tyr Gln Glu Leu
            100                 105                 110

Pro Val Thr Lys Ile Leu His Ser Leu Leu Lys Lys Glu Leu Val Pro
        115                 120                 125

Leu Ala Thr Leu Leu Ile Thr Ile Lys Thr Trp Phe Val Arg Asp Leu
    130                 135                 140

Lys Ala Ser Leu Val Asn Pro Cys Phe Val Gln Ile Thr Gly Phe Thr
145                 150                 155                 160

Gly Asp Asp Leu Arg Val Tyr Phe Met Arg His Phe Asp Asp Ser Ser
                165                 170                 175

Glu Val Glu Lys Ile Leu Gln Gln Leu Arg Lys Asn Glu Thr Leu Phe
            180                 185                 190

His Ser Cys Ser Ala Pro Met Val Cys Trp Thr Val Cys Ser Cys Leu
        195                 200                 205

Lys Gln Pro Lys Val Arg Tyr Tyr Asp Leu Gln Ser Ile Thr Gln Thr
    210                 215                 220

Thr Thr Ser Leu Tyr Ala Tyr Phe Phe Ser Asn Leu Phe Ser Thr Ala
225                 230                 235                 240

Glu Val Asp Leu Ala Asp Asp Ser Trp Pro Gly Gln Trp Arg Ala Leu
                245                 250                 255

Cys Ser Leu Ala Ile Glu Gly Leu Trp Ser Met Asn Phe Thr Phe Asn
            260                 265                 270

Lys Glu Asp Thr Glu Ile Glu Gly Leu Glu Val Pro Phe Ile Asp Ser
        275                 280                 285

Leu Tyr Glu Phe Asn Ile Leu Gln Lys Ile Asn Asp Cys Gly Gly Cys
    290                 295                 300

Thr Thr Phe Thr His Leu Ser Phe Gln Glu Phe Phe Ala Ala Met Ser
305                 310                 315                 320

Phe Val Leu Glu Glu
            325

<210> SEQ ID NO 126
<211> LENGTH: 112
<212> TYPE: PRT
<213> ORGANISM: Artificial Sequence
<220> FEATURE:
<223> OTHER INFORMATION: Synthetic construct

<400> SEQUENCE: 126

Leu Leu Gln His Val Leu Leu Asp Lys Glu Ala Tyr Trp Thr Pro Val
 1               5                  10                  15

Val Leu Phe Phe Phe Gly Leu Leu Asn Lys Asn Ile Ala Arg Glu Leu
                20                  25                  30

Glu Asp Thr Leu His Cys Lys Ile Ser Pro Arg Val Met Glu Glu Leu
            35                  40                  45

Leu Lys Trp Gly Glu Glu Leu Gly Lys Ala Glu Ser Ala Ser Leu Gln
 50                  55                  60
```

```
Phe His Ile Leu Arg Leu Phe His Cys Leu His Glu Ser Gln Glu Glu
 65                  70                  75                  80

Asp Phe Thr Lys Lys Met Leu Gly Arg Ile Phe Glu Val Asp Leu Asn
                 85                  90                  95

Ile Leu Glu Asp Glu Glu Leu Gln Ala Leu Lys His Cys Lys Arg Leu
            100                 105                 110

<210> SEQ ID NO 127
<211> LENGTH: 77
<212> TYPE: PRT
<213> ORGANISM: Artificial Sequence
<220> FEATURE:
<223> OTHER INFORMATION: Synthetic construct

<400> SEQUENCE: 127

Phe Asp Leu Leu Trp Tyr Leu Glu Asn Leu Ser Asp Lys Glu Phe Gln
  1               5                  10                  15

Ser Phe Lys Lys Tyr Leu Ala Arg Lys Ile Leu Asp Phe Lys Leu Pro
                 20                  25                  30

Gln Phe Pro Leu Ile Gln Met Thr Lys Glu Glu Leu Ala Asn Val Leu
             35                  40                  45

Pro Ile Ser Tyr Glu Gly Gln Tyr Ile Trp Asn Met Leu Phe Ser Ile
 50                  55                  60

Phe Ser Met Met Arg Lys Glu Asp Leu Cys Arg Lys Ile
 65                  70                  75

<210> SEQ ID NO 128
<211> LENGTH: 321
<212> TYPE: PRT
<213> ORGANISM: Artificial Sequence
<220> FEATURE:
<223> OTHER INFORMATION: Synthetic construct

<400> SEQUENCE: 128

Asn Leu Asn Val Phe Leu Met Gly Glu Arg Ala Ser Gly Lys Thr Ile
  1               5                  10                  15

Val Ile Asn Leu Ala Val Leu Arg Trp Ile Lys Gly Glu Met Trp Gln
                 20                  25                  30

Asn Met Ile Ser Tyr Val Val His Leu Thr Ala His Glu Ile Asn Gln
             35                  40                  45

Met Thr Asn Ser Ser Leu Ala Glu Leu Ile Ala Lys Asp Trp Pro Asp
 50                  55                  60

Gly Gln Ala Pro Ile Ala Asp Ile Leu Ser Asp Pro Lys Lys Leu Leu
 65                  70                  75                  80

Phe Ile Leu Glu Asp Leu Asp Asn Ile Arg Phe Glu Leu Asn Val Asn
                 85                  90                  95

Glu Ser Ala Leu Cys Ser Asn Ser Thr Gln Lys Val Pro Ile Pro Val
            100                 105                 110

Leu Leu Val Ser Leu Leu Lys Arg Lys Met Ala Pro Gly Cys Trp Phe
            115                 120                 125

Leu Ile Ser Ser Arg Pro Thr Arg Gly Asn Asn Val Lys Thr Phe Leu
            130                 135                 140

Lys Glu Val Asp Cys Cys Thr Thr Leu Gln Leu Ser Asn Gly Lys Arg
145                 150                 155                 160

Glu Ile Tyr Phe Asn Ser Phe Phe Lys Asp Arg Gln Arg Ala Ser Ala
                165                 170                 175

Ala Leu Gln Leu Val His Glu Asp Glu Ile Leu Val Gly Leu Cys Arg
            180                 185                 190
```

```
Val Ala Ile Leu Cys Trp Ile Thr Cys Thr Val Leu Lys Arg Gln Met
        195                 200                 205
Asp Lys Gly Arg Asp Phe Gln Leu Cys Cys Gln Thr Pro Thr Asp Leu
        210                 215                 220
His Ala His Phe Leu Ala Asp Ala Leu Thr Ser Glu Ala Gly Leu Thr
225                 230                 235                 240
Ala Asn Gln Tyr His Leu Gly Leu Leu Lys Arg Leu Cys Leu Leu Ala
                245                 250                 255
Ala Gly Gly Leu Phe Leu Ser Thr Leu Asn Phe Ser Gly Glu Asp Leu
                260                 265                 270
Arg Cys Val Gly Phe Thr Glu Ala Asp Val Ser Val Leu Gln Ala Ala
                275                 280                 285
Asn Ile Leu Leu Pro Ser Asn Thr His Lys Asp Arg Tyr Lys Phe Ile
        290                 295                 300
His Leu Asn Val Gln Glu Phe Cys Thr Ala Ile Ala Phe Leu Met Ala
305                 310                 315                 320
Val

<210> SEQ ID NO 129
<211> LENGTH: 111
<212> TYPE: PRT
<213> ORGANISM: Artificial Sequence
<220> FEATURE:
<223> OTHER INFORMATION: Synthetic construct

<400> SEQUENCE: 129

Lys Arg Glu Gln Tyr Ser Asp Phe Asn Gln Val Phe Thr Phe Ile Phe
1               5                   10                  15
Gly Leu Leu Asn Ala Asn Arg Arg Lys Ile Leu Glu Thr Ser Phe Gly
                20                  25                  30
Tyr Gln Leu Pro Met Val Asp Ser Phe Lys Trp Tyr Ser Val Gly Tyr
            35                  40                  45
Met Lys His Leu Asp Arg Asp Pro Glu Lys Leu Thr His His Met Pro
        50                  55                  60
Leu Phe Tyr Cys Leu Tyr Glu Asn Arg Glu Glu Glu Phe Val Lys Thr
65                  70                  75                  80
Ile Val Asp Ala Leu Met Glu Val Thr Val Tyr Leu Gln Ser Asp Lys
                85                  90                  95
Asp Met Met Val Ser Leu Tyr Cys Leu Asp Tyr Cys Cys His Leu
                100                 105                 110
```